(12) United States Patent
Unkefer et al.

(10) Patent No.: US 9,068,194 B2
(45) Date of Patent: Jun. 30, 2015

(54) INCREASING PLANT GROWTH BY MODULATING OMEGA-AMIDASE EXPRESSION IN PLANTS

(75) Inventors: Pat J. Unkefer, Los Alamos, NM (US); Penelope S. Anderson, Los Alamos, NM (US); Thomas J. Knight, Raymond, ME (US)

(73) Assignees: Los Alamos National Security, LLC, Los Alamos, NM (US); University of Maine System Board of Trustees, Bangor, ME (US)

( * ) Notice: Subject to any disclaimer, the term of this patent is extended or adjusted under 35 U.S.C. 154(b) by 816 days.

(21) Appl. No.: 13/037,307

(22) Filed: Feb. 28, 2011

(65) Prior Publication Data

US 2012/0144528 A1    Jun. 7, 2012

Related U.S. Application Data

(60) Provisional application No. 61/308,971, filed on Feb. 28, 2010.

(51) Int. Cl.
*C12N 15/82* (2006.01)
*C12N 9/80* (2006.01)

(52) U.S. Cl.
CPC .............. *C12N 15/8261* (2013.01); *C12N 9/80* (2013.01); *C12N 15/8262* (2013.01)

(58) Field of Classification Search
None
See application file for complete search history.

(56) References Cited

U.S. PATENT DOCUMENTS

| | | | |
|---|---|---|---|
| 6,555,500 B1 | 4/2003 | Unkefer et al. | |
| 6,831,040 B1 * | 12/2004 | Unkefer et al. | 504/287 |
| 2008/0250527 A1 | 10/2008 | Stewart et al. | |

FOREIGN PATENT DOCUMENTS

WO    2010/025466 A2    3/2010

OTHER PUBLICATIONS

Chilley et al 2006 The Plant Cell 18: p. 3058-3072.*
Calderon et al Journal of Bacteriology Feb. 1985: p. 807-809.*
Mosca et al 1994 FEBS Letters 353: p. 21-24.*
Campbell and Gowri 1990 Plant Physiology 92: p. 1-11.*
European Search Report dated Jul. 17, 2013 in EP 11748246.3, 7 pages.
Mazelis et al., "In Vivo Conversion of 5-Oxoproline to Glutamate by Higher Plants," *Plant Physiol.* (1976) 57, 85-87.
Jaisson, et al., "Molecular Identification of ω-amidase, the Enzyme that is Functionally Coupled with Glutamine Transminases, as Putative Tumor Suporessor Nit2," *Biochimie* 91 (2009), 1066-1071.
EMBL Accession No. AY0755592, "*Arabidopsis thaliana* AT5g12040/F14F18_210 mRNA, complete cds", Apr. 16, 2005. http://www.ebi.ac.uk/Tools/dbfetch/emblfetch?id=AY075592.1&Submit=Go.
International Search Report dated Jul. 8, 2011 for International Patent Application No. PCT/US2011/026552, 2 pages.

* cited by examiner

*Primary Examiner* — Eileen B O Hara
*Assistant Examiner* — Matthew Keogh
(74) *Attorney, Agent, or Firm* — Kilpatrick Townsend & Stockton LLP

(57) ABSTRACT

The present disclosure relates to compositions and methods for increasing the leaf-to-root ratio of the signal metabolite 2-oxoglutaramate and related proline molecules in plants by modulating levels of ω-amidase to increase nitrogen use efficiency, resulting in enhanced growth, faster growth rates, greater seed and fruit/pod yields, earlier and more productive flowering, increased tolerance to high salt conditions, and increased biomass yields.

33 Claims, 5 Drawing Sheets

```
Medicago_trunca   ------------------------------------------------------------
Ricinus_communi   ------------------------------------------------------------
Populus_trichoc   MKSAISSTTTLLSSKNLSLKLNLNHSPLSRLPSSLFRSKSNTHFPSLLPRNNSTHNQKSQ
vitis_vinifera    ---MKSAALSALLSSTLSYASPPNLNLLRPATAVLCRSLLPTSTP-----NPFHTQLRTA
Arabidopsis_tha   ------------------------------------------------------------
Oryza_sativa      ------------------------------------------------------------
Zea_mays          ------------MVAAAAAAAAATATAAALLAPGLKLCAGRARVSS-----PSGLPLRRVTA
Picea_sitchensi   ------------MTPLLSYSLRVVASALRPKSSIASAVGRLSAT-----PKRFPANRLRI
consensus         ----------------------------------l-------------------------

Medicago_trunca   ----MAASSINSELARSPAIPLPTPPLTN----------------FKIGLCQLSVTSDK
Ricinus_communi   -----MSAS-FNPEQARSPPALPLPTPPLTKAQFLLTSYLTILIYMIFKIGLCQLLVTPDK
Populus_trichoc   INTPIMASSFMPEQARAPPALPLNVPP------------------FKIGLCQLSVTADK
vitis_vinifera    KTRASMSSSFKPFQARVPATPPPTPPLSK----------------FKIGLCQLSVTADK
Arabidopsis_tha   -----MASSFNPEQARVPSALPLPAPPLTK---------------FNIGLCQLSVTSDK
Oryza_sativa      MATA--ASFR-PEAARSPPAVQPPAPPLS----------------KFKVALCQLSVTADK
Zea_mays          MASAPNSSFR-PEEARSPPALELPIPPLS----------------KFKVALCQLSVTADK
Picea_sitchensi   SYRNYNAAMAKPEDARSPPALPLPSAPNGG---------------KFKIALCQLSVTENK
consensus         --t----assf-pEqARsPpAlplPtpPlt----------------FkigLCQLsVTadk Medicago_trunca   DKNIAHARTAIQDAAAKGAKLILLPEIWNSPYSNDSFPVTAEDIDAGGDASPSTAMLSEL
Ricinus_communi   AKNIAHARKAIEEAAAKGAKLVLLPEIWNSPYSNDSFPVTAEDIDAGHVASPSTAMLSQL
Populus_trichoc   ERNIAHARKAIEEAAAKGAKLVNLPEIWNSPYSNDCFPVYAEDIDAGGEASPSTAMLSEA
vitis_vinifera    AKNIAHARKAIEEAVEKGAQLVLLPEIWNSPYSNDSFPVYAEDIDAGSDASPSTAMLSEV
Arabidopsis_tha   KRNISHAKKAIEEAASKGAKLVLLPEIWNSPYSNDSFPVYAEEIDAGGDASPSTAMLSEV
Oryza_sativa      ARNIARAREAIEAAAAGGAKLVLLPEIWNGPYSNDSFPETAEDIEAGGDAAPSFSMHSEV
Zea_mays          SRNIAKAAAIEKAASDGAKLVLLPEIWNGPYSNDSFPEYAEDIAAGGDAAPSFSMLSEV
Picea_sitchensi   ERNIAHARDAIEAAADNGAQLVVLPEIWNGPYSNASFPVYAEDIDAGGSASPSTSMLSEV
consensus         drNIahArkAIeeAaakGAkLvlLPEIWNsPYSNdsFPvYAEdIdAGgdAsPStamLsev Medicago_trunca   SSLLKITIVGGSIPERSGDRLYNTCCVFGTDGKLKAKHRKIHLFDIDIPGKITFIESLTL
Ricinus_communi   ARLLNITIVGGSIPERSGDRLYNTCCVFDTQGNLIAKHRKIHLFDIDIPGKITFIESKTL
Populus_trichoc   AGLLKVTIVGGSIPERSGDRLYNTCCVFDSDGKLKAKHRKIHLFDIDIPGKITFIESKTL
vitis_vinifera    SHALKITIVGGSIPERCGDQLYNTCCVFGSDGKLKAKHRKIHLFDINIPGKITFMESKTL
Arabidopsis_tha   SKRLKITIIGGSIPERVGDRLYNTCCVFGSDGEELKAKHRKIHLFDIDIPGKITFMESKTL
Oryza_sativa      ARSLQIFLVGGSISERSGNKLYNTCCVFGSDGELKGKHRKIHLFDIDIPGKITFKESKTL
Zea_mays          ARSLQITLVGGSIAERSGNNLYNTCCVFGSDGQLKGKHRKIHLFDIDIPGKITFKESKTL
Picea_sitchensi   ARSKGIFIVGGSISLSLDNLYNTCCVFSKDGELKAKHRKIHLFDIDIPGKISFMESKSL
consensus         ar-lkiTivGGSIpERsGdrLYNTCCvFgsdG-LkaKHRKIHLFDIdIPGKItFiEskTL Medicago_trunca   TAGDTPTIVDTEVGRIGIGICYDIRFPELAMIYAARGAHRLLCYPGAFNHTTGPLNWELLQ
Ricinus_communi   TAGETPNIVDTEVGRIGIGICYDIRFQELAVLYAARGAHLICYPGAFNHTTGPLNWELLQ
Populus_trichoc   TAGETPTIVDTEVGRIGIGICYDIRFQELAIIYAARGAHLICYPGAFNHTTGPLNWELLQ
vitis_vinifera    TAGGSPTIVDTEVGRIGIGICYDIRFSELAMLYAARGAHLICYPGAFNHTTGPLNWELLQ
Arabidopsis_tha   TAGETPTIVDTDVGRIGIGICYDIRFQELAMIYAARGAHLLCYPGAFNHTTGPLNWELLQ
Oryza_sativa      TAGQDLTVVDTDVGRIGIGICYDIRFQELAMLYAARGAHLLCYPGAFNHTTGPLNWELLQ
Zea_mays          TAGQSPTVVDTDVGRIGIGICYDIRFQELAMLYAARGAHLLCYPGAFNHTTGPLNWELLQ
Picea_sitchensi   TAGNTPTIVDTDVGRIGIGICYDIRFQELAMLYAARGAHLICYPGAFNHTTGPLNWELLQ
consensus         TAGdtptiVDTeVGRIGIGICYDIRFqELAmlYAARGAHLlCYPGAFNHTTGPLNWELLQ Medicago_trunca   RARATDNQLYVATCSPARDTTGWLCGLEVTPLL------------LVLLEKFWLLQN
Ricinus_communi   RARAADNQLYVATCSPARDVGAGYIVAWGHSTLVGPFGEILATTEHQDIIIAEIDYSLLE
Populus_trichoc   RARAADNQLYVATCSPARDVAAGYIVAWGHSTLVGPFGEVLATTEHEEDIIIAEIDYSLLE
vitis_vinifera    RARAADNQLYVATCSPARDAGAGYIVAWGHSTLVGPFGEVLATTEHEEAIIISEIDYSLIE
Arabidopsis_tha   RARATDNQLYVATCSPARDSGAGYIAWGHSTLVGPFGEVLATTEHEEAIIIAEIDYSILE
Oryza_sativa      RARAADNQLFVATCAPARDTSAGYIVAWGHSTLVGPFGEVIATTEHEETTIMAEIDYSLID
Zea_mays          RARAADNQLFVATCAPARDTSAGYIVAWGHSTLVGPFGEVIATTEHEEATIIADIDYSLIE
Picea_sitchensi   RARAIDNQLYVATCSPARDINAGYIVAWGHSTLVAPFGEIVATTEHEEATVIADIDYSRIE
consensus         RARAaDNQLyVATCsPARDtgagyvawGHstLvgpfgevlatteheeailiaeidyslie Medicago_trunca   ARRQ------PL------------------- (SEQ ID NO: 13)
Ricinus_communi   LHSQLSTTNLPLPTPTTTRDSTILEEDDLVYIYI (SEQ ID NO: 10)
Populus_trichoc   VRRTN----LPLTKQRRGDLYQLVDVQRLKSDS- (SEQ ID NO: 6)
vitis_vinifera    LRRTN----LPLLNQRRGDLYQLVDVQRLDSQ-- (SEQ ID NO: 4)
Arabidopsis_tha   QRRTS----LPLNRQRRGDLYQLVDVQRLDSK-- (SEQ ID NO: 3)
Oryza_sativa      QRRQF----LPLQYQRRGDLYQLVDVQRSGSDE- (SEQ ID NO: 8)
Zea_mays          QRRQF----LPLQHQRRGDLYQLVDVQRLGSQ-- (SEQ ID NO: 5)
Picea_sitchensi   ERRHN----MPLEKQRHGDLYQLVDVSRLDTAKH (SEQ ID NO: 7)
consensus         -Rrq-----lPL--qrrgdlyqlvdvqrl-s--- (SEQ ID NO: 44)
```

FIG. 2

```
Mus_musculus      ------------------------------------MSTFRLALIQLQVSSIKSDNL
Equus_caballus    MAAHSILDLSGLDRESQIDLQRPLKARPGKAKDLSSGSACTFRLALIQLQVSSVKSDNL
Homo_sapiens      ------------------------------------MTSFRLALIQLQISSIKSDNV
Danio_rerio       ------------------------------------MSKFRLAVVQLHVSKIKADNL
Xenopus_Siluran   ------------------------------------MAKFRLSLVQFLVSPVKSENL
Arabidopsis_tha   ---------------MASSFNPEQARVPSALPLPAPPLTKFNIGLCQLSVTSDNKRNI
consensus         ------------------------------------makFrlaliQlqvssiKsdnl Mus_musculus      RACSLVREAAKQGANIVSLPECFNSPYGTTYFPDYAEKIPG-----ESTQKLSEVAKES
Equus_caballus    RACGLVREAAAQGAKIVCLPECFNSPIGTNYFPQYAEKIPG-----ESTQKLSEVAKEC
Homo_sapiens      RACSFIREAATQGAKIVSLPECFNSPYGAKYFPEYAEKIPG-----ESTQKLSEVAKEC
Danio_rerio       RAQTLVTEAAGQGAKVVVLPECFNSPYGTGFFKEYAEKIPG-----ESTQVLSETAKKC
Xenopus_Siluran   RACKLIREAAQKGAQIVALPECFNSPYGTKYFPEYAEKIPG-----ESTERLSQVAKEC
Arabidopsis_tha   HAKKAIEEAASKGAKLVLLPEIWNSPYSNDSFPVYAEEIDAGGDASFSTAMLSEVSKRL
consensus         rAcslvrEAA-qGAkiV-LPEcfNSPYgt-yFpeYAEkIpg-----eSTqkLSevaKec Mus_musculus      IYLIGGSIPEEDAGKLYNTCSVFGPDGSLLVKHRKIHLFDIDVPGKITFQESKTLSPGD
Equus_caballus    IYLIGGSIPEEDAGKLYNTCAVFGPDGALLVKHRKLHLFDIDVPGKITFQESKTLSPGD
Homo_sapiens      IYLIGGSIPEEDAGKLYNTCAVFGPDGTLLAKYRKIHLFDIDVPGKITFQESKTLSPGD
Danio_rerio       IYLVGGSIPEEDGGKLYNTCSVFGPDGTLLVTHRKIHLFDIDVPGKIRFQESETLSPGK
Xenopus_Siluran   IYLIGGSIPEEDSGKLYNTCAVFGPDGTLLVKHRKIHLFDIDVPGKIRFQESETLSPGD
Arabidopsis_tha   ITIIGGSIPERVGDRLYNTCCVFGSDGELKAKHRKIHLFDIDIPGKITFMESKTLTAGE
consensus         IyliGGSIPEedagkLYNTCaVFGpDGtLlvkhRKiHLFDIDvPGKItFqESkTLspGd Mus_musculus      FSTFDTPYCKVGLGICYDMRFAELAQIYAQRGCQLLVYPGAFNLTTGPAHWELLQRARA
Equus_caballus    FSTFDTPYCRVGLGICYDLRFAELAQIYAQRGCQLLVYPGAFNLTTGPAHWELLQRGRA
Homo_sapiens      FSTFDTPYCRVGLGICYDMRFAELAQIYAQRGCQLLVYPGAFNLTTGPAHWELLQRSRA
Danio_rerio       LSMFETPYCKVGVGICYDIRFAELAQIYAKEGCQLLVYPGAFNMTTGPAHWELLQRGRA
Xenopus_Siluran   FSVFETPYCKVGVGICYDIRFAELAQLISKEGCQLLVYPGAFNMTTGPAHWELLQRARA
Arabidopsis_tha   PEIVDDDVGRIGIGICYDIRFQELMTFAARGAHLLCFPGAFNMTTGRFHWELLQRARA
consensus         fstfdTpyckvGlGICYDiRFaELAqiYaqrGcqLLvYPGAFNlTTGPaHWELLQRaRA Mus_musculus      DNQVYVATASPARDDKASYVAWGHSTVVDFWGQVLTKAGTEETILYSDIDLKKLAEIRQ
Equus_caballus    DNQVYVATASPARDDKASYVAWGHSTVVTPWGEVLATAGTEEMIVYSDIDLKKLAEIRQ
Homo_sapiens      DNQVYVATASPARDDKASYVAWGHSTVVNPWGEVLAKAGTE-------------------
Danio_rerio       DNQVYVATASPARDETASVVAWGHSSVINFWGEVISKAGSEESVVYADIDLQYLADVRQ
Xenopus_Siluran   DNQVYVATASPARDEKASYVAWGHSTIVSPWGEVIAKAGSEETVISADIDLEYLAEIRE
Arabidopsis_tha   DNQLYVATCSPARDSGAGYTAWGHSTLVGFFGEVLATTEHEEAIIIAEIDYSILEQRRT
consensus         DNQvYVATaSPARDdkAsYvAWGHStvv-PwGeVlakagtEetilyadidl--laeirq Mus_musculus      IPILKQKRADLYTVESKKP---- (SEQ ID NO: 38)
Equus_caballus    IPIFSQKRLDLYAVEAKKP---- (SEQ ID NO: 34)
Homo_sapiens      ----------------------- (SEQ ID NO: 33)
Danio_rerio       IPITKQRRHDLYSVNSVQEG--- (SEQ ID NO: 36)
Xenopus_Siluran   IPIRRQRRHDLYSVEEKKN---- (SEQ ID NO: 35)
Arabidopsis_tha   LPLNRQRRGDLYQLVDVQRLDSK (SEQ ID NO: 3)
consensus         ipi-kqrr-dlytve-kk----- (SEQ ID NO: 45)
```

FIG. 3

INCREASING PLANT GROWTH BY MODULATING OMEGA-AMIDASE EXPRESSION IN PLANTS

RELATED APPLICATION

This application claims the benefit under 35 USC 119(e) of U.S. Provisional Patent Application No. 61/308,971, filed Feb. 28, 2010, the disclosure of which is hereby incorporated by reference in its entirety.

STATEMENT AS TO RIGHTS TO INVENTIONS MADE UNDER FEDERALLY SPONSORED RESEARCH OR DEVELOPMENT

This invention was made with government support under Contract No. DE-AC52-06NA25396, awarded by the United States Department of Energy to Los Alamos National Security, LLC. The government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -13-1.TXT, created on Oct. 23, 2013, 184,320 bytes, machine format IBM-PC, MS-Windows operating system, is hereby incorporated by reference in its entirety for all purposes.

BACKGROUND OF THE INVENTION

As the human population increases worldwide, and available farmland continues to be destroyed or otherwise compromised, the need for more effective and sustainable agriculture systems is of paramount interest to the human race. Improving crop yields, protein content, and plant growth rates represent major objectives in the development of agriculture systems that can more effectively respond to the challenges presented.

In recent years, the importance of improved crop production technologies has only increased as yields for many well-developed crops have tended to plateau. Many agricultural activities are time sensitive, with costs and returns being dependent upon rapid turnover of crops or upon time to market. Therefore, rapid plant growth is an economically important goal for many agricultural businesses that involve high-value crops such as grains, vegetables, berries and other fruits.

Genetic engineering has and continues to play an increasingly important yet controversial role in the development of sustainable agriculture technologies. A large number of genetically modified plants and related technologies have been developed in recent years, many of which are in widespread use today (Factsheet: Genetically Modified Crops in the United States, Pew Initiative on Food and Biotechnology, August 2004,). The adoption of transgenic plant varieties is now very substantial and is on the rise, with approximately 250 million acres planted with transgenic plants in 2006.

While acceptance of transgenic plant technologies may be gradually increasing, particularly in the United States, Canada and Australia, many regions of the World remain slow to adopt genetically modified plants in agriculture, notably Europe. Therefore, consonant with pursuing the objectives of responsible and sustainable agriculture, there is a strong interest in the development of genetically engineered plants that do not introduce toxins or other potentially problematic substances into plants and/or the environment. There is also a strong interest in minimizing the cost of achieving objectives such as improving herbicide tolerance, pest and disease resistance, and overall crop yields. Accordingly, there remains a need for transgenic plants that can meet these objectives.

The goal of rapid plant growth has been pursued through numerous studies of various plant regulatory systems, many of which remain incompletely understood. In particular, the plant regulatory mechanisms that coordinate carbon and nitrogen metabolism are not fully elucidated. These regulatory mechanisms are presumed to have a fundamental impact on plant growth and development.

The metabolism of carbon and nitrogen in photosynthetic organisms must be regulated in a coordinated manner to assure efficient use of plant resources and energy. Current understanding of carbon and nitrogen metabolism includes details of certain steps and metabolic pathways which are subsystems of larger systems. In photosynthetic organisms, carbon metabolism begins with $CO_2$ fixation, which proceeds via two major processes, termed C-3 and C-4 metabolism. In plants with C-3 metabolism, the enzyme ribulose bisphosphate carboxylase (RuBisCo) catalyzes the combination of $CO_2$ with ribulose bisphosphate to produce 3-phosphoglycerate, a three carbon compound (C-3) that the plant uses to synthesize carbon-containing compounds. In plants with C-4 metabolism, $CO_2$ is combined with phosphoenol pyruvate to form acids containing four carbons (C-4), in a reaction catalyzed by the enzyme phosphoenol pyruvate carboxylase. The acids are transferred to bundle sheath cells, where they are decarboxylated to release $CO_2$, which is then combined with ribulose bisphosphate in the same reaction employed by C-3 plants.

Numerous studies have found that various metabolites are important in plant regulation of nitrogen metabolism. These compounds include the organic acid malate and the amino acids glutamate and glutamine. Nitrogen is assimilated by photosynthetic organisms via the action of the enzyme glutamine synthetase (GS) which catalyzes the combination of ammonia with glutamate to form glutamine. GS plays a key role in the assimilation of nitrogen in plants by catalyzing the addition of ammonium to glutamate to form glutamine in an ATP-dependent reaction (Miflin and Habash, 2002, Journal of Experimental Botany, Vol. 53, No. 370, pp. 979-987). GS also reassimilates ammonia released as a result of photorespiration and the breakdown of proteins and nitrogen transport compounds. GS enzymes may be divided into two general classes, one representing the cytoplasmic form (GS1) and the other representing the plastidic (i.e., chloroplastic) form (GS2).

Previous work has demonstrated that increased expression levels of GS1 result in increased levels of GS activity and plant growth, although reports are inconsistent. For example, Fuentes et al. reported that CaMV S35 promoter-driven overexpression of Alfalfa GS1 (cytoplasmic form) in tobacco resulted in increased levels of GS expression and GS activity in leaf tissue, increased growth under nitrogen starvation, but no effect on growth under optimal nitrogen fertilization conditions (Fuentes et al., 2001, J. Exp. Botany 52: 1071-81). Temple et al. reported that transgenic tobacco plants overexpressing the full length Alfalfa GS1 coding sequence contained greatly elevated levels of GS transcript, and GS polypeptide which assembled into active enzyme, but did not report phenotypic effects on growth (Temple et al., 1993, Molecular and General Genetics 236: 315-325). Corruzi et al. have reported that transgenic tobacco overexpressing a pea cytosolic GS1 transgene under the control of the CaMV S35 promoter show increased GS activity, increased cytosolic GS protein, and improved growth characteristics (U.S. Pat. No. 6,107,547). Unkefer et al. have more recently reported that transgenic tobacco plants overexpressing the Alfalfa GS1 in foliar tissues, which had been screened for increased leaf-to-root GS activity following genetic segregation by selfing to achieve increased GS1 transgene copy number, were found to produce increased 2-hydroxy-5-oxoproline levels in their foliar portions, which was found to lead to markedly increased growth rates over wild type tobacco plants (see, U.S. Pat. Nos. 6,555,500; 6,593,275; and 6,831,040).

Unkefer et al. have further described the use of 2-hydroxy-5-oxoproline (also known as 2-oxoglutaramate) to improve plant growth (U.S. Pat. Nos. 6,555,500; 6,593,275; 6,831, 040). In particular, Unkefer et al. disclose that increased concentrations of 2-hydroxy-5-oxoproline in foliar tissues (relative to root tissues) trigger a cascade of events that result in increased plant growth characteristics. Unkefer et al. describe methods by which the foliar concentration of 2-hydroxy-5-oxoproline may be increased in order to trigger increased plant growth characteristics, specifically, by applying a solution of 2-hydroxy-5-oxoproline directly to the foliar portions of the plant and over-expressing glutamine synthetase preferentially in leaf tissues.

SUMMARY OF THE INVENTION

The present disclosure is based on the surprising discovery that increasing ω-amidase (omega-amidase) expression in the root tissues of a plant results in an increase in the plant's leaf-to-root ratio of the signal metabolite 2-oxoglutaramate and related proline molecules. Additionally, increasing ω-amidase expression in the root tissues of a plant results in decreased ω-amidase expression in leaf tissue. Advantageously, modulating the expression of ω-amidase in plants results in plants with increased nitrogen use efficiency, which in turn results in enhanced growth and other agronomic characteristics, including faster growth rates, greater seed and fruit/pod yields, earlier and more productive flowering, increased tolerance to high salt conditions, and increased biomass yields.

Accordingly, one aspect of the present disclosure relates to a transgenic plant containing an ω-amidase transgene, where the ω-amidase transgene is operably linked to a root-preferred promoter.

Another aspect of the present disclosure provides a transgenic plant having inhibited expression of endogenous ω-amidase in leaf tissue.

Still another aspect of the present disclosure relates to a method for increasing nitrogen use efficiency of a plant relative to a wild type or untransformed plant of the same species, by: (a) introducing an ω-amidase transgene into the plant, where the ω-amidase transgene is operably linked to a root-preferred promoter; (b) expressing the ω-amidase transgene in root tissue of the plant or the progeny of the plant; and (c) selecting a plant having an increased leaf-to-root ratio of 2-oxoglutaramate relative to a plant of the same species that does not contain an ω-amidase transgene, where the increased leaf-to-root ratio of 2-oxoglutaramate results in increased nitrogen use efficiency.

Yet another aspect of the present disclosure relates to a method for increasing nitrogen use efficiency of a plant relative to a wild type or untransformed plant of the same species, by: (a) inhibiting endogenous ω-amidase expression in leaf tissue of the plant; and (b) selecting a plant having an increased leaf-to-root ratio of 2-oxoglutaramate relative to a plant of the same species that does not have inhibited endogenous ω-amidase expression in leaf tissue, where the increased leaf-to-root ratio of 2-oxoglutaramate results in increased nitrogen use efficiency

BRIEF DESCRIPTION OF THE DRAWINGS

FIG. 2 depicts amino acid sequence alignments of an *Arabidopsis thaliana* ω-amidase with other putative plant ω-amidases.

FIG. 3 depicts amino acid sequence alignments of an *Arabidopsis thaliana* ω-amidase with other putative animal ω-amidases.

DETAILED DESCRIPTION OF THE INVENTION

Definitions

Figure 1:
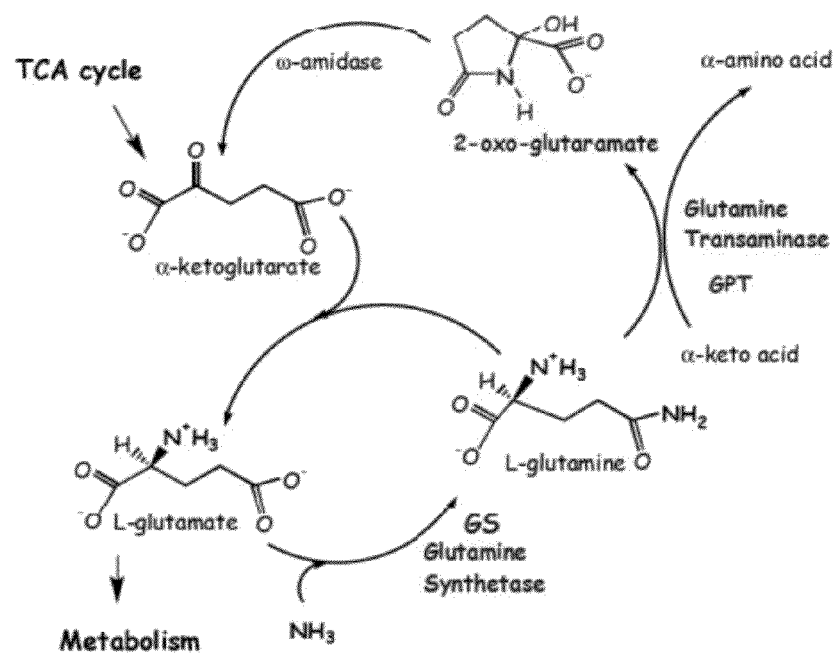
FIG. 1 depicts a schematic of a metabolic pathway of nitrogen assimilation and 2-oxoglutaramate biosynthesis.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y.; Current Protocols in Molecular Biology (Ausbel et al., eds., John Wiley & Sons, Inc. 2001; Transgenic Plants: Methods and Protocols (Leandro Pena, ed., Humana Press, $1^{st}$ edition, 2004); and, *Agrobacterium* Protocols (Wan, ed., Humana Press, $2^{nd}$ edition, 2006). As appropriate, procedures involving the use of commercially available kits and reagents are generally carried out in accordance with manufacturer defined protocols and/or parameters unless otherwise noted.

Each document, reference, patent application or patent cited in this text is expressly incorporated herein in its entirety by reference, and each should be read and considered as part of this specification. That the document, reference, patent application or patent cited in this specification is not repeated herein is merely for conciseness.

The term "nucleic acid" refers to deoxyribonucleotides or ribonucleotides and polymers thereof ("polynucleotides") in either single- or double-stranded form.

Unless specifically limited, the term "polynucleotide" encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

The term "promoter" refers to a nucleic acid control sequence or sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. As used herein, a promoter may include the full nucleotide sequence, or may only include the core domain or sequence that directs transcription of the operably linked nucleic acid. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "plant" includes whole plants, plant organs (e.g., leaves, stems, flowers, roots, reproductive organs, embryos and parts thereof, etc.), seedlings, seeds and plant cells and progeny thereof. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

The terms "GPT polynucleotide" and "GPT nucleic acid" are used interchangeably herein, and refer to a full length or partial length polynucleotide sequence of a gene which encodes a polypeptide involved in catalyzing the synthesis of 2-oxoglutaramate, and includes polynucleotides containing both translated (coding) and un-translated sequences, as well as the complements thereof. The term "GPT coding sequence" refers to the part of the gene which is transcribed and encodes a GPT protein. The term "targeting sequence" and "transit peptide" are used interchangeably and refer to the amino terminal part of a protein which directs the protein into a subcellular compartment of a cell, such as a chloroplast in a plant cell. GPT polynucleotides are further defined by their ability to hybridize under defined conditions to the GPT polynucleotides specifically disclosed herein, or to PCR products derived therefrom.

A "GPT transgene" is a nucleic acid molecule comprising a GPT polynucleotide which is exogenous to transgenic plant, or plant embryo, organ or seed, harboring the nucleic acid molecule, or which is exogenous to an ancestor plant, or plant embryo, organ or seed thereof, of a transgenic plant harboring the GPT polynucleotide. A "GPT transgene" may encompass a polynucleotide that encodes either a full length GPT protein or a truncated GPT protein, including but not limited to a GPT protein lacking a chloroplast transit peptide. More particularly, the exogenous GPT transgene will be heterogeneous with any GPT polynucleotide sequence present in wild-type plant, or plant embryo, organ or seed into which the GPT transgene is inserted. To this extent the scope of the heterogeneity required need only be a single nucleotide difference. However, preferably the heterogeneity will be in the order of an identity between sequences selected from the following identities: 0.01%, 0.05%, 0.1%, 0.5%, 1%, 5%, 10%, 15%, and 20%.

The terms "GS polynucleotide" and "GS nucleic acid" are used interchangeably herein, and refer to a full length or partial length polynucleotide sequence of a gene which encodes a glutamine synthetase protein, and includes polynucleotides containing both translated (coding) and un-translated sequences, as well as the complements thereof. The term "GS coding sequence" refers to the part of the gene which is transcribed and encodes a GS protein. The terms "GS1 polynucleotide" and "GS1 nucleic acid" are used interchangeably herein, and refer to a full length or partial length polynucleotide sequence of a gene which encodes a glutamine synthetase isoform 1 protein, and includes polynucleotides containing both translated (coding) and un-translated sequences, as well as the complements thereof. The term "GS1 coding sequence" refers to the part of the gene which is transcribed and encodes a GS1 protein.

A "GS transgene" is a nucleic acid molecule comprising a GS polynucleotide which is exogenous to transgenic plant, or plant embryo, organ or seed, harboring the nucleic acid molecule, or which is exogenous to an ancestor plant, or plant embryo, organ or seed thereof, of a transgenic plant harboring the GS polynucleotide. A "GS transgene" may encompass a polynucleotide that encodes either a full length GS protein or a truncated GS protein, including but not limited to a GS protein lacking a transit peptide. A "GS1 transgene" is a nucleic acid molecule comprising a GS1 polynucleotide which is exogenous to transgenic plant, or plant embryo, organ or seed, harboring the nucleic acid molecule, or which is exogenous to an ancestor plant, or plant embryo, organ or seed thereof, of a transgenic plant harboring the GS1 polynucleotide. A "GS1 transgene" may encompass a polynucleotide that encodes either a full length GS protein or a truncated GS1 protein, including but not limited to a GS1 protein lacking a transit peptide. More particularly, the exogenous GS or GS1 transgene will be heterogeneous with any GS or GS1 polynucleotide sequence present in wild-type plant, or plant embryo, organ or seed into which the GS or GS1 transgene is inserted. To this extent the scope of the heterogeneity required need only be a single nucleotide difference. However, preferably the heterogeneity will be in the order of an identity between sequences selected from the following identities: 0.01%, 0.05%, 0.1%, 0.5%, 1%, 5%, 10%, 15%, and 20%.

The terms "ω-amidase (omega-amidase) polynucleotide" and "ω-amidase nucleic acid" are used interchangeably herein, and refer to a polynucleotide sequence of a gene which encodes a polypeptide involved in the enzymatic breakdown of 2-oxoglutaramate, and includes polynucleotides containing both translated (coding) and un-translated sequences, as well as the complements thereof. The term "ω-amidase coding sequence" refers to the part of the gene which is transcribed and encodes an ω-amidase protein. The ω-amidase polynucleotides are further defined by their ability to hybridize under defined conditions to the ω-amidase polynucleotide specifically disclosed herein, or to PCR products derived therefrom.

An "ω-amidase transgene" is a nucleic acid molecule comprising an ω-amidase polynucleotide which is exogenous to transgenic plant, or plant embryo, organ or seed, harboring the nucleic acid molecule, or which is exogenous to an ancestor plant, or plant embryo, organ or seed thereof, of a transgenic plant harboring the ω-amidase polynucleotide. An "ω-amidase" may encompass a polynucleotide that encodes either a full length ω-amidase protein or a truncated ω-amidase protein, including but not limited to an ω-amidase protein lacking a chloroplast transit peptide. More particularly, the exogenous ω-amidase transgene will be heterogeneous with any ω-amidase polynucleotide sequence present in wild-type plant, or plant embryo, organ or seed into which the ω-amidase transgene is inserted. To this extent the scope of the heterogeneity required need only be a single nucleotide difference. However, preferably the heterogeneity will be in the order of an identity between sequences selected from the following identities: 0.01%, 0.05%, 0.1%, 0.5%, 1%, 5%, 10%, 15%, and 20%.

The term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "isolated" refers to material which is substantially or essentially free from components which normally accompany the material as it is found in its native or natural state. However, the term "isolated" is not intended refer to the components present in an electrophoretic gel or other separation medium. An isolated component is free from such separation media and in a form ready for use in another application or already in use in the new application/milieu. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity) over a specified region, when compared and aligned for maximum correspondence over a comparison window, or designated region as measured using a sequence comparison algorithms, or by manual alignment and visual inspection. This definition also refers to the complement of a test sequence, which has substantial sequence or subsequence complementarity when the test sequence has substantial identity to a reference sequence. This definition also refers to the complement of a test sequence, which has substantial sequence or subsequence complementarity when the test sequence has substantial identity to a reference sequence.

When percentage of sequence identity is used in reference to polypeptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the polypeptide. Where sequences differ in conservative substitutions, the percent sequence identity may be adjusted upwards to correct for the conservative nature of the substitution.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from about 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, highly stringent conditions are selected to be about 5-10° C. lower than the thermal melting point (Tm) for the specific sequence at a defined ionic strength pH. Low stringency conditions are generally selected to be about 15-30° C. below the Tm. Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

Genomic DNA or cDNA comprising GPT polynucleotides may be identified in standard Southern blots under stringent conditions using the GPT polynucleotide sequences disclosed here. For this purpose, suitable stringent conditions for such hybridizations are those which include a hybridization in a buffer of 40% formamide, 1M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions may be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

Transgenic Plants with Altered Levels of Ω-Amidase Expression:

The present disclosure provides transgenic plants containing higher levels of the signal metabolite 2-oxoglutaramate and its analogs in foliar tissues versus root or below-ground tissues and methods for increasing nitrogen use efficiency of a plant generating plants. 2-oxoglutaramate is a metabolite which is an extremely potent effector of gene expression, metabolism and plant growth (U.S. Pat. No. 6,555,500), and which may play a pivotal role in the coordination of the carbon and nitrogen metabolism systems (Lancien et al., 2000, *Enzyme Redundancy and the Importance of 2-Oxoglutarate in Higher Plants Ammonium Assimilation*, Plant Physiol. 123: 817-824).

The levels of 2-oxoglutaramate in leaf tissue may be increased by increasing the biosynthesis of 2-oxoglutaramate. The biosynthesis of 2-oxoglutaramte in leaf tissue may be preferentially increased to a level sufficient to exceed the breakdown rate by, for example, by decreasing the activity of the enzyme catalyzing the breakdown of 2-oxoglutaramate (FIG. 1). Additionally, the levels of 2-oxoglutaramate in root tissue may be decreased by increasing the breakdown of 2-oxoglutaramate. The breakdown rate of 2-oxoglutaramte in root tissue may be preferentially increased by, for example, increasing the activity of the enzyme catalyzing the breakdown of 2-oxoglutaramate (FIG. 1).

The methods disclosed herein are used to generate transgenic plants exhibiting higher leaf-to-root ratios of 2-oxoglutaramate when compared to wild type or progenitor plants. In the practice of the disclosed methods, 2-oxoglutaramate concentration in the leaf and root tissues may be modulated by any one of or a combination of several approaches disclosed herein. For example, the leaf-to-root ratio of 2 may be increased by increasing the activity of ω-amidases in root tissues or by inhibiting the activity of ω-amidases in leaf tissues.

Modulation of the Ω-Amidase Pathway in Plants:

The present disclosure is based on the surprising discovery that the leaf-to-root ratio of 2-oxoglutaramate may be increased in plants by modulating ω-amidase expression in the root and/or leaf tissue of plants. Moreover, increasing the leaf-to-root ratio of 2-oxoglutaramate results in increased nitrogen use efficiency.

Applicants have identified an ω-amidase pathway that may be modulated to achieve the objective of increasing the relative leaf to root concentration of 2-oxoglutaramate thereby triggering higher Nitrogen assimilation and carbon metabolism dynamics resulting in enhanced growth rates and agronomic characteristics. The only intermediate in this pathway, 2-oxoglutaramate, ostensibly functions as a signal metabolite that reflects the flux of assimilated nitrogen. Increased levels of 2-oxoglutaramate trigger a striking increase in resource acquisition rates, carbon and nitrogen metabolism, and overall growth. Plants treated with 2-oxoglutaramate or engineered to produce increased 2-oxoglutaramate levels in leaf show greater leaf nitrogen and media nitrogen use efficiency. The resulting increase in overall growth metabolism is accompanied by increased leaf-to-root ratios in 2-oxoglutaramate pools, which are in turn controlled by glutamine synthetase, glutamine phenylpyruvate transaminase and ω-amidase activities, as well as by the availability of nitrogen, in a complex, interrelated and tissue-specific manner. Moreover, increasing the leaf-to-root ratio of 2-oxoglutaramate results in increased nitrogen use efficiency. As used herein, "increased nitrogen use efficiency" and "increasing nitrogen use efficiency" refers to plants that have enhanced growth and better agronomic characteristics. Agronomic characteristics include, without limitation, faster growth rates, greater seed and fruit/pod yields, earlier and more productive flowering, increased tolerance to high salt conditions, and/or increased biomass yields resulting from increased nitrogen utilization mediated by an increased leaf-to-root ratio of 2-oxoglutaramate.

As described in Example 1, infra, transgenic plants engineered to over-express GS and/or GPT show lower ω-amidase activities in the leaves and greater ω-amidase activity in the roots. GPT and GS+GPT transgenic plants showed the largest increases in root ω-amidase activity. These plants responded to expression of the transgenes by altering their ω-amidase activities such that they tend to increase the leaf 2-oxoglutaramate pool and maintain the root 2-oxoglutaramate pool. These responses combined in the GS+GPT over-expressing plants to generate the highest leaf and lowest root 2-oxoglutaramate pools and the highest leaf and lowest GS and GPT activities.

Without wishing to be bound by theory, it is believed that the signal metabolite, 2-oxoglutaramate, provides two different messages, depending upon the tissue. Increased 2-oxoglutaramate in the leaves is stimulatory (Tables 2-4) and appears to effectively convey the message that nitrogen is abundant and carbon must be fixed to take advantage of the increased nitrogen. The increased nitrogen supply-driven faster growth is accompanied by an increase in leaf-to-root 2-oxoglutaramate pools. The increase in the leaf 2-oxoglutaramate pool is apparently key to the stimulation. Without wishing to be bound by theory, it is believed that the plant's strategy to maintain near normal or diminished 2-oxoglutaramate pool in the roots is a mechanism they may be using to overcome the apparent contradiction of how plants grow faster when fertilized with nitrogen and yet display the long-observed inhibition of nitrate uptake and assimilation in roots by a "N metabolite downstream of $NH_3$" (Foyer et al., 2002, Kluwer Academic Publishers, The Netherlands). If the inhibitory nitrogen metabolite is 2-oxoglutaramate, then the mechanism could be to manage its concentration downward when nitrogen is abundant to let the plant prosper and, conversely keep 2-oxoglutaramate higher when nitrogen is scarce and the plant tries to conserve a limiting resource to survive to reproduce.

Without wishing to be bound by theory, it is believed that the results disclosed herein indicate that modulating ω-amidase activity in plants is useful in driving increased levels of 2-oxoglutaramate in leaves relative to roots. Two approaches are hereinafter described: (1) promoting the breakdown of 2-oxoglutaramate by upregulating ω-amidase activity in root tissues, and (2) impairing the breakdown of 2-oxoglutaramate in leaf tissues by impairing, downregulating, or deactivating leaf ω-amidase activity.

Promoting the Breakdown of 2-Oxoglutaramate by Upregulating Ω-Amidase Activity in Root Tissues:

Certain aspects of the present disclosure relate to transgenic plants containing an ω-amidase transgene, where the ω-amidase transgene is operably linked to a root-preferred promoter.

It has been previously shown that an ω-amidase-like pathway in plants that is possibly involved in 2-oxoglutaramate breakdown (Von Gusgtav Schwab 1936, Planta Archiv fur wissenschaftliche botanik. 25.Band, 4. Heft. p 579-606. [German publication]; Olenicheva, LS1955, Biokhimiia 20(2): 165-172. [Russian publication]; and Yamamoto, Y. 1955, Journal of Biochemistry 42:763-774). However, none of these studies identified an ω-amidase protein.

Accordingly, it is believed that that an ω-amidase pathway is involved in the breakdown of 2-oxoglutaramate and its analogs in plants (FIG. 1). Additionally, an ω-amidase enzyme has been shown to be capable of catalyzing the breakdown of 2-oxoglutaramate in animal cells by opening the ring of 2-oxoglutaramate and removing the nitrogen to yield a keto acid (Cooper and Meister, 1977, CRC Critical Reviews in Biochemistry, pages 281-303; Meister, 1952, J. Biochem. 197: 304).

Applicants have identified a putative plant ω-amidase gene and protein (*Arabidopsis thaliana* gene AT5g12040, F14F18_210 mRNA). The identification of the putative plant ω-amidase was based on sequence homology analysis to ω-amidase gene sequences from other organisms including human and rat. The nucleotide coding and translated amino acid sequences thereof are shown below.

```
Arabidopsis ω-amidase nucleotide coding sequence
(Genbank accessions AY075592.1 with GI 19715573
corresponding to protein NP445766 (full-length
protein AAL91613.1 = SEQ ID NO: 46)) [SEQ ID NO: 2]:
AAAGTGAAATGAAGTCAGCAATTTCATCGTCACTCTTCTTCAATTCGAAG

AATCTTTTAAACCCTAATCCTCTTTCTCGCTTCATTTCTCTCAAATCTA

ACTTCCTCCCTAAATTATCTCCGAGATCGATCACTAGTCACACCTTGAA

GCTCCCATCTTCGTCAACCTCAGCTTTAAGATCCATTTCCTCTTCCATG

GCTTCTTCTTTCAACCCTGAACAAGCTAGAGTTCCCTCTGCTCTTCCTC

TCCCAGCTCCTCCGTTGACCAAATTCAACATCGGATTGTGTCAGCTATC

TGTTACATCTGACAAAAAGAGAAACATCTCTCATGCTAAAAAAGCCATT

GAAGAAGCTGCTTCTAAAGGAGCTAAGCTTGTTCTCTTACCCGAAATTT

GGAACAGTCCGTATTCCAATGATAGTTTTCCAGTTTATGCGGAGGAGAT

TGATGCAGGTGGTGATGCTTCTCCTTCAACGGCAATGCTTTCTGAAGTT

TCCAAACGTCTCAAGATTACAATCATTGGTGGATCTATACCAGAAAGAG

TTGGAGATCGTTTGTATAACACTTGCTGTGTCTTTGGTTCCGATGGAGA

GCTAAAAGCTAAGCATCGGAAGATACATTTATTTGATATAGACATTCCC

GGGAAGATTACTTTTATGGAATCCAAAACTCTTACTGCTGGAGAGACAC

CAACAATCGTTGACACAGATGTAGGGCGTATTGGAATAGGCATCTGTTA

TGATATCAGGTTCCAGGAGTTAGCTATGATATATGCTGCAAGAGGGGCT

CATTTGCTGTGCTACCCGGGAGCCTTTAACATGACAACTGGACCATTGC

ATTGGGAATTACTACAAAGGGCCAGGGCTACGGATAATCAGTTATATGT

GGCGACATGCTCACCTGCCAGAGATTCAGGAGCTGGCTACACTGCTTGG

GGGCACTCAACACTCGTTGGGCCTTTTGGAGAAGTACTAGCAACGACTG

AGCATGAGGAGGCCATTATCATAGCAGAGATTGATTACTCTATCCTTGA

ACAACGAAGGACTAGCCTTCCATTGAATAGGCAGCGGCGGGAGATCTT

TACCAGCTTGTAGACGTACAGCGCTTAGACTCTAAATGAACGCAGCAGTA

ACTGTATATCTGAGAGATATTGCGAGTTGAGCACGATTTGGTTACTTACA

ACTTCATGCATGATCAGTCATTTCTCCACAACTTTGCTGAGATATGTAAA

AGAATAAAAATCAAACTTTTGAGTTAAAATCGAACAAAGGCAAGTAAATT

CTGCTTAGATAATGTGAACTCCACCCACTTGCCATGTGTTTGTTGTTTAT

AAACTTCAATGCATTCTGATAACG

Mature Arabidopsis ω-amidase amino acid sequence;
and derived from the translation product of SEQ ID
NO: 2, above (Genbank accession AAL91613.1)
[SEQ ID NO: 3]:
MASSFNPEQARVPSALPLPAPPLTKFNIGLCQLSVTSDKKRNISHAKKA

IEEAASKGAKLVLLPEIWNSPYSNDSFPVYAEEIDAGGDASPSTAMLSE

VSKRLKITIIGGSIPERVGDRLYNTCCVFGSDGELKAKHRKIHLFDIDI

PGKITFMESKTLTAGETPTIVDTDVGRIGIGICYDIRFQELAMIYAARG

AHLLCYPGAFNMTTGPLHWELLQRARATDNQLYVATCSPARDSGAGYTA

WGHSTLVGPFGEVLATTEHEEAIIIAEIDYSILEQRRTSLPLNRQRRGD

LYQLVDVQRLDSK
```

Based on initial BLAST analysis in Genbank, the *Arabidopsis* ω-amidase has homologs in other plant species, as well as in bacteria, fungi, frogs, fish, and mammal. None of the identified homologs were annotated as ω-amidases. However, without wishing to be bound by theory, it is believed that these sequences also encode ω-amidases. The amino acid sequences of the identified putative ω-amidases are shown below.

*Vitis vinifera* amino acid sequence (Genbank accession XP_002279687.1) [SEQ ID NO: 4]:
MKSAALSALLSSTLSYASPPHLNLLRPATAVLCRSLLPTSTPNPFHTQL

RTAKISASMSSSFKPEQARVPPAIPPPTPPLSKFKIGLCQLSVTADKER

NIAHARKAIEEAVEKGAQLVLLPEIWNSPYSNDSFPVYAEDIDAGSDAS

PSTAMLSEVSHALKITIVGGSIPERCGDQLYNTCCVFGSDGKLKAKHRK

IHLFDINIPGKITFMESKTLTAGGSPTIVDTEVGRIGIGICYDIRFSEL

AMLYAARGAHLICYPGAFNMTTGPLHWELLQRARAADNQLYVATCSPAR

DAGAGYVAWGHSTLVGPFGEVLATTEHEEAIIISEIDYSLIELRRTNLP

LLNQRRGDLYQLVDVQRLDSQ

*Zea mays* amino acid sequence (Genbank accession ACN30911.1) [SEQ ID NO: 5]:
MVAAAAAAAATATAAALLAPGLKLCAGRARVSSPSGLPLRRVTAMASA

PNSSFRPEEARSPPALELPIPPLSKFKVALCQLSVTADKSRNIAHARAA

IEKAASDGAKLVVLPEIWNGPYSNDSFPEYAEDIEAGGDAAPSFSMLSE

VARSLQITLVGGSIAERSGNNLYNTCCVFGSDGQLKGKHRKIHLFDIDI

PGKITFKESKTLTAGQSPTVVDTDVGRIGIGICYDIRFQELAMLYAARG

AHLLCYPGAFNMTTGPLHWELLQRARAADNQLFVATCAPARDTSAGYVA

WGHSTLVGPFGEVIATTEHEEATIIADIDYSLIEQRRQFLPLQHQRRGD

LYQLVDVQRLGSQ

*Populus trichocarpa* amino acid sequence (Genbank accession XP_002309478.1) [SEQ ID NO: 6]:
MKSAISSTTTLLSSKNLSLKLHLNHSPLSRLPSSLFRSKSNTHFPSLLP

RNNSTHNQKSQIHTPIMASSFMPEQARAPPALPLPVPPFKIGLCQLSVT

ADKERNIAHARKAIEEAAAKGAKLVMLPEIWNSPYSNDCFPVYAEDIDA

GGEASPSTAMLSEAAGLLKVTIVGGSIPERSGDRLYNTCCVFDSDGKLK

AKHRKIHLFDIDIPGKITFIESKTLTAGETPTIVDTEVGRIGIGICYDI

RFQELAIIYAARGAHLICYPGAFNMTTGPLHWELLQRARAADNQLYVAT

CSPARDVAAGYVAWGHSTLVGPFGEVLATTEHEEDIIIAEIDYSLLEVR

RTNLPLTKQRRGDLYQLVDVQRLKSDS

*Picea sitchensis* amino acid sequence (Genbank accession ABK22312.1) [SEQ ID NO: 7]:
MTPLLSYSLRVVASALRPKSSIASAVGRLSATPKRFPANRLRISYRNYN

AAMAKPEDARSPPALPLPSAPNGGKFKIALCQLSVTENKERNIAHARDA

IEAAADNGAQLVVLPEIWNGPYSNASFPVYAEDIAGGSASPSTSMLSE

VARSKGITIVGGSISERSGDHLYNTCCIFGKDGELKAKHRKIHLFDIDI

PGKISFMESKTLTAGNTPTIVDTDVGRIGIGICYDIRFQELAMLYAARG

AHLICYPGAFNMTTGPLHWELLQRARAIDNQLYVATCSPARDINAGYVA

WGHSTLVAPFGEIVATTEHEEATVIADIDYSRIEERRMNMPLEKQRHGD

LYQLVDVSRLDTAKH

*Oryza sativa* amino acid sequence (Genbank accession NP_001049134.1) [SEQ ID NO: 8]:
MATAASFRPEAARSPPAVQPPAPPLSKFKVALCQLSVTADKARNIARAR

EAIEAAAAGGAKLVLLPEIWNGPYSNDSFPEYAEDIEAGGDAAPSFSMM

SEVARSLQITLVGGSISERSGNKLYNTCCVFGSDGELKGKHRKIHLFDI

DIPGKITFKESKTLTAGQDLTVVDTDVGRIGIGICYDIRFQELAMLYAA

RGAHLLCYPGAFNMTTGPLHWELLQRARAADNQLFVATCAPARDTSAGY

IAWGHSTLVGPFGEVIATAEHEETTIMAEIDYSLIDQRRQFLPLQYQRR

GDLYQLVDVQRSGSDE

*Sorghum bicolor* amino acid sequence (Genbank accession XP_002468410.1) [SEQ ID NO: 9]:
MRAAAAAAATSTAAALLAPGLKLCAGRARVSSCRLPLRRVAAMASAPNS

SFRPEEARSPPALELPTPPLSKFKVALCQLSVTADKSRNIAHARAAIEK

AASDGAKLVLLPEIWNGPYSNDSFPEYAEDIEAGGDAAPSFSMMSEVAR

SLQITLVDGQLKGKHRKIHLFDIDIPGKITFKESKTLTAGQSPTVVDTD

VGRIGIGICYDIRFQELAMLYAARGAHLLCYPGAFNMTTGPLHWELLQR

ARQPAVCCNVRSSSRYQCRLCCLGTLHACWTFWRGDCNN

*Ricinus communis* amino acid sequence (Genbank accession XP_002516116.1) [SEQ ID NO: 10]:
MSASFNPEQARSPPALPLPTPPLTKAQFLLTSYLTILIYMIFKIGLCQL

LVTPDKAKNIAHARKAIEEAAAKGAKLVLLPEIWNSPYSNDSFPVYAED

IDAGHVASPSTAMLSQLARLLNITIVGGSIPERSGDRLYNTCCVFDTQG

NLIAKHRKIHLFDIDIPGKITFIESKTLTAGETPNIVDTEVGRIGIGIC

YDIRFQELAVLYAARGAHLICYPGAFNMTTGPLHWELLQRARAADNQLY

VATCSPARDVGAGYVAWGHSTLVGPFGEILATTEHEQDIIIAEIDYSLI

ELRSQLSTTHLPLPTPTTTRDSTIEEEDDLVYIYI

*Physcomitrella patens* subsp. *patens* amino acid sequence (Genbank accession XP_001766085.1) [SEQ ID NO: 11]:
MASDFQPHMARQPPSESLPNAPNGGKYKLAVCQLSVTSDKAANIAHARQ

KIEAAADSGAQLIVLPEMWNCPYSNDSFPTYAEDIDAGLEASPSSHMLS

EVARKKKVTIVGGSIPERNDGKLYNTCCVFDKNGELKAKFRKIHLFDID

IPGKITFKESDTLTPGEGLCVVDTDVGRIAVGICYDIRFPEMAMLYSAR

GAHIICYPGAFNMTTGPLHWELLQKARAVDNQIFVVTCSPARDTEAGYI

AWGHSTVVGPFGEILATTEHEEATIFADIDYSQLD TRRQNMPLESQRR

GDLYHLIDVTRKDTVKSS

*Selaginella moellendorffii* amino acid sequence (Genbank accession XP_002969787.1) [SEQ ID NO: 12]:
MPSSRYFWFLWQFKLAVCQLSICADKEQNIRHAREAIQTAADGGSKLVL

LPEMWNCPYSNASFPIYAEDIDAGDSPSSKMLSDMAKSKEVTIIGGSIP

ERSGNHLYNTCCIYGKDGSLKGKHRKVHLFDIDIPGKIQFKESDTLTPG

DKYTVVDTDVGRIGVGICYDIRFPEMAMTYAARGVHMICYPGAFNMTTG

PAHWELLQKARAVDNQLFVATCSPARNPSAGYVAWGHSSVIGPFGEILA

STGREEAIFYADIDYAQIKERRMNMPLDHQRRGDLYQLVDLTFTT

*Medicago truncatula* amino acid sequence (Genbank accession ACJ85250.1) [SEQ ID NO: 13]:
MAASSINSELARSPPAIPLPTPPLTNFKIGLCQLSVTSDKDKNIAHART
AIQDAAAKGAKLILLPEIWNSPYSNDSFPVYAEDIDAGGDASPSTAMLS
ELSSLLKITIVGGSIPERSGDRLYNTCCVFGTDGKLAKHRKIHLFDID
IPGKITFIESLTLTAGDTPTIVDTEVGRIGIGICYDIRFPELAMIYAAR
GAHLLCYPGAFNMTTGPLHWELLQRARATDNQLYVATCSPARDTTGWLC
GLGVTPLLLVLLEKFWLLQNARRQPL

*Chlorella variabilis* amino acid sequence (Genbank accession EFN54567.1) [SEQ ID NO: 14]:
MQALAKGMALVGVAGLSAAAGRRAACLRPLSSYTSATADVIDPPPPQKV
PPPLPCCRCRHCCHRLASNQQLARPLLAGPSAQIKVALCQLAVGADKQA
NLTTARSAIEEAATAGADLVVLPEMWNCPYSNDSFPTYAEDVEAGDSPS
TSMLSAAAAANRVVLVGGSIPERANGGRLYNTCFVYGRDGRLLGRHRKV
HLFDIDIPGKITFKESLTLTPGEGLTVVGRLGIGICYDIRFPELALLYA
ARGVQLIVYPGAFNMTTGPVHWELLQRARAVDGQLFVATCSPARSEGTG
YIAWGHSTAVGPFAEVLATTDEKAGIVYCHMDFAQLGERRANMPLRHQK
RADLYSLLDLTRPNSLSNAGLHNGPVQRTLAGSSGIVGSGITRQLLMEG
AKVVALLRKVDQKAGLLRDCQGAPIENLYPAVVEDVSKEEQCAAFVHEV
VEQHGAIDHAVSCFGAWWQGGLLTEQSYAEFSRVLANFAGSHFTFVKYI
LPAMRQSHTSSMLFVTGGVGKRVLSADSGLATVGGAALYGIVRAAQAQY
QGRPPRINELRIFALVTRHGEMPRSHSSIVEGLRAHSNRKVGNLAAEAL
AAAADDELLEVTSERLDGVMLMVGD

*Volvox carteri* f. *nagariensis* amino acid sequence (Genbank accession XP_002948137.1) [SEQ ID NO: 15]:
MHVTADKAQNLQTAKRAIEDAAAQGAKLVVLPEMWNCPYSNDSFPTYAE
DIEGGASGSVAMLSAAAAAACVTLVAGSIPERCGDRLYNTCCVFNSRGE
LLAKHRKVHLFDIDIPGKITFKESLTLSPGPGPTVVDTEAGRLGIGICY
DIRFPELAQLYAARGCQVLIYPGAFNMTTGPVHWELLARARAVDNQIFV
ITCSPARNPSSSYQAWGHSTVVGPFAEILATTDHQPGTIYTELDYSQLA
ERRANMPLRQQKRHDLYVLLDKTA

*Chlamydomonas reinhardtii* amino acid sequence (Genbank accession XP_001690839.1) [SEQ ID NO: 19]:
KVALCQLHVTADKEQNLRTARKAIEDAAAAGAKLVVLPEMFNCPYSNDS
FPTYAEDIEGGASGSVAALSAAAAAARVTLVAGSIPERCQGKLYNTCCV
FDSSGKLLAKHRKVHLFDIDIPGKITFKESLTLSPGPGPTVVDTEAGRL
GIGICYDIRFPELAQIYAARGCQVLIYPGAFNMTTGPVHWELLAKARAV
DNQVFVLTCSPARNPDSSYQAWGHSTALGPFAEVLATTEHSPATVFAEL
DYAQLDERRAAMPLRQQKRHDLYLLLDKTA

*Micromonas pusilla* CCMP1545 amino acid sequence (Genbank accession XP_003064056.1) [SEQ ID NO: 20]:
MRATKTTAAAAAAAASSSGAGAPVPFARVPAPWSASGASASDAATPTP
TPAPRVVKVALCQLACPTADKVANIARAREAIRNAAEGGAALVVLPEMW
NCPYANESFPAHAETIGANDPTPSVTMLSEAAAAHDIVLVGGSIPERGV
GVGGGGGADEEDVLYNACCVFDGKRGLIARHRKTHLFDVDIPGEISFRE
SDTLTEGEGLTVVDTAVGRVGVGICFDVRFGEMAAAMANRGADVLIYPG
AFNTVTGPHHWELLQRARAVDNQARSIHWSPYDRCFVLTCSPARNTTGE
GYQAWGHSTAVGPFAEVLATTDERPGIVFADLDLGEVTRRRRNMPLATQ
RRGDLYALHDLGAVRGDA

*Ectocarpus siliculosus* amino acid sequence (Genbank accession CBJ25483.1) [SEQ ID NO: 21]:
MFLAAARRASPILLSLAVKTSTTAAFCSPRLANARTNTAAGATRTAYAA
CSISRNISLLSRPLSSMSASGASEGATAGAGSRRFVVAACQILCGSDKL
ANIATAESAVRDAAAAGAQVVVLPECWNGPYDTASFPVYAEPVPDPQGD
ETAADMPSAEQSPSAAMLCRAAAENKVWLVGGSVPEAGKDGGVYNTCIV
VGPSGRIVAKHRKVHLFDIDVPGGITFKESDTLSPGDSITTVETPFGTI
GVGICYDMRFPELSMAMRAAGSVLLCFPGAFNMTTGPAHWELLQRARAL
MDNQCFVVTASPARNPDSKYQAWGHSSIVDPWGTVVATTEHEEALVAEV
DVGRVAEVRTSIPVSLQKRPDLYRLELP

*Phaeodactylum tricornutum* CCAP 1 055/1 amino acid sequence (Genbank accession XP_002183613.1) [SEQ ID NO: 22]:
MSASRQNDDDDDDDPSVLRVALCQLPVTNDKAQNHQTAREYLNRAANQG
ARLVVLPEIWNSPYATAAFPEYAEQLPDVLAQDGDGHTGVYESPSADLL
RESAKEHKLWIVGGSIPERDDDDKIYNTSLVFDPQGNLVAKHRKMHLFD
IDVPGGITFFESDTLSPGNTVSHFATPWGNIGLGICYDIRFPEYAMLLA
KEHDCGILIYPGAFNLTTGPAHWELLQRGRAVDNQCFVLTASPARTEPP
SKAGLYPHYTAWGHSTAVSPWGEVIATTNEKAGIVFADLDLSKVTEMRT
SIPIGKQKRTDLYQLVGKS

*Schizosaccharomyces pombe* 972h amino acid sequence (Genbank accession NP_594154.1) [SEQ ID NO: 23]:
MNSKFFGLVQKGTRSFFPSLNFCYTRNIMSVSASSLVPKDFRAFRIGLV
QLANTKDKSENLQLARLKVLEAAKNGSNVIVLPEIFNSPYGTGYFNQYA
EPIEESSPSYQALSSMAKDTKTYLFGGSIPERKDGKLYNTAMVFDPSGK
LIAVHRKIHLFDIDIPGGVSFRESDSLSPGDAMTMVDTEYGKFGLGICY
DIRFPELAMIAARNGCSVMIYPGAFNLSTGPLHWELLARARAVDNEMFV
ACCAPARDMNADYHSWGHSTVVDPFGKVIATTDEKPSIVYADIDPSVMS
TARNSVPIYTQRRFDVYSEVLPALKKEE

*Aspergillus oryzae* RIB40 amino acid sequence (Genbank accession XP_001819629.1) [SEQ ID NO: 24]:
MAALLKQPLKLALVQLASGADKAVNLAHARTKVLEAAQAGAKLIVLPEC
FNSPYGTQYFPKYAETLLPSPPTEDQSPSYHALSAIAAEEAKAYLVGGSI
PELEPTTKKYYNTSLVFSPTGSLIGTHRKTHLFDIDIPGKITFKESEVL
SPGNQLTIVDLPDYGKIGLAICYDIRFPEAAMIAARKGAFALIYPGAFN
MTTGPMHWSLLARARAVDNQLYVGLCSPARDMEATYHAWGHSLIANPAA
EVLVEAEDKETIVYADLNDTIQSTRKGIPVYTQRRFDLYPDVSAEK

*Neurospora crassa* OR74A amino acid sequence (Genbank accession XP_960906.1) [SEQ ID NO: 25]:
MASSTKHPILLKKPVKLACIQLASGADKSANLSHAADKVREAASGGANI
VVLPECFNSPYGCDFFPSYAEQLLPSPPTVEQSPSFHALSAMARDNGIY
LVGGSIPELAIEEGTEDKKTYYNTSLVFGPDGKLLASHRKVHLFDIDIP

GKIKFKESDVLSPGNSVTLVDLPDYGRIAVAICYDIRFPELAMIAARKG

CFALVYPGAFNTTTGPLHWRLQGQARAMDNQIYVALCSPARDISASYHA

YGHSLIVDPMARVLVEAEESETIVSAELDGTKIEE ARSGIPLRDQRRF

DIYPDVSQAKPFF

*Rhizobium leguminosarum* bv. *viciae* 3841 amino acid
sequence (Genbank accession YP_769862.1)
[SEQ ID NO: 26]:
MSFKAAAVQMCSGVDPVRNAAAMARLVREAAGQGAIYVQTPEMTGMLQR

DRAAARAVLADEAHDIIVKTGSDLARELGIHMHVGSTAIALADGKIANR

GFLFGPDGRILNRYDKIHMFDVDLDNGESWRESAAYTAGSEARVLSLPF

AEMGFAICYDVRFPALFRAQAMAGAEVMTVPAAFTKQTGEAHWEILLRA

RAIENGVFVIAAAQAGRHEDGRESFGHSMIIDPWGTVLASAGATGEAVI

VAEIDPSAVKAAHDKIPNLRNGREFSVEKIAGAIAGGVAA

*Rhizobium etli* CFN 42 amino acid sequence
(Genbank accession YP_471237.1) [SEQ ID NO: 27]:
MSFKAAAIQMCSGVDPVKNAASMARLVREAAAQGATYVQTPEMTGMLQR

DRAAARAVLADEAHDIIVKTGSELARELGIHVHVGSTAIALSDGKIANR

GFLFGPDGRILNRYDKIHMFDVDLDNGESWRESAAYTAGSEARVLSLPF

AEMGFAICYDVRFPALFRAQAVAGAEVMTVPSSFSRQTGEAHWEILLRA

RAIENGVFVIAAAQAGRHEDGRETFGHSIIIDPWGTVLASAGATGEAVI

LAEIDPGAVKAAHDKIPNLRDGREFSVEKIAGAVAGGVAA

*Rhizobium leguminosarum* bv. *trifolii* WSM1325
amino acid sequence (Genbank accession
YP_002977603.1) [SEQ ID NO: 28]:
MSFKAAAVQMCSGVDPVKNAAAMARLVREAAGQGATYVQTPEMTGMLQR

DRTAARAVLADEAHDIIVKTGSELAIELGIHMHVGSTAIALADGKIANR

GFLFGPDGRVLNRYDKIHMFDVDLDNGESWRESAAYTAGSEARVLSLPF

AEMGFAICYDVRFPALFCAQAVAGAEVMTVPAAFTKQTGEAHWEILLRA

RAIENGVFVIAAAQAGRHEDGRETFGHSMIIDPWGTVLASAGATGEAVI

VAEIDPAAVKAAHDKIPNLRNGREFSVEKIAGAIAGGVAA

*Bradyrhizobium* sp. ORS278 amino acid sequence
(Genbank accession YP_001202760.1) [SEQ ID NO: 29]:
MSNDRSFTAAMVQMRTALLPEPSLEQGRTLIREAVAQGAQYVQTPEVSN

MMQLNRTALFEQLKSEEEDPSLKAYRALAKELNIHLHIGSLALRFSAEK

AVNRSFLIGPDGQVLASYDKIHMFDIDLPGGESYRESANYQPGETAVIS

DLPWGRLGLTICYDVRFPALYRALAESGASFISVPSAFTRKTGEAHWHT

LLRARAIETGCFVFAAAQCGLHENKRETFGHSLIIDPWGEILAEGGVEP

GVILARIDPSRVESVRQTIPSLQHGRRFGIADPKGGPDYLHLVRGSA

*Sinorhizobium meliloti* BL225C amino acid sequence
(Genbank accession ZP_07592670.1) [SEQ ID NO: 30]:
MPSSRYFWFLWQFKLAVCQLSICADKEQNIRHAREAIQTAADGGSKLVL

LPEMWNCPYSNASFPIYAEDIDAGDSPSSKMLSDMAKSKEVTIIGGSIP

ERSGNHLYNTCCIYGKDGSLKGKHRKVHLFDIDIPGKIQFKESDTLTPG

DKYTVVDTDVGRIGVGICYDIRFPEMAMTYAARGVHMICYPGAFNMTTG

PAHWELLQKARAVDNQLFVATCSPARNPSAGYVAWGHSSVIGPFGEILA

STGREEAIFYADIDYAQIKERRMNMPLDHQRRGDLYQLVDLTFTT

*Sinorhizobium meliloti* 1021 amino acid sequence
(Genbank accession NP_386723.1) [SEQ ID NO: 31]:
MTFKAAAVQICSGVDPAGNAETMAKLVREAASRGATYVQTPEMTGAVQR

DRTGLRSVLKDGENDVVVREASRLARELGIYLHVGSTPIARADGKIANR

GFLFGPDGAKICDYDKIHMFDVDLENGESWRESAAYHPGNTARTADLPF

GKLGFSICYDVRFPELFRQQAVAGAEIMSVPAAFTRQTGEAHWEILLRA

RAIENGLFVIAAAQAGTHEDGRETFGHSMIVDPWGRVLAEAGATGEEII

VAEIDVAAVHAARAKIPNLRNARSFVLDEVVPVGK GGAAA

*Phytophthora infestans* T30-4 amino acid sequence
(Genbank accession XP_002999170.1) [SEQ ID NO: 32]:
MLGRTIRSQARHLRSPFLRLSSPMSTTAPKFKLALCQIAVGDDKQKNIA

TATAAVTEAAQNAAQVVSLPECWNSPYATTSFPQYAEEIPEKKAALNEK

EHPSTFALSQLAAKLQIFLVGGSIPEKDATGKVYNTSVIFSPEGEILGK

HRKVHLFDIDVPGKITFKESDTLSPGNSMTLFDTPYGKMGVGICYDIRF

PELSMLMKKQGAKVLLFPGAFNTTGPAHWELLQRARAVDNQLYVAATS

PARGPEGGYQAWGHSTVISPWGEVVATCGHGESIVYAEVDLEKVEEMRR

NIPTTNQTRSDLYELVQK

*Homo sapiens* amino acid sequence (Genbank
accession NP_064587.1) [SEQ ID NO: 33]:
MTSFRLALIQLQISSIKSDNVTRACSFIREAATQGAKIVSLPECFNSPY

GAKYFPEYAEKIPGESTQKLSEVAKECSIYLIGGSIPEEDAGKLYNTCA

VFGPDGTLLAKYRKIHLFDIDVPGKITFQESKTLSPGDSFSTFDTPYCR

VGLGICYDMRFAELAQIYAQRGCQLLVYPGAFNLTTGPAHWELLQRSRA

VDNQVYVATASPARDDKASYVAWGHSTVVNPWGEVLAKAGTEEAIVYSD

IDLKKLAEIRQQIPVFRQKRSDLYAVEMKKP

*Equus caballus* amino acid sequence (Genbank
accession XP_001502234.1) [SEQ ID NO: 34]:
MAAHSILDLSGLDRESQIDLQRPLKARPGKAKDLSSGSACTFRLALIQL

QVSSVKSDNLTRACGLVREAAAQGAKIVCLPECFNSPYGTNYFPQYAEK

IPGESTQKLSEVAKECSIYLIGGSIPEEDAGKLYNTCAVFGPDGALLVK

HRKLHLFDIDVPGKITFQESKTLSPGDSFSTFDTPYCRVGLGICYDLRF

AELAQIYAQRGCQLLVYPGAFNLTTGPAHWELLQRGRAVDNQVYVATAS

PARDDKASYVAWGHSTVVTPWGEVLATAGTEEMIV YSDIDLKKLAEIR

QQIPIFSQKRLDLYAVEAKKP

*Xenopus* (*Silurana*) *tropicalis* amino acid sequence
(Genbank accession NP_001016633.1) [SEQ ID NO: 35]:
MAKFRLSLVQFLVSPVKSENLNRACKLIKEAAQKGAQIVALPECFNSPY

GTKYFPEYAEKIPGESTERLSQVAKECGIYLIGGSIPEEDSGKLYNTCA

VFGPDGTLLVKHRKIHLFDIDVPGKIRFQESETLSPGDSFSVFETPYCK

VGVGICYDIRFAELAQLYSKKGCQLLVYPGAFNMTTGPAHWELLQRARA

LDNQVYVATASPARDEKASYVAWGHSTIVSPWGEVIAKAGSEETVISAD

IDLEYLAEIREQIPIRRQRRHDLYSVEEKKN

*Danio rerio* amino acid sequence (Genbank accession AAQ97821.1) [SEQ ID NO: 36]:
MSKFRLAVVQLHVSKIKADNLGRAQTLVTEAAGQGAKVVVLPECFNSPY

GTGFFKEYAEKIPGESTQVLSETAKKCGIYLVGGSIPEEDGGKLYNTCS

VFGPDGTLLVTHRKIHLFDIDVPGKIRFQESETLSPGKSLSMFETPYCK

VGVGICYDIRFAELAQIYAKKGCQLLVYPGAFNMTTGPAHWELLQRGRA

VDNQVYVATASPARDETASYVAWGHSSVINPWGEVISKAGSEESVVYAD

IDLQYLADVRQQIPITKQRRNDLYSVNSVQEG

*Nematostella vectensis* amino acid sequence (Genbank accession XP_001622809.1) [SEQ ID NO: 37]:
MAVPILVFRIGLVQLAVTANKLQNLQRAREKIKEAVAAGAKIVALPECF

NSPYGTQYFKDYAEEIPGESSNMLAEVAKETGAYIVGGSIPERASNGKL

YNTSLSYDPSGNLMGKHRKIHLFDIDVPGKIRFQESEVLSPGENLTILD

TEYCKIGIGICYDMRFPELAQLYAKKGCHLLLYPGAFNMTTGPAHWELL

TRARALDNQLYVATISPARDDNATYIAWGHSTVVNPWGKIVSKADHTEQ

ILYAEIDLKYLNEVRSQIPVQFQKRDDVYELQVK

*Mus musculus* amino acid sequence (Genbank accession NP_075664.1) [SEQ ID NO: 38]:
MSTFRLALIQLQVSSIKSDNLTRACSLVREAAKQGANIVSLPECFNSPY

GTTYFPDYAEKIPGESTQKLSEVAKESSIYLIGGSIPEEDAGKLYNTCS

VFGPDGSLLVKHRKIHLFDIDVPGKITFQESKTLSPGDSFSTFDTPYCK

VGLGICYDMRFAELAQIYAQRGCQLLVYPGAFNLTTGPAHWELLQRARA

VDNQVYVATASPAR DDKASYVAWGHSTVVDPWGQVLTKAGTEETILYS

DIDLKKLAEIRQQIPILKQKRADLYTVESKKP

The *Arabidopsis thaliana* ω-amidase amino acid sequence was aligned with the amino acid sequence of other putative plant ω-amidases and with other putative animal ω-amidases to identify conserved regions. The results of the sequence alignments are shown in FIG. 2 and FIG. 3. Regions of homology are depicted in color shading and in the consensus sequences (SEQ ID NO: 44 for FIG. 2, and SEQ ID NO: 45 for FIG. 3).

Additional homologs of the *Arabidopsis thaliana* ω-amidase are listed in Table 1 below.

TABLE 1

| Genbank Accession No. | Source Organism |
|---|---|
| AAL91613.1 | *Arabidopsis thaliana* |
| NP_196765.2 | *Arabidopsis thaliana* |
| XP_002871509.1 | *Arabidopsis lyrata* subsp. *lyrata* |
| NP_974769.1 | *Arabidopsis thaliana* |
| XP_002309478.1 | *Populus trichocarpa* |
| XP_002279687.1 | *Vitis vinifera* |
| NP_001146676.1 | *Zea mays* |
| NP_001146295.1 | *Zea mays* |
| NP_001049134.1 | *Oryza sativa Japonica* Group |
| XP_002516116.1 | *Ricinus communis* |
| XP_001766085.1 | *Physcomitrella patens* subsp. *patens* |
| XP_001756522.1 | *Physcomitrella patens* subsp. *patens* |
| XP_002969787.1 | *Selaginella moellendorffii* |
| XP_002985119.1 | *Selaginella moellendorffii* |
| XP_002948137.1 | *Volvox carteri f. nagariensis* |
| XP_001690839.1 | *Chlamydomonas reinhardtii* |
| NP_001057093.1 | *Oryza sativa Japonica* Group |
| XP_002468410.1 | *Sorghum bicolor* |
| NP_064587.1 | *Homo sapiens* |
| XP_001089575.2 | *Macaca mulatta* |
| XP_001502234.1 | *Equus caballus* |

TABLE 1-continued

| Genbank Accession No. | Source Organism |
|---|---|
| XP_002502298.1 | *Micromonas* sp. RCC299 |
| XP_526254.2 | *Pan troglodytes* |
| XP_535718.2 | *Canis familiaris* |
| XP_002716659.1 | *Oryctolagus cuniculus* |
| NP_001033222.1 | *Bos taurus* |
| NP_001029298.1 | *Rattus norvegicus* |
| NP_001016633.1 | *Xenopus (Silurana) tropicalis* |
| NP_001085409.1 | *Xenopus laevis* |
| XP_002758928.1 | *Callithrix jacchus* |
| XP_003064056.1 | *Micromonas pusilla* CCMP1545 |
| NP_001135127.1 | *Salmo salar* |
| XP_001622809.1 | *Nematostella vectensis* |
| NP_991174.2 | *Danio rerio* |
| XP_002594716.1 | *Branchiostoma floridae* |
| NP_075664.1 | *Mus musculus* |
| XP_001370849.1 | *Monodelphis domestica* |
| NP_001090454.1 | *Xenopus laevis* |
| XP_002999170.1 | *Phytophthora infestans* T30-4 |
| XP_002917137.1 | *Ailuropoda melanoleuca* |
| XP_002741281.1 | *Saccoglossus kowalevskii* |
| XP_002131764.1 | *Ciona intestinalis* |
| NP_594154.1 | *Schizosaccharomyces pombe* 972h- |
| XP_001742101.1 | *Monosiga brevicollis* MX1 |
| XP_416604.2 | *Gallus gallus* |
| XP_002194275.1 | *Taeniopygia guttata* |
| XP_001599587.1 | *Nasonia vitripennis* |
| XP_002410555.1 | *Ixodes scapularis* |
| XP_003035898.1 | *Schizophyllum commune* H4-8 |
| XP_002183613.1 | *Phaeodactylum tricornutum* CCAP 1055/1 |
| XP_001875493.1 | *Laccaria bicolor* S238N-H82 |
| XP_002112209.1 | *Trichoplax adhaerens* |
| XP_636983.1 | *Dictyostelium discoideum* AX4 |
| XP_002158547.1 | *Hydra magnipapillata* |
| XP_002839272.1 | *Tuber melanosporum* Mel28 |
| XP_307722.3 | *Anopheles gambiae* str. PEST |
| XP_001819629.1 | *Aspergillus oryzae* RIB40 *Aspergillus flavus* NRRL3357 |
| XP_001268376.1 | *Aspergillus clavatus* NRRL 1 |
| ZP_08115581.1 | *Desulfotomaculum nigrificans* DSM 574 |
| YP_001320997.1 | *Alkaliphilus metalliredigens* QYMF |
| XP_369268.1 | *Magnaporthe oryzae* 70-15 |
| XP_002626458.1 | *Ajellomyces dermatitidis* SLH14081 |
| XP_751200.1 | *Aspergillus fumigatus* Af293 |
| XP_001657673.1 | *Aedes aegypti* |
| XP_002173486.1 | *Schizosaccharomyces japonicus* yFS275 |
| XP_001212538.1 | *Aspergillus terreus* NIH2624 |
| XP_001258462.1 | *Neosartorya fischeri* NRRL 181 |
| XP_002434512.1 | *Ixodes scapularis* |
| XP_960906.1 | *Neurospora crassa* OR74A |
| XP_002847679.1 | *Arthroderma otae* CBS 113480 |
| XP_967861.1 | *Tribolium castaneum* |
| XP_002426154.1 | *Pediculus humanus corporis* |
| XP_003176259.1 | *Arthroderma gypseum* CBS 118893 |
| XP_500602.1 | *Yarrowia lipolytica* |
| XP_001428419.1 | *Paramecium tetraurelia* strain d4-2 |
| XP_003014235.1 | *Arthroderma benhamiae* CBS 112371 |
| XP_001393123.1 | *Aspergillus niger* CBS 513.88 |
| ZP_03608460.1 | *Methanobrevibacter smithii* DSM 2375 |
| XP_002147261.1 | *Penicillium marneffei* ATCC 18224 |
| ZP_03293831.1 | *Clostridium hiranonis* DSM 13275 |
| XP_002290043.1 | *Thalassiosira pseudonana* CCMP1335 |
| XP_003065597.1 | *Coccidioides posadasii* C735 delta SOWgp |
| XP_001588734.1 | *Sclerotinia sclerotiorum* 1980 |
| YP_001273073.1 | *Methanobrevibacter smithii* ATCC 35061 >*Methanobrevibacter smithii* DSM 2374 |
| XP_001552800.1 | *Botryotinia fuckeliana* B05.10 |
| XP_446414.1 | *Candida glabrata* CBS 138 |
| XP_002792830.1 | *Paracoccidioides brasiliensis* Pb01 |
| XP_001998501.1 | *Drosophila mojavensis* |
| YP_003780301.1 | *Clostridium ljungdahlii* DSM 13528 |
| NP_013455.1 | *Saccharomyces cerevisiae* S288c |
| XP_002404736.1 | *Ixodes scapularis* |
| YP_001086961.1 | *Clostridium difficile* 630 |
| ZP_05328587.1 | *Clostridium difficile* QCD-63q42 |

TABLE 1-continued

| Genbank Accession No. | Source Organism |
|---|---|
| ZP_05399936.1 | *Clostridium difficile* QCD-23m63 |
| | *Clostridium difficile* NAP08 |
| | *Clostridium difficile* NAP07 |
| YP_001113615.1 | *Desulfotomaculum reducens* MI-1 |
| XP_001247884.1 | *Coccidioides immitis* RS |
| XP_390426.1 | *Gibberella zeae* PH-1 |
| XP_003025334.1 | *Trichophyton verrucosum* HKI 0517 |
| XP_002052999.1 | *Drosophila virilis* |
| ZP_07325748.1 | *Acetivibrio cellulolyticus* CD2 |
| ZP_05349666.1 | *Clostridium difficile* ATCC 43255 |

Accordingly, in certain embodiments, the ω-amidase transgene encodes a polypeptide having an amino acid sequence that is at least 75%, at least 80%, at least 85%, at last 90%, at last 91%, at last 92%, at last 93%, at last 94%, at last 95%, at last 96%, at last 97%, at last 98%, at last 99%, or 100% identical to an amino acid sequence encoded by a polypeptide selected from AAL91613.1, ACN30911.1, ABK22312.1, ACJ85250.1, AAQ97821.1, CBJ25483.1, EFN54567.1, NP_196765.2, XP_002871509.1, NP_974769.1, XP_002309478.1, XP_002279687.1, NP_001146676.1, NP_001146295.1, NP_001049134.1, XP_002516116.1, XP_001766085.1, XP_001756522.1, XP_002969787.1, XP_002985119.1, XP_002948137.1, XP_001690839.1, NP_001057093.1, XP_002468410.1, NP_064587.1, XP_001089575.2, XP_001502234.1, XP_002502298.1, XP_526254.2, XP_535718.2, XP_002716659.1, NP_001033222.1, NP_001029298.1, NP_001016633.1, NP_001085409.1, XP_002758928.1, XP_003064056.1, NP_001135127.1, XP_001622809.1, NP_991174.2, XP_002594716.1, NP_075664.1, XP_001370849.1, NP_001090454.1, XP_002999170.1, XP_002917137.1, XP_002741281.1, XP_002131764.1, NP_594154.1, XP_001742101.1, XP_416604.2, XP_002194275.1, XP_001599587.1, XP_002410555.1, XP_003035898.1, XP_002183613.1, XP_001875493.1, XP_002112209.1, XP_636983.1, XP_002158547.1, XP_002839272.1, XP_307722.3, XP_001819629.1, XP_001268376.1, ZP_08115581.1, YP_001320997.1, XP_369268.1, XP_002626458.1, XP_751200.1, XP_001657673.1, XP_002173486.1, XP_001212538.1, XP_001258462.1, XP_002434512.1, XP_960906.1, XP_002847679.1, XP_967861.1, XP_002426154.1, XP_003176259.1, XP_500602.1, XP_001428419.1, XP_003014235.1, XP_001393123.1, ZP_03608460.1, XP_002147261.1, ZP_03293831.1, XP_002290043.1, XP_003065597.1, XP_001588734.1, YP_001273073.1, XP_001552800.1, XP_446414.1, XP_002792830.1, XP_001998501.1, YP_003780301.1, NP_013455.1, XP_002404736.1, YP_001086961.1, ZP_05328587.1, ZP_05399936.1, YP_001113615.1, XP_001247884.1, XP_390426.1, XP_003025334.1, XP_002052999.1, YP_769862.1, ZP_07325748.1, ZP_05349666.1, YP_471237.1, YP_002977603.1, YP_001202760.1, ZP_07592670.1, and NP_386723.1. In other embodiments, the ω-amidase transgene is incorporated into the genome of the transgenic plants.

Certain aspects of the present disclosure relate to an ω-amidase transgene that is operably linked to a root-preferred promoter. As used herein, a "root-preferred promoter" refers to expression driven by a promoter that is selectively enhanced in root cells or tissues, in comparison to one or more non-root cells or tissues. For example, a root-preferred promoter may preferentially drive high levels of expression of a gene in root cells or tissue but may still drive low levels of expression of the gene in other non-root cells or tissues, such as leaves. Root tissues include but are not limited to at least one of root cap, apical meristem, protoderm, ground meristem, procambium, endodermis, cortex, vascular cortex, epidermis, and the like.

In certain other embodiments, 2-oxoglutaramate levels in root tissues are decreased in order to increase the leaf-to-root ratio thereof by increasing the natural breakdown of 2-oxoglutaramate in root tissue. For example, the breakdown of 2-oxoglutaramate in root tissue may be increased by upregulating ω-amidase activity in the roots. Thus, in one embodiment, an ω-amidase transgene, including without limitation any of the ω-amidase genes and coding sequences disclosed herein, is introduced into the plant under the control of a root-preferred promoter, such as the rolD promoter of *Agrobacterium rhizogenes* (Kamo and Bowers, 1999, Plant Cell Reports 18: 809-815 and references cited therein). The rolD promoter controls the expression of rolD, which functions to promote root elongation. GUS protein expression under control of the rolD-promoter has been shown to yield mainly root-preferred GUS expression (Leach and Aoyagi, 1991, Plant Sci. 79, 69-76). Root-preferred promoters may be either constitutive or inducible.

Additional constitutive and/or inducible root-preferred promoters include, without limitation, the RolD-2 promoter; glycine rich promoters (GRP); ADH promoters, including the maize ADH1 promoter (Kyozuka, J et al., 1994, The Plant Cell 6:799-810); PHT promoters, including the Pht1 gene family promoters (Schunmann et al., 2004, J. Experimental Botany 55:855-865); metal uptake protein promoters, including the maize metallothionein promoter (Diehn, S, 2006 Maize, U.S. Pat. Application Publication US 2006/0005275); the 35S CaMV domain A promoter (Elmayan, T and M. Tepfer. 1995, Transgenic Research 4:388-396); the pDJ3S, SIREO, and pMe1 promoters (Arango et al., Plant Cell Rep. 2010 June; 29 (6):651-9. Epub 2010 Apr. 6.); the Sad1 and Sad2 promoters (U.S. Patent Application Publication US 2008/0244791); the TobRB7 promoter (Yamamoto et al., 1991, Plant Cell 3:371-3); the RCc3 promoter (Xu et al., 1995, Plant Mol. Biol. 27:237-248); the FaRB7 promoter (Vaugn et al., Exp. Bot. (2006) 57 (14): 3901-3910); the SPmads promoter (Noh et al., American Society of Plant Biologists, Plant Biology 2005 Conference, Abstract #1097); the IDS2 promoter (Kobayashi et al., The Plant Journal, Vol. 36(6): 780-793, December 2003); the pyk10 promoter (Nitz et al., Plant Sci. 2001 July; 161(2):337-346); the Pt2L4 promoter (De Souza et al., Genet. Mol. Res. 8 (1): 334-344 (2009)); the Lbc3 leghemoglobin promoter (Bak, K, et al., 1993, The Plant Journal 4(3) 577-580); the PEPC promoter (Kawamura et al. 1990, J. Biochem 107: 165-168); the Gns1 Glucanase root promoter (Simmons, C et al., 1992, Plant Molecular Biology 18: 33-45), the $35S^2$ promoter (Elmayan, T and M. Tepfer. 1995, Transgenic Research 4:388-396); the GI4 and GI5 promoters (European Patent EP 1 862 473 B1; and the GRP promoter. Additionally, any of the disclosed root-preferred promoters may be in a truncated form that contains only the core domain or functional domain of the promoter sufficient to drive expression in root tissue. Moreover, root-preferred promoters also include isoforms of any of the root-preferred promoters disclosed herein. For example, the RolD-2 promoter is one of several truncated isoforms of the RolD promoter described in Leach and Aoyagi, 1991, Plant Sci. 79, 69-76. Moreover, Leach and Aoyagi describe the RolD2 promoter as being a highly root-preferred promoter. Accordingly, a root-preferred promoter also includes any of the RolD isomers described by Leach and Aoyagi.

Thus, in certain embodiments, the root-preferred promoter is selected from RolD promoter, RolD-2 promoter, glycine rich protein promoter, GRP promoter, ADH promoter, maize ADH1 promoter, PHT promoter, Pht1 gene family promoter, metal uptake protein promoter, maize metallothionein protein promoter, 35S CaMV domain A promoter. pDJ3S promoter, SIREO promoter, pMe1 promoter, Sad1 promoter, Sad2 promoter, TobRB7 promoter, RCc3 promoter, FaRB7 promoter, SPmads promoter, IDS2 promoter, pyk10 promoter, Lbc3 leghemoglobin promoter, PEPC promoter, Gns1 glucanase root promoter, $35S^2$ promoter, GI4 promoter, GI5 promoter, and GRP promoter.

In stable transformation embodiments, one or more copies of the ω-amidase transgene become integrated into the genome of the transgenic plant, thereby providing increased ω-amidase enzyme capacity into the root tissue of the plant, which serves to mediate synthesis of 2-oxoglutaramate, which in turn signals metabolic gene expression, resulting in increased nitrogen use efficiency, which in turn results in increased plant growth and the enhancement of other agronomic characteristics.

In other embodiments, root-preferred expression of the ω-amidase transgene results in an increased leaf-to-root ratio of 2-oxoglutaramte relative to a plant of the same species that does not contain an ω-amidase transgene. In certain preferred embodiments, the leaf-to-root ratio of 2-oxoglutaramate is at least two times, at least three times, at least four times, at least five times, at least six times, at least seven times, at least eight times, at least nine times, at least ten times, or more higher than that of a plant of the same species that does not contain an ω-amidase transgene.

In further embodiments, the transgenic plant has increased nitrogen use efficiency. The disclosed transgenic plants with increased nitrogen use efficiency may further contain other transgenes known to increase nitrogen utilization efficiency, including without limitation those described in U.S. Pat. No. 7,560,626.

Impairing the Breakdown of 2-Oxoglutaramate in Leaf Tissues by Inhibiting Ω-Amidase Activity:

Other aspects of the present disclosure relate to transgenic plants having inhibited expression of endogenous ω-amidase in leaf tissue.

Accordingly, in certain embodiments, the breakdown of 2-oxoglutaramate or its analogs may be impaired by decreasing ω-amidase activity in order allow accumulation of 2-oxoglutaramate in the leaves, thereby increasing the leaf-to-root ratio. More specifically, the following approaches to impeding the 2-oxoglutaramate breakdown pathway may be used.

In one specific embodiment, the normal metabolic breakdown of 2-oxogluataramate catalyzed by an ω-amidase enzyme, including but not limited to any of the ω-amidase enzymes disclosed herein, is inhibited in leaf tissue of any of the disclosed transgenic plants by the application of a chemical inhibitor, including without limitation 6-diazo-5-oxo-nor-leucine, p-hydroxymercuribenzoate, diisopropyl fluorophosphates, sodium cyanide, phenylmercuriacetate, Iodoacetate, silver nitrate, chloromercuricphenylsulfonic acid, and copper sulfate. Accordingly, in certain embodiments, endogenous ω-amidase expression in leaf tissue of any of the disclosed transgenic plants is inhibited by a chemical inhibitor selected from 6-diazo-5-oxo-nor-leucine, p-hydroxymercuribenzoate, diisopropyl fluorophosphates, sodium cyanide, phenylmercuriacetate, Iodoacetate, silver nitrate, chloromercuricphenylsulfonic acid, and copper sulfate.

In another embodiment, ω-amidase function may be inhibited in leaf tissue of any of the disclosed transgenic plants by genetically impeding the transcription and/or translation of an ω-amidase gene, including but not limited to the ω-amidase genes and coding sequences disclosed herein. Methods for impeding ω-amidase expression and function include, without limitation, recessive gene disruption and dominant gene silencing.

As used herein, "recessive gene disruption" refers to mutating a target ω-amidase sequence to eliminate either expression or function. Methods for mutating a target sequence are known in the art, and include, without limitation, the generation of mutations via chemical or radiation damage followed by isolation of the mutant. In addition, known molecular biology approaches for decreasing the expression of a functional phenotype may be used, and include without limitation, various knockout or knockdown methods. These methods capitalize upon knowledge of sequence either in the gene of interest or in the DNA sequence flanking the gene. Such sequences are then examined to find suitable sequences that can be targeted to accomplish either excision of the target gene or fragments of the gene. Thus, in certain embodiments, the endogenous ω-amidase expression in leaf tissue of any of the disclosed transgenic plants is inhibited by a recessive gene disruption selected from a mutant ω-amidase gene that eliminates endogenous ω-amidase expression, an endogenous ω-amidase knockout mutant, and an endogenous ω-amidase knockdown mutant.

As used herein, "dominant gene silencing" refers to inducing or destroying/inhibiting the mRNA transcript of the gene, a means which provides the benefit of being done in a spatial or temporal manner by the selection of specific promoters. Of the dominant gene silencing approaches, dsRNA-triggered RNAi is one of the most powerful and the most efficient at gene silencing, and allows one to enhance or capitalize upon a natural regulatory mechanism which destroys intact mRNA by providing an antisense oligonucleotide that is specific for an endogenous ω-amidase gene (For review, see, Behlke, 2006, Molecular Therapy 13(4): 644-670; see also, Tang and Galili, 2004, Trends Biotechnology 22:463-469; Rajewsky and Socci, 2004, Developmental Biology 267:529-535; Hamilton et al., 2002, EMBO J. 21:4671-4679J). In one embodiment, a construct comprising a suitable RNAi sequence under the control of a leaf specific promoter such as the RuBisCo small subunit promoter is introduced into the plant in order to silence ω-amidase protein expression. Accordingly, in certain embodiments, the endogenous ω-amidase expression in leaf tissue of any of the disclosed transgenic plants is inhibited by an RNAi antisense oligonucleotide that is specific for an endogenous ω-amidase gene.

In certain embodiments, inhibition of endogenous ω-amidase expression in leaf tissue results in an increased leaf-to-root ratio of 2-oxoglutaramte relative to a plant of the same species that does not comprise inhibited endogenous ω-amidase expression in leaf tissue. In certain preferred embodiments, the leaf-to-root ratio of 2-oxoglutaramate is at least two times, at least three times, at least four times, at least five times, at least six times, at least seven times, at least eight times, at least nine times, at least ten times, or more higher than that of a plant of the same species that does not comprise inhibited endogenous ω-amidase expression in leaf tissue. In further embodiments, the transgenic plant has increased nitrogen use efficiency.

Similarly, the expression of the substrate GS and/or the catalytic protein GPT may be impaired in root tissue using any of the approaches disclosed herein.

Embodiments Relating to Transgenic Plants with Increased Ω-Amidase Activity in Root Tissues and Inhibited Ω-Amidase Activity in Leaf Tissue:

Certain aspects of the present disclosure relate to transgenic plants with increased ω-amidase expression in root tissue and inhibited endogenous ω-amidase expression in leaf tissue, which results in an increased leaf-to-root ratio of 2-oxoglutaramte.

Accordingly, in certain embodiments, transgenic plants containing an ω-amidase transgene that is operably linked to a root-preferred promoter, further have inhibited endogenous ω-amidase expression in leaf tissue. Exemplary transgenic plants ω-amidase transgenes, and root-preferred promoters are as described in previous sections. In other embodiments, the endogenous ω-amidase expression in leaf tissue is inhibited by recessive gene disruption, dominant gene silencing, or a chemical inhibitor. In still other embodiments, the endogenous ω-amidase expression in leaf tissue is inhibited by a recessive gene disruption selected a mutant ω-amidase gene that eliminates endogenous ω-amidase expression, an endogenous ω-amidase knockout mutant, and an endogenous ω-amidase knockdown mutant. In yet other embodiments, the endogenous ω-amidase expression in leaf tissue is inhibited by an RNAi antisense oligonucleotide that is specific for an endogenous ω-amidase gene. In further embodiments, the endogenous ω-amidase expression in leaf tissue is inhibited by a chemical inhibitor selected from 6-diazo-5-oxo-nor-leucine, p-hydroxymercuribenzoate, diisopropyl fluorophosphates, sodium cyanide, phenylmercuriacetate, Iodoacetate, silver nitrate, chloromercuricphenylsulfonic acid, and copper sulfate. In further embodiments, the transgenic plant has an increased leaf-to-root ratio of 2-oxoglutaramte. In certain preferred embodiments, the leaf-to-root ratio of 2-oxoglutaramate is at least two times, at least three times, at least four times, at least five times, at least six times, at least seven times, at least eight times, at least nine times, at least ten times, or more higher than that of an unmodified plant of the same species. In still further embodiments, the transgenic plant has increased nitrogen use efficiency.

In certain embodiments, transgenic plants having inhibited expression of endogenous ω-amidase in leaf tissue relative to a plant of the same species that does not comprise inhibited expression of endogenous ω-amidase in leaf tissue, where the endogenous ω-amidase expression in leaf tissue is inhibited by recessive gene disruption or dominant gene silencing of at least one endogenous ω-amidase gene, further contain an ω-amidase transgene, where the ω-amidase transgene is operably linked to a root-preferred promoter. Exemplary transgenic plants, recessive gene disruption, dominant gene silencing, ω-amidase transgenes, and root-preferred promoters are as described in previous sections. In further embodiments, the transgenic plant has an increased leaf-to-root ratio of 2-oxoglutaramte. In certain preferred embodiments, the leaf-to-root ratio of 2-oxoglutaramate is at least two times, at least three times, at least four times, at least five times, at least six times, at least seven times, at least eight times, at least nine times, at least ten times, or more higher than that of an unmodified plant of the same species. In still further embodiments, the transgenic plant has increased nitrogen use efficiency.

Expression of Glutamine Phenylpyruvate Transaminase and Glutamine Synthetase:

Other aspects of the present disclosure relate to transgenic plants with increased ω-amidase expression in root tissue or inhibited endogenous ω-amidase expression in leaf tissue that further contain increased expression of glutamine phenylpyruvate transaminase (GPT) and/or glutamine synthetase (GS).

In a particular embodiment, any of the transgenic plants disclosed herein further over-express the GPT protein, which is directly involved in the synthesis of 2-oxoglutaramate, which results in higher leaf-to-root ratios of the 2-oxoglutaramate compound. In a related embodiment, any of the transgenic plants disclosed herein further over-express the GPT protein and the GS protein. These transgenic plants further containing GPT and GS have an even higher leaf-to-root ratios of 2-oxoglutaramate, resulting in a further increase in nitrogen use efficiency. This increase in nitrogen use efficiency also results in plants that grow faster, produce greater seed and fruit/pod yields, display earlier and more productive flowering, demonstrate increased tolerance to high salt conditions, and produce superior biomass yields (See, co-owned, co-pending U.S. patent application Ser. No. 12/551,271).

More particularly, applicants have determined that the over-expression of GPT and GS in transgenic plants results in a disproportionate increase in the relative concentrations of 2-oxoglutaramate in the foliar and below ground tissues. Moreover, the ratio of the concentration of 2-oxoglutaramate in above ground tissue to below ground tissue (leaf-to-root ratio) is positively correlated with plant biomass. Faster growing, larger genetically-engineered plants have a greater ratio of the concentrations of 2-oxoglutaramate in leaf tissue versus root tissue when compared to wild type plants. In one particular embodiment, transgenic tobacco plants carrying GPT and GS1 transgenes under the control of robust constitutive promoters showed substantially greater leaf-to-root ratios of 2-oxoglutaramate and demonstrated high growth phenotypes when compared to wild type tobacco plants. In particular, two transgenic tobacco lines over-expressing GPT and GS1 transgenes were found to have: (1) well over two-times the fresh weight of wild type plants, (2) two-times the 2-oxoglutaramate foliar concentration compared to the wild type plants, and (3) between two- and three-times the leaf-to-root ratio seen in wild type plants.

In a wild type or engineered plant, the ratio can be expected to reflect the relative concentrations of 2-oxoglutaramate, as well as glutamine, the substrate from which it is made, in the leaves versus the roots of the plant. The actual ratios would be expected to differ from species to species. This is due to the fact that leaves and roots house differing fractions of the nitrogen assimilation machinery and activity, as a function of plant species (Pate, 1980, Ann. Rev. Plant Physiol. 31: 313-340). In fact, some plant species assimilate most of their nitrogen in their roots, and thus have high amino acid concentrations in their roots and xylem sap, and lower concentrations in their leaves. Other plants assimilate most of their nitrogen in their leaves, and thus have high amino acid concentrations in their leaves, and lower concentrations in their roots. Plant species distribute themselves along a continuum of this distribution of labor and amino acid concentrations between leaves and roots.

In addition to the over-expression of natural GPT proteins in transgenic plant systems, genetically-engineered, enhanced GPT enzymes may be developed and used to improve 2-oxoglutaramate synthesis kinetics, thereby increasing the rate of 2-oxoglutaramate accumulation in leaves. The GPT enzyme may be broadly classed as being a member of aspartate amino transferase type enzymes, based on sequence homology with known well characterized aspartate amino transferase enzymes. The major gene sequence databases include this classification of the transferase enzymes as a part of their sequence analysis (Gen Bank for example). Characteristically these are vitamin B6-dependent enzymes which catalyze transamination reactions between an amino acid and a ketoacid. The kinetic properties of these many (~1000) transaminases differ in such properties as substrate specificities, binding constants, maximal velocity (Vmax) and unimolecular turnover rates (Kcat). The specific arginine residues involved directly in the hydrogen-bonding of the substrate dicarboxlyic acid substrates have been highly conserved (Fotheringham et al., 1986, Biochem J. 234:593-604; Seville et al., 1988, Biochemistry 27:8344-8349: Jager et al., 1992, FEBS Lett. 306:234-238) and thus the changes in specificities and kinetic properties are often conferred by changes in other amino acid residues. The enzyme's performance has proven to be very sensitive to subtle changes in the structure of the residue, for example the addition of a single $CH_2$ group in a residue not in direct contact with either substrate or co-factor (Jansonius and Vincent, 1987; Seville et al., 1988, supra). Various studies have shown that it is possible to change an aspartate amino transferase enzyme's properties with directed mutation of the wild type protein (Kohler et al., 1994, Biochemistry 33:90-97; Jager et al., 1994, Protein Engineering. 7:605-612).

Within the plant GPT sequences, the region NLGQGFP (SEQ ID NO: 18) is highly conserved (and completely conserved among soybean, grape, rice *hordeum*, and *Arabidopsis* sequences (See, U.S. patent application Ser. No. 12/551,271 and U.S. patent application Ser. No. 12/551,193). Applicants have used such a directed mutation approach to generate a mutant GPT from the natural *Arabidopsis* GPT, by substituting V (valine) for the F (phenylalanine) residue in the wild type sequence. The resulting GPT/F:V mutant was expressed in *E. coli*, using the common PET vector system, and showed improved maximal velocity and unimolecular turnover. Maximal velocity was determined using the formula: $V_{max}=K_{cat}[E]_{tot}$. The apparent unimolecular rate constant $k_{cat}$ is also called turnover number and denotes the maximum number of enzymatic reactions catalyzed per second.

Vmax for the mutant increased to 6.04, a 20% increase over the wild type Vmax value of 5.07. Care was taken to assure that the same amount of protein was used in these experiments and thus the relationship of $V_{max}=K_{cat}[E]_{tot}$ can be applied to show that the mutant's unimolecular turnover rate has increased. The glutamine Km for the mutant is 0.75 millimolar, a slight increase from the 0.30 mM Km measured for the wild type enzyme. This mutant GPT enzyme may be expected to produce more product, the 2-oxoglutaramate, per unit time than the wild type GPT when the concentration of the substrate glutamine is present in millimolar or greater quantities, thus assuring that the mutant is saturating. A survey of the plant and agricultural literature shows that well nourished plants contain millimolar glutamine concentrations (Dzuibany et al., 1998, Plants 206:515-522; Knight and Weissman, 1982, Plant Physiol 70:1683-1688; Sivasankar and Oaks, 1995, Plant Physiol. 107: 1225-1231; Yanagisawa et al., 2004, Proc. Natl. Acad. Sci. USA 101:7833-7838; Udy and Dennison, 1997, Australia J Experimental Marine Biology and Ecology 217:253-277).

The amino acid sequence of the GPT/F:V mutant protein is as follows (V substitution shown in bold) [SEQ ID NO: 1]:
MYLDINGVMIKQFSFKASLLPFSSNFRQSSAKIHRPIGATMTTVSTQNES

TQKPVQVAKRLEKFKTTIFTQMSILAVKHGAINLGQGVPNFDGPDFVKE

AAIQAIKDGKNQYARGYGIPQLNSAIAARFREDTGLVVDPEKEVTVTSG

CTEAIAAAMLGLINPGDEVILFAPFYDSYEATLSMAGAKVKGITLRPPDF

SIPLEELKAAVTNKTRAILMNTPHNPTGKMFTREELETIASLCIENDVLV

FSDEVYDKLAFEMDHISIASLPGMYERTVTMNSLGKTFSLTGWKIGWA

IAPPHLTWGVRQAHSYLTFATSTPAQWAAVAALKAPESYFKELKRDY

NVKKETLVKGLKEVGFTVFPSSGTYFVVADHTPFGMENDVAFCEYL

IEEVGVVAIPTSVFYLNPEEGKNLVRFAFCKDEETLRGAIERMKQKLK

RKV

Two other substitution mutants were made at this residue, and one was also expressed in *E. coli* and analyzed kinetically (F:L mutation), but showed a higher (less desirable) Km value of 1.98 mM and a decreased Vmax value of 4.0.

In another approach to this aspect of the present disclosure, GPT and/or GS transgenes may be designed to utilize the codon usage preferred by the target plant species. Codon usage in plants is well established to vary particularly between monocots and dicots; in general, monocots seem to have higher GC usage overall with a very pronounced GC preference at the third base position (Kawabe and Miyashita, 2003, Genes & Genetic Systems 78(5): 343-52). Codon usage bias has been correlated with protein expression levels (Hiroaka et al., 2009). Thus one skilled in the art can refer to such sources as the Codon Usage Database or the work of Kawabe and Miyashita comparing several monocots and dicots or other genome sequence information and use or deduce the preferred codon usage for the target plant and simply design and synthesize the optimized gene sequence.

In yet a further approach to this aspect of the present disclosure, consensus engineering of the GPT and/or GS structures is used to generate consensus variants showing significant increases in protein stability in order to improve the amount of GPT activity in the plant. In this approach the native sequence is modified to more closely resemble a consensus sequence derived from the alignment of numerous proteins of a particular family (Schiller et al., 1994, J Mol. Biol. 240:188-192).

Accordingly, in certain embodiments, any of the transgenic plants with modulated ω-amidase expression disclosed herein further contain a GPT transgene. In certain embodiments, the GPT transgene is a GPT/F:V mutant given by SEQ ID NO:1. In other embodiments, any of the transgenic plants disclosed herein further contain a GPT transgene and a GS transgene. In yet other embodiments, the GPT transgene and GS transgene are each operably linked to a leaf-preferred promoter. As used herein, a "leaf-preferred promoter" refers to expression driven by a promoter that is selectively enhanced in leaf cells or tissues, in comparison to one or more non-leaf cells or tissues. For example, a leaf-preferred promoter may preferentially drive high levels of expression of a gene in leaf cells or tissue but may also drive low levels of expression of the gene in other non-leaf cells or tissues, such as roots.

In other embodiments, any of the disclosed transgenes are codon optimized for expression in the plant. In further embodiments, the transgenic plant has an increased leaf-to-root ratio of 2-oxoglutaramte. In certain preferred embodiments, the leaf-to-root ratio of 2-oxoglutaramate is at least two times, at least three times, at least four times, at least five times, at least six times, at least seven times, at least eight times, at least nine times, at least ten times, or more higher than that of an unmodified plant of the same species. In still further embodiments, the transgenic plant has increased nitrogen use efficiency.

Increasing 2-Oxoglutaramate Biosynthesis in Leaf Tissues by Gene Activation:

As yet another approach, genes encoding proteins involved in the metabolic pathway which produces 2-oxoglutaramate, which genes may be "silent" and not expressed in particular cell type in a plant, may be activated, or turned-on, via gene activation methodologies, such as the homologous recombination methods developed by Transkaryotic Therapies, Inc. (see, for example U.S. Pat. No. 6,187,305). In these methods, the endogenous regulatory region of a gene is replaced with a regulatory sequence from a different gene or a novel regulatory whose presence in the cell results in expression of the gene. Such regulatory sequences may be comprised of promoters, enhancers, scaffold-attachment regions, negative regulatory elements, transcriptional initiation sites, regulatory protein binding sites or combinations of these sequences. As a result, an endogenous copy of a gene encoding a desired gene product is turned on and expressed, and an exogenous copy of the gene need not be introduced.

In a related embodiment, transcription factor upregulation or over-expression may be used to increase the transcription of genes which promote higher leaf-to-root ratios of 2-oxoglutaramate and/or its analogs. In one embodiment, the Dof-1 transcription factor is introduced as a transgene in order to induce the up-regulation of genes encoding enzymes for carbon skeleton production, a marked increase in amino acid content and a reduction in the glucose level, as previously reported in transgenic *Arabidopsis*. Over-expression of the Dof-1 transcription factor has been shown to improved nitrogen assimilation and growth under low-nitrogen conditions (Yanagisawa et al., 2004, PNAS 101:7833-7838). In this report, the transcription factor was expressed constitutively in the plant. Over expression of the Dof-1 transcription factor, alone, or in combination with other measures such as the over-expression of GS and GPT (or functionally-improved mutants thereof) in above-ground plant tissues can be expected to increase the leaf to root ratio of 2-oxoglutaramate.

Accordingly, in certain embodiments, any of the transgenic plants with modulated ω-amidase expression disclosed herein also contain increased endogenous GPT expression, where the endogenous GPT expression is increased by gene activation. In still further embodiments, any of the transgenic plants disclosed herein contain increased endogenous GS expression, where the endogenous GS expression is increased by gene activation. In further embodiments, the transgenic plant has an increased leaf-to-root ratio of 2-oxoglutaramte. In certain preferred embodiments, the leaf-to-root ratio of 2-oxoglutaramate is at least two times, at least three times, at least four times, at least five times, at least six times, at least seven times, at least eight times, at least nine times, at least ten times, or more higher than that of an unmodified plant of the same species. In still further embodiments, the transgenic plant has increased nitrogen use efficiency.

Suitable Transgenic Plants:

Certain aspects of the present disclosure relate to transgenic plants. The transgenic plants disclosed herein may be any vascular plant of the phylum Tracheophyta, including angiosperms and gymnosperms. Angiosperms may be a monocotyledonous (monocot) or a dicotyledonous (dicot) plant. Important monocots include those of the grass families, such as the family Poaceae and Gramineae, including plants of the genus *Avena* (*Avena sativa*, oats), genus *Hordeum* (i.e., *Hordeum vulgare*, Barley), genus *Oryza* (i.e., *Oryza sativa*, rice, cultivated rice varieties), genus *Panicum* (*Panicum* spp., *Panicum virgatum*, Switchgrass), genus *Phleum* (*Phleum pratense*, Timothy-grass), genus *Saccharum* (i.e., *Saccharum officinarum*, *Saccharum spontaneum*, hybrids thereof, Sugarcane), genus *Secale* (i.e., *Secale cereale*, Rye), genus *Sorghum* (*Sorghum vulgare*, Sorghum), genus *Triticum* (wheat, various classes, including *T. aestivum* and *T. durum*), genus *Fagopyrum* (buckwheat, including *F. esculentum*), genus *Triticosecale* (*Triticale*, various hybrids of wheat and rye), genus *Chenopodium* (quinoa, including *C. quinoa*), genus *Zea* (i.e., *Zea mays*, numerous varieties) as well as millets (i.e., *Pennisetum glaucum*) including the genus *Digitaria* (*D. exilis*).

Important dicots include those of the family Solanaceae, such as plants of the genus *Lycopersicon* (*Lycopersicon esculentum*, tomato), genus *Capiscum* (*Capsicum annuum*, peppers), genus *Solanum* (*Solanum tuberosum*, potato, *S. lycopersicum*, tomato); genus *Manihot* (cassava, *M. esculenta*), genus *Ipomoea* (sweet potato, *I. batatas*), genus *Olea* (olives, including *O. europaea*); plants of the *Gossypium* family (i.e., *Gossypium* spp., *G. hirsutum*, *G. herbaceum*, cotton); the Legumes (family Fabaceae), such as peas (*Pisum* spp, *P. sativum*), beans (*Glycine* spp., *Glycine max*(soybean); *Phaseolus vulgaris*, common beans, *Vigna radiata*, mung bean), chickpeas (*Cicer arietinum*)), lentils (*Lens culinaris*), peanuts (*Arachis hypogaea*); coconuts (*Cocos nucifera*) as well as various other important crops such as camelina (*Camelina sativa*, family Brassicaceae), citrus (*Citrus* spp, family Rutaceae), coffee (*Coffea* spp, family Rubiaceae), melon (*Cucumis* spp, family Cucurbitaceae), squash (*Cucurbita* spp, family Cucurbitaceae), roses (*Rosa* spp, family Rosaceae), sunflower (*Helianthus annuus*, family Asteraceae), sugar beets (*Beta* spp, family Amaranthaceae), including sugarbeet, *B. vulgaris*), genus *Daucus* (carrots, including *D. carota*), genus *Pastinaca* (parsnip, including *P. sativa*), genus *Raphanus* (radish, including *R. sativus*), genus *Dioscorea* (yams, including *D. rotundata* and *D. cayenensis*), genus *Armoracia* (horseradish, including *A. rusticana*), genus *Elaeis* (Oil palm, including *E. guineensis*), genus *Linum* (flax, including *L. usitatissimum*), genus *Carthamus* (safflower, including *C. tinctorius* L.), genus *Sesamum* (sesame, including *S. indicum*), genus *Vitis* (grape, including *Vitis vinifera*), and plants of the genus *Brassica* (family Brassicaceae, i.e., broccoli, brussel sprouts, cabbage, swede, turnip, rapeseed *B. napus*, and cauliflower).

Other specific plants which may be transformed to generate the transgenic plants of the present disclosure include various other fruits and vegetables, such as apples, asparagus, avocado, banana, blackberry, blueberry, brussel sprout, cabbage, cotton, canola, carrots, radish, cucumbers, cherries, cranberries, cantaloupes, eggplant, grapefruit, lemons, limes, nectarines, oranges, peaches, pineapples, pears, plums, tangelos, tangerines, papaya, mango, strawberry, raspberry, lettuce, onion, grape, kiwi fruit, okra, parsnips, pumpkins, and spinach. In addition various flowering plants, trees and ornamental plants may be used to generate transgenic varietals, including without limitation lily, carnation, chrysanthemum, petunia, geranium, violet, gladioli, lupine, orchid and lilac.

In certain embodiments, the transgenic plant is selected from wheat, oats, rice, corn, bean, soybean, tobacco, alfalfa, *Arabidopsis*, grasses, fruits, vegetables, flowering plants, and trees.

Other aspects of the present disclosure also relate to a progeny of any generation of any of the transgenic plants disclosed herein. A further aspect relates to a seed of any generation of the transgenic plants disclosed herein.

Production of Transgenic Plants:

Certain aspects of the present disclosure relate to methods for generating transgenic plants with increased nitrogen use efficiency. Exemplary methods for the production of transgenic plants are described below. Further examples are described in co-owned, co-pending U.S. patent application Ser. Nos. 12/551,271, and 12/660,501, both of which are incorporated in their entireties by reference herein.

Transgene Constructs/Expression Vectors:

In order to generate the transgenic plants of the present disclosure, the gene coding sequence for the desired transgene(s) must be incorporated into a nucleic acid construct (also interchangeably referred to herein as a/an (transgene) expression vector, expression cassette, expression construct or expressible genetic construct), which can direct the expression of the transgene sequence in transformed plant cells. Such nucleic acid constructs carrying the transgene(s) of interest may be introduced into a plant cell or cells using a number of methods known in the art, including but not limited to electroporation, DNA bombardment or biolistic approaches, microinjection, and via the use of various DNA-based vectors such as *Agrobacterium tumefaciens* and *Agrobacterium rhizogenes* vectors. Once introduced into the transformed plant cell, the nucleic acid construct may direct the expression of the incorporated transgene(s) (i.e., ω-amidase), either in a transient or stable fashion. Stable expression is preferred, and is achieved by utilizing plant transformation vectors which are able to direct the chromosomal integration of the transgene construct. Once a plant cell has been successfully transformed, it may be cultivated to regenerate a transgenic plant.

A large number of expression vectors suitable for driving the constitutive or induced expression of inserted genes in transformed plants are known. In addition, various transient expression vectors and systems are known. To a large extent, appropriate expression vectors are selected for use in a particular method of gene transformation (see, infra). Broadly speaking, a typical plant expression vector for generating transgenic plants will comprise the transgene of interest under the expression regulatory control of a promoter, a selectable marker for assisting in the selection of transformants, and a transcriptional terminator sequence.

More specifically, the basic elements of a nucleic acid construct for use in generating the transgenic plants of the present disclosure are: a suitable promoter, such as a root-preferred promoter, capable of directing the functional expression of the transgene(s) in a transformed plant cell, the transgene (s) (i.e., ω-amidase coding sequence) operably linked to the promoter, preferably a suitable transcription termination sequence (i.e., nopaline synthetic enzyme gene terminator) operably linked to the transgene, and sometimes other elements useful for controlling the expression of the transgene, as well as one or more selectable marker genes suitable for selecting the desired transgenic product (i.e., antibiotic resistance genes).

As *Agrobacterium tumefaciens* is the primary transformation system used to generate transgenic plants, there are numerous vectors designed for *Agrobacterium* transformation. For stable transformation, *Agrobacterium* systems utilize "binary" vectors that permit plasmid manipulation in both *E. coli* and *Agrobacterium*, and typically contain one or more selectable markers to recover transformed plants (Hellens et al., 2000, *Technical focus: A guide to Agrobacterium binary Ti vectors*. Trends Plant Sci 5:446-451). Binary vectors for use in *Agrobacterium* transformation systems typically comprise the borders of T-DNA, multiple cloning sites, replication functions for *Escherichia coli* and *A. tumefaciens*, and selectable marker and reporter genes.

So-called "super-binary" vectors provide higher transformation efficiencies, and generally comprise additional virulence genes from a Ti (Komari et al., 2006, Methods Mol. Biol. 343: 15-41). Super binary vectors are typically used in plants which exhibit lower transformation efficiencies, such as cereals. Such additional virulence genes include without limitation virB, virE, and virG (Vain et al., 2004, *The effect of additional virulence genes on transformation efficiency, transgene integration and expression in rice plants using the pGreen/pSoup dual binary vector system*. Transgenic Res. 13: 593-603; Srivatanakul et al., 2000, *Additional virulence genes influence transgene expression: transgene copy number, integration pattern and expression*. J. Plant Physiol. 157, 685-690; Park et al., 2000, *Shorter T-DNA or additional virulence genes improve Agrobacterium-mediated transformation*. Theor. Appl. Genet. 101, 1015-1020; Jin et al., 1987, *Genes responsible for the supervirulence phenotype of Agrobacterium tumefaciens A281*. J. Bacteriol. 169: 4417-4425).

Plant Promoters:

In order to generate the transgenic plants of the present disclosure, the gene coding sequence for the desired transgene(s) is are operably linked to a promoter in order to drive expression of the transgene. A large number of promoters which are functional in plants are known in the art. In constructing ω-amidase, GPT, or GS transgene constructs and ω-amidase RNAi constructs, the selected promoter(s) may be constitutive, non-specific promoters such as the Cauliflower Mosaic Virus 35S ribosomal promoter (CaMV 35S promoter), which is widely employed for the expression of transgenes in plants. Examples of other strong constitutive promoters include without limitation the rice actin 1 promoter, the CaMV 19S promoter, the Ti plasmid nopaline synthase promoter, the alcohol dehydrogenase promoter and the sucrose synthase promoter.

Alternatively, in some embodiments, it may be desirable to select a promoter based upon the desired plant cells to be transformed by the transgene construct, the desired expression level of the transgene, the desired tissue or subcellular compartment for transgene expression, the developmental stage targeted, and the like. For example, a root-preferred promoter may include, without limitation, a RolD promoter, a RolD-2 promoter, a glycine rich protein promoter, a GRP promoter, an ADH promoter, a maize ADH1 promoter, a PHT promoter, a Pht1 gene family promoter, a metal uptake protein promoter, a maize metallothionein protein promoter, a 35S CaMV domain A promoter, a pDJ3S promoter, an SIREO promoter, a pMe1 promoter, an Sad1 promoter, an Sad2 promoter, a TobRB7 promoter, an RCc3 promoter, an FaRB7 promoter, an SPmads promoter, an IDS2 promoter, a pyk10 promoter, an Lbc3 leghemoglobin promoter, a PEPC promoter, a Gns1 glucanase root promoter, a $35S^2$ promoter, a GI4 promoter, a GI5 promoter, and a GRP promoter In addition to constitutive promoters, various inducible promoter sequences may be employed in cases where it is desirable to regulate transgene expression as the transgenic plant regenerates, matures, flowers, etc. Examples of such inducible promoters include promoters of heat shock genes, protection responding genes (i.e., phenylalanine ammonia lyase; see, for example Bevan et al., 1989, EMBO J. 8(7): 899-906), wound responding genes (i.e., cell wall protein genes), chemically inducible genes (i.e., nitrate reductase, chitinase) and dark inducible genes (i.e., asparagine synthetase; see, for example U.S. Pat. No. 5,256,558). Also, a number of plant nuclear genes are activated by light, including gene families encoding the major chlorophyll a/b binding proteins (cab) as well as the small subunit of ribulose-1,5-bisphosphate carboxylase (rbcS) (see, for example, Tobin and Silverthorne, 1985, Annu. Rev. Plant Physiol. 36: 569-593; Dean et al., 1989, Annu. Rev. Plant Physiol. 40: 415-439.).

Other inducible promoters include ABA- and turgor-inducible promoters, the auxin-binding protein gene promoter (Schwob et al., 1993, Plant J. 4(3): 423-432), the UDP glucose flavonoid glycosyl-transferase gene promoter (Ralston et al., 1988, Genetics 119(1): 185-197); the MPI proteinase inhibitor promoter (Cordero et al., 1994, Plant J. 6(2): 141-150), the glyceraldehyde-3-phosphate dehydrogenase gene promoter (Kohler et al., 1995, Plant Mol. Biol. 29(6): 1293-1298; Quigley et al., 1989, J. Mol. Evol. 29(5): 412-421; Martinez et al., 1989, J. Mol. Biol. 208(4): 551-565) and light inducible plastid glutamine synthetase gene from pea (U.S. Pat. No. 5,391,725; Edwards et al., 1990, supra).

For a review of plant promoters used in plant transgenic plant technology, see Potenza et al., 2004, In Vitro Cell. Devel. Biol—Plant, 40(1): 1-22. For a review of synthetic plant promoter engineering, see, for example, Venter, M., 2007, Trends Plant Sci., 12(3): 118-124.

In certain embodiments, a 3' transcription termination sequence is also incorporated downstream of the transgene in order to direct the termination of transcription and permit correct polyadenylation of the mRNA transcript. Suitable transcription terminators are those which are known to function in plants, including without limitation, the nopaline synthase (NOS) and octopine synthase (OCS) genes of *Agrobacterium tumefaciens*, the T7 transcript from the octopine synthase gene, the 3' end of the protease inhibitor I or II genes from potato or tomato, the CaMV 35S terminator, the tml terminator and the pea rbcS E9 terminator. In addition, a gene's native transcription terminator may be used. In specific embodiments, described by way of the Examples, infra, the nopaline synthase transcription terminator is employed.

Selectable Markers:

Selectable markers are typically included in transgene expression vectors in order to provide a means for selecting plant transformants. While various types of markers are available, various negative selection markers are typically utilized, including those which confer resistance to a selection agent that inhibits or kills untransformed cells, such as genes which impart resistance to an antibiotic (such as kanamycin, gentamycin, anamycin, hygromycin and hygromycinB) or resistance to a herbicide (such as sulfonylurea, gulfosinate, phosphinothricin and glyphosate). Screenable markers include, for example, genes encoding β-glucuronidase (Jefferson, 1987, Plant Mol. Biol. Rep 5: 387-405), genes encoding luciferase (Ow et al., 1986, Science 234: 856-859) and various genes encoding proteins involved in the production or control of anthocyanin pigments (See, for example, U.S. Pat. No. 6,573,432). The *E. coli* glucuronidase gene (gus, gusA or uidA) has become a widely used selection marker in plant transgenics, largely because of the glucuronidase enzyme's stability, high sensitivity and ease of detection (e.g., fluorometric, spectrophotometric, various histochemical methods). Moreover, there is essentially no detectable glucuronidase in most higher plant species.

Transformation Methodologies and Systems:

Various methods for introducing the transgene expression vector constructs of the present disclosure into a plant or plant cell are well known to those skilled in the art, and any capable of transforming the target plant or plant cell may be utilized.

*Agrobacterium*-mediated transformation is perhaps the most common method utilized in plant transgenics, and protocols for *Agrobacterium*-mediated transformation of a large number of plants are extensively described in the literature (see, for example, *Agrobacterium* Protocols, Wan, ed., Humana Press, 2$^{nd}$ edition, 2006). *Agrobacterium tumefaciens* is a Gram negative soil bacteria that causes tumors (Crown Gall disease) in a great many dicot species, via the insertion of a small segment of tumor-inducing DNA ("T-DNA", 'transfer DNA') into the plant cell, which is incorporated at a semi-random location into the plant genome, and which eventually may become stably incorporated there. Directly repeated DNA sequences, called T-DNA borders, define the left and the right ends of the T-DNA. The T-DNA can be physically separated from the remainder of the Ti-plasmid, creating a 'binary vector' system.

*Agrobacterium* transformation may be used for stably transforming dicots, monocots, and cells thereof (Rogers et al., 1986, Methods Enzymol., 118: 627-641; Hernalsteen et al., 1984, EMBO J., 3: 3039-3041; Hoykass-Van Slogteren et al., 1984, Nature, 311: 763-764; Grimsley et al., 1987, Nature 325: 167-1679; Boulton et al., 1989, Plant Mol. Biol. 12: 31-40; Gould et al., 1991, Plant Physiol. 95: 426-434). Various methods for introducing DNA into *Agrobacteria* are known, including electroporation, freeze/thaw methods, and triparental mating. The most efficient method of placing foreign DNA into *Agrobacterium* is via electroporation (Wise et al., 2006, *Three Methods for the Introduction of Foreign DNA into Agrobacterium*, Methods in Molecular Biology, vol. 343: *Agrobacterium* Protocols, 2/e, volume 1; Ed., Wang, Humana Press Inc., Totowa, N.J., pp. 43-53). In addition, given that a large percentage of T-DNAs do not integrate, *Agrobacterium*-mediated transformation may be used to obtain transient expression of a transgene via the transcriptional competency of unincorporated transgene construct molecules (Helens et al., 2005, Plant Methods 1:13).

A large number of *Agrobacterium* transformation vectors and methods have been described (Karimi et al., 2002, Trends Plant Sci. 7(5): 193-5), and many such vectors may be obtained commercially (for example, Invitrogen, Carlsbad, Calif.). In addition, a growing number of "open-source" *Agrobacterium* transformation vectors are available (for example, pCambia vectors; Cambia, Can berra, Australia). See, also, subsection herein on TRANSGENE CONSTRUCTS, supra. In a specific embodiment described further in the Examples, a pMON316-based vector was used in the leaf disc transformation system of Horsch et. al. (Horsch et al., 1995, Science 227:1229-1231) to generate growth enhanced transgenic tobacco and tomato plants.

Other commonly used transformation methods that may be employed in generating the transgenic plants of the present disclosure include, without limitation microprojectile bombardment, or biolistic transformation methods, protoplast transformation of naked DNA by calcium, polyethylene glycol (PEG) or electroporation (Paszkowski et al., 1984, EMBO J. 3: 2727-2722; Potrykus et al., 1985, Mol. Gen. Genet. 199: 169-177; Fromm et al., 1985, Proc. Nat. Acad. Sci. USA 82: 5824-5828; Shimamoto et al., 1989, Nature, 338: 274-276.

Biolistic transformation involves injecting millions of DNA-coated metal particles into target cells or tissues using a biolistic device (or "gene gun"), several kinds of which are available commercially. Once inside the cell, the DNA elutes off the particles and a portion may be stably incorporated into one or more of the cell's chromosomes (for review, see Kikkert et al., 2005, *Stable Transformation of Plant Cells by Particle Bombardment/Biolistics*, in: Methods in Molecular Biology, vol. 286: Transgenic Plants: Methods and Protocols, Ed. L. Peña, Humana Press Inc., Totowa, N.J.).

Electroporation is a technique that utilizes short, high-intensity electric fields to permeabilize reversibly the lipid bilayers of cell membranes (see, for example, Fisk and Dandekar, 2005, *Introduction and Expression of Transgenes in Plant Protoplasts*, in: Methods in Molecular Biology, vol. 286: Transgenic Plants: Methods and Protocols, Ed. L. Peña, Humana Press Inc., Totowa, N.J., pp. 79-90; Fromm et al., 1987, *Electroporation of DNA and RNA into plant protoplasts*, in Methods in Enzymology, Vol. 153, Wu and Grossman, eds., Academic Press, London, UK, pp. 351-366; Joersbo and Brunstedt, 1991, *Electroporation: mechanism and transient expression, stable transformation and biological effects in plant protoplasts*. Physiol. Plant. 81, 256-264; Bates, 1994, *Genetic transformation of plants by protoplast electroporation*. Mol. Biotech. 2: 135-145; Dillen et al., 1998, *Electroporation-mediated DNA transfer to plant protoplasts and intact plant tissues for transient gene expression assays*, in Cell Biology, Vol. 4, ed., Celis, Academic Press, London, UK, pp. 92-99). The technique operates by creating aqueous pores in the cell membrane, which are of sufficiently large size to allow DNA molecules (and other macromolecules) to enter the cell, where the transgene expression construct (as T-DNA) may be stably incorporated into plant genomic DNA, leading to the generation of transformed cells that can subsequently be regenerated into transgenic plants.

Newer transformation methods include so-called "floral dip" methods, which offer the promise of simplicity, without requiring plant tissue culture, as is the case with all other commonly used transformation methodologies (Bent et al., 2006, *Arabidopsis thaliana Floral Dip Transformation Method*, Methods Mol Biol, vol. 343: *Agrobacterium Protocols*, 2/e, volume 1; Ed., Wang, Humana Press Inc., Totowa, N.J., pp. 87-103; Clough and Bent, 1998, *Floral dip: a simplified method for Agrobacterium-mediated transformation of Arabidopsis thaliana*, Plant J. 16: 735-743). However, with the exception of *Arabidopsis*, these methods have not been widely used across a broad spectrum of different plant species. Briefly, floral dip transformation is accomplished by dipping or spraying flowering plants in with an appropriate strain of *Agrobacterium tumefaciens*. Seeds collected from these $T_0$ plants are then germinated under selection to identify transgenic $T_1$ individuals. Example 16 demonstrated floral dip inoculation of *Arabidopsis* to generate transgenic *Arabidopsis* plants.

Other transformation methods include those in which the developing seeds or seedlings of plants are transformed using vectors such as *Agrobacterium* vectors. For example, such vectors may be used to transform developing seeds by injecting a suspension or mixture of the vector (i.e., *Agrobacteria*) directly into the seed cavity of developing pods (i.e., pepper pods, bean pods, pea pods and the like). Still other transformation methods include those in which the flower structure is targeted for vector inoculation.

In addition, although transgenes are most commonly inserted into the nuclear DNA of plant cells, transgenes may also be inserted into plastidic DNA (i.e., into the plastome of the chloroplast). In most flowering plants, plastids do not occur in the pollen cells, and therefore transgenic DNA incorporated within a plastome will not be passed on through propagation, thereby restricting the trait from migrating to wild type plants. Plastid transformation, however, is more complex than cell nucleus transformation, due to the presence of many thousands of plastomes per cell (as high as 10,000). Transplastomic lines are genetically stable only if all plastid copies are modified in the same way, i.e. uniformly. This is typically achieved through repeated regeneration under certain selection conditions to eliminate untransformed plastids, by segregating transplastomic and untransformed plastids, resulting in the selection of homoplasmic cells carrying the transgene construct and the selectable marker stably integrated therein. Plastid transformation has been successfully performed in various plant species, including tobacco, potatoes, oilseed rape, rice, and *Arabidopsis*.

To generate transplastomic lines carrying an ω-amidase transgene, the transgene expression cassette is inserted into flanking sequences from the plastome. Using homologous recombination, the transgene expression cassette becomes integrated into the plastome via a natural recombination process. The basic DNA delivery techniques for plastid transformation include particle bombardment of leaves or polyethylene glycol-mediated DNA transformation of protoplasts. Transplastomic plants carrying transgenes in the plastome may be expressed at very high levels, due to the fact that many plastids (i.e., chloroplasts) per cell, each carrying many copies of the plastome. This is particularly the case in foliar tissue, where a single mature leaf cell may contain over 10,000 copies of the plastome. Following a successful transformation of the plastome, the transplastomic events carry the transgene on every copy of the plastid genetic material. This can result in the transgene expression levels representing as much as half of the total protein produced in the cell.

Plastid transformation methods and vector systems are described, for example, in recent U.S. Pat. Nos. 7,528,292; 7,371,923; 7,235,711; and, 7,193,131. See also U.S. Pat. Nos. 6,680,426 and 6,642,053.

The foregoing plant transformation methodologies may be used to introduce at least one transgene into a number of different plant cells and tissues, including without limitation, whole plants, tissue and organ explants including chloroplasts, flowering tissues and cells, protoplasts, meristem cells, callus, immature embryos and gametic cells such as microspores, pollen, sperm and egg cells, tissue cultured cells of any of the foregoing, any other cells from which a fertile regenerated transgenic plant may be generated. Callus is initiated from tissue sources including, but not limited to, immature embryos, seedling apical meristems, microspores and the like. Cells capable of proliferating as callus are also recipient cells for genetic transformation.

Methods of regenerating individual plants from transformed plant cells, tissues or organs are known and are described for numerous plant species.

As an illustration, transformed plantlets (derived from transformed cells or tissues) are cultured in a root-permissive growth medium supplemented with the selective agent used in the transformation strategy. Once rooted, transformed plantlets are then transferred to soil and allowed to grow to maturity. Upon flowering, the mature plants are preferably selfed (self-fertilized), and the resultant seeds harvested and used to grow subsequent generations.

$T_0$ transgenic plants may be used to generate subsequent generations (e.g., $T_1$, $T_2$, etc.) by selfing of primary or secondary transformants, or by sexual crossing of primary or secondary transformants with other plants (transformed or untransformed). During the mature plant growth stage, the plants are typically examined for growth phenotype, nitrogen use efficiency, $CO_2$ fixation rate, etc. (see following subsection).

Selection of Transgenic Plants with Increased Nitrogen Use Efficiency:

Transgenic plants may be selected, screened and characterized using standard methodologies. The preferred transgenic plants of the present disclosure will exhibit one or more phenotypic characteristics indicative of increased nitrogen use efficiency, including without limitation, faster growth rates, greater seed and fruit/pod yields, earlier and more productive flowering, increased tolerance to high salt conditions, and increased biomass yields. Transgenic plants are typically regenerated under selective pressure in order to select transformants prior to creating subsequent transgenic plant generations. In addition, the selective pressure used may be employed beyond $T_0$ generations in order to ensure the presence of the desired transgene expression construct or cassette.

$T_0$ transformed plant cells, calli, tissues or plants may be identified and isolated by selecting or screening for the genetic composition of and/or the phenotypic characteristics encoded by marker genes contained in the transgene expression construct used for the transformation. For example, selection may be conducted by growing potentially-transformed plants, tissues or cells in a growth medium containing a repressive amount of antibiotic or herbicide to which the transforming genetic construct can impart resistance. Further, the transformed plant cells, tissues and plants can be identified by screening for the activity of marker genes (i.e., β-glucuronidase) which may be present in the transgene expression construct.

Various physical and biochemical methods may be employed for identifying plants containing the desired transgene expression construct, as is well known. Examples of such methods include Southern blot analysis or various nucleic acid amplification methods (i.e., PCR) for identifying the transgene, transgene expression construct or elements thereof, Northern blotting, 51 RNase protection, reverse transcriptase PCR (RT-PCR) amplification for detecting and determining the RNA transcription products, and protein gel electrophoresis, Western blotting, immunoprecipitation, enzyme immunoassay, and the like may be used for identifying the protein encoded and expressed by the transgene.

In another approach, expression levels of genes, proteins and/or metabolic compounds that are know to be modulated by transgene expression in the target plant may be used to identify transformants. In one embodiment of the present disclosure, increased levels of the signal metabolite 2-oxoglutaramate in leaf tissue, or decreased levels in the root tissue, or a higher leaf-to-root ratio of 2-oxoglutaramate may be used to screen for desirable transformants.

Ultimately, the transformed plants of the present disclosure may be screened for increased nitrogen use efficiency. Nitrogen use efficiency may be expressed as plant yield per given amount of nitrogen. Indeed, some degree of phenotypic screening is generally desirable in order to identify transformed lines with the fastest growth rates, the highest seed yields, etc., particularly when identifying plants for subsequent selfing, cross-breeding and back-crossing. Various parameters may be used for this purpose, including without limitation, growth rates, total fresh weights, dry weights, seed and fruit yields (number, weight), seed and/or seed pod sizes, seed pod yields (e.g., number, weight), leaf sizes, plant sizes, increased flowering, time to flowering, overall protein content (in seeds, fruits, plant tissues), specific protein content (i.e., ω-amidase), nitrogen content, free amino acid, and specific metabolic compound levels (i.e., 2-oxoglutaramate). Generally, these phenotypic measurements are compared with those obtained from a parental identical or analogous plant line, an untransformed identical or analogous plant, or an identical or analogous wild-type plant (i.e., a normal or parental plant). Preferably, and at least initially, the measurement of the chosen phenotypic characteristic(s) in the target transgenic plant is done in parallel with measurement of the same characteristic(s) in a normal or parental plant. Typically, multiple plants are used to establish the phenotypic desirability and/or superiority of the transgenic plant in respect of any particular phenotypic characteristic.

Preferably, initial transformants are selected and then used to generate $T_1$ and subsequent generations by selfing (self-fertilization), until the transgene genotype breeds true (i.e., the plant is homozygous for the transgene). In practice, this is accomplished by screening at each generation for the desired traits and selfing those individuals, often repeatedly (i.e., 3 or 4 generations). As exemplified herein, transgenic plant lines propagated through at least one sexual generation (Tobacco, Arabidopsis, Tomato) demonstrated higher transgene product activities compared to lines that did not have the benefit of sexual reproduction and the concomitant increase in transgene copy number.

Stable transgenic lines may be crossed and back-crossed to create varieties with any number of desired traits, including those with stacked transgenes, multiple copies of a transgene, etc. Various common breeding methods are well known to those skilled in the art (see, e.g., Breeding Methods for Cultivar Development, Wilcox J. ed., American Society of Agronomy, Madison Wis. (1987)). Additionally, stable transgenic plants may be further modified genetically, by transforming such plants with further transgenes or additional copies of the parental transgene. Also contemplated are transgenic plants created by single transformation events which introduce multiple copies of a given transgene or multiple transgenes.

Nitrogen use efficiency may be expressed as plant yield per given amount of nitrogen.

Methods for Increasing Nitrogen Use Efficiency:

Certain aspects of the present disclosure relate to methods for increasing nitrogen use efficiency of a plant.

One particular aspect relates to a method for increasing nitrogen use efficiency of a plant relative to a wild type or untransformed plant of the same species, by: (a) introducing an ω-amidase transgene into the plant, where the ω-amidase transgene is operably linked to a root-preferred promoter; (b) expressing the ω-amidase transgene in root tissue of the plant or the progeny of the plant; and (c) selecting a plant having an increased leaf-to-root ratio of 2-oxoglutaramate relative to a plant of the same species that does not contain an ω-amidase transgene, where the increased leaf-to-root ratio of 2-oxoglutaramate results in increased nitrogen use efficiency.

In certain embodiments, the ω-amidase transgene encodes a polypeptide having an amino acid sequence that is at least 90% identical to an amino acid sequence encoded by a polypeptide selected from AAL91613.1, ACN30911.1, ABK22312.1, ACJ85250.1, AAQ97821.1, CBJ25483.1, EFN54567.1, NP_196765.2, XP_002871509.1, NP_974769.1, XP_002309478.1, XP_002279687.1, NP_001146676.1, NP_001146295.1, NP_001049134.1, XP_002516116.1, XP_001766085.1, XP_001756522.1, XP_002969787.1, XP_002985119.1, XP_002948137.1, XP_001690839.1, NP_001057093.1, XP_002468410.1, NP_064587.1, XP_001089575.2, XP_001502234.1, XP_002502298.1, XP_526254.2, XP_535718.2, XP_002716659.1, NP_001033222.1, NP_001029298.1, NP_001016633.1, NP_001085409.1, XP_002758928.1, XP_003064056.1, NP_001135127.1, XP_001622809.1, NP_991174.2, XP_002594716.1, NP_075664.1, XP_001370849.1, NP_001090454.1, XP_002999170.1, XP_002917137.1, XP_002741281.1, XP_002131764.1, NP_594154.1, XP_001742101.1, XP_416604.2, XP_002194275.1, XP_001599587.1, XP_002410555.1, XP_003035898.1, XP_002183613.1, XP_001875493.1, XP_002112209.1, XP_636983.1, XP_002158547.1, XP_002839272.1, XP_307722.3, XP_001819629.1, XP_001268376.1, ZP_08115581.1, YP_001320997.1, XP_369268.1, XP_002626458.1, XP_751200.1, XP_001657673.1, XP_002173486.1, XP_001212538.1, XP_001258462.1, XP_002434512.1, XP_960906.1, XP_002847679.1, XP_967861.1, XP_002426154.1, XP_003176259.1, XP_500602.1, XP_001428419.1, XP_003014235.1, XP_001393123.1, ZP_03608460.1, XP_002147261.1, ZP_03293831.1, XP_002290043.1, XP_003065597.1, XP_001588734.1, YP_001273073.1, XP_001552800.1, XP_446414.1, XP_002792830.1, XP_001998501.1, YP_003780301.1, NP_013455.1, XP_002404736.1, YP_001086961.1, ZP_05328587.1, ZP_05399936.1, YP_001113615.1, XP_001247884.1, XP_390426.1, XP_003025334.1, XP_002052999.1, YP_769862.1, ZP_07325748.1, ZP_05349666.1, YP_471237.1, YP_002977603.1, YP_001202760.1, ZP_07592670.1, and NP_386723.1. In other embodiments, the ω-amidase transgene is incorporated into the genome of the plant. In still other embodiments, the root-preferred promoter is selected from RolD promoter, RolD-2 promoter, glycine rich protein promoter, GRP promoter, ADH promoter, maize ADH1 promoter, PHT promoter, Pht1 gene family promoter, metal uptake protein promoter, maize metallothionein protein promoter, 35S CaMV domain A promoter. pDJ3S promoter, SIREO promoter, pMe1 promoter, Sad1 promoter, Sad2 promoter, TobRB7 promoter, RCc3 promoter, FaRB7 promoter, SPmads promoter, IDS2 promoter, pyk10 promoter, Lbc3 leghemoglobin promoter, PEPC promoter, Gns1 glucanase root promoter, 35S$^2$promoter, GI4 promoter, GI5 promoter, and GRP promoter.

In other embodiments, endogenous ω-amidase expression in leaf tissue is inhibited. In still other embodiments, the endogenous ω-amidase expression in leaf tissue is inhibited by recessive gene disruption, dominant gene silencing, or a chemical inhibitor. In yet other embodiments, the endogenous ω-amidase expression in leaf tissue is inhibited by a recessive gene disruption selected from a mutant ω-amidase gene that eliminates endogenous ω-amidase expression, an endogenous ω-amidase knockout mutant, and an endogenous ω-amidase knockdown mutant. In further embodiments, the endogenous ω-amidase expression in leaf tissue is inhibited by an RNAi antisense oligonucleotide that is specific for an endogenous ω-amidase gene. In still further embodiments, the endogenous ω-amidase expression in leaf tissue is inhibited by a chemical inhibitor selected from 6-diazo-5-oxo-nor-leucine, p-hydroxymercuribenzoate, diisopropyl fluorophosphates, sodium cyanide, phenylmercuriacetate, Iodoacetate, silver nitrate, chloromercuricphenylsulfonic acid, and copper sulfate.

In other embodiments, the leaf-to-root ratio of 2-oxoglutaramate is at least two times higher than that of a progenitor or wild type plant of the same species. In still other embodiments, the plant further contains a GPT transgene. In yet other embodiments, the GPT transgene is a GPT/F:V mutant given by SEQ ID NO:1. In further embodiments, the plant further comprises a GPT transgene and a GS transgene. In other embodiments, the GPT transgene and GS transgene are each operably linked to a leaf-preferred promoter. In still further embodiments, endogenous GPT expression in the plant is increased by gene activation. In yet other embodiments, endogenous GS expression in the plant is increased by gene activation. In other embodiments, each transgene is codon optimized for expression in the plant.

Another aspect relates to a method for increasing nitrogen use efficiency of a plant relative to a wild type or untransformed plant of the same species, by: (a) inhibiting endogenous ω-amidase expression in leaf tissue of the plant; and (b) selecting a plant having an increased leaf-to-root ratio of 2-oxoglutaramate relative to a plant of the same species that does not have inhibited endogenous ω-amidase expression in leaf tissue, where the increased leaf-to-root ratio of 2-oxoglutaramate results in increased nitrogen use efficiency.

In certain embodiments, the endogenous ω-amidase expression in leaf tissue is inhibited by recessive gene disruption, dominant gene silencing, or a chemical inhibitor. In other embodiments, the endogenous ω-amidase expression in leaf tissue is inhibited by a recessive gene disruption selected from a mutant ω-amidase gene that eliminates endogenous ω-amidase expression, an endogenous ω-amidase knockout mutant, and an endogenous ω-amidase knockdown mutant. In still other embodiments, the endogenous ω-amidase expression in leaf tissue is inhibited by an RNAi antisense oligonucleotide that is specific for an endogenous ω-amidase gene. In yet other embodiments, the chemical inhibitor selected from 6-diazo-5-oxo-nor-leucine, p-hydroxymercuribenzoate, diisopropyl fluorophosphates, sodium cyanide, phenylmercuriacetate, Iodoacetate, silver nitrate, chloromercuricphenylsulfonic acid, and copper sulfate.

In other embodiments, the plant further contains an [omega]-amidase transgene, wherein the [omega]-amidase transgene is operably linked to a root-preferred promoter. In still other embodiments, the leaf-to-root ratio of 2-oxoglutaramate is at least two times higher than that of a progenitor or wild type plant of the same species. In yet other embodiments, the plant further contains a GPT transgene. In further embodiments, the GPT transgene is a GPT/F:V mutant given by SEQ ID NO:1. In still further embodiments, the plant further contains a GPT transgene and a GS transgene. In other embodiments, the GPT transgene and GS transgene are each operably linked to a leaf-preferred promoter. In yet further embodiments, endogenous GPT expression in the plant is increased by gene activation. In other embodiments, endogenous GS expression in the plant is increased by gene activation. In still other embodiments, each transgene is codon optimized for expression in the plant.

In further embodiments of the methods for increasing nitrogen use efficiency of a plant, the plant may contain other transgenes known to increase nitrogen utilization efficiency, including without limitation those described in U.S. Pat. No. 7,560,626.

In the Examples provided herein, the transgene and control plants all received the same nutrient solutions in the same amounts. The transgenic plants were consistently characterized by higher yields, and thus have higher nitrogen use efficiencies.

EXAMPLES

Example 1

Effects of Increasing Expression Levels of GS and GPT on Ω-Amidase Pathway

Materials and Methods:
Generation of Transgenic Plants:

Plants were genetically engineered to over-produce 2-oxoglutaramate by over expressing GS and GPT transgenes, as described in U.S. patent application Ser. No. 12/551,271. The resulting phenotypic effects were evaluated. Three sets of transgenic tobacco lines were generated: one set over-expressing GPT to increase GRMT catalytic capacity; a second set over-expressing GS to increase, in the leaves only, the catalytic capacity to make the glutamine substrate of GPT; and a third set over expressing GS and GPT, produced by sexually crossing fast-growing progeny of the single transgene lines.

Growth of Engineered Tobacco and *Arabidopsis*:

Wild type and engineered tobacco seeds were surface sterilized and germinated in phytotrays containing M&S medium. The medium for the engineered plants contained kanamycin (10 ug/ml). The vigorously growing seedlings were transferred at 17 d to a sand culture, covered to control humidity for 4 d to aid adaptation to ambient conditions; plants were continuously provided a nutrient solution (Knight and Langston-Unkefer, 1988, Science 241: 951) containing 10 mM $KNO_3$. The growth conditions were as described previously (Knight and Langston-Unkefer, supra). Tissue was harvested between 32-35 d after the transplant unless the plants were being grown for seed production. Wild type and engineered *Arabidopsis* seeds were surface sterilized and germinated in phytotrays containing M&S medium. For the engineered plants the medium contained kanamycin (10 ug/ml).

The seedlings were transferred to the ArabiSystem using the Promix (Lehle Seeds) growth medium and grown at 24° C. with 16 h light and 8 h dark periods. Plants were grown to maturity.

Results:

The over-expression of GS in tobacco generated two classes of progeny; those that grew faster and over-expressed GS only in their leaves, thus increasing their leaf-to ratio of GS, and a second class that grew at normal rates and over-expressed GS in both leaves and roots, thereby maintaining a normal leaf-to-root ratio. Regulation of GS and GPT expression in these plants appears complex and expression of each gene appears to influence the other (see Tables 2 and 3); over-expression of only GPT in leaves and roots was accompanied by increased GS activity in the leaf and only normal GS activity in the root. Increased GS expression only in the leaf was accompanied by increased GPT activity in the leaf and lower GPT activity in the root. These responses were evident in the GS+GPT transgenic plants as well. Over-expression of either GS or GPT was accompanied by lower ω-amidase activity in the leaves and greater ω-amidase activity in the roots. GPT and GS+GPT transgenic plants showed the largest increases in root ω-amidase activity. These plants responded to expression of the transgenes by altering their ω-amidase activities such that they tend to increase the leaf root 2-oxoglutaramate pool, and maintain the root 2-oxoglutaramate pool. These responses combined in the GS+GPT over-expressing plants to generate the highest leaf and lowest root 2-oxoglutaramate pools and the highest leaf and lowest GS and GPT activities.

Tables 2, 3, and 4 below depict the effects of engineering for greater 2-oxoglutaramate (2-OGM) biosynthesis. Tables 2 and 3 depict results from tobacco plants, and Table 4 depicts results from *Arabidopsis thaliana* plants.

TABLE 2

Effects of engineering greater 2-oxoglutaramate biosynthesis capability

| Tobacco Genotype | Leaf 2-OGM nmol/gfwt | Root 2-OGM nmol/gfwt (Leaf/Root) | Leaf GS umol/gfwt/m | Leaf GPT nmol/gfwt/h | Leaf Amidase nmol/gfwt/h (GPT/Amidase) | Root GS umol/gfwt/m (Leaf/Root) | Root GPT nmol/gfwt/h | Root Amidase nmol/gfwt/h (GPT/Amidase) |
|---|---|---|---|---|---|---|---|---|
| Wild type | 191 | 116 (1.6) | 7.8 | 100 | 191 (0.5) | 2.1 (3.7) | 236 | 252 (0.9) |
| +GPT | 384 | 143 (2.7) | 10.5 | 196 | 118 (1.7) | 1.9 (5.5) | 566 | 440 (1.3) |
| +GS | 502 | 131 (3.8) | 11.6 | 288 | 112 (2.6) | 1.7 (6.8) | 136 | 372 (0.4) |
| +GS +GPT | 701 | 80 (8.7) | 16.3 | 731 | 149 (4.9) | 1.8 (9.1) | 117 | 292 (0.4) |

In Table 2 above, "gfwt" refers to grams fresh weight and "nmol/gfwt/h" refers to nano moles per grams fresh weight per hour.

TABLE 3

Effects of engineering greater 2-oxoglutaramate biosynthesis capability

| Tobacco Genotype | $NO_3$ uptake rate mm/gfwth | Leaf $NO_3$ μmol/gfwt | Root $NO_3$ μmol/gfwt | Leaf Protein Mg/gfwt | Chlorophyll μg/gfwt | $CO_2$ Fixed Rate $mm/m^2/s$ | RGR Mg/g/d | Seed yield g/plt | Whole Plant gfwt |
|---|---|---|---|---|---|---|---|---|---|
| Wild type | 4.3 ± 2.8 | 69.3 ± 4.9 | 29.9 ± 2.2 | 4.3 (100%) | 818 + 10 | 7.7 | 226 | 1.0 | 21.0 (100%) |
| +GPT | 10.9 ± 2.4 | 77.6 ± 8.2 | 57.5 ± 6.0 | 5.2 (120%) | 1044 ± 3 | 12.9 | ND | NM | 31 (147%) |
| +GS | 11.3 ± 1.9 | 22.8 ± 2.7 | 12.1 ± 3.2 | 6.9 (160%) | 1109 + 6 | 13.5 | 269 | NM | 35.6 (169%) |
| +GS +GPT | 19.5 ± 3.1 | 51.1 ± 1.8 | 30.1 ± 3.5 | 7.3 (170%) | 1199 ± 11 | 20.6 | 346 | 2.87 | 71.9 (342%) |

TABLE 4

Arabidopsis engineered to over-produce 2-oxoglutaramate

| Arabidopsis Genotype | Leaf GS Activity μmol/ gfwt, m | Leaf GPT Activity nmol/ gfwt/h | Leaf 2-OGM nmol · gfwt/ h | Leaf Protein mg/gfwt (% wt) | Whole Plant Fresh Wt, g (% wt) |
|---|---|---|---|---|---|
| Wild type | 6.99 | 184 | 184 | 6.06* | 0.246 |
| +GS + GPT | 18.7 | 1077 | 395.6 | 7.46* (123%) | 1.106 (449%) |

Example 2

Plant Expression Vector Modulating Root Ω-Amidase Expression Levels

Ω-amidase expression levels are increased in root tissues by generating transgenic plants transformed with expression constructs containing an ω-amidase coding sequence, including but not limited to any of the ω-amidase coding sequences disclosed herein, under the control of a root-preferred promoter. It is believed that increased levels of ω-amidase in root tissues result in increased breakdown of the signal metabolite 2-oxoglutaramate.

A construct for transforming plants includes an expression cassette encoding a suitable root-preferred promoter, a sequence encoding a plant ω-amidase, and a terminator sequence. In this example, the expression cassette contains the glycine-rich protein (GRP) promoter (Goddemeier et al., 1998, Plant Mol. Biol. 36(5): 799-802), the *Arabidopsis thaliana* ω-amidase coding sequence, and the NOS terminator. The GRP promoter sequence is shown below [SEQ ID NO: 16]:

```
GAAATTAAACCCAGGGTCGACAGCGCCCACTATAGAGAAAAATTG
AAATGTTTTGAGAATCGGATGATTTTTTTTAACTATTAGGTCTAGTTTG
AAAACCCTATTTTCTAACAAAGGGATTTTCATTTTTATAAGAGAAAAT
AAACTAACTTTTCTTGAGAAAATAAAATTCTTTGGAAAAATGGATTTC
TCAAACTAGCTCTTACGGCTAGTTTGGAAACCCCAATTTCACACGG
GATTCTCATTTTCCCAAGGGAAAAATGAACTAATTTCCCTTAGAAAA
ATGAGAATCCCGTGGGAAATTGGGATTTTCAAAGTAGCCCTTATAGT
GGAAATAAGTTATGGTGTCTCGCTCGTATGGTTATGTAGGGCCGCGC
GTGTATTCCAGCGCCGGCCGCATGGATACCCTATCGATTCTGACTT
CTCTGTCTCAGGAAAATAATACAGCCACGATTAACGGAACCTGCTG
GCTGGATCCATGATTACTCACTTGACTTCACATCGATCCAAATTATC
TAGCTTGCACGTTCATGGGTCGCCTCGCTCGCCCGATCGATATTAC
GTACACCATAGATTAGTACTATATGGAGTGGAGTGTTGAATGGATGC
TCTTTATTATTCTAGCCAAGTTATCAAGCCGGGCACTTGCATCGGAAG
GAGTACCAGTGTACGCATCAGATCAGACGATAATCGATCAAGATGG
GTACGAGATTTGCCGCTTGCTTCCTGTTCTTGATGGGCAATCTTTTC
GGGCCTTGAACGTCGGAGAATCGACTATACGAAATCCTAGGTCAAC
TATACATTGGTTGATGCTTCCGTGTAGTTTTACCAGTTCATCGGTCTC
TAGCTTGTTGTTTGCGACGACTTCACGTGGCCACGCGTTTACTGCGC
TCTGCTCAAAGAAATTGCCTACAGTGCCTGGCGTCAGCTGCAGGCG
TTGAATCCGAGGTCGCGCGCCGCAGAATAAGTACGAGTCAAAGGCT
GAGCTGCATGCCGTACCGGCCTTTATTAATAGCTGAGCTCTACTCGC
TACGTCAGTATAGTATAGCACGGTCATATATATACTATAGCTATAGCT
GTGGGGTACCGTGTCCGTATCGTGAATCTGAAGTCGAACAGTGATAT
GGCGTACTATCTAATAATGTCCCGTGCAGTAATATCACTGTTGCCGAC
GATGGGAATCTCTAGTTTTGACAGAAACCAAAGCAACTGCTAGCTAAT
TAATTCCAGAGAGATCGATTTCTACAGTGCTGCAACAATCAATGCAAT
TGGCATCAGACGATATATGCTAATGGTTTCTTTATCGATACGTGGTCAA
CAGAGCTCTCTCGCCCGCCCTGATCAGATCTCATCGCACATGGACAC
CCATCTGCCAACCCAACACGGGCGGGGAACCACCGTGAAACATCG
CGTTCATGCACGACCCCCCCGCAGGCCGCAGCTATAAATACCCATG
CAATGCAATGCAGCGGGTCATCATCGACTCCACCTGGACTCGCTCAC
TGGCAATGGCTACCACCAGC
```

Alternatively, an expression cassette containing the rolD promoter and the *Arabidopsis thaliana* ω-amidase coding sequence may be used. The sequence of this construct is shown below: (ATG start codon of the ω-amidase gene shown in bold) [SEQ ID NO: 17]:

```
GACGTCGGTACCGAATTTGTTCGTGAACTATTAGTTGCGGGCCTTGG
CATCCGACTACCTCTGCGGCAATATTATATTCCCTGGGCCCACCGT
GAACCCAATTTCGCCTATTTATTCATTACCCCCATTAACATTGAAGTA
GTCATGATGGGCCTGCAGCACGTTGGTGAGGCTGGCACAACTCATC
CATATACTTTCTGACCGGATCGGCACATTATTGTAGAAAACGCGGAC
CCACAGCGCACTTTCCAAAGCGGTGCCGCGTCAGAATGCGCTGGC
AGAAAAAAATTAATCCAAAAGTACCCTCCAAGCAGCCCATATAAAC
GCGTTTACAAATCCGCTAACCTCAACAATTTGAGCAGAGAAAATTCG
CACCTACAAGGCAGATGGCATCATCATTCAATCCAGAGCAGGCAAG
AGTTCCTTCAGCATTACCTTTACCAGCACCACCACTTACCAAATTCA
ACATCGGACTTTGTCAATTGAGTGTTACTTCTGATAAGAAAAGAAACA
TTTCACATGCTAAGAAAGCAATCGAAGAGGCTGCTAGTAAGGGAGC
TAAACTCGTTCTTTTGCCTGAAATATGGAACTCACCATACAGTAACG
ATTCTTTTCCTGTGTACGCAGAAGAGATCGATGCTGGAGGTGATGC
ATCTCCATCAACTGCTATGCTCTCAGAAGTTAGTAAGAGACTCAAGA
TTACAATTATCGGAGGTTCAATTCCTGAGAGAGTTGGAGATAGGTTG
TATAACACATGTTGCGTGTTCGGATCTGATGGAGAGCTCAAGGCTAA
GCATAGGAAGATTCACCTCTTCGATATAGATATTCCTGGAAAGATCA
CCTTCATGGAATCAAAAACACTTACCGCTGGAGAGACTCCAACAAT
TGTTGATACAGATGTGGGTAGAATCGGAATAGGTATATGTTAC
GATATCAGGTTCCAAGAATTGGCTATGATATATGCTGCAAGAGGAGC
```

-continued

```
ACATCTCTTATGCTACCCTGGAGCTTTCAATATGACTACAGGTCCATT

GCACTGGGAGCTTTTGCAAAGAGCTAGGGCAACAGATAACCAGCTC

TATGTTGCTACCTGCTCTCCTGCAAGAGATTCAGGAGCTGGTTACAC

CGCATGGGGTCATTCTACTCTTGTTGGACCATTTGGTGAAGTGTTGGC

TACCACTGAGCACGAAGAGGCTATTATAATCGCAGAAATCGATTACA

GTATACTTGAGCAGAGAAGGACTTCTCTCCCATTAAATAGGCAGAGG

AGGGGTGATTTATACCAGTTAGTTGATGTTCAGAGATTAGATAGTAAGT

GACACGTGTGAATTACAGGTGACCAGCTCGAATTTCCCCGATCGTTC

AAACATTTGGCAATAAAGTTTCTTAAGATTGAATCCTGTTGCCGGTCTT

GCGATGATTATCATATAATTTCTGTTGAATTACGTTAAGCATGTAATAA

TTAACATGTAATGCATGACGTTATTTATGAGATGGGTTTTTATGATTAG

AGTCCCGCAATTATACATTTAATACGCGATAGAAAACAAAATATAGCG

CGCAAACTAGGATAAATTATCGCGCGCGGTGTCATCTATGTTACTAGA

TCGGGGGTACCGACGTC
```

For transformation of plants, the expression cassette, above, is cloned into a suitable vector. For *Agrobacterium* mediated transformation, the above construct is cloned into the TF101.1 vector, which carries the spectinomycin resistance selectable marker gene.

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Example 3

Increased Growth of Transgenic Alfalfa Plants Carrying Root-Preferred Ω-Amidase Transgene In this example, alfalfa plant growth was increased by introducing an ω-amidase transgene under the control of a highly root-preferred promoter. The resulting transgenic alfalfa plants showed decreased 2-oxoglutaramate concentration in roots, increased leaf-to-root ratio of 2-oxoglutaramate, and enhanced growth relative to wild type alfalfa plants. Alfalfa plants (*Medicago sativa*, var *Ladak*) were transformed with the *Arabidopsis* ω-amidase coding sequence truncated to remove the chloroplast transit peptide, under the control of a truncated *Agrobacterium rhizogenes* RolD promoter within the expression vector pTF101.1.

Materials and Methods:

*Agrobacterium* Vectors:

The expression vector pTF101.1 was engineered to carry the ω-amidase transgene expression cassette of SEQ ID NO: 39 (RolD promoter+ω-amidase+NOS terminator) and was transferred to *Agrobacterium tumefaciens* strain LBA4404 cultures using a standard electroporation method (McCormac et al., 1998, Molecular Biotechnology 9:155-159). The truncated *Agrobacterium rhizogenes* RolD promoter utilized is the pD-02 isoform (RolD2) described in Leach and Aoyagi, 1991, Plant Sci. 79, 69-76. Leach and Aoyagi describe the RolD2 promoter as being a highly root-preferred promoter that drove high levels of expression in root tissue. Transformed *Agrobacterium* were selected on media containing 50 µg/ml of chloroamphenicol. Transformed *Agrobacterium* cells were grown in LB culture media containing 25 µg/ml of antibiotic for 36 hours. At the end of the 36 hr growth period cells were collected by centrifugation and cells from each transformation were resuspended in 100 ml LB broth without antibiotic.

The nucleotide sequence of the pTF101.1 vector+rolD-02promoter+*Arabidopsis* ω-amidase (codon optimized for *Arabidopsis*)+nos terminator (SEQ ID NO: 39) is set forth below. Underlined nucleotides=rolD-02 promoter, bold nucleotides=ω-amidase coding region, italicized nucleotides include the nos terminator region (and some Cambia vector sequence), and other nucleotides=pTF101.1 vector.

```
AGTACTTTAAAGTACTTTAAAGTACTTTAAAGTACTTTGATCCAACCCCT

CCGCTGCTATAGTGCAGTCGGCTTCTGACGTTCAGTGCAGCCGTCTTCT

GAAAACGACATGTCGCACAAGTCCTAAGTTACGCGACAGGCTGCCGCCC

TGCCCTTTTCCTGGCGTTTTCTTGTCGCGTGTTTTAGTCGCATAAAGTA

GAATACTTGCGACTAGAACCGGAGACATTACGCCATGAACAAGAGCGCC

GCCGCTGGCCTGCTGGGCTATGCCCGCGTCAGCACCGACGACCAGGACT

TGACCAACCAACGGGCCGAACTGCACGCGGCCGGCTGCACCAAGCTGTT

TTCCGAGAAGATCACCGGCACCAGGCGCGACCGCCCGGAGCTGGCCAGG

ATGCTTGACCACCTACGCCCTGGCGACGTTGTGACAGTGACCAGGCTAG

ACCGCCTGGCCCGCAGCACCCGCGACCTACTGGACATTGCCGAGCGCAT

CCAGGAGGCCGGCGCGGGCCTGCGTAGCCTGGCAGAGCCGTGGGCCGAC

ACCACCACGCCGGCCGGCCGCATGGTGTTGACCGTGTTCGCCGGCATTG

CCGAGTTCGAGCGTTCCCTAATCATCGACCGCACCCGGAGCGGGCGCGA

GGCCGCCAAGGCCCGAGGCGTGAAGTTTGGCCCCCGCCCTACCCTCACC

CCGGCACAGATCGCGCACGCCCGCGAGCTGATCGACCAGGAAGGCCGCA

CCGTGAAAGAGGCGGCTGCACTGCTTGGCGTGCATCGCTCGACCCTGTA

CCGCGCACTTGAGCGCAGCGAGGAAGTGACGCCCACCGAGGCCAGGCGG

CGCGGTGCCTTCCGTGAGGACGCATTGACCGAGGCCGACGCCCTGGCGG

CCGCCGAGAATGAACGCCAAGAGGAACAAGCATGAAACCGCACCAGGAC

GGCCAGGACGAACCGTTTTTCATTACCGAAGAGATCGAGGCGGAGATGA

TCGCGGCCGGGTACGTGTTCGAGCCGCCCGCGCACGTCTCAACCGTGCG

GCTGCATGAAATCCTGGCCGGTTTGTCTGATGCCAAGCTGGCGGCCTGG

CCGGCCAGCTTGGCCGCTGAAGAAACCGAGCGCCGCCGTCTAAAAAGGT

GATGTGTATTTGAGTAAAACAGCTTGCGTCATGCGGTCGCTGCGTATAT

GATGCGATGAGTAAATAAACAAATACGCAAGGGGAACGCATGAAGGTTA

TCGCTGTACTTAACCAGAAAGGCGGGTCAGGCAAGACGACCATCGCAAC
```

-continued

```
CCATCTAGCCCGCGCCCTGCAACTCGCCGGGGCCGATGTTCTGTTAGTC
GATTCCGATCCCCAGGGCAGTGCCCGCGATTGGGCGGCCGTGCGGGAAG
ATCAACCGCTAACCGTTGTCGGCATCGACCGCCCGACGATTGACCGCGA
CGTGAAGGCCATCGGCCGGCGCGACTTCGTAGTGATCGACGGAGCGCCC
CAGGCGGCGGACTTGGCTGTGTCCGCGATCAAGGCAGCCGACTTCGTGC
TGATTCCGGTGCAGCCAAGCCCTTACGACATATGGGCCACCGCCGACCT
GGTGGAGCTGGTTAAGCAGCGCATTGAGGTCACGGATGGAAGGCTACAA
GCGGCCTTTGTCGTGTCGCGGGCGATCAAAGGCACGCGCATCGGCGGTG
AGGTTGCCGAGGCGCTGGCCGGGTACGAGCTGCCCATTCTTGAGTCCCG
TATCACGCAGCGCGTGAGCTACCCAGGCACTGCCGCCGCCGGCACAACC
GTTCTTGAATCAGAACCCGAGGGCGACGCTGCCCGCGAGGTCCAGGCGC
TGGCCGCTGAAATTAAATCAAAACTCATTTGAGTTAATGAGGTAAAGAG
AAAATGAGCAAAAGCACAAACACGCTAAGTGCCGGCCGTCCGAGCGCAC
GCAGCAGCAAGGCTGCAACGTTGGCCAGCCTGGCAGACACGCCAGCCAT
GAAGCGGGTCAACTTTCAGTTGCCGGCGGAGGATCACACCAAGCTGAAG
ATGTACGCGGTACGCCAAGGCAAGACCATTACCGAGCTGCTATCTGAAT
ACATCGCGCAGCTACCAGAGTAAATGAGCAAATGAATAAATGAGTAGAT
GAATTTTAGCGGCTAAAGGAGGCGGCATGGAAAATCAAGAACAACCAGG
CACCGACGCCGTGGAATGCCCCATGTGTGGAGGAACGGGCGGTTGGCCA
GGCGTAAGCGGCTGGGTTGTCTGCCGGCCCTGCAATGGCACTGGAACCC
CCAAGCCCGAGGAATCGGCGTGACGGTCGCAAACCATCCGGCCCGGTAC
AAATCGGCGCGGCGCTGGGTGATGACCTGGTGGAGAAGTTGAAGGCCGC
GCAGGCCGCCCAGCGGCAACGCATCGAGGCAGAAGCACGCCCCGGTGAA
TCGTGGCAAGCGGCCGCTGATCGAATCCGCAAAGAATCCCGGCAACCGC
CGGCAGCCGGTGCGCCGTCGATTAGGAAGCCGCCCAAGGGCGACGAGCA
ACCAGATTTTTTCGTTCCGATGCTCTATGACGTGGGCACCCGCGATAGT
CGCAGCATCATGGACGTGGCCGTTTTCCGTCTGTCGAAGCGTGACCGAC
GAGCTGGCGAGGTGATCCGCTACGAGCTTCCAGACGGGCACGTAGAGGT
TTCCGCAGGGCCGGCCGGCATGGCCAGTGTGTGGGATTACGACCTGGTA
CTGATGGCGGTTTCCCATCTAACCGAATCCATGAACCGATACCGGGAAG
GGAAGGGAGACAAGCCCGGCCGCGTGTTCCGTCCACACGTTGCGGACGT
ACTCAAGTTCTGCCGGCGAGCCGATGGCGGAAAGCAGAAAGACGACCTG
GTAGAAACCTGCATTCGGTTAAACACCACGCACGTTGCCATGCAGCGTA
CGAAGAAGGCCAAGAACGGCCGCCTGGTGACGGTATCCGAGGGTGAAGC
CTTGATTAGCCGCTACAAGATCGTAAAGAGCGAAACCGGGCGGCCGGAG
TACATCGAGATCGAGCTAGCTGATTGGATGTACCGCGAGATCACAGAAG
GCAAGAACCCGGACGTGCTGACGGTTCACCCCGATTACTTTTTGATCGA
TCCCGGCATCGGCCGTTTTCTCTACCGCCTGGCACGCCGCGCCGCAGGC
AAGGCAGAAGCCAGATGGTTGTTCAAGACGATCTACGAACGCAGTGGCA
GCGCCGGAGAGTTCAAGAAGTTCTGTTTCACCGTGCGCAAGCTGATCGG
```

```
GTCAAATGACCTGCCGGAGTACGATTTGAAGGAGGAGGCGGGGCAGGCT
GGCCCGATCCTAGTCATGCGCTACCGCAACCTGATCGAGGGCGAAGCAT
CCGCCGGTTCCTAATGTACGGAGCAGATGCTAGGGCAAATTGCCCTAGC
AGGGGAAAAAGGTCGAAAAGGTCTCTTTCCTGTGGATAGCACGTACATT
GGGAACCCAAAGCCGTACATTGGGAACCGGAACCCGTACATTGGGAACC
CAAAGCCGTACATTGGGAACCGGTCACACATGTAAGTGACTGATATAAA
AGAGAAAAAGGCGATTTTTCCGCCTAAAACTCTTTAAAACTTATTAAA
ACTCTTAAAACCCGCCTGGCCTGTGCATAACTGTCTGGCCAGCGCACAG
CCGAAGAGCTGCAAAAAGCGCCTACCCTTCGGTCGCTGCGCTCCCTACG
CCCCGCCGCTTCGCGTCGGCCTATCGCGGCCGCTGGCCGCTCAAAAATG
GCTGGCCTACGGCCAGGCAATCTACCAGGGCGCGGACAAGCCGCGCCGT
CGCCACTCGACCGCCGGCGCCCACATCAAGGCACCCTGCCTCGCGCGTT
TCGGTGATGACGGTGAAAACCTCTGACACATGCAGCTCCCGGAGACGGT
CACAGCTTGTCTGTAAGCGGATGCCGGGAGCAGACAAGCCCGTCAGGGC
GCGTCAGCGGGTGTTGGCGGGTGTCGGGGCGCAGCCATGACCCAGTCAC
GTAGCGATAGCGGAGTGTATACTGGCTTAACTATGCGGCATCAGAGCAG
ATTGTACTGAGAGTGCACCATATGCGGTGTGAAATACCGCACAGATGCG
TAAGGAGAAAATACCGCATCAGGCGCTCTTCCGCTTCCTCGCTCACTGA
CTCGCTGCGCTCGGTCGTTCGGCTGCGGCGAGCGGTATCAGCTCACTCA
AAGGCGGTAATACGGTTATCCACAGAATCAGGGGATAACGCAGGAAAGA
ACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAA
AATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGAC
CCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCG
CTGCGCCTTATCCGGTAACTATCGTCTTGAGTCCAACCCGGTAAGACAC
GACTTATCGCCACTGGCAGCAGCCACTGGTAACAGGATTAGCAGAGCGA
GGTATGTAGGCGGTGCTACAGAGTTCTTGAAGTGGTGGCCTAACTACGG
CTACACTAGAAGGACAGTATTTGGTATCTGCGCTCTGCTGAAGCCAGTT
ACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCT
CAGTGGAACGAAAACTCACGTTAAGGGATTTTGGTCATGCATGATATAT
CTCCCAATTTGTGTAGGGCTTATTATGCACGCTTAAAAATAATAAAAGC
AGACTTGACCTGATAGTTTGGCTGTGAGCAATTATGTGCTTAGTGCATC
TAATCGCTTGAGTTAACGCCGGCGAAGCGGCGTCGGCTTGAACGAATTT
CTAGCTAGACATTATTTGCCGACTACCTTGGTGATCTCGCCTTTCACGT
AGTGGACAAATTCTTCCAACTGATCTGCGCGCGAGGCCAAGCGATCTTC
```

-continued

TTCTTGTCCAAGATAAGCCTGTCTAGCTTCAAGTATGACGGGCTGATAC
TGGGCCGGCAGGCGCTCCATTGCCCAGTCGGCAGCGACATCCTTCGGCG
CGATTTTGCCGGTTACTGCGCTGTACCAAATGCGGGACAACGTAAGCAC
TACATTTCGCTCATCGCCAGCCCAGTCGGGCGGCGAGTTCCATAGCGTT
AAGGTTTCATTTAGCGCCTCAAATAGATCCTGTTCAGGAACCGGATCAA
AGAGTTCCTCCGCCGCTGGACCTACCAAGGCAACGCTATGTTCTCTTGC
TTTTGTCAGCAAGATAGCCAGATCAATGTCGATCGTGGCTGGCTCGAAG
ATACCTGCAAGAATGTCATTGCGCTGCCATTCTCCAAATTGCAGTTCGC
GCTTAGCTGGATAACGCCACGGAATGATGTCGTCGTGCACAACAATGGT
GACTTCTACAGCGCGGAGAATCTCGCTCTCTCCAGGGGAAGCCGAAGTT
TCCAAAAGGTCGTTGATCAAAGCTCGCCGCGTTGTTTCATCAAGCCTTA
CGGTCACCGTAACCAGCAAATCAATATCACTGTGTGGCTTCAGGCCGCC
ATCCACTGCGGAGCCGTACAAATGTACGGCCAGCAACGTCGGTTCGAGA
TGGCGCTCGATGACGCCAACTACCTCTGATAGTTGAGTCGATACTTCGG
CGATCACCGCTTCCCCCATGATGTTTAACTTTGTTTTAGGGCGACTGCC
CTGCTGCGTAACATCGTTGCTGCTCCATAACATCAAACATCGACCCACG
GCGTAACGCGCTTGCTGCTTGGATGCCCGAGGCATAGACTGTACCCCAA
AAAAACATGTCATAACAAGAAGCCATGAAAACCGCCACTGCGCCGTTAC
CACCGCTGCGTTCGGTCAAGGTTCTGGACCAGTTGCGTGACGGCAGTTA
CGCTACTTGCATTACAGCTTACGAACCGAACGAGGCTTATGTCCACTGG
GTTCGTGCCCGAATTGATCACAGGCAGCAACGCTCTGTCATCGTTACAA
TCAACATGCTACCCTCCGCGAGATCATCCGTGTTTCAAACCCGGCAGCT
TAGTTGCCGTTCTTCCGAATAGCATCGGTAACATGAGCAAAGTCTGCCG
CCTTACAACGGCTCTCCCGCTGACGCCGTCCCGGACTGATGGGCTGCCT
GTATCGAGTGGTGATTTTGTGCCGAGCTGCCGGTCGGGGAGCTGTTGGC
TGGCTGGTGGCAGGATATATTGTGGTGTAAACAAATTGACGCTTAGACA
ACTTAATAACACATTGCGGACGTTTTTAATGTACTGAATTAACGCCGAA
TTGCTCTAGCATTCGCCATTCAGGCTGCGCAACTGTTGGGAAGGGCGAT
CGGTGCGGGCCTCTTCGCTATTACGCCAGCTGGCGAAAGGGGATGTGC
TGCAAGGCGATTAAGTTGGGTAACGCCAGGGTTTTCCCAGTCACGACGT
TGTAAAACGACGGCCAGTGCCAAGCTAATTCTTCAAGACGTGCTCAAAT
CACTATTTCCACACCCCTATATTTCTATTGCACTCCCTTTTAACTGTTT
TTTATTACAAAAATGCCCTGGAAAATGCACTCCCTTTTTGTGTTTGTTT
TTTTGTGAAACGATGTTGTCAGGTAATTTATTTGTCAGTCTACTATGGT
GGCCCATTATATTAATAGCAACTGTCGGTCCAATAGACGACGTCGATTT
TCTGCATTTGTTTAACCACGTGGATTTTATGACATTTTATATTAGTTAA
TTTGTAAAACCTACCCAATTAAAGACCTCATATGTTCTAAAGACTAATA
CTTAATGATAACAATTTTCTTTTAGTGAAGAAAGGGATAATTAGTAAAT
ATGGAACAAGGGCAGAAGATTTATTAAAGCCGCGTAAGAGACAACAAGT
AGGTACGTGGAGTGTCTTAGGTGACTTACCCACATAACATAAAGTGACA

-continued

TTAACAAACATAGCTAATGCTCCTATTTGAATAGTGCATATCAGCATAC
CTTATTACATATAGATAGGAGCAAACTCTAGCTAGATTGTTGAGAGCAG
ATCTCGGTGACGGGCAGGACCGGACGGGGCGGTACCGGCAGGCTGAAGT
CCAGCTGCCAGAAACCCACGTCATGCCAGTTCCCGTGCTTGAAGCCGGC
CGCCCGCAGCATGCCGCGGGGGGCATATCCGAGCGCCTCGTGCATGCGC
ACGCTCGGGTCGTTGGGCAGCCCGATGACAGCGACCACGCTCTTGAAGC
CCTGTGCCTCCAGGGACTTCAGCAGGTGGGTGTAGAGCGTGGAGCCCAG
TCCCGTCCGCTGGTGGCGGGGGGAGACGTACACGGTCGACTCGGCCGTC
CAGTCGTAGGCGTTGCGTGCCTTCCAGGGGCCCGCGTAGGCGATGCCGG
CGACCTCGCCGTCCACCTCGGCGACGAGCCAGGGATAGCGCTCCCGCAG
ACGGACGAGGTCGTCCGTCCACTCCTGCGGTTCCTGCGGCTCGGTACGG
AAGTTGACCGTGCTTGTCTCGATGTAGTGGTTGACGATGGTGCAGACCG
CCGGCATGTCCGCCTCGGTGGCACGGCGGATGTCGGCCGGGCGTCGTTC
TGGGCTCATGGTAGATCCCCCGTTCGTAAATGGTGAAAATTTTCAGAAA
ATTGCTTTTGCTTTAAAAGAAATGATTTAAATTGCTGCAATAGAAGTAG
AATGCTTGATTGCTTGAGATTCGTTTGTTTTGTATATGTTGTGTTGAGA
ATTAATTCTCGAGGTCCTCTCCAAATGAAATGAACTTCCTTATATAGAG
GAAGGGTCTTGCGAAGGATAGTGGGATTGTGCGTCATCCCTTACGTCAG
TGGAGATATCACATCAATCCACTTGCTTTGAAGACGTGGTTGGAACGTC
TTCTTTTTCCACGATGCTCCTCGTGGGTGGGGGTCCATCTTTGGGACCA
CTGTCGGTAGAGGCATCTTGAACGATAGCCTTTCCTTTATCGCAATGAT
GGCATTTGTAGGAGCCACCTTCCTTTTCCACTATCTTCACAATAAAGTG
ACAGATAGCTGGGCAATGGAATCCGAGGAGGTTTCCGGATATTACCCTT
TGTTGAAAAGTCTCAATTGCCCTTTGGTCTTCTGAGACTGTATCTTTGA
TATTTTTGGAGTAGACAAGTGTGTCGTGCTCCACCATGTTATCACATCA
ATCCACTTGCTTTGAAGACGTGGTTGGAACGTCTTCTTTTTCCACGATG
CTCCTCGTGGGTGGGGGTCCATCTTTGGGACCACTGTCGGCAGAGGCAT
CTTCAACGATGGCCTTTCCTTTATCGCAATGATGGCATTTGTAGGAGCC
ACCTTCCTTTTCCACTATCTTCACAATAAAGTGACAGATAGCTGGGCAA
TGGAATCCGAGGAGGTTTCCGGATATTACCCTTTGTTGAAAAGTCTCAA
TTGCCCTTTGGTCTTCTGAGACTGTATCTTTGATATTTTTGGAGTAGAC
AAGTGTGTCGTGCTCCACCATGTTGACCTGCAGGCATGCAAGCTTGCAT
GCCTGCAGGTCGACTCTAGAGGATCCCCGTCGGTACC<u>GAATTTGTTCGT</u>
<u>GAACTATTAGTTGCGGGCCTTGGCATCCGACTACCTCTGCGGCAATATT</u>
<u>ATATTCCCTGGGCCCACCGTGAACCCAATTTCGCCTATTTATTCATTAC</u>
<u>CCCCATTAACATTGAAGTAGTCATGATGGGCCTGCAGCACGTTGGTGAG</u>
<u>GCTGGCACAACTCATCCATATACTTTCTGACCGGATCGGCACATTATTG</u>
<u>TAGAAAACGCGGACCCACAGCGCACTTTCCAAAGCGGTGCCGCGTCAGA</u>
<u>ATGCGCTGGCAGAAAAAAATTAATCCAAAGTACCCTCCAAGCAGCCCA</u>
<u>TATAAACGCGTTTACAAATCCGCTAACCTCAACAATTTGAGCAGAGAAA</u>

-continued

ATTCGCACCTACAAGGCAGATGGCATCATCATTCAATCCAGAGCAGGCA

AGAGTTCCTTCAGCATTACCTTTACCAGCACCACCACTTACCAAATTCAA

CATCGGACTTTGTCAATTGAGTGTTACTTCTGATAAGAAAAGAAACATTT

CACATGCTAAGAAAGCAATCGAAGAGGCTGCTAGTAAGGGAGCTAAACTC

GTTCTTTTGCCTGAAATATGGAACTCACCATACAGTAACGATTCTTTTCC

TGTGTACGCAGAAGAGATCGATGCTGGAGGTGATGCATCTCCATCAACTG

CTATGCTCTCAGAAGTTAGTAAGAGACTCAAGATTACAATTATCGGAGGT

TCAATTCCTGAGAGAGTTGGAGATAGGTTGTATAACACATGTTGCGTGTT

CGGATCTGATGGAGAGCTCAAGGCTAAGCATAGGAAGATTCACCTCTTCG

ATATAGATATTCCTGGAAAGATCACCTTCATGGAATCAAAAACACTTACC

GCTGGAGAGACTCCAACAATTGTTGATACAGATGTGGGTAGAATCGGAAT

AGGTATATGTTACGATATCAGGTTCCAAGAATTGGCTATGATATATGCTG

CAAGAGGAGCACATCTCTTATGCTACCCTGGAGCTTTCAATATGACTACA

GGTCCATTGCACTGGGAGCTTTTGCAAAGAGCTAGGGCAACAGATAACCA

GCTCTATGTTGCTACCTGCTCTCCTGCAAGAGATTCAGGAGCTGGTTACA

CCGCATGGGGTCATTCTACTCTTGTTGGACCATTTGGTGAAGTGTTGGCT

ACCACTGAGCACGAAGAGGCTATTATAATCGCAGAAATCGATTACAGTAT

ACTTGAGCAGAGAAGGACTTCTCTCCCATTAAATAGGCAGAGGAGGGGTG

ATTTATACCAGTTAGTTGATGTTCAGAGATTAGATAGTAAGTGACACGTG

TGAATTACAGGTGACCAGCTCGAATTTCCCCGATCGTTCAAACATTTGGC

AATAAAGTTTCTTAAGATTGAATCCTGTTGCCGGTCTTGCGATGATTATC

ATATAATTTCTGTTGAATTACGTTAAGCATGTAATAATTAACATGTAATG

CATGACGTTATTTATGAGATGGGTTTTTATGATTAGAGTCCCGCAATTAT

ACATTTAATACGCGATAGAAAACAAAATATAGCGCGCAAACTAGGATAAA

TTATCGCGCGGTGTCATCTATGTTACTAGATCGGGGGTACCGACGGGT

ACCGAGCTCGAATTCGTAATCATGGTCATAGCTGTTTCCTGTGTGAAATT

GTTATCCGCTCACAATTCCACACAACATACGAGCCGGAAGCATAAAGTGT

AAAGCCTGGGGTGCCTAATGAGTGAGCTAACTCACATTAATTGCGTTGC

GCTCACTGCCCGCTTTCCAGTCGGGAAACCTGTCGTGCCAGCTGCATTA

ATGAATCGGCCAACGCGCGGGAGAGGCGGTTTGCGTATTGGAGCTTGA

GCTTGGATCAGATTGTCGTTTCCCGCCTTCAGTTTAAACTATCAGTGTT

TGACAGGATATATTGGCGGGTAAACCTAAGAGAAAAGAGCGTTTATTAG

AATAACGGATATTTAAAAGGGCGTGAAAAGGTTTATCCGTTCGTCCATT

TGTATGTGCATGCCAACCACAGGGTTCCCCTCGGGATCAA

Seedling Inoculations:

Alfalfa seedlings were grown to less than about ½ inch tall, and were then soaked in paper toweling that had been flooded with the *Agrobacteria* containing the TF101.1 vector carrying the ω-amidase transgene expression cassette. The seedlings were left in the paper toweling for two to three days, removed and then planted in potting soil. Resulting T0 and control plants were then grown for 27 days in a growth chamber, harvested and analyzed for biochemical and physical characteristics.

Biochemical Characterization:

HPLC Assay for 2-oxoglutaramate: HPLC was used to assay 2-oxoglutaramate, following a modification of Calderon et al., 1985, J Bacteriol 161(2): 807-809. Briefly, 2-oxoglutaramate was extracted from plant tissue in distilled de-ionized water acidified to less than pH 2.0 with HCl using a weight to volume ratio of 2:1. 2-Oxoglutaramate was detected and quantified by HPLC, using an ION-300 7.8 mm ID×30 cm L column, with a mobile phase in $0.01 NH_2SO_4$, a flow rate of approximately 0.2 ml/min, at 40° C. Injection volume is approximately 20 and retention time between about 38 and 39 minutes. Detection is achieved with 210 nm UV light. Authentic 2-oxoglutaramate was used to calibrate the assay.

HPLC Assays for GPT and GS Activities:

GPT was extracted from fresh plant tissue after grinding in cold 100 mM Tris-HCl, pH 7.6, containing 1 mm ethylenediaminetetraacetic, 200 mM pyridoxal phosphate and 6 mM mercaptoethanol in a ratio of 3 ml per gram of tissue. The extract was clarified by centrifugation and used in the assay. GS activity was extracted from fresh plant tissue after grinding in cold 50 mM Imidazole, pH 7.5 containing 10 mM MgCl2, and 12.5 mM mercaptoethanol in a ratio of 3 ml per gram of tissue. The extract was clarified by centrifugation and used in the assay. GPT activity was assayed as described in Calderon and Mora, 1985, Journal Bacteriology 161:807-809. GS activity was measured as described in Shapiro and Stadtmann, 1970, Methods in Enzymology 17A: 910-922. Both assays involve an incubation with substrates and cofactor at the proper pH. Detection was by HPLC.

HPLC Assay for Ω-Amidase Activity:

Ω-amidase activity was determined using the 96-well plate assay as described in Krasnikov et al., 2009, Analytical Biochemistry 391: 144-150.

Figure 4:
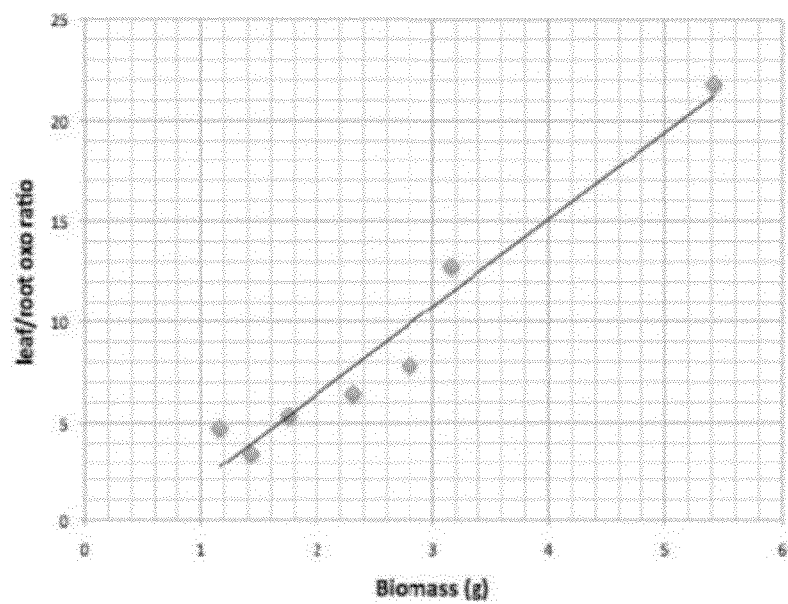
FIG. 4 graphically depicts a plot of plant fresh weight values plotted against 2-oxoglutaramate concentration.
Figure 5:
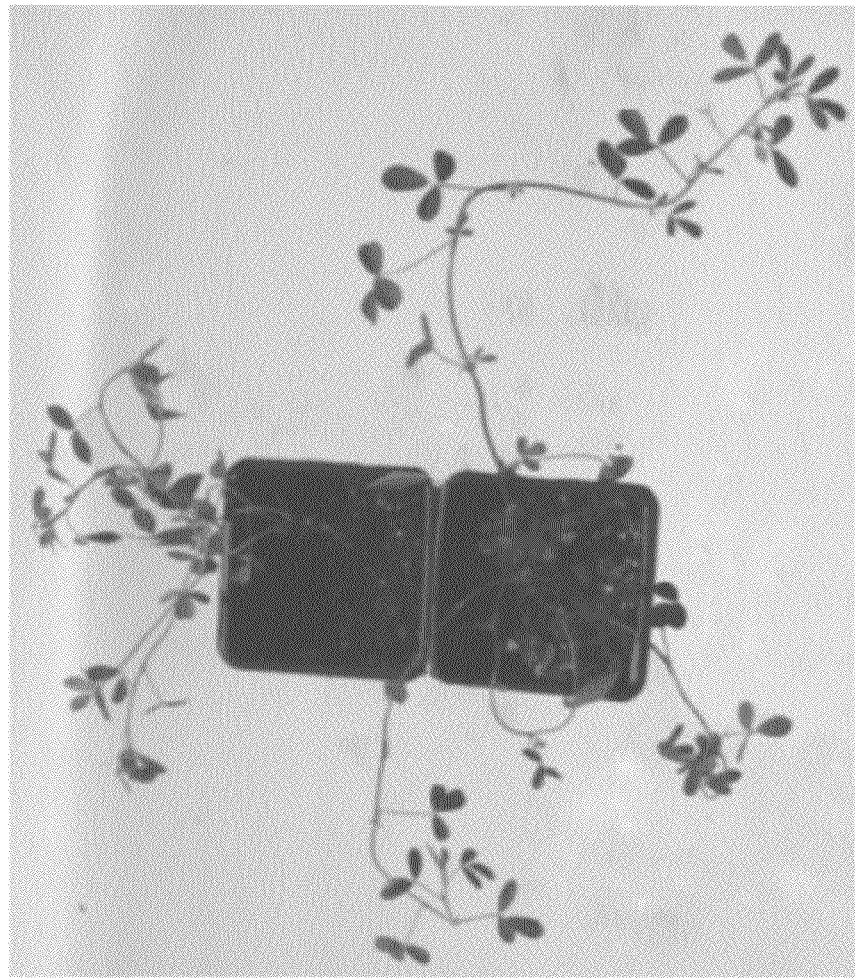
FIG. 5 depicts a photograph comparing ω-amidase transgenic and control alfalfa plants.

Results:

Plant fresh weight and leaf and root 2-oxoglutaramate concentrations and ratios in wild type and transgenic alfalfa plants were measured and are shown in Table 5 below. A comparison of the GS and GPT activities in the best performing transgenic alfalfa with a wild type control plant average values is shown in Table 6. Plant fresh weight values are plotted against 2-oxoglutaramate concentrations in FIG. 4. A photograph comparing transgenic and control alfalfa plants is shown in FIG. 5.

Transgenic alfalfa plants carrying the ω-amidase directed for root expression showed significantly reduced root 2-oxoglutaramate concentrations, presumably as a result of the added ω-amidase activity introduced by the transgene (Table 5). Activity levels for both GS and GPT remain constant in root tissues but are very significantly elevated in transgenic alfalfa (Table 6). The transgenic plants also showed faster growth, yielding substantially increased biomass (Table 5), which correlated in near-linear fashion with the level of reduced 2-oxoglutaramate in these plants (FIG. 4). The fastest growing transgenic alfalfa line exhibited a 274% increase in biomass relative to the average biomass of the controls. This line also showed the most reduction in 2-oxoglutaramate root concentration.

TABLE 5

| ALFALFA GENOTYPE | FRESH WEIGHT (g) | ROOT 2-OGM (nmol/g) | LEAF 2-OGM (nmol/g) | LEAF/ROOT 2-OGM |
|---|---|---|---|---|
| Control 1 | 1.43 | 259.7 | 910.7 | 3.5 |
| Control 2 | 1.75 | 286 | 1538.5 | 5.4 |

TABLE 5-continued

| ALFALFA GENOTYPE | FRESH WEIGHT (g) | ROOT 2-OGM (nmol/g) | LEAF 2-OGM (nmol/g) | LEAF/ROOT 2-OGM |
|---|---|---|---|---|
| Control 3 | 1.16 | 383.4 | 1826.6 | 4.8 |
| Transgene 4 | 2.31 | 332 | 2144.6 | 6.5 |
| Transgene 6 | 2.80 | 189 | 1479.4 | 7.8 |
| Transgene 13 | 3.16 | 241.2 | 3038.5 | 12.8 |
| Transgene 5 | 5.42 | 125.14 | 2729.9 | 21.8 |

TG = Transgenic

TABLE 6

| ALFALFA GENOTYPE | GS Activity micromoles/gfwt/min | | GPT Activity nmoles/gfw/hr | |
|---|---|---|---|---|
| | Leaf | Root | Leaf | Root |
| Control, avg | 4.3 | 3.3 | 339.1 | 66.3 |
| Transgene 5 | 15.9 | 3.5 | 951.6 | 63.6 |

Example 4

Increased Growth of Transgenic *Arabidopsis* Plants Carrying Root-Preferred Ω-Amidase Transgene In this example, *Arabidopsis* plant growth was increased by introducing an ω-amidase transgene under the control of a highly root-preferred promoter. The resulting transgenic *Arabidopsis* plants showed markedly decreased 2-oxoglutaramate concentration in roots, very significantly increased leaf-to-root ratios of 2-oxoglutaramate, highly elevated GS and GPT levels in leaf, greatly reduced ω-amidase levels in leaves, and astounding enhanced growth relative to wild type *Arabidopsis* plants.

Materials and Methods:

*Agrobacterium* Vectors:

The ω-amidase transgene expression vector and *Agrobacteria* preparation were generated as described in Example 3, supra.

Transformation:

Transformation of *Arabidopsis* was achieved using *Agrobacterium*-mediated "floral dip" transfer as described (Harrison et al., 2006, Plant Methods 2:19-23; Clough and Bent, 1998, Plant J. 16:735-743). *Agrobacteria* transformed with the TF101.1 vector carrying the ω-amidase transgene expression cassette were grown under antibiotic selection, collected by centrifugation resuspended in LB broth with antibiotic and used to floral dip *Arabidopsis* inflorescence. Floral dipped *Arabidopsis* plants were taken to maturity and self-fertilized and seeds were collected.

Germination and Selection:

Seeds from plants transformed with the TF101.1 vector carrying the ω-amidase transgene expression cassette were germinated on a media containing 15 mg/L of BASTA or an equivalent amount of phosphinothricin. For the additional constructs and combinations described in Examples 5-7: Seeds derived from plants transformed with glutamine synthetase construct were germinated on a media contain 20 micrograms hygromycin and regular selection procedures were followed to obtain the surviving seedlings. Seeds derived from plants transformed with glutamine phenylpyruvate transaminase were geminated on a media containing 20 ug/ml of kanamycin and regular selection procedures were followed to obtain the surviving seedlings. For seedlings containing more than one of these genes the seedlings were transferred to media containing the next selection chemical and surviving seedlings were obtained. The surviving seedlings were examined.

Biochemical Characterization:

Assays for 2-oxoglutaramate, ω-amidase, GS and GPT were conducted as described in Example 3, supra.

Results:

GPT activity and GS activity of wild type and transgenic *Arabidopsis* plants were measured and are shown in Table 7, below. Ω-amidase activities and 2-oxoglutaramate concentrations in wild type and transgenic *Arabidopsis* plants were measured in both leaf and root tissues, and are shown in Table 8, below.

TABLE 7

| Arabidopsis Genotype | FWt mg Whole plant | GS Activity umoles/gfwt/min | | | GPT Activity nmoles/gfwt/hr | | |
|---|---|---|---|---|---|---|---|
| | | Root | Leaf | L/R | Root | Leaf | L/R |
| Wild type* | 77 | 1.5 | 3.4 | 2.3 | 167 | 132 | 0.8 |
| TG Amidase** | 479 | 1.4 | 5.8 | 4.1 | 192 | 486 | 2.5 |

TG = Transgenic
*Average values of 9 plants
**Average values of 6 plants

TABLE 8

| Arabidopsis Genotype | FWt mg Whole plant | Ω-amidase nmoles/gfwt/hr | | | 2-Oxoglutaramate Concentration nmoles/gfwt | | |
|---|---|---|---|---|---|---|---|
| | | Root | Leaf | Ratio L/R | Root | Leaf | L/R Ratio |
| Wild type* | 77 | 86 | 1090 | 12.7 | 410 | 163 | 0.4 |
| TG ω-amidase** | 479 | 243 | 127 | 0.5 | 98 | 305 | 3.1 |

TG = Transgenic
*Average values of 9 plants
**Average values of 6 plants

Compared to wild type control *Arabidopsis* plants, the transgenic *Arabidopsis* plants carrying the ω-amidase directed for root expression showed dramatic biochemical changes within the ω-amidase pathway, including increased root ω-amidase activity (186% increase), reduced levels of root 2-oxoglutaramate (76% reduction) and increased leaf-to-root 2-oxoglutaramate ratios. Moreover, these transgenic plants also show great reductions in leaf ω-amidase activity levels (88% reduction), a near-doubling of leaf 2-oxoglutaramate levels, and higher leaf GS and leaf GPT activities (70% and 533%, respectively). The resulting impact on growth was astounding, with the transgenic plants weighing more than six times the weight of the wild type plants, on average.

Example 5

Increased Growth of Transgenic *Arabidopsis* Plants Carrying Root-Preferred Ω-Amidase Transgene and Leaf-Directed GPT In this example, *Arabidopsis* plant growth was increased by introducing an ω-amidase transgene under the control of a highly root-preferred promoter and a GPT transgene under the control of a leaf-directing promoter. The resulting transgenic *Arabidopsis* plants show astounding increases in growth, as well as various biochemical changes, relative to wild type *Arabidopsis* plants.

Materials and Methods:

*Agrobacterium* Vectors:

The ω-amidase transgene expression vector and *Agrobacterium* preparation were generated as described in Example 3, supra. For the leaf-directed GPT transgene, an expression cassette comprising the tomato rubisco small subunit promoter and an *Arabidopsis* codon-optimized GPT truncated to delete the first 45 codons of the full length GPT (eliminating the chloroplast transit peptide) was constructed and cloned into the Cambia 2201 expression vector. The resulting GPT transgene expression vector construct (6c) is shown below, and was used to transform *Agrobacteria* as described in Example 3.

The nucleotide sequence of the Cambia 2201 with tomato rubisco SSU promoter+(−45) truncated, optimized for *Arabidopsis* GPT+nos terminator is set forth below as SEQ ID NO: 40. Underlined nucleotides=tomato rubisco promoter, bold nucleotides=GPT coding region (codon optimized for *Arabidopsis*), italicized nucleotides=nos terminator region (and some Cambia vector sequence), and other nucleotides=Cambia 2201 vector and additional cloning sites.

```
CCCGCGCGTTGGCCGATTCATTAATGCAGCTGGCACGACAGGTTTCCCGA
CTGGAAAGCGGGCAGTGAGCGCAACGCAATTAATGTGAGTTAGCTCACT
CATTAGGCACCCCAGGCTTTACACTTTATGCTTCCGGCTCGTATGTTGT
GTGGAATTGTGAGCGGATAACAATTTCACACAGGAAACAGCTATGACCA
TGATTACGAATTCGAGCTCGGTACCCGGGGATCCTCTAGATCTAGAGAAT
TCATCGATGTTTGAATCCTCCTTAAAGTTTTTCTCTGGAGAAACTGTAGT
AATTTTACTTTGTTGTGTTCCCTTCATCTTTTGAATTAATGGCATTTGTT
TTAATACTAATCTGCTTCTGAAACTTGTAATGTATGTATATCAGTTTCTT
ATAATTTATCCAAGTAATATCTTCCATTCTCTATGCAATTGCCTGCATAA
GCTCGACAAAAGAGTACATCAACCCCTCCTCCTCTGGACTACTCTAGCTA
AACTTGAATTTCCCCTTAAGATTATGAAATTGATATATCCTTAACAAACG
ACTCCTTCTGTTGGAAAATGTAGTACTTGTCTTTCTTCTTTTGGGTATAT
ATAGTTTATATACACCATACTATGTACAACATCCAAGTAGAGTGAAATGG
ATACATGTACAAGACTTATTTGATTGATTGATGACTTGAGTTGCCTTAGG
AGTAACAAATTCTTAGGTCAATAAATCGTTGATTTGAAATTAATCTCTCT
GTCTTAGACAGATAGGAATTATGACTTCCAATGGTCCAGAAAGCAAAGTT
CGCACTGAGGGTATACTTGGAATTGAGACTTGCACAGGTCCAGAAACCAA
AGTTCCCATCGAGCTCTAAAATCACATCTTTGGAATGAAATTCAATTAGA
GATAAGTTGCTTCATAGCATAGGTAAAATGGAAGATGTGAAGTAACCTGC
AATAATCAGTGAAATGACATTAATACACTAAATACTTCATATGTAATTAT
CCTTTCCAGGTTAACAATACTCTATAAAGTAAGAATTATCAGAAATGGGC
TCATCAAACTTTTGTACTATGTATTTCATATAAGGAAGTATAACTATACA
TAAGTGTATACACAACTTTATTCCTATTTTGTAAAGGTGGAGAGACTGTT
TTCGATGGATCTAAAGCAATATGTCTATAAAATGCATTGATATAATAATT
ATCTGAGAAAATCCAGAATTGGCGTTGGATTATTTCAGCCAAATAGAAGT
TTGTACCATACTTGTTGATTCCTTCTAAGTTAAGGTGAAGTATCATTCAT
AAACAGTTTTCCCCAAAGTACTACTCACCAAGTTTCCCTTTGTAGAATTA
ACAGTTCAAATATATGGCGCAGAAATTACTCTATGCCCAAAACCAAACGA
GAAAGAAACAAAATACAGGGGTTGCAGACTTTATTTTCGTGTTAGGGTGT
GTTTTTTCATGTAATTAATCAAAAAATATTATGACAAAAACATTTATACA
TATTTTTACTCAACACTCTGGGTATCAGGGTGGGTTGTGTTCGACAATCA
ATATGGAAAGGAAGTATTTTCCTTATTTTTTAGTTAATATTTTCAGTTA
TACCAAACATACCTTGTGATATTATTTTTAAAAATGAAAAACTCGTCAGA
AGAAAAAGCAAAAGCAACAAAAAAATTGCAAGTATTTTTTAAAAAAGAA
AAAAAAAACATATCTTGTTTGTCAGTATGGGAAGTTTGAGATAAGGACGA
GTGAGGGGTTAAAATTCAGTGGCCATTGATTTTGTAATGCCAAGAACCAC
AAAATCCAATGGTTACCATTCCTGTAAGATGAGGTTTGCTAACTCTTTTT
GTCCGTTAGATAGGAAGCCTTATCACTATATATACAAGGCGTCCTAATAA
CCTCTTAGTAACCAATTATTTCAGCAACTAGTATGGCGACTCAAAATGAG
TCAACACAAAAGCCTGTTCAGGTGGCTAAGAGACTTGAGAAGTTTAAAAC
TACAATTTTCACTCAAATGTCTATCCTCGCAGTTAAGCACGGAGCTATTA
ATCTTGGACAGGGTTTTCCTAACTTCGATGGTCCAGATTTCGTGAAAGAA
GCTGCAATTCAAGCAATCAAGGATGGAAAAAATCAGTATGCTAGAGGATA
CGGTATTCCTCAGTTGAACTCTGCTATCGCTGCAAGATTCAGAGAAGATA
CAGGACTTGTTGTGGATCCAGAAAAAGAGGTTACTGTGACATCAGGTTGT
ACTGAGGCTATTGCTGCAGCTATGCTCGGACTTATTAACCCTGGAGATGA
AGTTATCCTTTTTGCACCATTCTATGATTCTTACGAGGCTACATTGTCAA
TGGCAGGAGCTAAGGTGAAAGGTATTACTCTCAGACCTCCAGATTTCTCT
ATCCCTTTGGAAGAGCTCAAGGCAGCTGTTACTAATAAGACAAGAGCTAT
CTTGATGAATACTCCTCATAACCCAACAGGAAAGATGTTTACTAGAGAAG
AGCTCGAAACTATTGCTTCTCTTTGCATCGAGAACGATGTTTTGGTGTTC
TCAGATGAAGTGTATGATAAACTCGCATTTGAGATGGATCACATTTCTAT
CGCTTCACTTCCAGGAATGTACGAAAGAACTGTTACTATGAATTCTTTGG
GAAAGACTTTTTCTCTCACAGGATGGAAAATTGGTTGGGCAATCGCTCCT
CCACATCTCACATGGGTGTTAGACAAGCACACTCTTATCTTACTTTCGC
AACTTCAACACCTGCTCAGTGGGCAGCTGTGGCAGCTCTTAAGGCTCCAG
AATCTTACTTCAAGGAGTTGAAGAGAGATTACAACGTTAAGAAAGAAACA
CTTGTGAAGGGATTGAAAGAGGTTGGTTTTACAGTGTTCCCTTCTTCAGG
AACTTACTTTGTTGTGGCAGATCATACTCCATTCGGTATGGAAAACGATG
TTGCTTTTTGTGAGTATCTTATTGAAGAGGTTGGAGTTGTGGCTATCCCT
ACATCTGTGTTTTACCTTAATCCAGAAGAGGGAAAGAATCTTGTTAGATT
TGCATTCTGCAAAGATGAAGAGACTTTGAGAGGTGCTATTGAGAGGATGA
AGCAAAAACTCAAGAGAAAAGTTTGACACGTGTGAATTACAGGTGACCAG
```
*CTCGAATTTCCCCGATCGTTCAAACATTTGGCAATAAAGTTTCTTAAGAT*

*TGAATCCTGTTGCCGGTCTTGCGATGATTATCATATAATTTCTGTTGAAT*

*TACGTTAAGCATGTAATAATTAACATGTAATGCATGACGTTATTTATGAG*

*ATGGGTTTTTATGATTAGAGTCCCGCAATTATACATTTAATACGCGATAG*

```
AAAACAAAATATAGCGCGCAAACTAGGATAAATTATCGCGCGCGGTGTCA
TCTATGTTACTAGATCGGGAATTAAACTATCAGTGTTTGACAGGATATAT
TGGCGGGTAAACCTAAGAGAAAAGAGCGTTTATTAGAATAACGGATATT
TAAAAGGGCGTGAAAAGGTTTATCCGTTCGTCCATTTGTATGTGCATGC
CAACCACAGGGTTCCCCTCGGGATCAAAGTACTTTGATCCAACCCCTCC
GCTGCTATAGTGCAGTCGGCTTCTGACGTTCAGTGCAGCCGTCTTCTGA
AAACGACATGTCGCACAAGTCCTAAGTTACGCGACAGGCTGCCGCCCTG
CCCTTTTCCTGGCGTTTTCTTGTCGCGTGTTTTAGTCGCATAAAGTAGA
ATACTTGCGACTAGAACCGGAGACATTACGCCATGAACAAGAGCGCCGC
CGCTGGCCTGCTGGGCTATGCCCGCGTCAGCACCGACGACCAGGACTTG
ACCAACCAACGGGCCGAACTGCACGCGGCCGGCTGCACCAAGCTGTTTT
CCGAGAAGATCACCGGCACCAGGCGCGACCGCCCGGAGCTGGCCAGGAT
GCTTGACCACCTACGCCCTGGCGACGTTGTGACAGTGACCAGGCTAGAC
CGCCTGGCCCGCAGCACCCGCGACCTACTGGACATTGCCGAGCGCATCC
AGGAGGCCGGCGCGGGCCTGCGTAGCCTGGCAGAGCCGTGGGCCGACAC
CACCACGCCGGCCGGCCGCATGGTGTTGACCGTGTTCGCCGGCATTGCC
GAGTTCGAGCGTTCCCTAATCATCGACCGCACCCGGAGCGGGCGCGAGG
CCGCCAAGGCCCGAGGCGTGAAGTTTGGCCCCCGCCCTACCCTCACCCC
GGCACAGATCGCGCACGCCCGCGAGCTGATCGACCAGGAAGGCCGCACC
GTGAAAGAGGCGGCTGCACTGCTTGGCGTGCATCGCTCGACCCTGTACC
GCGCACTTGAGCGCAGCGAGGAAGTGACGCCCACCGAGGCCAGGCGGCG
CGGTGCCTTCCGTGAGGACGCATTGACCGAGGCCGACGCCCTGGCGGCC
GCCGAGAATGAACGCCAAGAGGAACAAGCATGAAACCGCACCAGGACGG
CCAGGACGAACCGTTTTTCATTACCGAAGAGATCGAGGCGGAGATGATC
GCGGCCGGGTACGTGTTCGAGCCGCCCGCGCACGTCTCAACCGTGCGGC
TGCATGAAATCCTGGCCGGTTTGTCTGATGCCAAGCTGGCGGCCTGGCC
GGCCAGCTTGGCCGCTGAAGAAACCGAGCGCCGCCGTCTAAAAAGGTGA
TGTGTATTTGAGTAAAACAGCTTGCGTCATGCGGTCGCTGCGTATATGA
TGCGATGAGTAAATAAACAAATACGCAAGGGGAACGCATGAAGGTTATC
GCTGTACTTAACCAGAAAGGCGGGTCAGGCAAGACGACCATCGCAACCC
ATCTAGCCCGCGCCCTGCAACTCGCCGGGGCCGATGTTCTGTTAGTCGA
TTCCGATCCCCAGGGCAGTGCCCGCGATTGGCGGCCGTGCGGGAAGAT
CAACCGCTAACCGTTGTCGGCATCGACCGCCCGACGATTGACCGCGACG
TGAAGGCCATCGGCCGGCGCGACTTCGTAGTGATCGACGGAGCGCCCA
GGCGGCGGACTTGGCTGTGTCCGCGATCAAGGCAGCCGACTTCGTGCTG
ATTCCGGTGCAGCCAAGCCCTTACGACATATGGGCCACCGCCGACCTGG
TGGAGCTGGTTAAGCAGCGCATTGAGGTCACGGATGGAAGGCTACAAGC
GGCCTTTGTCGTGTCGCGGGCGATCAAAGGCACGCGCATCGGCGGTGAG
GTTGCCGAGGCGCTGGCCGGGTACGAGCTGCCCATTCTTGAGTCCCGTA
TCACGCAGCGCGTGAGCTACCCAGGCACTGCCGCCGCCGGCACAACCGT
```
```
TCTTGAATCAGAACCCGAGGGCGACGCTGCCCGCGAGGTCCAGGCGCTG
GCCGCTGAAATTAAATCAAAACTCATTTGAGTTAATGAGGTAAAGAGAA
AATGAGCAAAAGCACAAACACGCTAAGTGCCGGCCGTCCGAGCGCACGC
AGCAGCAAGGCTGCAACGTTGGCCAGCCTGGCAGACACGCCAGCCATGA
AGCGGGTCAACTTTCAGTTGCCGGCGGAGGATCACACCAAGCTGAAGAT
GTACGCGGTACGCCAAGGCAAGACCATTACCGAGCTGCTATCTGAATAC
ATCGCGCAGCTACCAGAGTAAATGAGCAAATGAATAAATGAGTAGATGA
ATTTTAGCGGCTAAAGGAGGCGGCATGGAAAATCAAGAACAACCAGGCA
CCGACGCCGTGGAATGCCCCATGTGTGGAGGAACGGGCGGTTGGCCAGG
CGTAAGCGGCTGGGTTGTCTGCCGGCCCTGCAATGGCACTGGAACCCCC
AAGCCCGAGGAATCGGCGTGACGGTCGCAAACCATCCGGCCCGGTACAA
ATCGGCGCGGCGCTGGGTGATGACCTGGTGGAGAAGTTGAAGGCCGCGC
AGGCCGCCCAGCGGCAACGCATCGAGGCAGAAGCACGCCCCGGTGAATC
GTGGCAAGCGGCCGCTGATCGAATCCGCAAAGAATCCCGGCAACCGCCG
GCAGCCGGTGCGCCGTCGATTAGGAAGCCGCCCAAGGGCGACGAGCAAC
CAGATTTTTTCGTTCCGATGCTCTATGACGTGGGCACCCGCGATAGTCG
CAGCATCATGGACGTGGCCGTTTTCCGTCTGTCGAAGCGTGACCGACGA
GCTGGCGAGGTGATCCGCTACGAGCTTCCAGACGGGCACGTAGAGGTTT
CCGCAGGGCCGGCCGGCATGGCCAGTGTGTGGGATTACGACCTGGTACT
GATGGCGGTTTCCCATCTAACCGAATCCATGAACCGATACCGGGAAGGG
AAGGGAGACAAGCCCGGCCGCGTGTTCCGTCCACACGTTGCGGACGTAC
TCAAGTTCTGCCGGCGAGCCGATGGCGGAAAGCAGAAAGACGACCTGGT
AGAAACCTGCATTCGGTTAAACACCACGCACGTTGCCATGCAGCGTACG
AAGAAGGCCAAGAACGGCCGCCTGGTGACGGTATCCGAGGGTGAAGCCT
TGATTAGCCGCTACAAGATCGTAAAGAGCGAAACCGGGCGGCCGGAGTA
CATCGAGATCGAGCTAGCTGATTGGATGTACCGCGAGATCACAGAAGGC
AAGAACCCGGACGTGCTGACGGTTCACCCCGATTACTTTTTGATCGATC
CCGGCATCGGCCGTTTTCTCTACCGCCTGGCACGCCGCGCCGCAGGCAA
GGCAGAAGCCAGATGGTTGTTCAAGACGATCTACGAACGCAGTGGCAGC
GCCGGAGAGTTCAAGAAGTTCTGTTTCACCGTGCGCAAGCTGATCGGGT
CAAATGACCTGCCGGAGTACGATTTGAAGGAGGAGGCGGGGCAGGCTGG
CCCGATCCTAGTCATGCGCTACCGCAACCTGATCGAGGGCGAAGCATCC
GCCGGTTCCTAATGTACGGAGCAGATGCTAGGGCAAATTGCCCTAGCAG
GGGAAAAAGGTCGAAAAGGTCTCTTTCCTGTGGATAGCACGTACATTGG
GAACCCAAAGCCGTACATTGGGAACCGGAACCCGTACATTGGGAACCCA
AAGCCGTACATTGGGAACCGGTCACACATGTAAGTGACTGATATAAAAG
AGAAAAAGGCGATTTTTCCGCCTAAAACTCTTTAAAACTTATTAAAAC
TCTTAAAACCCGCCTGGCCTGTGCATAACTGTCTGGCCAGCGCACAGCC
GAAGAGCTGCAAAAAGCGCCTACCCTTCGGTCGCTGCGCTCCCTACGCC
CCGCCGCTTCGCGTCGGCCTATCGCGGCCGCTGGCCGCTCAAAAATGGC
```

-continued

TGGCCTACGGCCAGGCAATCTACCAGGGCGCGGACAAGCCGCGCCGTCG
CCACTCGACCGCCGGCGCCCACATCAAGGCACCCTGCCTCGCGCGTTTC
GGTGATGACGGTGAAAACCTCTGACACATGCAGCTCCCGGAGACGGTCA
CAGCTTGTCTGTAAGCGGATGCCGGGAGCAGACAAGCCCGTCAGGGCGC
GTCAGCGGGTGTTGGCGGGTGTCGGGGCGCAGCCATGACCCAGTCACGT
AGCGATAGCGGAGTGTATACTGGCTTAACTATGCGGCATCAGAGCAGAT
TGTACTGAGAGTGCACCATATGCGGTGTGAAATACCGCACAGATGCGTA
AGGAGAAAATACCGCATCAGGCGCTCTTCCGCTTCCTCGCTCACTGACT
CGCTGCGCTCGGTCGTTCGGCTGCGGCGAGCGGTATCAGCTCACTCAAA
GGCGGTAATACGGTTATCCACAGAATCAGGGGATAACGCAGGAAAGAAC
ATGTGAGCAAAAGGCCAGCAAAAGGCCAGGAACCGTAAAAAGGCCGCGT
TGCTGGCGTTTTTCCATAGGCTCCGCCCCCCTGACGAGCATCACAAAAA
TCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCT
GCGCCTTATCCGGTAACTATCGTCTTGAGTCCAACCCGGTAAGACACGA
CTTATCGCCACTGGCAGCAGCCACTGGTAACAGGATTAGCAGAGCGAGG
TATGTAGGCGGTGCTACAGAGTTCTTGAAGTGGTGGCCTAACTACGGCT
ACACTAGAAGGACAGTATTTGGTATCTGCGCTCTGCTGAAGCCAGTTAC
CTTCGGAAAAGAGTTGGTAGCTCTTGATCCGGCAAACAAACCACCGCT
GGTAGCGGTGGTTTTTTGTTTGCAAGCAGCAGATTACGCGCAGAAAAA
AAGGATCTCAAGAAGATCCTTTGATCTTTTCTACGGGGTCTGACGCTCA
GTGGAACGAAAACTCACGTTAAGGGATTTTGGTCATGCATGATATATCT
CCCAATTTGTGTAGGGCTTATTATGCACGCTTAAAAATAATAAAAGCAG
ACTTGACCTGATAGTTTGGCTGTGAGCAATTATGTGCTTAGTGCATCTA
ATCGCTTGAGTTAACGCCGGCGAAGCGGCGTCGGCTTGAACGAATTTCTA
GCTAGAGGATCGCACCAATAACTGCCTTAAAAAAATTACGCCCCGCCCT
GCCACTCATCGCAGTACTGTTGTAATTCATTAAGCATTCTGCCGACATG
GAAGCCATCACAAACGGCATGATGAACCTGAATCGCCAGCGGCATCAGC
ACCTTGTCGCCTTGCGTATAATATTTGCCCATTGTGAAAACGGGGGCGA
AGAAGTTGTCCATATTGGCCACGTTTAAATCAAAACTGGTGAAACTCAC
CCAGGGATTGGCTGAGACGAAAAACATATTCTCAATAAACCCTTTAGGG
AAATAGGCCAGGTTTTCACCGTAACACGCCACATCTTGCGAATATATGT
GTAGAAACTGCCGGAAATCGTCGTGGTATTCACTCCAGAGCGATGAAAA
CGTTTCAGTTTGCTCATGGAAAACGGTGTAACAAGGGTGAACACTATCC
CATATCACCAGCTCACCGTCTTTCATTGCCATACGGAACTCCGGATGAG
CATTCATCAGGCGGGCAAGAATGTGAATAAAGGCCGGATAAAACTTGTG
CTTATTTTTCTTTACGGTCTTTAAAAAGGCCGTAATATCCAGCTGAACG

GTCTGGTTATAGGTACATTGAGCAACTGACTGAAATGCCTCAAAATGTT
CTTTACGATGCCATTGGGATATATCAACGGTGGTATATCCAGTGATTTT
TTTCTCCATGATGTTTAACTTTGTTTTAGGGCGACTGCCCTGCTGCGTA
ACATCGTTGCTGCTCCATAACATCAAACATCGACCCACGGCGTAACGCG
CTTGCTGCTTGGATGCCCGAGGCATAGACTGTACCCCAAAAAAACATGT
CATAACAAGAAGCCATGAAAACCGCCACTGCGCCGTTACCACCGCTGCG
TTCGGTCAAGGTTCTGGACCAGTTGCGTGACGGCAGTTACGCTACTTGC
ATTACAGCTTACGAACCGAACGAGGCTTATGTCCACTGGGTTCGTGCCC
GAATTGATCACAGGCAGCAACGCTCTGTCATCGTTACAATCAACATGCT
ACCCTCCGCGAGATCATCCGTGTTTCAAACCCGGCAGCTTAGTTGCCGT
TCTTCCGAATAGCATCGGTAACATGAGCAAAGTCTGCCGCCTTACAACG
GCTCTCCCGCTGACGCCGTCCCGGACTGATGGGCTGCCTGTATCGAGTG
GTGATTTTGTGCCGAGCTGCCGGTCGGGGAGCTGTTGGCTGGCTGGTGG
CAGGATATATTGTGGTGTAAACAAATTGACGCTTAGACAACTTAATAAC
ACATTGCGGACGTTTTTAATGTACTGAATTAACGCCGAATTAATTCGGG
GGATCTGGATTTTAGTACTGGATTTTGGTTTTAGGAATTAGAAATTTTA
TTGATAGAAGTATTTTACAAATACAAATACATACTAAGGGTTTCTTATA
TGCTCAACACATGAGCGAAACCCTATAGGAACCCTAATTCCCTTATCTG
GGAACTACTCACACATTATTATGGAGAAACTCGAGCTTGTCGATCGACT
CTAGCTAGAGGATCGATCCGAACCCCAGAGTCCCGCTCAGAAGAACTCG
TCAAGAAGGCGATAGAAGGCGATGCGCTGCGAATCGGGAGCGGCGATAC
CGTAAAGCACGAGGAAGCGGTCAGCCCATTCGCCGCCAAGCTCTTCAGC
AATATCACGGGTAGCCAACGCTATGTCCTGATAGCGGTCCGCCACACCC
AGCCGGCCACAGTCGATGAATCCAGAAAAGCGGCCATTTTCCACCATGA
TATTCGGCAAGCAGGCATCGCCATGTGTCACGACGAGATCCTCGCCGTC
GGGCATGCGCGCCTTGAGCCTGGCGAACAGTTCGGCTGGCGCGAGCCCC
TGATGCTCTTCGTCCAGATCATCCTGATCGACAAGACCGGCTTCCATCC
GAGTACGTGCTCGCTCGATGCGATGTTTCGCTTGGTGGTCGAATGGGCA
GGTAGCCGGATCAAGCGTATGCAGCCGCCGCATTGCATCAGCCATGATG
GATACTTTCTCGGCAGGAGCAAGGTGAGATGACAGGAGATCCTGCCCCG
GCACTTCGCCCAATAGCAGCCAGTCCCTTCCCGCTTCAGTGACAACGTC
GAGCACAGCTGCGCAAGGAACGCCCGTCGTGGCCAGCCACGATAGCCGC
GCTGCCTCGTCCTGGAGTTCATTCAGGGCACCGGACAGGTCGGTCTTGA
CAAAAGAACCGGGCGCCCTGCGCTGACAGCCGGAACACGGCGGCATC
AGAGCAGCCGATTGTCTGTTGTGCCCAGTCATAGCCGAATAGCCTCTCC
ACCCAAGCGGCCGGAGAACCTGCGTGCAATCCATCTTGTTCAATCCCCA
TGGTCGATCGACAGATCTGCGAAAGCTCGAGAGAGATAGATTTGTAGAG
AGAGACTGGTGATTTCAGCGTGTCCTCTCCAAATGAAATGAACTTCCTT
ATATAGAGGAAGGTCTTGCGAAGGATAGTGGGATTGTGCGTCATCCCTT
ACGTCAGTGGAGATATCACATCAATCCACTTGCTTTGAAGACGTGGTTG

-continued

```
GAACGTCTTCTTTTTCCACGATGCTCCTCGTGGGTGGGGTCCATCTTT

GGGACCACTGTCGGCAGAGGCATCTTGAACGATAGCCTTTCCTTTATCG

CAATGATGGCATTTGTAGGTGCCACCTTCCTTTTCTACTGTCCTTTTGA

TGAAGTGACAGATAGCTGGGCAATGGAATCCGAGGAGGTTTCCCGATAT

TACCCTTTGTTGAAAAGTCTCAATAGCCCTTTGGTCTTCTGAGACTGTA

TCTTTGATATTCTTGGAGTAGACGAGAGTGTCGTGCTCCACCATGTTAT

CACATCAATCCACTTGCTTTGAAGACGTGGTTGGAACGTCTTCTTTTTC

CACGATGCTCCTCGTGGGTGGGGTCCATCTTTGGGACCACTGTCGGCA

GAGGCATCTTGAACGATAGCCTTTCCTTTATCGCAATGATGGCATTTGT

AGGTGCCACCTTCCTTTTCTACTGTCCTTTTGATGAAGTGACAGATAGC

TGGGCAATGGAATCCGAGGAGGTTTCCCGATATTACCCTTTGTTGAAAA

GTCTCAATAGCCCTTTGGTCTTCTGAGACTGTATCTTTGATATTCTTGG

AGTAGACGAGAGTGTCGTGCTCCACCATGTTGGCAAGCTGCTCTAGCCA

ATACGCAAACCGCCTCTC
```

Transformation and Selection:

Transformation of *Arabidopsis* was achieved using *Agrobacterium*-mediated "floral dip" transfer as described in Example 4. Transformed plants were grown under selection as described in Example 4.

Biochemical Characterization:

Assays for 2-oxoglutaramate, ω-amidase, GS and GPT were conducted as described in Example 3, supra.

Results:

GPT activity and GS activity of wild type and transgenic *Arabidopsis* plants were measured and are shown in Table 9, below. Ω-amidase activities and 2-oxoglutaramate concentrations in wild type and transgenic *Arabidopsis* plants were measured in both leaf and root tissues, and are shown in Table 10, below.

TABLE 9

| Arabidopsis Genotype | FWt mg Whole plant | GS Activity umoles/gfwt/min | | | GPT Activity nmoles/gfwt/hr | | |
|---|---|---|---|---|---|---|---|
| | | Root | Leaf | L/R | Root | Leaf | L/R |
| Wild type* | 77 | 1.5 | 3.4 | 2.3 | 167 | 132 | 0.8 |
| TG GPT (6c) + ω-amidase** | 513 | 1.8 | 8.25 | 4.6 | 232 | 389 | 1.7 |

TG = Transgenic
GPT (6c) = –45 truncated GPT [SEQ ID NO: 40]
*Average values of 9 plants
**Average values of 5 plants

TABLE 10

| Arabidopsis Genotype | FWt mg Whole plant | Ω-amidase nmoles/gfwt/hr | | | 2-Oxoglutaramate Concentration nmoles/gfwt | | |
|---|---|---|---|---|---|---|---|
| | | Root | Leaf | L/R Ratio | Root | Leaf | L/R Ratio |
| Wild type* | 77 | 86 | 1090 | 12.7 | 410 | 163 | 0.4 |
| TG GPT (6c) + ω-amidase** | 513 | 308 | 584 | 1.9 | 268 | 275 | 1.0 |

TG = Transgenic
GPT (6c) = –45 truncated GPT [SEQ ID NO: 40]
*Average values of 9 plants
**Average values of 5 plants Compared to wild type control *Arabidopsis* plants, the transgenic *Arabidopsis* plants carrying the ω-amidase directed for root expression and the truncated GPT (for cyosolic expression) directed for leaf expression showed biochemical changes within the ω-amidase pathway similar to those observed in the transgenic plants of Example 5, supra. More specifically, transgenic GPT+ω-amidase plants showed increased root ω-amidase activity, reduced root 2-oxoglutaramate concentration, and increased leaf-to-root 2-oxoglutaramate ratios. Also, similar to the results seen in the transgenic plants of Example 5, the GPT+ω-amidase transgenic plants showed significant reductions in leaf ω-amidase activity levels, increased leaf 2-oxoglutaramate, and higher leaf GS and leaf GPT activities. The resulting impact on growth was even greater than observed for the transgenic plants of Example 5, with the transgenic plants weighing more than 6.7 times the weight of the wild type plants, on average.

Example 6

Increased Growth of Transgenic *Arabidopsis* Plants Carrying Root-Preferred Ω-Amidase Transgene and Leaf-Directed GPT and GS In this example, *Arabidopsis* plant growth was increased by introducing an ω-amidase transgene under the control of a highly root-preferred promoter and GPT and GS transgenes under the control of leaf-directing promoters. The resulting transgenic *Arabidopsis* plants showed astounding increases in growth, as well as various biochemical changes, relative to wild type *Arabidopsis* plants.

Materials and Methods:

*Agrobacterium* Vectors:

The ω-amidase transgene expression vector and *Agrobacteria* preparation were generated as described in Example 3, supra. For the leaf-directed GPT transgene, an expression cassette comprising the tomato rubisco small subunit promoter and the coding sequence for an *Arabidopsis* codon-optimized GPT truncated to delete the first 45 codons of the full length GPT (eliminating the chloroplast transit peptide), and containing an F to V mutation at amino acid residue 45, was constructed and cloned into the Cambia 2201 expression vector. The resulting GPT transgene expression vector construct (9c) is shown in SEQ ID NO: 41 below, and was used to transform *Agrobacteria* as described in Example 5.

The nucleotide sequence of the Cambia 2201 with tomato rubisco SSU promoter+(–45) truncated, optimized for *Arabidopsis* GPT F-to-V mutation+nos terminator is set forth below as SEQ ID NO: 41. Underlined nucleotides=tomato rubisco promoter, bold nucleotides=GPT coding region (codon optimized for *Arabidopsis*), italicized nucleotides=nos terminator region (and some Cambia vector sequence), and other nucleotides=Cambia 2201 vector and additional cloning sites.

CCCGCGCGTTGGCCGATTCATTAATGCAGCTGGCACGACAGGTTTCCCGA

CTGGAAAGCGGGCAGTGAGCGCAACGCAATTAATGTGAGTTAGCTCACT

CATTAGGCACCCCAGGCTTTACACTTTATGCTTCCGGCTCGTATGTTGT

GTGGAATTGTGAGCGGATAACAATTTCACACAGGAAACAGCTATGACCA

TGATTACGAATTCGAGCTCGGTACCCGGGGATCCTCTAGATCTAGAAT

TCATCGATGTTTGAATCCTCCTTAAAGTTTTTCTCTGGAGAAACTGTAGT

AATTTTACTTTGTTGTGTTCCCTTCATCTTTTGAATTAATGGCATTTGTT

TTAATACTAATCTGCTTCTGAAACTTGTAATGTATGTATATCAGTTTCTT

ATAATTTATCCAAGTAATATCTTCCATTCTCTATGCAATTGCCTGCATAA

GCTCGACAAAAGAGTACATCAACCCCTCCTCCTCTGGACTACTCTAGCTA

AACTTGAATTTCCCCTTAAGATTATGAAATTGATATATCCTTAACAAACG

ACTCCTTCTGTTGGAAAATGTAGTACTTGTCTTTCTTCTTTTGGGTATAT

ATAGTTTATATACACCATACTATGTACAACATCCAAGTAGAGTGAAATGG

ATACATGTACAAGACTTATTTGATTGATTGATGACTTGAGTTGCCTTAGG

AGTAACAAATTCTTAGGTCAATAAATCGTTGATTTGAAATTAATCTCTCT

GTCTTAGACAGATAGGAATTATGACTTCCAATGGTCCAGAAAGCAAAGTT

CGCACTGAGGGTATACTTGGAATTGAGACTTGCACAGGTCCAGAAACCAA

AGTTCCCATCGAGCTCTAAAATCACATCTTTGGAATGAAATTCAATTAGA

GATAAGTTGCTTCATAGCATAGGTAAAATGGAAGATGTGAAGTAACCTGC

AATAATCAGTGAAATGACATTAATACACTAAATACTTCATATGTAATTAT

CCTTTCCAGGTTAACAATACTCTATAAAGTAAGAATTATCAGAAATGGGC

TCATCAAACTTTTGTACTATGTATTTCATATAAGGAAGTATAACTATACA

TAAGTGTATACACAACTTTATTCCTATTTTGTAAAGGTGGAGAGACTGTT

TTCGATGGATCTAAAGCAATATGTCTATAAAATGCATTGATATAATAATT

ATCTGAGAAAATCCAGAATTGGCGTTGGATTATTTCAGCCAAATAGAAGT

TTGTACCATACTTGTTGATTCCTTCTAAGTTAAGGTGAAGTATCATTCAT

AAACAGTTTTCCCCAAAGTACTACTCACCAAGTTTCCCTTTGTAGAATTA

ACAGTTCAAATATATGGCGCAGAAATTACTCTATGCCCAAAACCAAACGA

GAAAGAAACAAAATACAGGGGTTGCAGACTTTATTTTCGTGTTAGGGTGT

GTTTTTTCATGTAATTAATCAAAAAATATTATGACAAAAACATTTATACA

TATTTTTACTCAACACTCTGGGTATCAGGGTGGGTTGTGTTCGACAATCA

ATATGGAAAGGAAGTATTTTCCTTATTTTTTAGTTAATATTTTCAGTTA

TACCAAACATACCTTGTGATATTATTTTAAAAATGAAAAACTCGTCAGA

AAGAAAAAGCAAAGCAACAAAAAAATTGCAAGTATTTTTAAAAAAGAA

AAAAAAAACATATCTTGTTTGTCAGTATGGGAAGTTTGAGATAAGGACGA

GTGAGGGGTTAAAATTCAGTGGCCATTGATTTTGTAATGCCAAGAACCAC

AAAATCCAATGGTTACCATTCCTGTAAGATGAGGTTTGCTAACTCTTTTT

GTCCGTTAGATAGGAAGCCTTATCACTATATATACAAGGCGTCCTAATAA

CCTCTTAGTAACCAATTATTTCAGCAACTAGTATGGCGACTCAAAATGAG

TCAACACAAAAGCCTGTTCAGGTGGCTAAGAGACTTGAGAAGTTTAAAAC

TACAATTTTCACTCAAATGTCTATCCTCGCAGTTAAGCACGGAGCTATTA

ATCTTGGACAGGGTGTTCCTAACTTCGATGGTCCAGATTTCGTGAAAGAA

GCTGCAATTCAAGCAATCAAGGATGGAAAAAATCAGTATGCTAGAGGATA

CGGTATTCCTCAGTTGAACTCTGCTATCGCTGCAAGATTCAGAGAAGATA

CAGGACTTGTTGTGGATCCAGAAAAAGAGGTTACTGTGACATCAGGTTGT

ACTGAGGCTATTGCTGCAGCTATGCTCGGACTTATTAACCCTGGAGATGA

AGTTATCCTTTTTGCACCATTCTATGATTCTTACGAGGCTACATTGTCAA

TGGCAGGAGCTAAGGTGAAAGGTATTACTCTCAGACCTCCAGATTTCTCT

ATCCCTTTGGAAGAGCTCAAGGCAGCTGTTACTAATAAGACAAGAGCTAT

CTTGATGAATACTCCTCATAACCCAACAGGAAAGATGTTTACTAGAGAAG

AGCTCGAAACTATTGCTTCTCTTTGCATCGAGAACGATGTTTTGGTGTTC

TCAGATGAAGTGTATGATAAACTCGCATTTGAGATGGATCACATTTCTAT

CGCTTCACTTCCAGGAATGTACGAAAGAACTGTTACTATGAATTCTTTGG

GAAAGACTTTTCTCTCACAGGATGGAAAATTGGTTGGGCAATCGCTCCT

CCACATCTCACATGGGGTGTTAGACAAGCACACTCTTATCTTACTTTCGC

AACTTCAACACCTGCTCAGTGGGCAGCTGTGGCAGCTCTTAAGGCTCCAG

AATCTTACTTCAAGGAGTTGAAGAGAGATTACAACGTTAAGAAAGAAACA

CTTGTGAAGGGATTGAAAGAGGTTGGTTTTACAGTGTTCCCTTCTTCAGG

AACTTACTTTGTTGTGGCAGATCATACTCCATTCGGTATGGAAAACGATG

TTGCTTTTTGTGAGTATCTTATTGAAGAGGTTGGAGTTGTGGCTATCCCT

ACATCTGTGTTTTACCTTAATCCAGAAGAGGGAAAGAATCTTGTTAGATT

TGCATTCTGCAAAGATGAAGAGACTTTGAGAGGTGCTATTGAGAGGATGA

AGCAAAAACTCAAGAGAAAAGTTTGACACGTGTGAATTACAGGTGACCAG

CTCGAATTTCCCCGAT*CGTTCAAACATTTGGCAATAAAGTTTCTTAAGAT*

*TGAATCCTGTTGCCGGTCTTGCGATGATTATCATATAATTTCTGTTGAAT*

*TACGTTAAGCATGTAATAATTAACATGTAATGCATGACGTTATTTATGAG*

*ATGGGTTTTTATGATTAGAGTCCCGCAATTATACATTTAATACGCGATAG*

*AAAACAAAATATAGCGCGCAAACTAGGATAAATTATCGCGCGCGGTGTCA*

*TCTATGTTACTAGATCGGGAATTAAACTATCAGTGTTTGACAGGATATAT*

*TGGCGGGTAAACCTAAGAGAAAAGAGCGTTTATTAGAATAACGGATATTT*

*AAAAGGGCGTGAAAAGGTTTATCCGTTCGTCCATTTGTATGTGCATGCC*

*AACCACAGGGTTCCCCTCGGGATCAAAGTACTTTGATCCAACCCCTCCG*

*CTGCTATAGTGCAGTCGGCTTCTGACGTTCAGTGCAGCCGTCTTCTGAA*

*AACGACATGTCGCACAAGTCCTAAGTTACGCGACAGGCTGCCGCCCTGC*

*CCTTTTCCTGGCGTTTTCTTGTCGCGTGTTTTAGTCGCATAAAGTAGAA*

*TACTTGCGACTAGAACCGGAGACATTACGCCATGAACAAGAGCGCCGCC*

*GCTGGCCTGCTGGGCTATGCCCGCGTCAGCACCGACGACCAGGACTTGA*

*CCAACCAACGGGCCGAACTGCACGCGGCCGGCTGCACCAAGCTGTTTTC*

-continued

```
CGAGAAGATCACCGGCACCAGGCGCGACCGCCCGGAGCTGGCCAGGATG
CTTGACCACCTACGCCCTGGCGACGTTGTGACAGTGACCAGGCTAGACC
GCCTGGCCCGCAGCACCCGCGACCTACTGGACATTGCCGAGCGCATCCA
GGAGGCCGGCGCGGGCCTGCGTAGCCTGGCAGAGCCGTGGGCCGACACC
ACCACGCCGGCCGGCCGCATGGTGTTGACCGTGTTCGCCGGCATTGCCG
AGTTCGAGCGTTCCCTAATCATCGACCGCACCCGGAGCGGGCGCGAGGC
CGCCAAGGCCCGAGGCGTGAAGTTTGGCCCCCGCCCTACCCTCACCCCG
GCACAGATCGCGCACGCCCGCGAGCTGATCGACCAGGAAGGCCGCACCG
TGAAAGAGGCGGCTGCACTGCTTGGCGTGCATCGCTCGACCCTGTACCG
CGCACTTGAGCGCAGCGAGGAAGTGACGCCCACCGAGGCCAGGCGGCGC
GGTGCCTTCCGTGAGGACGCATTGACCGAGGCCGACGCCCTGGCGGCCG
CCGAGAATGAACGCCAAGAGGAACAAGCATGAAACCGCACCAGGACGGC
CAGGACGAACCGTTTTTCATTACCGAAGAGATCGAGGCGGAGATGATCG
CGGCCGGGTACGTGTTCGAGCCGCCCGCGCACGTCTCAACCGTGCGGCT
GCATGAAATCCTGGCCGGTTTGTCTGATGCCAAGCTGGCGGCCTGGCCG
GCCAGCTTGGCCGCTGAAGAAACCGAGCGCCGCCGTCTAAAAAGGTGAT
GTGTATTTGAGTAAAACAGCTTGCGTCATGCGGTCGCTGCGTATATGAT
GCGATGAGTAAATAAACAAATACGCAAGGGGAACGCATGAAGGTTATCG
CTGTACTTAACCAGAAAGGCGGGTCAGGCAAGACGACCATCGCAACCCA
TCTAGCCCGCGCCCTGCAACTCGCCGGGGCCGATGTTCTGTTAGTCGAT
TCCGATCCCCAGGGCAGTGCCCGCGATTGGGCGGCCGTGCGGGAAGATC
AACCGCTAACCGTTGTCGGCATCGACCGCCCGACGATTGACCGCGACGT
GAAGGCCATCGGCCGGCGCGACTTCGTAGTGATCGACGGAGCGCCCCAG
GCGGCGGACTTGGCTGTGTCCGCGATCAAGGCAGCCGACTTCGTGCTGA
TTCCGGTGCAGCCAAGCCCTTACGACATATGGGCCACCGCCGACCTGGT
GGAGCTGGTTAAGCAGCGCATTGAGGTCACGGATGGAAGGCTACAAGCG
GCCTTTGTCGTGTCGCGGGCGATCAAAGGCACGCGCATCGGCGGTGAGG
TTGCCGAGGCGCTGGCCGGGTACGAGCTGCCCATTCTTGAGTCCCGTAT
CACGCAGCGCGTGAGCTACCCAGGCACTGCCGCCGCCGGCACAACCGTT
CTTGAATCAGAACCCGAGGGCGACGCTGCCCGCGAGGTCCAGGCGCTGG
CCGCTGAAATTAAATCAAAACTCATTTGAGTTAATGAGGTAAAGAGAAA
ATGAGCAAAAGCACAAACACGCTAAGTGCCGGCCGTCCGAGCGCACGCA
GCAGCAAGGCTGCAACGTTGGCCAGCCTGGCAGACACGCCAGCCATGAA
GCGGGTCAACTTTCAGTTGCCGGCGGAGGATCACACCAAGCTGAAGATG
TACGCGGTACGCCAAGGCAAGACCATTACCGAGCTGCTATCTGAATACA
TCGCGCAGCTACCAGAGTAAATGAGCAAATGAATAAATGAGTAGATGAA
TTTTAGCGGCTAAAGGAGGCGGCATGGAAAATCAAGAACAACCAGGCAC
CGACGCCGTGGAATGCCCCATGTGTGGAGGAACGGGCGGTTGGCCAGGC
GTAAGCGGCTGGGTTGTCTGCCGGCCCTGCAATGGCACTGGAACCCCCA
AGCCCGAGGAATCGGCGTGACGGTCGCAAACCATCCGGCCCGGTACAAA
```

```
TCGGCGCGGCGCTGGGTGATGACCTGGTGGAGAAGTTGAAGGCCGCGCA
GGCCGCCCAGCGGCAACGCATCGAGGCAGAAGCACGCCCCGGTGAATCG
TGGCAAGCGGCCGCTGATCGAATCCGCAAAGAATCCCGGCAACCGCCGG
CAGCCGGTGCGCCGTCGATTAGGAAGCCGCCCAAGGGCGACGAGCAACC
AGATTTTTTCGTTCCGATGCTCTATGACGTGGGCACCCGCGATAGTCGC
AGCATCATGGACGTGGCCGTTTTCCGTCTGTCGAAGCGTGACCGACGAG
CTGGCGAGGTGATCCGCTACGAGCTTCCAGACGGGCACGTAGAGGTTTC
CGCAGGGCCGGCCGGCATGGCCAGTGTGTGGGATTACGACCTGGTACTG
ATGGCGGTTTCCCATCTAACCGAATCCATGAACCGATACCGGGAAGGGA
AGGGAGACAAGCCCGGCCGCGTGTTCCGTCCACACGTTGCGGACGTACT
CAAGTTCTGCCGGCGAGCCGATGGCGGAAAGCAGAAAGACGACCTGGTA
GAAACCTGCATTCGGTTAAACACCACGCACGTTGCCATGCAGCGTACGA
AGAAGGCCAAGAACGGCCGCCTGGTGACGGTATCCGAGGGTGAAGCCTT
GATTAGCCGCTACAAGATCGTAAAGAGCGAAACCGGGCGGCCGGAGTAC
ATCGAGATCGAGCTAGCTGATTGGATGTACCGCGAGATCACAGAAGGCA
AGAACCCGGACGTGCTGACGGTTCACCCCGATTACTTTTTGATCGATCC
CGGCATCGGCCGTTTTCTCTACCGCCTGGCACGCCGCGCCGCAGGCAAG
GCAGAAGCCAGATGGTTGTTCAAGACGATCTACGAACGCAGTGGCAGCG
CCGGAGAGTTCAAGAAGTTCTGTTTCACCGTGCGCAAGCTGATCGGGTC
AAATGACCTGCCGGAGTACGATTTGAAGGAGGAGGCGGGGCAGGCTGGC
CCGATCCTAGTCATGCGCTACCGCAACCTGATCGAGGGCGAAGCATCCG
CCGGTTCCTAATGTACGGAGCAGATGCTAGGGCAAATTGCCCTAGCAGG
GGAAAAAGGTCGAAAAGGTCTCTTTCCTGTGGATAGCACGTACATTGGG
AACCCAAAGCCGTACATTGGGAACCGGAACCCGTACATTGGGAACCCAA
AGCCGTACATTGGGAACCGGTCACACATGTAAGTGACTGATATAAAAGA
GAAAAAAGGCGATTTTTCCGCCTAAAACTCTTTAAAACTTATTAAAACT
CTTAAAACCCGCCTGGCCTGTGCATAACTGTCTGGCCAGCGCACAGCCG
AAGAGCTGCAAAAAGCGCCTACCCTTCGGTCGCTGCGCTCCCTACGCCC
CGCCGCTTCGCGTCGGCCTATCGCGGCCGCTGGCCGCTCAAAAATGGCT
GGCCTACGGCCAGGCAATCTACCAGGGCGCGGACAAGCCGCGCCGTCGC
CACTCGACCGCCGGCGCCCACATCAAGGCACCCTGCCTCGCGCGTTTCG
GTGATGACGGTGAAAACCTCTGACACATGCAGCTCCCGGAGACGGTCAC
AGCTTGTCTGTAAGCGGATGCCGGGAGCAGACAAGCCCGTCAGGGCGCG
TCAGCGGGTGTTGGCGGGTGTCGGGGCGCAGCCATGACCCAGTCACGTA
GCGATAGCGGAGTGTATACTGGCTTAACTATGCGGCATCAGAGCAGATT
GTACTGAGAGTGCACCATATGCGGTGTGAAATACCGCACAGATGCGTAA
GGAGAAAATACCGCATCAGGCGCTCTTCCGCTTCCTCGCTCACTGACTC
GCTGCGCTCGGTCGTTCGGCTGCGGCGAGCGGTATCAGCTCACTCAAAG
GCGGTAATACGGTTATCCACAGAATCAGGGGATAACGCAGGAAAGAACA
TGTGAGCAAAAGGCCAGCAAAAGGCCAGGAACCGTAAAAAGGCCGCGTT
```

```
GCTGGCGTTTTTCCATAGGCTCCGCCCCCCTGACGAGCATCACAAAAAT
CGACGCTCAAGTCAGAGGTGGCGAAACCCGACAGGACTATAAAGATACC
AGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTG
CGCCTTATCCGGTAACTATCGTCTTGAGTCCAACCCGGTAAGACACGAC
TTATCGCCACTGGCAGCAGCCACTGGTAACAGGATTAGCAGAGCGAGGT
ATGTAGGCGGTGCTACAGAGTTCTTGAAGTGGTGGCCTAACTACGGCTA
CACTAGAAGGACAGTATTTGGTATCTGCGCTCTGCTGAAGCCAGTTACC
TTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAG
TGGAACGAAAACTCACGTTAAGGGATTTTGGTCATGCATGATATATCTC
CCAATTTGTGTAGGGCTTATTATGCACGCTTAAAAATAATAAAAGCAGA
CTTGACCTGATAGTTTGGCTGTGAGCAATTATGTGCTTAGTGCATCTAA
TCGCTTGAGTTAACGCCGGCGAAGCGGCGTCGGCTTGAACGAATTTCTA
GCTAGAGGATCGCACCAATAACTGCCTTAAAAAAATTACGCCCCGCCCT
GCCACTCATCGCAGTACTGTTGTAATTCATTAAGCATTCTGCCGACATG
GAAGCCATCACAAACGGCATGATGAACCTGAATCGCCAGCGGCATCAGC
ACCTTGTCGCCTTGCGTATAATATTTGCCCATTGTGAAAACGGGGGCGA
AGAAGTTGTCCATATTGGCCACGTTTAAATCAAAACTGGTGAAACTCAC
CCAGGGATTGGCTGAGACGAAAAACATATTCTCAATAAACCCTTTAGGG
AAATAGGCCAGGTTTTCACCGTAACACGCCACATCTTGCGAATATATGT
GTAGAAACTGCCGGAAATCGTCGTGGTATTCACTCCAGAGCGATGAAAA
CGTTTCAGTTTGCTCATGGAAAACGGTGTAACAAGGGTGAACACTATCC
CATATCACCAGCTCACCGTCTTTCATTGCCATACGGAACTCCGGATGAG
CATTCATCAGGCGGGCAAGAATGTGAATAAAGGCCGGATAAAACTTGTG
CTTATTTTCTTTACGGTCTTTAAAAAGGCCGTAATATCCAGCTGAACG
GTCTGGTTATAGGTACATTGAGCAACTGACTGAAATGCCTCAAAATGTT
CTTTACGATGCCATTGGGATATATCAACGGTGGTATATCCAGTGATTTT
TTTCTCCATGATGTTTAACTTTGTTTAGGGCGACTGCCCTGCTGCGTA
ACATCGTTGCTGCTCCATAACATCAAACATCGACCCACGGCGTAACGCG
CTTGCTGCTTGGATGCCCGAGGCATAGACTGTACCCCAAAAAAACATGT
CATAACAAGAAGCCATGAAAACCGCCACTGCGCCGTTACCACCGCTGCG
TTCGGTCAAGGTTCTGGACCAGTTGCGTGACGGCAGTTACGCTACTTGC
ATTACAGCTTACGAACCGAACGAGGCTTATGTCCACTGGGTTCGTGCCC
GAATTGATCACAGGCAGCAACGCTCTGTCATCGTTACAATCAACATGCT
ACCCTCCGCGAGATCATCCGTGTTTCAAACCCGGCAGCTTAGTTGCCGT
CTTCCGAATAGCATCGGTAACATGAGCAAAGTCTGCCGCCTTACAACG

GCTCTCCCGCTGACGCCGTCCCGGACTGATGGGCTGCCTGTATCGAGTG
GTGATTTTGTGCCGAGCTGCCGGTCGGGGAGCTGTTGGCTGGCTGGTGG
CAGGATATATTGTGGTGTAAACAAATTGACGCTTAGACAACTTAATAAC
ACATTGCGGACGTTTTTAATGTACTGAATTAACGCCGAATTAATTCGGG
GGATCTGGATTTTAGTACTGGATTTTGGTTTTAGGAATTAGAAATTTTA
TTGATAGAAGTATTTTACAAATACAAATACATCTAAGGGTTTCTTATA
TGCTCAACACATGAGCGAAACCCTATAGGAACCCTAATTCCCTTATCTG
GGAACTACTCACACATTATTATGGAGAAACTCGAGCTTGTCGATCGACT
CTAGCTAGAGGATCGATCCGAACCCCAGAGTCCCGCTCAGAAGAACTCG
TCAAGAAGGCGATAGAAGGCGATGCGCTGCGAATCGGGAGCGGCGATAC
CGTAAAGCACGAGGAAGCGGTCAGCCCATTCGCCGCCAAGCTCTTCAGC
AATATCACGGGTAGCCAACGCTATGTCCTGATAGCGGTCCGCCACACCC
CAGCCGGCCACAGTCGATGAATCCAGAAAAGCGGCCATTTTCCACATGA
TATTCGGCAAGCAGGCATCGCCATGTGTCACGACGAGATCCTCGCCGTC
GGGCATGCGCGCCTTGAGCCTGGCGAACAGTTCGGCTGGCGCGAGCCCC
TGATGCTCTTCGTCCAGATCATCCTGATCGACAAGACCGGCTTCCATCC
GAGTACGTGCTCGCTCGATGCGATGTTTCGCTTGGTGGTCGAATGGGCA
GGTAGCCGGATCAAGCGTATGCAGCCGCCGCATTGCATCAGCCATGATG
TGATACTTCTCGGCAGGAGCAAGGTGAGATGACAGGAGATCCTGCCCCG
GCACTTCGCCCAATAGCAGCCAGTCCCTTCCCGCTTCAGTGACAACGTC
GAGCACAGCTGCGCAAGGAACGCCCGTCGTGGCCAGCCACGATAGCCGC
GCTGCCTCGTCCTGGAGTTCATTCAGGGCACCGGACAGGTCGGTCTTGA
CAAAAGAACCGGGCGCCCCTGCGCTGACAGCCGGAACACGGCGGCATC
AGAGCAGCCGATTGTCTGTTGTGCCCAGTCATAGCCGAATAGCCTCTCC
ACCCAAGCGGCCGGAGAACCTGCGTGCAATCCATCTTGTTCAATCCCCA
TGGTCGATCGACAGATCTGCGAAAGCTCGAGAGAGATAGATTTGTAGAG
AGAGACTGGTGATTTCAGCGTGTCCTCTCCAAATGAAATGAACTTCCTT
ATATAGAGGAAGGTCTTGCGAAGGATAGTGGGATTGTGCGTCATCCCTT
ACGTCAGTGGAGATATCACATCAATCCACTTGCTTTGAAGACGTGGTTG
GAACGTCTTCTTTTTCCACGATGCTCCTCGTGGGTGGGGGTCCATCTTT
GGGACCACTGTCGGCAGAGGCATCTTGAACGATAGCCTTTCCTTTATCG
CAATGATGGCATTTGTAGGTGCCACCTTCCTTTTCTACTGTCCTTTTGA
TGAAGTGACAGATAGCTGGGCAATGGAATCCGAGGAGGTTTCCCGATAT
TACCCTTTGTTGAAAAGTCTCAATAGCCCTTTGGTCTTCTGAGACTGTA
TCTTTGATATTCTTGGAGTAGACGAGAGTGTCGTGCTCCACCATGTTAT
CACATCAATCCACTTGCTTTGAAGACGTGGTTGGAACGTCTTCTTTTTC
CACGATGCTCCTCGTGGGTGGGGGTCCATCTTTGGGACCACTGTCGGCA
GAGGCATCTTGAACGATAGCCTTTCCTTTATCGCAATGATGGCATTTGT
AGGTGCCACCTTCCTTTTCTACTGTCCTTTTGATGAAGTGACAGATAGC
TGGGCAATGGAATCCGAGGAGGTTTCCCGATATTACCCTTTGTTGAAAA
```

-continued

GTCTCAATAGCCCTTTGGTCTTCTGAGACTGTATCTTTGATATTCTTGG

AGTAGACGAGAGTGTCGTGCTCCACCATGTTGGCAAGCTGCTCTAGCCA

ATACGCAAACCGCCTCTC

For the leaf-directed GS transgene, an expression cassette comprising the tomato rubisco small subunit promoter and an *Arabidopsis* GS1 coding sequence was constructed and cloned into the Cambia 1305.1 expression vector with the tomato rubisco small subunit promoter (rbcS3C). The resulting GS transgene expression vector construct (4c) is set forth as SEQ ID NO: 43, and was used to transform *Agrobacteria* as described in Example 5.

The nucleotide sequence of the Cambia 1305.1 with rubisco small subunit promoter (rbcS3C)+ARGS (*Arabidopsis* GS1) is set forth below as SEQ ID NO: 43. Underlined nucleotides=tomato rubisco promoter, double underlined nucleotides=catI intron in the Cambia 1305.1 vector first 10 amino acids are from GUSplus enzyme and cloning sites in 1305.1 vector, bold nucleotides=*Arabidopsis* GS1 coding region (cloned into SpeI to pmII sites), italicized nucleotides=nos terminator region (and some Cambia vector sequence), and other nucleotides=Cambia 2201 vector and additional cloning sites.

*GGTACC*GTTTGAATCCTCCTTAAAGTTTTTCTCTGGAGAAACTGTAGTAA

TTTTACTTTGTTGTGTTCCCTTCATCTTTTGAATTAATGGCATTTGTTTT

AATACTAATCTGCTTCTGAAACTTGTAATGTATGTATATCAGTTTCTTAT

AATTTATCCAAGTAATATCTTCCATTCTCTATGCAATTGCCTGCATAAGC

TCGACAAAAGAGTACATCAACCCCTCCTCCTCTGGACTACTCTAGCTAAA

CTTGAATTTCCCCTTAAGATTATGAAATTGATATATCCTTAACAAACGAC

TCCTTCTGTTGGAAAATGTAGTACTTGTCTTTCTTCTTTTGGGTATATAT

AGTTTATATACACCATACTATGTACAACATCCAAGTAGAGTGAAATGGAT

ACATGTACAAGACTTATTTGATTGATTGATGACTTGAGTTGCCTTAGGAG

TAACAAATTCTTAGGTCAATAAATCGTTGATTTGAAATTAATCTCTCTGT

CTTAGACAGATAGGAATTATGACTTCCAATGGTCCAGAAAGCAAAGTTCG

CACTGAGGGTATACTTGGAATTGAGACTTGCACAGGTCCAGAAACCAAAG

TTCCCATCGAGCTCTAAAATCACATCTTTGGAATGAAATTCAATTAGAGA

TAAGTTGCTTCATAGCATAGGTAAAATGGAAGATGTGAAGTAACCTGCAA

TAATCAGTGAAATGACATTAATACACTAAATACTTCATATGTAATTATCC

TTTCCAGGTTAACAATACTCTATAAAGTAAGAATTATCAGAAATGGGCTC

ATCAAACTTTTGTACTATGTATTTCATATAAGGAAGTATAACTATACATA

AGTGTATACACAACTTTATTCCTATTTTGTAAAGGTGGAGAGACTGTTTT

CGATGGATCTAAAGCAATATGTCTATAAAATGCATTGATATAATAATTAT

CTGAGAAAATCCAGAATTGGCGTTGGATTATTTCAGCCAAATAGAAGTTT

GTACCATACTTGTTGATTCCTTCTAAGTTAAGGTGAAGTATCATTCATAA

ACAGTTTTCCCCAAAGTACTACTCACCAAGTTTCCCTTTGTAGAATTAAC

AGTTCAAATATATGGCGCAGAAATTACTCTATGCCCAAAACCAAACGAGA

AAGAAACAAAATACAGGGGTTGCAGACTTTATTTTCGTGTTAGGGTGTGT

-continued

TTTTTCATGTAATTAATCAAAAAATATTATGACAAAAACATTTATACATA

TTTTTACTCAACACTCTGGGTATCAGGGTGGGTTGTGTTCGACAATCAAT

ATGGAAAGGAAGTATTTTCCTTATTTTTTTAGTTAATATTTTCAGTTATA

CCAAACATACCTTGTGATATTATTTTTAAAAATGAAAAACTCGTCAGAAA

GAAAAAGCAAAAGCAACAAAAAAATTGCAAGTATTTTTTAAAAAAGAAAA

AAAAAACATATCTTGTTTGTCAGTATGGGAAGTTTGAGATAAGGACGAGT

GAGGGGTTAAAATTCAGTGGCCATTGATTTTGTAATGCCAAGAACCACAA

AATCCAATGGTTACCATTCCTGTAAGATGAGGTTTGCTAACTCTTTTTGT

CCGTTAGATAGGAAGCCTTATCACTATATATACAAGGCGTCCTAATAACC

TCTTAGTAACCAATTATTTCAGCA*CC*ATGGTAGATCTGAGG<ins>GTAAATTTC</ins>

<ins>TAGTTTTTCTCCTTCATTTTCTTGGTTAGGACCCTTTTCTCTTTTTATTT</ins>

<ins>TTTTGAGCTTTGATCTTTCTTTAAACTGATCTATTTTTTAATTGATTGGT</ins>

<ins>TATGGTGTAAATATTACATAGCTTTAACTGATAATCTGATTACTTTATTT</ins>

<ins>CGTGTGTCTATGATGATGATGATAGTTACAG</ins>AACCGACGAACTAGTATGT

CTCTGCTCTCAGATCTCGTTAACCTCAACCTCACCGATGCCACCGGGAAA

ATCATCGCCGAATACATATGGATCGGTGGATCTGGAATGGATATCAGAAG

CAAAGCCAGGACACTACCAGGACCAGTGACTGATCCATCAAAGCTTCCA

AGTGGAACTACGACGGATCCAGCACCGGTCAGGCTGCTGGAAGACAGT

GAAGTCATTCTATACCCTCAGGCAATATTCAAGGATCCCTTCAGGAAAGG

CAACAACATCCTGGTGATGTGTGATGCTTACACACCAGCTGGTGATCCTA

TTCCAACCAACAAGAGGCACAACGCTGCTAAGATCTTCAGCCACCCCGAC

GTTGCCAAGGAGGAGCCTTGGTATGGGATTGAGCAAGAATACACTTTGAT

GCAAAAGGATGTGAACTGGCCAATTGGTTGGCCTGTTGGTGGCTACCCTG

GCCCTCAGGGACCTTACTACTGTGGTGTGGGAGCTGACAAAGCCATTGGT

CGTGACATTGTGGATGCTCACTACAAGGCCTGTCTTTACGCCGGTATTGG

TATTTCTGGTATCAATGGAGAAGTCATGCCAGGCCAGTGGGAGTTCCAAG

TCGGCCCTGTTGAGGGTATTAGTTCTGGTGATCAAGTCTGGGTTGCTCGA

TACCTTCTCGAGAGGATCACTGAGATCTCTGGTGTAATTGTCAGCTTCGA

CCCGAAACCAGTCCCGGGTGACTGGAATGGAGCTGGAGCTCACTGCAACT

ACAGCACTAAGACAATGAGAAACGATGGAGGATTAGAAGTGATCAAGAAA

GCGATAGGGAAGCTTCAGCTGAAACACAAAGAACACATTGCTGCTTACGG

TGAAGGAAACGAGCGTCGTCTCACTGGAAAGCACGAAACCGCAGACATCA

ACACATTCTCTTGGGGAGTCGCGAACCGTGGAGCGTCAGTGAGAGTGGGA

CGTGACACAGAAGGAAGGTAAAGGGTACTTCGAAGACAGAAGGCCAGC

TTCTAACATGGATCCTTACGTTGTCACCTCCATGATCGCTGAGACGACCA

TACTCGGTTGACACGTGTGAATTGGTGACCAGCTCGAATTTCCCCGATC*G*

*TTCAAACATTTGGCAATAAAGTTTCTTAAGATTGAATCCTGTTGCCGGTC*

*TTGCGATGATTATCATATAATTTCTGTTGAATTACGTTAAGCATGTAATA*

*ATTAACATGTAATGCATGACGTTATTTATGAGATGGGTTTTTATGATTAG*

*AGTCCCGCAATTATACATTTAATACGCGATAGAAAACAAAATATAGCGCG*

CAAACTAGGATAAATTATCGCGCGCGGTGTCATCTATGTTACTAGATCGG
GAATTAAACTATCAGTGTTTGACAGGATATATTGGCGGGTAAACCTAAGA
GAAAAGAGCGTTTATTAGAATAACGGATATTTAAAAGGGCGTGAAAAGG
TTTATCCGTTCGTCCATTTGTATGTGCATGCCAACCACAGGGTTCCCCT
CGGGATCAAAGTACTTTGATCCAACCCCTCCGCTGCTATAGTGCAGTCG
GCTTCTGACGTTCAGTGCAGCCGTCTTCTGAAAACGACATGTCGCACAA
GTCCTAAGTTACGCGACAGGCTGCCGCCCTGCCCTTTTCCTGGCGTTTT
CTTGTCGCGTGTTTTAGTCGCATAAAGTAGAATACTTGCGACTAGAACC
GGAGACATTACGCCATGAACAAGAGCGCCGCCGCTGGCCTGCTGGGCTA
TGCCCGCGTCAGCACCGACGACCAGGACTTGACCAACCAACGGGCCGAA
CTGCACGCGGCCGGCTGCACCAAGCTGTTTTCCGAGAAGATCACCGGCA
CCAGGCGCGACCGCCCGGAGCTGGCCAGGATGCTTGACCACCTACGCCC
TGGCGACGTTGTGACAGTGACCAGGCTAGACCGCCTGGCCCGCAGCACC
CGCGACCTACTGGACATTGCCGAGCGCATCCAGGAGGCCGGCGCGGGCC
TGCGTAGCCTGGCAGAGCCGTGGGCCGACACCACCACGCCGGCCGGCCG
CATGGTGTTGACCGTGTTCGCCGGCATTGCCGAGTTCGAGCGTTCCCTA
ATCATCGACCGCACCCGGAGCGGGCGCGAGGCCGCCAAGGCCCGAGGCG
TGAAGTTTGGCCCCCGCCCTACCCTCACCCCGGCACAGATCGCGCACGC
CCGCGAGCTGATCGACCAGGAAGGCCGCACCGTGAAAGAGGCGGCTGCA
CTGCTTGGCGTGCATCGCTCGACCCTGTACCGCGCACTTGAGCGCAGCG
AGGAAGTGACGCCCACCGAGGCCAGGCGGCGCGGTGCCTTCCGTGAGGA
CGCATTGACCGAGGCCGACGCCCTGGCGGCCGCCGAGAATGAACGCCAA
GAGGAACAAGCATGAAACCGCACCAGGACGGCCAGGACGAACCGTTTTT
CATTACCGAAGAGATCGAGGCGGAGATGATCGCGGCCGGGTACGTGTTC
GAGCCGCCCGCGCACGTCTCAACCGTGCGGCTGCATGAAATCCTGGCCG
GTTTGTCTGATGCCAAGCTGGCGGCCTGGCCGGCCAGCTTGGCCGCTGA
AGAAACCGAGCGCCGCCGTCTAAAAAGGTGATGTGTATTTGAGTAAAAC
AGCTTGCGTCATGCGGTCGCTGCGTATATGATGCGATGAGTAAATAAAC
AAATACGCAAGGGGAACGCATGAAGGTTATCGCTGTACTTAACCAGAAA
GGCGGGTCAGGCAAGACGACCATCGCAACCCATCTAGCCCGCGCCCTGC
AACTCGCCGGGGCCGATGTTCTGTTAGTCGATTCCGATCCCCAGGGCAG
TGCCCGCGATTGGGCGGCCGTGCGGGAAGATCAACCGCTAACCGTTGTC
GGCATCGACCGCCCGACGATTGACCGCGACGTGAAGGCCATCGGCCGGC
GCGACTTCGTAGTGATCGACGGAGCGCCCCAGGCGGCGGACTTGGCTGT
GTCCGCGATCAAGGCAGCCGACTTCGTGCTGATTCCGGTGCAGCCAAGC
CCTTACGACATATGGGCCACCGCCGACCTGGTGGAGCTGGTTAAGCAGC
GCATTGAGGTCACGGATGGAAGGCTACAAGCGGCCTTTGTCGTGTCGCG
GGCGATCAAAGGCACGCGCATCGGCGGTGAGGTTGCCGAGGCGCTGGCC
GGGTACGAGCTGCCCATTCTTGAGTCCCGTATCACGCAGCGCGTGAGCT
ACCCAGGCACTGCCGCCGCCGGCACAACCGTTCTTGAATCAGAACCCGA

GGGCGACGCTGCCCGCGAGGTCCAGGCGCTGGCCGCTGAAATTAAATCA
AAACTCATTTGAGTTAATGAGGTAAAGAGAAAATGAGCAAAAGCACAAA
CACGCTAAGTGCCGGCCGTCCGAGCGCACGCAGCAGCAAGGCTGCAACG
TTGGCCAGCCTGGCAGACACGCCAGCCATGAAGCGGGTCAACTTTCAGT
TGCCGGCGGAGGATCACACCAAGCTGAAGATGTACGCGGTACGCCAAGG
CAAGACCATTACCGAGCTGCTATCTGAATACATCGCGCAGCTACCAGAG
TAAATGAGCAAATGAATAAATGAGTAGATGAATTTTAGCGGCTAAAGGA
GGCGGCATGGAAAATCAAGAACAACCAGGCACCGACGCCGTGGAATGCC
CCATGTGTGGAGGAACGGGCGGTTGGCCAGGCGTAAGCGGCTGGGTTGT
CTGCCGGCCCTGCAATGGCACTGGAACCCCCAAGCCCGAGGAATCGGCG
TGACGGTCGCAAACCATCCGGCCCGGTACAAATCGGCGCGGCGCTGGGT
GATGACCTGGTGGAGAAGTTGAAGGCCGCGCAGGCCGCCCAGCGGCAAC
GCATCGAGGCAGAAGCACGCCCCGGTGAATCGTGGCAAGCGGCCGCTGA
TCGAATCCGCAAAGAATCCCGGCAACCGCCGGCAGCCGGTGCGCCGTCG
ATTAGGAAGCCGCCCAAGGGCGACGAGCAACCAGATTTTTTCGTTCCGA
TGCTCTATGACGTGGGCACCCGCGATAGTCGCAGCATCATGGACGTGGC
CGTTTTCCGTCTGTCGAAGCGTGACCGACGAGCTGGCGAGGTGATCCGC
TACGAGCTTCCAGACGGGCACGTAGAGGTTTCCGCAGGGCCGGCCGGCA
TGGCCAGTGTGTGGGATTACGACCTGGTACTGATGGCGGTTTCCCATCT
AACCGAATCCATGAACCGATACCGGGAAGGGAAGGGAGACAAGCCCGGC
CGCGTGTTCCGTCCACACGTTGCGGACGTACTCAAGTTCTGCCGGCGAG
CCGATGGCGGAAAGCAGAAAGACGACCTGGTAGAAACCTGCATTCGGTT
AAACACCACGCACGTTGCCATGCAGCGTACGAAGAAGGCCAAGAACGGC
CGCCTGGTGACGGTATCCGAGGGTGAAGCCTTGATTAGCCGCTACAAGA
TCGTAAAGAGCGAAACCGGGCGGCCGGAGTACATCGAGATCGAGCTAGC
TGATTGGATGTACCGCGAGATCACAGAAGGCAAGAACCCGGACGTGCTG
ACGGTTCACCCCGATTACTTTTTGATCGATCCCGGCATCGGCCGTTTTC
TCTACCGCCTGGCACGCCGCGCCGCAGGCAAGGCAGAAGCCAGATGGTT
GTTCAAGACGATCTACGAACGCAGTGGCAGCGCCGGAGAGTTCAAGAAG
TTCTGTTTCACCGTGCGCAAGCTGATCGGGTCAAATGACCTGCCGGAGT
ACGATTTGAAGGAGGAGGCGGGGCAGGCTGGCCCGATCCTAGTCATGCG
CTACCGCAACCTGATCGAGGGCGAAGCATCCGCCGGTTCCTAATGTACG
GAGCAGATGCTAGGGCAAATTGCCCTAGCAGGGGAAAAAGGTCGAAAAG
GTCTCTTTCCTGTGGATAGCACGTACATTGGGAACCCAAAGCCGTACAT
TGGGAACCGGAACCCGTACATTGGGAACCCAAAGCCGTACATTGGGAAC
CGGTCACACATGTAAGTGACTGATATAAAAGAGAAAAAAGGCGATTTTT
CCGCCTAAAACTCTTTAAAACTTATTAAAACTCTTAAAACCCGCCTGGC
CTGTGCATAACTGTCTGGCCAGCGCACAGCCGAAGAGCTGCAAAAAGCG
CCTACCCTTCGGTCGCTGCGCTCCCTACGCCCCGCCGCTTCGCGTCGGC
CTATCGCGGCCGCTGGCCGCTCAAAAATGGCTGGCCTACGGCCAGGCAA

```
TCTACCAGGGCGCGGACAAGCCGCGCCGTCGCCACTCGACCGCCGGCGC
CCACATCAAGGCACCCTGCCTCGCGCGTTTCGGTGATGACGGTGAAAAC
CTCTGACACATGCAGCTCCCGGAGACGGTCACAGCTTGTCTGTAAGCGG
ATGCCGGGAGCAGACAAGCCCGTCAGGGCGCGTCAGCGGGTGTTGGCGG
GTGTCGGGGCGCAGCCATGACCCAGTCACGTAGCGATAGCGGAGTGTAT
ACTGGCTTAACTATGCGGCATCAGAGCAGATTGTACTGAGAGTGCACCA
TATGCGGTGTGAAATACCGCACAGATGCGTAAGGAGAAAATACCGCATC
AGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATC
CACAGAATCAGGGGATAACGCAGGAAAGAACATGTGAGCAAAAGGCCAG
CAAAAGGCCAGGAACCGTAAAAAGGCCGCGTTGCTGGCGTTTTTCCATA
GGCTCCGCCCCCTGACGAGCATCACAAAAATCGACGCTCAAGTCAGAG
GTGGCGAAACCCGACAGGACTATAAAGATACCAGGCGTTTCCCCCTGGA
AGCTCCCTCGTGCGCTCTCCTGTTCCGACCCTGCCGCTTACCGGATACC
TGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGT
GTGCACGAACCCCCCGTTCAGCCCGACCGCTGCGCCTTATCCGGTAACT
ATCGTCTTGAGTCCAACCCGGTAAGACACGACTTATCGCCACTGGCAGC
AGCCACTGGTAACAGGATTAGCAGAGCGAGGTATGTAGGCGGTGCTACA
GAGTTCTTGAAGTGGTGGCCTAACTACGGCTACACTAGAAGGACAGTAT
TTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTT
GTTTGCAAGCAGCAGATTACGCGCAGAAAAAAAGGATCTCAAGAAGATC
CTTTGATCTTTTCTACGGGGTCTGACGCTCAGTGGAACGAAAACTCACG
TTAAGGGATTTTGGTCATGCATTCTAGGTACTAAAACAATTCATCCAGT
AAAATATAATATTTTATTTTCTCCCAATCAGGCTTGATCCCCAGTAAGT
CAAAAAATAGCTCGACATACTGTTCTTCCCCGATATCCTCCCTGATCGA
CCGGACGCAGAAGGCAATGTCATACCACTTGTCCGCCCTGCCGCTTCTC
CCAAGATCAATAAAGCCACTTACTTTGCCATCTTTCACAAAGATGTTGC
TGTCTCCCAGGTCGCCGTGGGAAAAGACAAGTTCCTCTTCGGGCTTTTC
CGTCTTTAAAAAATCATACAGCTCGCGCGGATCTTTAAATGGAGTGTCT
TCTTCCCAGTTTTCGCAATCCACATCGGCCAGATCGTTATTCAGTAAGTA
ATCCAATTCGGCTAAGCGGCTGTCTAAGCTATTCGTATAGGGACAATCC
GATATGTCGATGGAGTGAAAGAGCCTGATGCACTCCGCATACAGCTCGA
TAATCTTTTCAGGGCTTTGTTCATCTTCATACTCTTCCGAGCAAAGGAC
GCCATCGGCCTCACTCATGAGCAGATTGCTCCAGCCATCATGCCGTTCA
AAGTGCAGGACCTTTGGAACAGGCAGCTTTCCTTCCAGCCATAGCATCA
TGTCCTTTTCCCGTTCCACATCATAGGTGGTCCCTTTATACCGGCTGTC
CGTCATTTTTAAATATAGGTTTTCATTTTCTCCCACCAGCTTATATACC
TTAGCAGGAGACATTCCTTCCGTATCTTTTACGCAGCGGTATTTTTCGA
TCAGTTTTTTCAATTCCGGTGATATTCTCATTTTAGCCATTTATTATTT
CCTTCCTCTTTTCTACAGTATTTAAAGATACCCCAAGAAGCTAATTATA
ACAAGACGAACTCCAATTCACTGTTCCTTGCATTCTAAAACCTTAAATA
CCAGAAAACAGCTTTTTCAAAGTTGTTTTCAAAGTTGGCGTATAACATA
GTATCGACGGAGCCGATTTTGAAACCGCGGTGATCACAGGCAGCAACGC
TCTGTCATCGTTACAATCAACATGCTACCCTCCGCGAGATCATCCGTGT
TTCAAACCCGGCAGCTTAGTTGCCGTTCTTCCGAATAGCATCGGTAACA
TGAGCAAAGTCTGCCGCCTTACAACGGCTCTCCCGCTGACGCCGTCCCG
GACTGATGGGCTGCCTGTATCGAGTGGTGATTTTGTGCCGAGCTGCCGG
TCGGGGAGCTGTTGGCTGGCTGGTGGCAGGATATATTGTGGTGTAAACA
AATTGACGCTTAGACAACTTAATAACACATTGCGGACGTTTTTAATGTA
CTGAATTAACGCCGAATTAATTCGGGGGATCTGGATTTTAGTACTGGAT
TTTGGTTTTAGGAATTAGAAATTTTATTGATAGAAGTATTTTACAAATA
CAAATACATACTAAGGGTTTCTTATATGCTCAACACATGAGCGAAACCC
TATAGGAACCCTAATTCCCTTATCTGGGAACTACTCACACATTATTATG
GAGAAACTCGAGCTTGTCGATCGACAGATCCGGTCGGCATCTACTCTAT
TTCTTTGCCCTCGGACGAGTGCTGGGCGTCGGTTTCCACTATCGGCGA
GTACTTCTACACAGCCATCGGTCCAGACGGCCGCGCTTCTGCGGGCGAT
TTGTGTACGCCCGACAGTCCCGGCTCCGGATCGGACGATTGCGTCGCAT
CGACCCTGCGCCCAAGCTGCATCATCGAAATTGCCGTCAACCAAGCTCT
GATAGAGTTGGTCAAGACCAATGCGGAGCATATACGCCCGGAGTCGTGG
CGATCCTGCAAGCTCCGGATGCCTCCGCTCGAAGTAGCGCGTCTGCTGC
TCCATACAAGCCAACCACGGCCTCCAGAAGAAGATGTTGGCGACCTCGT
ATTGGGAATCCCCGAACATCGCCTCGCTCCAGTCAATGACCGCTGTTAT
GCGGCCATTGTCCGTCAGGACATTGTTGGAGCCGAAATCCGCGTGCACG
AGGTGCCGGACTTCGGGGCAGTCCTCGGCCCAAAGCATCAGCTCATCGA
GAGCCTGCGCGACGGACGCACTGACGGTGTCGTCCATCACAGTTTGCCA
GTGATACACATGGGGATCAGCAATCGCGCATATGAAATCACGCCATGTA
GTGTATTGACCGATTCTTGCGGTCCGAATGGGCCGAACCCGCTCGTCT
GGCTAAGATCGGCCGCAGCGATCGCATCCATAGCCTCCGCGACCGGTTG
TAGAACAGCGGGCAGTTCGGTTTCAGGCAGGTCTTGCAACGTGACACCC
TGTGCACGGCGGGAGATGCAATAGGTCAGGCTCTCGCTAAACTCCCCAA
TGTCAAGCACTTCCGGAATCGGGAGCGCGGCCGATGCAAAGTGCCGATA
AACATAACGATCTTTGTAGAAACCATCGGCGCAGCTATTTACCCGCAGG
ACATATCCACGCCCTCCTACATCGAAGCTGAAAGCACGAGATTCTTCGC
CCTCCGAGAGCTGCATCAGGTCGGAGACGCTGTCGAACTTTTCGATCAG
AAACTTCTCGACAGACGTCGCGGTGAGTTCAGGCTTTTTCATATCTCAT
TGCCCCCCGGGATCTGCGAAAGCTCGAGAGAGATAGATTTGTAGAGAGA
GACTGGTGATTTCAGCGTGTCCTCTCCAAATGAAATGAACTTCCTTATA
TAGAGGAAGGTCTTGCGAAGGATAGTGGGATTGTGCGTCATCCCTTACG
```

-continued

```
TCAGTGGAGATATCACATCAATCCACTTGCTTTGAAGACGTGGTTGGAA
CGTCTTCTTTTTCCACGATGCTCCTCGTGGGTGGGGGTCCATCTTTGGG
ACCACTGTCGGCAGAGGCATCTTGAACGATAGCCTTTCCTTTATCGCAA
TGATGGCATTTGTAGGTGCCACCTTCCTTTTCTACTGTCCTTTTGATGA
AGTGACAGATAGCTGGGCAATGGAATCCGAGGAGGTTTCCCGATATTAC
CCTTTGTTGAAAAGTCTCAATAGCCCTTTGGTCTTCTGAGACTGTATCT
TTGATATTCTTGGAGTAGACGAGAGTGTCGTGCTCCACCATGTTATCAC
ATCAATCCACTTGCTTTGAAGACGTGGTTGGAACGTCTTCTTTTTCCAC
GATGCTCCTCGTGGGTGGGGGTCCATCTTTGGGACCACTGTCGGCAGAG
GCATCTTGAACGATAGCCTTTCCTTTATCGCAATGATGGCATTTGTAGG
TGCCACCTTCCTTTTCTACTGTCCTTTTGATGAAGTGACAGATAGCTGG
GCAATGGAATCCGAGGAGGTTTCCCGATATTACCCTTTGTTGAAAAGTC
TCAATAGCCCTTTGGTCTTCTGAGACTGTATCTTTGATATTCTTGGAGT
AGACGAGAGTGTCGTGCTCCACCATGTTGGCAAGCTGCTCTAGCCAATA
CGCAAACCGCCTCTCCCCGCGCGTTGGCCGATTCATTAATGCAGCTGGC
ACGACAGGTTTCCCGACTGGAAAGCGGGCAGTGAGCGCAACGCAATTAA
TGTGAGTTAGCTCACTCATTAGGCACCCCAGGCTTTACACTTTATGCTT
CCGGCTCGTATGTTGTGTGGAATTGTGAGCGGATAACAATTTCACACAG
GAAACAGCTATGACCATGATTACGAATTCGAGCTC
```

Transformation and Selection:

Transformation of *Arabidopsis* was achieved using *Agrobacterium*-mediated "floral dip" transfer as described in Example 4. Transformed plants were grown under selection as described in Example 4.

Biochemical Characterization:

Assays for 2-oxoglutaramate, ω-amidase, GS and GPT were conducted as described in Example 3, supra.

Results:

GPT activity and GS activity of wild type and transgenic *Arabidopsis* plants were measured and are shown in Table 11, below. Ω-amidase activities and 2-oxoglutaramate concentrations in wild type and transgenic *Arabidopsis* plants were measured in both leaf and root tissues, and are shown in Table 12, below.

TABLE 11

| *Arabidopsis* Genotype | FWt mg Whole plant | GS Activity umoles/gfwt/min | | | | GPT Activity nmoles/gfwt/hr | | |
|---|---|---|---|---|---|---|---|---|
| | | Root | Leaf | L/R | | Root | Leaf | L/R |
| Wild type* | 77 | 1.5 | 3.4 | 2.3 | | 167 | 132 | 0.8 |
| TG GPT (9c) + GS (4c) + ω-amidase** | 709 | 1.6 | 9.4 | 5.9 | | 182 | 414 | 2.3 |

TG = Transgenic
GPT (9c) = –45 truncated GPT variant [SEQ ID NO: 41]
GS 4c = SEQ ID NO: 43
*Average values of 9 plants
**Average values of 5 plants

TABLE 12

| *Arabidopsis* Genotype | FWt mg Whole plant | Ω-amidase nmoles/gfwt/hr | | | 2-Oxoglutaramate Concentration nmoles/gfwt | | |
|---|---|---|---|---|---|---|---|
| | | Root | Leaf | L/R Ratio | Root | Leaf | L/R Ratio |
| Wild type* | 77 | 86 | 1090 | 12.7 | 410 | 163 | 0.4 |
| TG GPT (9c) + GS (4c) + ω-amidase** | 709 | 195 | 344 | 1.8 | 113 | 223 | 2.0 |

TG = Transgenic
GPT (9c) = –45 truncated GPT variant [SEQ ID NO: 41]
*Average values of 9 plants
**Average values of 5 plants Compared to wild type control *Arabidopsis* plants, the transgenic *Arabidopsis* plants carrying the ω-amidase directed for root expression, and truncated GPT (for cyosolic expression) and GS1 directed for leaf expression, showed biochemical changes within the ω-amidase pathway similar to those observed in the transgenic plants of Examples 4 and 5, supra. More specifically, transgenic GPT+ω-amidase plants showed increased root ω-amidase activity, reduced root 2-oxoglutaramate concentration, and increased leaf-to-root 2-oxoglutaramate ratios. Also, similar to the results seen in the transgenic plants of Examples 5 and 6, the GPT+GS+ω-amidase transgenic plants showed significant reductions in leaf ω-amidase activity levels, increased leaf 2-oxoglutaramate, and higher leaf GS and leaf GPT activities. The resulting impact on growth was greater than observed for the transgenic plants of either Example 4 or Example 5, with the transgenic plants weighing more than nine times the weight of the wild type plants, on average.

Example 7

Comparison of Transgenic *Arabidopsis* Genotypes Carrying Root-Preferred Ω-Amidase Transgene The data generated from the studies of Examples 4, 5, and 6, which were conducted in parallel, are presented together for comparison in Tables 13 and 14 below.

TABLE 13

| Genotype | FWt mg Whole plant | GS Activity umoles/gfwt/min | | | GPT Activity nmoles/gfwt/hr | | |
|---|---|---|---|---|---|---|---|
| | | Root | Leaf | L/R | Root | Leaf | L/R |
| Wild type* | 77 | 1.5 | 3.4 | 2.3 | 167 | 132 | 0.8 |
| WT + ω-amidase** | 479 | 1.4 | 5.8 | 4.1 | 192 | 486 | 2.5 |
| GPT (6c) + ω-amidase | 513 | 1.8 | 8.25 | 4.6 | 232 | 389 | 1.7 |
| GPT (9c) + GS + ω-amidase*** | 709 | 1.6 | 9.4 | 5.9 | 182 | 414 | 2.3 |

*Average values of 9 plants
**Average values of 6 plants
***Average values of 5 plants

TABLE 14

| Genotype | FWt mg Whole plant | Ω-amidase nmoles/gfwt/hr | | | 2-Oxoglutaramate Concentration nmoles/gfwt | | |
|---|---|---|---|---|---|---|---|
| | | Root | Leaf | L/R | Root | Leaf | L/R |
| Wild type* | 77 | 86 | 1090 | 12.7 | 410 | 163 | 0.4 |
| WT + ω-amidase** | 479 | 243 | 127 | 0.5 | 98 | 305 | 3.1 |
| GPT (6c) + ω-amidase*** | 513 | 308 | 584 | 1.9 | 268 | 275 | 1.0 |
| GPT (9c) + GS + ω-amidase*** | 709 | 195 | 344 | 1.8 | 113 | 223 | 2.0 |

*Average values of 9 plants
**Average values of 6 plants
***Average values of 5 plants Example 8

Chemical Inhibition of Ω-Amidase Activity in Leaf and Root Tissues and Modulation of Leaf-to-Root Ratio of 2-Oxoglutaramate This example demonstrates how the concentration of 2-oxoglutaramate changes in response to foliar and root treatment with 6-diazo-5-oxo-nor-leucine (DON), an inhibitor of the ω-amidase enzyme which breaks-down 2-oxoglutaramate (Duran and Calderon, 1995, Role of the glutamine transaminase-ω-amidase pathway and glutaminase in glutamine degradation in *Rhizobium etli*. Microbiology 141:589-595).

Materials and Methods:
Nutrient Solution:
Columbia nutrient solution was utilized (Knight and Weissman, 1982, Plant Physiol. 70: 1683).
Leaf Treatments:
Plants were grown in sand at 24° C. using a 16 hour/day light and 8 hour/day dark photoperiod. Seeds were germinated in the sand and allowed to grow for 9-14 days after seedling emergence. Seedlings (1 per 3 inch pot) were provided nutrients daily. The top of each pot was covered with Saran plastic film, with a slit cut to allow the seedlings room to emerge, in order to prevent treatment solution from reaching the soil. Leaves were treated by spraying DON treatment/nutrient solution twice daily. The DON treatment/nutrient solution contained 1 microgram/ml DON, 50 micoliters/liter SILWET L77 (a surfactant) and 0.02 vol/vol % glycerol (a humectant) at pH 6.3, dissolved in nutrient solution. Control plants were sprayed daily with the same solution without DON. An airbrush was used to apply the solutions until drip. Plants were sacrificed and analyzed for fresh weight, ω-amidase activity, and 2-oxoglutaramate concentrations in leaf and root tissue 14 days after initiation of treatment.
Root Treatments:
Plants were grown hydroponically at 24° C. using a 16 hour/day light and 8 hour/day dark photoperiod. Seeds were first germinated and seedlings were grown for 9 days, at which time the individual seedlings were suspended with their roots in the nutrient solution (600 ml of nutrient, pH 6.3) in an 800 ml beaker covered with aluminum foil, with a slit for the seedlings, to prevent algal growth. The beakers were aerated with air provided by a small pump and delivered into the solution through a glass Pasteur pipette. For the treatments, DON was added to the nutrient solution to a final concentration of 1 microgram per ml. Thus DON was supplied continuously to the treated seedlings. The controls were grown in the same nutrient solution without DON. The solutions were refreshed every third day. Plants were sacrificed and analyzed for fresh weight, ω-amidase activity, and 2-oxoglutaramate concentrations in leaf and root tissue 14 days after initiation of treatment.

Results:
Treatment of Roots with Ω-amidase Inhibitor:
Sweet corn and pole bean plant roots were treated with DON as described above. The results of the root treatments are shown in Tables 15 and 16 below. None of the DON treated plants had detectable levels of ω-amidase activity, whereas the control wild type plants maintained normal levels of ω-amidase activity. Indeed, all corn and bean plants subjected to continuous DON treatment of roots showed severely stunted growth, in contrast to vigorous growth of untreated control plants. Control plants increased their fresh weighs throughout the experimental period up to nearly eight-fold.

Dramatic reductions in the 2-oxoglutaramate leaf-to-root ratio were observed in both corn and bean plants treated with the ω-amidase inhibitor. Treated plants accumulated very large amounts of 2-oxoglutaramate in their roots (over 30-fold increase in corn; 15-fold increase in beans) while maintaining normal levels in their leaves.

TABLE 15

INHIBITION OF Ω-AMIDASE IN CORN ROOTS

| CORN | % INCREASE IN FWT (initial wt) | 2-OGM LEAF nmoles/gfwt | 2-OGM ROOT nmoles/gfwt | LEAF/ ROOT RATIO |
|---|---|---|---|---|
| CONTROL | 370% (1.26 g) | 276 | 65 | 4.25 |
| TREATED | 174% (0.96 g) | 300 | 2288 | 0.13 |

2-OGM = 2-oxoglutaramate

TABLE 16

INHIBITION OF Ω-AMIDASE IN BEAN ROOTS

| BEAN | % INCREASE IN FWT (initial wt) | 2-OGM LEAF nmoles/gfwt | 2-OGM ROOT nmoles/gfwt | LEAF/ ROOT RATIO |
|---|---|---|---|---|
| CONTROL | 839% (1.134 g) | 311.2 | 101.4 | 3.07 |
| TREATED | 198% (1.104 g) | 279 | 1586 | 0.18 |

2-OGM = 2-oxoglutaramate

Treatment of Leaves with Ω-Amidase Inhibitor:
Corn plant leaves were treated with DON as described above. The results are shown in Tables 17 and 18, below. Ω-amidase activity in leaf was effectively suppressed by DON, with the treated plants showing only about 50% the ω-amidase activity observed in untreated plants (Table 18). A dramatic increase in leaf 2-oxoglutaramate and the leaf-to-root 2-oxoglutaramate ratio was observed in the treated plants (Tables 17 and 18). Specifically, treated plants accumulated very large amounts of 2-oxoglutaramate in their leaves (more than 7-fold increase over untreated plants). Moreover, inhibition of ω-amidase activity in leaves also resulted in a near doubling of corn plant fresh weights (Table 18).

TABLE 17

INHIBITION OF Ω-AMIDASE IN CORN LEAVES RESULTS IN INCREASED LEAF-TO-ROOT RATIO 2-OXOGLUTARAMATE

| CORN | 2-OGM LEAF nmoles/gfwt | 2-OGM ROOT nmoles/gfwt | LEAF/ROOT RATIO |
|---|---|---|---|
| CONTROL | 101.3 | 344.1 | 0.29 |
| TREATED | 753.9 | 126.8 | 5.0 |

2-OGM = 2-oxoglutaramate
gfwt = grams fresh weight

TABLE 18

INHIBITION OF Ω-AMIDASE IN CORN LEAVES RESULTS IN INCREASED GROWTH

| | CORN | | | | | |
|---|---|---|---|---|---|---|
| | Whole Plant Fresh Wt, g | | Amidase activity Leaf, µmole/gfw/hr | | 2-Oxoglutaramate Concentration nmoles/gfwt | |
| | Control | Treated | Control | Treated | Control | Treated |
| | 9.3 | 20.9 | | | | |
| | 12.4 | 19.2 | | | | |
| | 11.3 | 24.3 | | | | |
| Average | 11.0 | 21.4 | 0.261 | 0.135 | 101.3 | 838.8 | gfwt = grams fresh weight

Example 9

Comparison of GPT Isoforms in Combination with Root-Preferred Ω-Amidase

This Example compares the growth-enhancing performance of three different GPT transgene isoforms in combination with root-preferred expression of an ω-amidase transgene on *Arabidopsis* plant growth. The ω-amidase expression construct used in all three combinations is as described in Example 3 [SEQ ID NO: 39]. The three GPT transgene isoforms were: (1) GPT 5c, full length *Arabidopsis* GPT codon optimized [SEQ ID NO: 42]; (2) GPT 6c, truncated −45 GPT (deleted chloroplast targeting sequence), codon optimized [SEQ ID NO: 40]; and, (3) GPT 9c, truncated −45 GPT (deleted chloroplast targeting sequence), codon optimized, mutation F to V at amino acid residue 45 [SEQ ID NO: 41].

The nucleotide sequence of the Cambia 1305.1 with rbcS3C promoter+catI intron with *Arabidopsis* GPT gene is set forth below as SEQ ID NO: 42. Underlined ATG is start site, parentheses are the catI intron and the underlined actagt is the speI cloning site used to splice in the *Arabidopsis* gene.

AAAAAAGAAAAAAAAAACATATCTTGTTTGTCAGTATGGGAAGTTTGAGA

TAAGGACGAGTGAGGGGTTAAAATTCAGTGGCCATTGATTTTGTAATGC

CAAGAACCACAAAATCCAATGGTTACCATTCCTGTAAGATGAGGTTTGC

TAACTCTTTTTGTCCGTTAGATAGGAAGCCTTATCACTATATATACAAG

GCGTCCTAATAACCTCTTAGTAACCAATTATTTCAGCACCATGGTA

GATCTGAGG(GTAAATTTCTAGTTTTTCTCCTTCATTTTCTTGGTTAGG

ACCCTTTTCTCTTTTTATTTTTTTGAGCTTTGATCTTTCTTTAAACTGAT

CTATTTTTAATTGATTGGTTATGGTGTAAATATTACATAGCTTTAACTG

ATAATCTGATTACTTTATTTCGTGTGTCTATGATGATGATGATAGTTACA

G)AACCGACGAACTAGTATGTACCTGGACATAAATGGTGTGATGATC

AAACAGTTTAGCTTCAAAGCCTCTCTTCTCCCATTCTCTTCTAATTTCCG

ACAAAGCTCCGCCAAAATCCATCGTCCTATCGGAGCCACCATGACCACAG

TTTCGACTCAGAACGAGTCTACTCAAAAACCCGTCCAGGTGGCGAAGAGA

TTAGAGAAGTTCAAGACTACTATTTTCACTCAAATGAGCATATTGGCAGT

TAAACATGGAGCGATCAATTTAGGCCAAGGCTTTCCCAATTTCGACGGTC

CTGATTTTGTTAAAGAAGCTGCGATCCAAGCTATTAAAGATGGTAAAAAC

CAGTATGCTCGTGGATACGGCATTCCTCAGCTCAACTCTGCTATAGCTGC

GCGGTTTCGTGAAGATACGGGTCTTGTTGTTGATCCTGAGAAAGAAGTTA

CTGTTACATCTGGTTGCACAGAAGCCATAGCTGCAGCTATGTTGGGTTTA

ATAAACCCTGGTGATGAAGTCATTCTCTTTGCACCGTTTTATGATTCCTA

TGAAGCAACACTCTCTATGGCTGGTGCTAAAGTAAAAGGAATCACTTTAC

GTCCACCGGACTTCTCCATCCCTTTGGAAGAGCTTAAAGCTGCGGTAACT

AACAAGACTCGAGCCATCCTTATGAACACTCCGCACAACCCGACCGGGAA

GATGTTCACTAGGGAGGAGCTTGAAACCATTGCATCTCTCTGCATTGAAA

ACGATGTGCTTGTGTTCTCGGATGAAGTATACGATAAGCTTGCGTTTGAA

ATGGATCACATTTCTATAGCTTCTCTTCCCGGTATGTATGAAAGAACTG

TGACCATGAATTCCCTGGGAAAGACTTTCTCTTTAACCGGATGGAAGAT

CGGCTGGGCGATTGCGCCGCCTCATCTGACTTGGGGAGTTCGACAAGCA

CACTCTTACCTCACATTCGCCACATCAACACCAGCACAATGGGCAGCCG

TTGCAGCTCTCAAGGCACCAGAGTCTTACTTCAAAGAGCTGAAAAGAGA

TTACAATGTGAAAAAGGAGACTCTGGTTAAGGGTTTGAAGGAAGTCGGA

TTTACAGTGTTCCCATCGAGCGGGACTTACTTTGTGGTTGCTGATCACA

CTCCATTTGGAATGGAGAACGATGTTGCTTTCTGTGAGTATCTTATTGA

AGAAGTTGGGGTCGTTGCGATCCCAACGAGCGTCTTTTATCTGAATCCA

GAAGAAGGGAAGAATTTGGTTAGGTTTGCGTTCTGTAAAGACGAAGAGA

CGTTGCGTGGTGCAATTGAGAGGATGAAGCAGAAGCTTAAGAGAAAAGT

CTGA

The results are shown in Table 19 below. Both of the GPT isoforms in which the chloroplast transit peptide was deleted outperform the wild type and full length GPT isoform plants.

TABLE 19

TRUNCATED GPT ISOFORMS OUTPERFORM NATIVE GPT

| Genotype | Fresh Wt, mg | Mean weight, mg | SD+/− | % Increase |
|---|---|---|---|---|
| Wild type (average of 9 plants) | | 77 | 27 | 0 |
| 5c GPT + ω-amidase | 357 | | | |
| | 456 | | | |
| | 459 | | | |
| | 198 | 371 | 149 | 482 |
| 6cGPT + ω-amidase | 525 | | | |
| | 438 | | | |
| | 560 | | | |
| | 501 | | | |
| | 552 | 513 | 56 | 666 |

TABLE 19-continued

TRUNCATED GPT ISOFORMS OUTPERFORM NATIVE GPT

| Genotype | Fresh Wt, mg | Mean weight, mg | SD+/− | % Increase |
|---|---|---|---|---|
| 9c GPT + ω-amidase | 390 | | | |
| | 359 | | | |
| | 405 | | | |
| | 387 | | | |
| | 574 | 431 | 99 | 560 |

What is claimed is:

1. A transgenic plant comprising an ω-amidase transgene, wherein the ω-amidase transgene is operably linked to a root-preferred promoter and wherein the ω-amidase transgene encodes an ω-amidase protein having an amino acid sequence that is at least 90% identical to SEQ ID NO: 3, wherein the transgenic plant has increased biomass relative to a plant of the same species that does not comprise the ω-amidase transgene.

2. The transgenic plant according to claim 1, wherein the ω-amidase transgene is incorporated into the genome of the plant.

3. The transgenic plant according to claim 1, wherein the root-preferred promoter is selected from the group consisting of RolD promoter, RolD-2 promoter, glycine rich protein promoter, GRP promoter, ADH promoter, maize ADH1 promoter, PHT promoter, Pht1 gene family promoter, metal uptake protein promoter, maize metallothionein protein promoter, 35S CaMV domain A promoter, pDJ3S promoter, SIREO promoter, pMe1 promoter, Sad1 promoter, Sad2 promoter, TobRB7 promoter, RCc3 promoter, FaRB7 promoter, SPmads promoter, IDS2 promoter, pyk10 promoter, Lbc3 leghemoglobin promoter, PEPC promoter, Gns1 glucanase root promoter, 35S2 promoter, GI4 promoter, GI5 promoter, and GRP promoter.

4. The transgenic plant according to claim 1, wherein endogenous ω-amidase expression in leaf tissue is inhibited.

5. The transgenic plant according to claim 4, wherein the endogenous ω-amidase expression in leaf tissue is inhibited by recessive gene disruption, dominant gene silencing, or a chemical inhibitor.

6. The transgenic plant according to claim 5, wherein the endogenous ω-amidase expression in leaf tissue is inhibited by a recessive gene disruption selected from the group consisting of a mutant ω-amidase gene that eliminates endogenous ω-amidase expression, an endogenous ω-amidase knockout mutant, and an endogenous ω-amidase knockdown mutant.

7. The transgenic plant according to claim 4, wherein the endogenous ω-amidase expression in leaf tissue is inhibited by an RNAi antisense oligonucleotide that is specific for an endogenous ω-amidase gene.

8. The transgenic plant according to claim 4, wherein the endogenous ω-amidase expression in leaf tissue is inhibited by a chemical inhibitor selected from the group consisting of 6-diazo-5-oxo-nor-leucine, p-hydroxymercuribenzoate, diisopropyl fluorophosphates, sodium cyanide, phenylmercuriacetate, iodoacetate, silver nitrate, chloromercuricphenylsulfonic acid, and copper sulfate.

9. The transgenic plant according to claim 1, wherein root-preferred expression of the ω-amidase transgene results in an increased leaf-to-root ratio of 2-oxoglutaramate relative to a plant of the same species that does not comprise the ω-amidase transgene.

10. The transgenic plant according to claim 9, wherein the leaf-to-root ratio of 2-oxoglutaramate is at least two times higher than that of a plant of the same species that does not comprise an ω-amidase transgene.

11. The transgenic plant according to claim 1, further comprising a GPT transgene.

12. The transgenic plant according to claim 11, wherein the GPT transgene is a GPT/F:V mutant given by SEQ ID NO:1.

13. The transgenic plant according to claim 1, further comprising a GPT transgene and a GS transgene.

14. The transgenic plant according to claim 13, wherein the GPT transgene and GS transgene are each operably linked to a leaf-preferred promoter.

15. The transgenic plant according to claim 1, wherein the transgene is codon optimized for expression in the plant.

16. The transgenic plant according to claim 1, wherein the transgenic plant has increased nitrogen use efficiency.

17. The transgenic plant according to claim 1, wherein the transgenic plant is selected from the group consisting of wheat, oats, rice, corn, bean, soybean, tobacco, alfalfa, *Arabidopsis*, grasses, fruits, vegetables, flowering plants, and trees.

18. A progeny of any generation of the transgenic plant according to claim 1, wherein the progeny comprises an ω-amidase transgene operably linked to a root-preferred promoter and wherein the ω-amidase transgene encodes an ω-amidase protein having an amino acid sequence that is at least 90% identical to SEQ ID NO: 3, wherein the transgenic plant has increased biomass relative to a plant of the same species that does not comprise the ω-amidase transgene.

19. A seed of any generation of the transgenic plant according to claim 1, wherein the seed comprises an ω-amidase transgene operably linked to a root-preferred promoter and wherein the ω-amidase transgene encodes an ω-amidase protein having an amino acid sequence that is at least 90% identical to SEQ ID NO: 3, wherein the seed germinates to produce a transgenic plant that has increased biomass relative to a plant of the same species that does not comprise the ω-amidase transgene.

20. A method for increasing biomass of a plant relative to a wild type or untransformed plant of the same species, comprising:

(a) introducing an ω-amidase transgene into the plant, wherein the ω-amidase transgene is operably linked to a root-preferred promoter and wherein the ω-amidase transgene encodes an ω-amidase protein having an amino acid sequence that is at least 90% identical to SEQ ID NO: 3;
(b) expressing the ω-amidase transgene in root tissue of the plant or the progeny of the plant; and
(c) selecting a plant having an increased biomass relative to a plant of the same species that does not comprise the ω-amidase transgene.

21. The method according to claim 20, wherein the ω-amidase transgene is incorporated into the genome of the plant.

22. The method according to claim 20, wherein the root-preferred promoter is selected from the group consisting of RolD promoter, RolD-2 promoter, glycine rich protein promoter, GRP promoter, ADH promoter, maize ADH1 promoter, PHT promoter, Pht1 gene family promoter, metal uptake protein promoter, maize metallothionein protein promoter, 35S CaMV domain A promoter, pDJ3S promoter, SIREO promoter, pMe1 promoter, Sad1 promoter, Sad2 promoter, TobRB7 promoter, RCc3 promoter, FaRB7 promoter, SPmads promoter, IDS2 promoter, pyk10 promoter, Lbc3 leghemoglobin promoter, PEPC promoter, Gns1 glucanase root promoter, 35S2 promoter, GI4 promoter, GI5 promoter, and GRP promoter.

23. The method according to claim 20, wherein endogenous ω-amidase expression in leaf tissue is inhibited.

24. The method according to claim 23, wherein the endogenous ω-amidase expression in leaf tissue is inhibited by recessive gene disruption, dominant gene silencing, or a chemical inhibitor.

25. The method according to claim 23, wherein the endogenous ω-amidase expression in leaf tissue is inhibited by a recessive gene disruption selected from the group consisting of a mutant ω-amidase gene that eliminates endogenous ω-amidase expression, an endogenous ω-amidase knockout mutant, and an endogenous ω-amidase knockdown mutant.

26. The method according to claim 23, wherein the endogenous ω-amidase expression in leaf tissue is inhibited by an RNAi antisense oligonucleotide that is specific for an endogenous ω-amidase gene.

27. The method according to claim 23, wherein the endogenous ω-amidase expression in leaf tissue is inhibited by a chemical inhibitor selected from the group consisting of 6-diazo-5-oxo-nor-leucine, p-hydroxymercuribenzoate, diisopropyl fluorophosphates, sodium cyanide, phenylmercuriacetate, Iodoacetate, silver nitrate, chloromercuricphenylsulfonic acid, and copper sulfate.

28. The method according to claim 20, wherein the leaf-to-root ratio of 2-oxoglutaramate is at least two times higher than that of a progenitor or wild type plant of the same species.

29. The method according to claim 20, wherein the plant further comprises a GPT transgene.

30. The method according to claim 29, wherein the GPT transgene is a GPT/F:V mutant given by SEQ ID NO:1.

31. The method according to claim 20, wherein the plant further comprises a GPT transgene and a GS transgene.

32. The method according to claim 31, wherein the GPT transgene and GS transgene are each operably linked to a leaf-preferred promoter.

33. The method according to claim 20, wherein the transgene is codon optimized for expression in the plant.

* * * * *

SEQUENCE LISTING

<160> NUMBER OF SEQ ID NOS: 46

<210> SEQ ID NO 1
<211> LENGTH: 440
<212> TYPE: PRT
<213> ORGANISM: Artificial Sequence
<220> FEATURE:
<223> OTHER INFORMATION: synthetic Arabidopsis glutamine phenylpyruvate
      transaminase (GPT) mutant GPT/F:V with V substitution in conserved
      region at position 88

<400> SEQUENCE: 1

```
Met Tyr Leu Asp Ile Asn Gly Val Met Ile Lys Gln Phe Ser Phe Lys
 1               5                  10                  15

Ala Ser Leu Leu Pro Phe Ser Ser Asn Phe Arg Gln Ser Ser Ala Lys
            20                  25                  30

Ile His Arg Pro Ile Gly Ala Thr Met Thr Thr Val Ser Thr Gln Asn
        35                  40                  45

Glu Ser Thr Gln Lys Pro Val Gln Val Ala Lys Arg Leu Glu Lys Phe
    50                  55                  60

Lys Thr Thr Ile Phe Thr Gln Met Ser Ile Leu Ala Val Lys His Gly
65                  70                  75                  80

Ala Ile Asn Leu Gly Gln Gly Val Pro Asn Phe Asp Gly Pro Asp Phe
                85                  90                  95

Val Lys Glu Ala Ala Ile Gln Ala Ile Lys Asp Gly Lys Asn Gln Tyr
            100                 105                 110

Ala Arg Gly Tyr Gly Ile Pro Gln Leu Asn Ser Ala Ile Ala Ala Arg
        115                 120                 125

Phe Arg Glu Asp Thr Gly Leu Val Val Asp Pro Glu Lys Glu Val Thr
    130                 135                 140

Val Thr Ser Gly Cys Thr Glu Ala Ile Ala Ala Ala Met Leu Gly Leu
145                 150                 155                 160

Ile Asn Pro Gly Asp Glu Val Ile Leu Phe Ala Pro Phe Tyr Asp Ser
                165                 170                 175

Tyr Glu Ala Thr Leu Ser Met Ala Gly Ala Lys Val Lys Gly Ile Thr
            180                 185                 190

Leu Arg Pro Pro Asp Phe Ser Ile Pro Leu Glu Glu Leu Lys Ala Ala
        195                 200                 205

Val Thr Asn Lys Thr Arg Ala Ile Leu Met Asn Thr Pro His Asn Pro
    210                 215                 220

Thr Gly Lys Met Phe Thr Arg Glu Glu Leu Glu Thr Ile Ala Ser Leu
225                 230                 235                 240

Cys Ile Glu Asn Asp Val Leu Val Phe Ser Asp Glu Val Tyr Asp Lys
                245                 250                 255

Leu Ala Phe Glu Met Asp His Ile Ser Ile Ala Ser Leu Pro Gly Met
            260                 265                 270

Tyr Glu Arg Thr Val Thr Met Asn Ser Leu Gly Lys Thr Phe Ser Leu
```

```
                        275                 280                 285
Thr Gly Trp Lys Ile Gly Trp Ala Ile Ala Pro Pro His Leu Thr Trp
    290                 295                 300

Gly Val Arg Gln Ala His Ser Tyr Leu Thr Phe Ala Thr Ser Thr Pro
305                 310                 315                 320

Ala Gln Trp Ala Ala Val Ala Ala Leu Lys Ala Pro Glu Ser Tyr Phe
                325                 330                 335

Lys Glu Leu Lys Arg Asp Tyr Asn Val Lys Lys Glu Thr Leu Val Lys
            340                 345                 350

Gly Leu Lys Glu Val Gly Phe Thr Val Phe Pro Ser Ser Gly Thr Tyr
        355                 360                 365

Phe Val Val Ala Asp His Thr Pro Phe Gly Met Glu Asn Asp Val Ala
370                 375                 380

Phe Cys Glu Tyr Leu Ile Glu Glu Val Gly Val Val Ala Ile Pro Thr
385                 390                 395                 400

Ser Val Phe Tyr Leu Asn Pro Glu Glu Gly Lys Asn Leu Val Arg Phe
                405                 410                 415

Ala Phe Cys Lys Asp Glu Glu Thr Leu Arg Gly Ala Ile Glu Arg Met
            420                 425                 430

Lys Gln Lys Leu Lys Arg Lys Val
        435                 440

<210> SEQ ID NO 2
<211> LENGTH: 1353
<212> TYPE: DNA
<213> ORGANISM: Arabidopsis thaliana
<220> FEATURE:
<223> OTHER INFORMATION: Arabidopsis omega-amidase, AT5g12040/F14F18_210
      cDNA
<220> FEATURE:
<221> NAME/KEY: CDS
<222> LOCATION: (9)..(1118)
<223> OTHER INFORMATION: omega-amidase

<400> SEQUENCE: 2
aaagtgaaat gaagtcagca atttcatcgt cactcttctt caattcgaag aatcttttaa    60
accctaatcc tctttctcgc ttcatttctc tcaaatctaa cttcctccct aaattatctc   120
cgagatcgat cactagtcac accttgaagc tcccatcttc gtcaacctca gctttaagat   180
ccatttcctc tttcatggct tcttctttca accctgaaca agctagagtt ccctctgctc   240
ttcctctccc agctcctccg ttgaccaaat tcaacatcgg attgtgtcag ctatctgtta   300
catctgacaa aaagagaaac atctctcatg ctaaaaagc cattgaagaa ctgcttcta    360 aaggagctaa gcttgttctc ttacccgaaa tttggaacag tccgtattcc aatgatagtt   420
ttccagttta tgcggaggag attgatgcag gtggtgatgc ttctccttca acggcaatgc   480
tttctgaagt ttccaaacgt ctcaagatta caatcattgg tggatctata ccagaaagag   540
ttggagatcg tttgtataac acttgctgtg tctttggttc cgatgagag ctaaaagcta    600 agcatcggaa gatacatta tttgatatag acattccggg gaagattact tttatggaat    660
ccaaaactct tactgctgga gagacaccaa caatcgttga cacagatgta gggcgtattg   720
gaataggcat ctgttatgat atcaggttcc aggagttagc tatgatatat gctgcaagag   780
gggctcattt gctgtgctac ccgggagcct ttaacatgac aactggacca ttgcattggg   840
aattactaca aagggccagg gctacggata tcagttata tgtggcgaca tgctcacctg    900
ccagagattc aggagctggc tacactgctt gggggcactc aacactcgtt gggccttttg   960
```

```
gagaagtact agcaacgact gagcatgagg aggccattat catagcagag attgattact    1020
ctatccttga acaacgaagg actagccttc cattgaatag gcagcggcgg ggagatcttt    1080
accagcttgt agacgtacag cgcttagact ctaaatgaac gcagcagtaa ctgtatatct    1140
gagagatatt gcgagttgag cacgatttgg ttacttacaa cttcatgcat gatcagtcat    1200
ttctccacaa ctttgctgag atatgtaaaa gaataaaaat caaacttttg agttaaaatc    1260
gaacaaaggc aagtaaattc tgcttagata atgtgaactc cacccacttg ccatgtgttt    1320
gttgtttata aacttcaatg cattctgata acg                                 1353

<210> SEQ ID NO 3
<211> LENGTH: 307
<212> TYPE: PRT
<213> ORGANISM: Arabidopsis thaliana
<220> FEATURE:
<223> OTHER INFORMATION: Arabidopsis mature omega-amidase,
      AT5g12040/F14F18_210

<400> SEQUENCE: 3
```

Met Ala Ser Ser Phe Asn Pro Glu Gln Ala Arg Val Pro Ser Ala Leu
1               5                   10                  15

Pro Leu Pro Ala Pro Pro Leu Thr Lys Phe Asn Ile Gly Leu Cys Gln
            20                  25                  30

Leu Ser Val Thr Ser Asp Lys Lys Arg Asn Ile Ser His Ala Lys Lys
        35                  40                  45

Ala Ile Glu Glu Ala Ala Ser Lys Gly Ala Lys Leu Val Leu Leu Pro
    50                  55                  60

Glu Ile Trp Asn Ser Pro Tyr Ser Asn Asp Ser Phe Pro Val Tyr Ala
65                  70                  75                  80

Glu Glu Ile Asp Ala Gly Gly Asp Ala Ser Pro Ser Thr Ala Met Leu
                85                  90                  95

Ser Glu Val Ser Lys Arg Leu Lys Ile Thr Ile Gly Gly Ser Ile
            100                 105                 110

Pro Glu Arg Val Gly Asp Arg Leu Tyr Asn Thr Cys Cys Val Phe Gly
        115                 120                 125

Ser Asp Gly Glu Leu Lys Ala Lys His Arg Lys Ile His Leu Phe Asp
    130                 135                 140

Ile Asp Ile Pro Gly Lys Ile Thr Phe Met Glu Ser Lys Thr Leu Thr
145                 150                 155                 160

Ala Gly Glu Thr Pro Thr Ile Val Asp Thr Asp Val Gly Arg Ile Gly
                165                 170                 175

Ile Gly Ile Cys Tyr Asp Ile Arg Phe Gln Glu Leu Ala Met Ile Tyr
            180                 185                 190

Ala Ala Arg Gly Ala His Leu Leu Cys Tyr Pro Gly Ala Phe Asn Met
        195                 200                 205

Thr Thr Gly Pro Leu His Trp Glu Leu Leu Gln Arg Ala Arg Ala Thr
    210                 215                 220

Asp Asn Gln Leu Tyr Val Ala Thr Cys Ser Pro Ala Arg Asp Ser Gly
225                 230                 235                 240

Ala Gly Tyr Thr Ala Trp Gly His Ser Thr Leu Val Gly Pro Phe Gly
                245                 250                 255

Glu Val Leu Ala Thr Thr Glu His Glu Glu Ala Ile Ile Ile Ala Glu
            260                 265                 270

Ile Asp Tyr Ser Ile Leu Glu Gln Arg Arg Thr Ser Leu Pro Leu Asn
        275                 280                 285

```
Arg Gln Arg Arg Gly Asp Leu Tyr Gln Leu Val Asp Val Gln Arg Leu
            290                 295                 300

Asp Ser Lys
305

<210> SEQ ID NO 4
<211> LENGTH: 364
<212> TYPE: PRT
<213> ORGANISM: Vitis vinifera
<220> FEATURE:
<223> OTHER INFORMATION: wine grape cultivar PN40024 omega-amidase
      NIT2-like, LOC100266241

<400> SEQUENCE: 4

Met Lys Ser Ala Ala Leu Ser Ala Leu Leu Ser Ser Thr Leu Ser Tyr
  1               5                  10                  15

Ala Ser Pro Pro His Leu Asn Leu Arg Pro Ala Thr Ala Val Leu
             20                  25                  30

Cys Arg Ser Leu Leu Pro Thr Ser Thr Pro Asn Pro Phe His Thr Gln
         35                  40                  45

Leu Arg Thr Ala Lys Ile Ser Ala Ser Met Ser Ser Phe Lys Pro
 50                  55                  60

Glu Gln Ala Arg Val Pro Pro Ala Ile Pro Pro Thr Pro Pro Leu
 65                  70                  75                  80

Ser Lys Phe Lys Ile Gly Leu Cys Gln Leu Ser Val Thr Ala Asp Lys
                 85                  90                  95

Glu Arg Asn Ile Ala His Ala Arg Lys Ala Ile Glu Glu Ala Val Glu
            100                 105                 110

Lys Gly Ala Gln Leu Val Leu Leu Pro Glu Ile Trp Asn Ser Pro Tyr
        115                 120                 125

Ser Asn Asp Ser Phe Pro Val Tyr Ala Glu Asp Ile Asp Ala Gly Ser
    130                 135                 140

Asp Ala Ser Pro Ser Thr Ala Met Leu Ser Glu Val Ser His Ala Leu
145                 150                 155                 160

Lys Ile Thr Ile Val Gly Gly Ser Ile Pro Glu Arg Cys Gly Asp Gln
                165                 170                 175

Leu Tyr Asn Thr Cys Cys Val Phe Gly Ser Asp Gly Lys Leu Lys Ala
            180                 185                 190

Lys His Arg Lys Ile His Leu Phe Asp Ile Asn Ile Pro Gly Lys Ile
        195                 200                 205

Thr Phe Met Glu Ser Lys Thr Leu Thr Ala Gly Gly Ser Pro Thr Ile
    210                 215                 220

Val Asp Thr Glu Val Gly Arg Ile Gly Ile Gly Ile Cys Tyr Asp Ile
225                 230                 235                 240

Arg Phe Ser Glu Leu Ala Met Leu Tyr Ala Ala Arg Gly Ala His Leu
                245                 250                 255

Ile Cys Tyr Pro Gly Ala Phe Asn Met Thr Thr Gly Pro Leu His Trp
            260                 265                 270

Glu Leu Leu Gln Arg Ala Arg Ala Ala Asp Asn Gln Leu Tyr Val Ala
        275                 280                 285

Thr Cys Ser Pro Ala Arg Asp Ala Gly Ala Gly Tyr Val Ala Trp Gly
    290                 295                 300

His Ser Thr Leu Val Gly Pro Phe Gly Glu Val Leu Ala Thr Thr Glu
305                 310                 315                 320

His Glu Glu Ala Ile Ile Ile Ser Glu Ile Asp Tyr Ser Leu Ile Glu
                325                 330                 335
```

```
Leu Arg Arg Thr Asn Leu Pro Leu Leu Asn Gln Arg Arg Gly Asp Leu
            340                 345                 350

Tyr Gln Leu Val Asp Val Gln Arg Leu Asp Ser Gln
            355                 360

<210> SEQ ID NO 5
<211> LENGTH: 356
<212> TYPE: PRT
<213> ORGANISM: Zea mays
<220> FEATURE:
<223> OTHER INFORMATION: maize strain B73 unknown protein

<400> SEQUENCE: 5

Met Val Ala Ala Ala Ala Ala Ala Ala Thr Ala Thr Ala Ala
  1               5                  10                  15

Ala Leu Leu Ala Pro Gly Leu Lys Leu Cys Ala Gly Arg Ala Arg Val
                20                  25                  30

Ser Ser Pro Ser Gly Leu Pro Leu Arg Arg Val Thr Ala Met Ala Ser
            35                  40                  45

Ala Pro Asn Ser Ser Phe Arg Pro Glu Glu Ala Arg Ser Pro Pro Ala
 50                  55                  60

Leu Glu Leu Pro Ile Pro Pro Leu Ser Lys Phe Lys Val Ala Leu Cys
 65                  70                  75                  80

Gln Leu Ser Val Thr Ala Asp Lys Ser Arg Asn Ile Ala His Ala Arg
                85                  90                  95

Ala Ala Ile Glu Lys Ala Ala Ser Asp Gly Ala Lys Leu Val Val Leu
            100                 105                 110

Pro Glu Ile Trp Asn Gly Pro Tyr Ser Asn Asp Ser Phe Pro Glu Tyr
            115                 120                 125

Ala Glu Asp Ile Glu Ala Gly Asp Ala Ala Pro Ser Phe Ser Met
            130                 135                 140

Leu Ser Glu Val Ala Arg Ser Leu Gln Ile Thr Leu Val Gly Gly Ser
145                 150                 155                 160

Ile Ala Glu Arg Ser Gly Asn Asn Leu Tyr Asn Thr Cys Cys Val Phe
                165                 170                 175

Gly Ser Asp Gly Gln Leu Lys Gly Lys His Arg Lys Ile His Leu Phe
            180                 185                 190

Asp Ile Asp Ile Pro Gly Lys Ile Thr Phe Lys Glu Ser Lys Thr Leu
            195                 200                 205

Thr Ala Gly Gln Ser Pro Thr Val Val Asp Thr Asp Val Gly Arg Ile
            210                 215                 220

Gly Ile Gly Ile Cys Tyr Asp Ile Arg Phe Gln Glu Leu Ala Met Leu
225                 230                 235                 240

Tyr Ala Ala Arg Gly Ala His Leu Leu Cys Tyr Pro Gly Ala Phe Asn
                245                 250                 255

Met Thr Thr Gly Pro Leu His Trp Glu Leu Leu Gln Arg Ala Arg Ala
            260                 265                 270

Ala Asp Asn Gln Leu Phe Val Ala Thr Cys Ala Pro Ala Arg Asp Thr
            275                 280                 285

Ser Ala Gly Tyr Val Ala Trp Gly His Ser Thr Leu Val Gly Pro Phe
            290                 295                 300

Gly Glu Val Ile Ala Thr Thr Glu His Glu Glu Ala Thr Ile Ile Ala
305                 310                 315                 320

Asp Ile Asp Tyr Ser Leu Ile Glu Gln Arg Arg Gln Phe Leu Pro Leu
                325                 330                 335
```

```
Gln His Gln Arg Arg Gly Asp Leu Tyr Gln Leu Val Asp Val Gln Arg
                340                 345                 350

Leu Gly Ser Gln
        355

<210> SEQ ID NO 6
<211> LENGTH: 370
<212> TYPE: PRT
<213> ORGANISM: Populus trichocarpa
<220> FEATURE:
<223> OTHER INFORMATION: western balsam poplar (black cottonwood)
      hypothetical protein, locus POPTRDRAFT_819468

<400> SEQUENCE: 6

Met Lys Ser Ala Ile Ser Ser Thr Thr Thr Leu Leu Ser Ser Lys Asn
  1               5                  10                  15

Leu Ser Leu Lys Leu His Leu Asn His Ser Pro Leu Ser Arg Leu Pro
             20                  25                  30

Ser Ser Leu Phe Arg Ser Lys Ser Asn Thr His Phe Pro Ser Leu Leu
         35                  40                  45

Pro Arg Asn Asn Ser Thr His Asn Gln Lys Ser Gln Ile His Thr Pro
 50                  55                  60

Ile Met Ala Ser Ser Phe Met Pro Glu Gln Ala Arg Ala Pro Pro Ala
 65                  70                  75                  80

Leu Pro Leu Pro Val Pro Pro Phe Lys Ile Gly Leu Cys Gln Leu Ser
                 85                  90                  95

Val Thr Ala Asp Lys Glu Arg Asn Ile Ala His Ala Arg Lys Ala Ile
            100                 105                 110

Glu Glu Ala Ala Ala Lys Gly Ala Lys Leu Val Met Leu Pro Glu Ile
        115                 120                 125

Trp Asn Ser Pro Tyr Ser Asn Asp Cys Phe Pro Val Tyr Ala Glu Asp
130                 135                 140

Ile Asp Ala Gly Gly Glu Ala Ser Pro Ser Thr Ala Met Leu Ser Glu
145                 150                 155                 160

Ala Ala Gly Leu Leu Lys Val Thr Ile Val Gly Gly Ser Ile Pro Glu
                165                 170                 175

Arg Ser Gly Asp Arg Leu Tyr Asn Thr Cys Cys Val Phe Asp Ser Asp
            180                 185                 190

Gly Lys Leu Lys Ala Lys His Arg Lys Ile His Leu Phe Asp Ile Asp
        195                 200                 205

Ile Pro Gly Lys Ile Thr Phe Ile Glu Ser Lys Thr Leu Thr Ala Gly
    210                 215                 220

Glu Thr Pro Thr Ile Val Asp Thr Glu Val Gly Arg Ile Gly Ile Gly
225                 230                 235                 240

Ile Cys Tyr Asp Ile Arg Phe Gln Glu Leu Ala Ile Ile Tyr Ala Ala
                245                 250                 255

Arg Gly Ala His Leu Ile Cys Tyr Pro Gly Ala Phe Asn Met Thr Thr
            260                 265                 270

Gly Pro Leu His Trp Glu Leu Leu Gln Arg Ala Arg Ala Ala Asp Asn
        275                 280                 285

Gln Leu Tyr Val Ala Thr Cys Ser Pro Ala Arg Asp Val Ala Ala Gly
    290                 295                 300

Tyr Val Ala Trp Gly His Ser Thr Leu Val Gly Pro Phe Gly Glu Val
305                 310                 315                 320

Leu Ala Thr Thr Glu His Glu Glu Asp Ile Ile Ile Ala Glu Ile Asp
```

```
                325                 330                 335
Tyr Ser Leu Leu Glu Val Arg Arg Thr Asn Leu Pro Leu Thr Lys Gln
            340                 345                 350
Arg Arg Gly Asp Leu Tyr Gln Leu Val Asp Val Gln Arg Leu Lys Ser
        355                 360                 365
Asp Ser
    370

<210> SEQ ID NO 7
<211> LENGTH: 358
<212> TYPE: PRT
<213> ORGANISM: Picea sitchensis
<220> FEATURE:
<223> OTHER INFORMATION: Sitka spruce cultivar FB3-425 unknown protein,
      similar to Arabidopsis At5g12040

<400> SEQUENCE: 7

Met Thr Pro Leu Leu Ser Tyr Ser Leu Arg Val Val Ala Ser Ala Leu
1               5                   10                  15
Arg Pro Lys Ser Ser Ile Ala Ser Ala Val Gly Arg Leu Ser Ala Thr
            20                  25                  30
Pro Lys Arg Phe Pro Ala Asn Arg Leu Arg Ile Ser Tyr Arg Asn Tyr
        35                  40                  45
Asn Ala Ala Met Ala Lys Pro Glu Asp Ala Arg Ser Pro Pro Ala Leu
    50                  55                  60
Pro Leu Pro Ser Ala Pro Asn Gly Gly Lys Phe Lys Ile Ala Leu Cys
65                  70                  75                  80
Gln Leu Ser Val Thr Glu Asn Lys Glu Arg Asn Ile Ala His Ala Arg
                85                  90                  95
Asp Ala Ile Glu Ala Ala Asp Asn Gly Ala Gln Leu Val Val Leu
            100                 105                 110
Pro Glu Ile Trp Asn Gly Pro Tyr Ser Asn Ala Ser Phe Pro Val Tyr
        115                 120                 125
Ala Glu Asp Ile Asp Ala Gly Gly Ser Ala Ser Pro Ser Thr Ser Met
    130                 135                 140
Leu Ser Glu Val Ala Arg Ser Lys Gly Ile Thr Ile Val Gly Gly Ser
145                 150                 155                 160
Ile Ser Glu Arg Ser Gly Asp His Leu Tyr Asn Thr Cys Cys Ile Phe
                165                 170                 175
Gly Lys Asp Gly Glu Leu Lys Ala Lys His Arg Lys Ile His Leu Phe
            180                 185                 190
Asp Ile Asp Ile Pro Gly Lys Ile Ser Phe Met Glu Ser Lys Thr Leu
        195                 200                 205
Thr Ala Gly Asn Thr Pro Thr Ile Val Asp Thr Asp Val Gly Arg Ile
    210                 215                 220
Gly Ile Gly Ile Cys Tyr Asp Ile Arg Phe Gln Glu Leu Ala Met Leu
225                 230                 235                 240
Tyr Ala Ala Arg Gly Ala His Leu Ile Cys Tyr Pro Gly Ala Phe Asn
                245                 250                 255
Met Thr Thr Gly Pro Leu His Trp Glu Leu Leu Gln Arg Ala Arg Ala
            260                 265                 270
Ile Asp Asn Gln Leu Tyr Val Ala Thr Cys Ser Pro Ala Arg Asp Ile
        275                 280                 285
Asn Ala Gly Tyr Val Ala Trp Gly His Ser Thr Leu Val Ala Pro Phe
    290                 295                 300
```

```
Gly Glu Ile Val Ala Thr Thr Glu His Glu Glu Ala Thr Val Ile Ala
305                 310                 315                 320

Asp Ile Asp Tyr Ser Arg Ile Glu Glu Arg Met Asn Met Pro Leu
            325                 330                 335

Glu Lys Gln Arg His Gly Asp Leu Tyr Gln Leu Val Asp Val Ser Arg
            340                 345                 350

Leu Asp Thr Ala Lys His
            355

<210> SEQ ID NO 8
<211> LENGTH: 310
<212> TYPE: PRT
<213> ORGANISM: Oryza sativa
<220> FEATURE:
<223> OTHER INFORMATION: rice Japonica group cultivar Nipponbare
      hypothetical protein Os03g0175600, similar to Nit protein 2
      (CUA002)

<400> SEQUENCE: 8

Met Ala Thr Ala Ala Ser Phe Arg Pro Glu Ala Ala Arg Ser Pro Pro
1               5                   10                  15

Ala Val Gln Pro Pro Ala Pro Pro Leu Ser Lys Phe Lys Val Ala Leu
            20                  25                  30

Cys Gln Leu Ser Val Thr Ala Asp Lys Ala Arg Asn Ile Ala Arg Ala
        35                  40                  45

Arg Glu Ala Ile Glu Ala Ala Ala Gly Gly Ala Lys Leu Val Leu
50                  55                  60

Leu Pro Glu Ile Trp Asn Gly Pro Tyr Ser Asn Asp Ser Phe Pro Glu
65                  70                  75                  80

Tyr Ala Glu Asp Ile Glu Ala Gly Gly Asp Ala Ala Pro Ser Phe Ser
                85                  90                  95

Met Met Ser Glu Val Ala Arg Ser Leu Gln Ile Thr Leu Val Gly Gly
            100                 105                 110

Ser Ile Ser Glu Arg Ser Gly Asn Lys Leu Tyr Asn Thr Cys Cys Val
        115                 120                 125

Phe Gly Ser Asp Gly Glu Leu Lys Gly Lys His Arg Lys Ile His Leu
130                 135                 140

Phe Asp Ile Asp Ile Pro Gly Lys Ile Thr Phe Lys Glu Ser Lys Thr
145                 150                 155                 160

Leu Thr Ala Gly Gln Asp Leu Thr Val Val Asp Thr Asp Val Gly Arg
                165                 170                 175

Ile Gly Ile Gly Ile Cys Tyr Asp Ile Arg Phe Gln Glu Leu Ala Met
            180                 185                 190

Leu Tyr Ala Ala Arg Gly Ala His Leu Leu Cys Tyr Pro Gly Ala Phe
        195                 200                 205

Asn Met Thr Thr Gly Pro Leu His Trp Glu Leu Leu Gln Arg Ala Arg
210                 215                 220

Ala Ala Asp Asn Gln Leu Phe Val Ala Thr Cys Ala Pro Ala Arg Asp
225                 230                 235                 240

Thr Ser Ala Gly Tyr Ile Ala Trp Gly His Ser Thr Leu Val Gly Pro
                245                 250                 255

Phe Gly Glu Val Ile Ala Thr Ala Glu His Glu Glu Thr Thr Ile Met
            260                 265                 270

Ala Glu Ile Asp Tyr Ser Leu Ile Asp Gln Arg Arg Gln Phe Leu Pro
        275                 280                 285

Leu Gln Tyr Gln Arg Arg Gly Asp Leu Tyr Gln Leu Val Asp Val Gln
```

```
              290                 295                 300
Arg Ser Gly Ser Asp Glu
305                 310
```

<210> SEQ ID NO 9
<211> LENGTH: 284
<212> TYPE: PRT
<213> ORGANISM: Sorghum bicolor
<220> FEATURE:
<223> OTHER INFORMATION: sorghum cultivar BTx623 hypothetical protein
      SORBIDRAFT_01g045480, similar to hydrolase, carbon-nitrogen
      family protein, expressed

<400> SEQUENCE: 9

```
Met Arg Ala Ala Ala Ala Ala Ala Thr Ser Thr Ala Ala Ala Leu
 1               5                  10                  15

Leu Ala Pro Gly Leu Lys Leu Cys Ala Gly Arg Ala Arg Val Ser Ser
            20                  25                  30

Cys Arg Leu Pro Leu Arg Arg Val Ala Ala Met Ala Ser Ala Pro Asn
        35                  40                  45

Ser Ser Phe Arg Pro Glu Glu Ala Arg Ser Pro Pro Ala Leu Glu Leu
    50                  55                  60

Pro Thr Pro Pro Leu Ser Lys Phe Lys Val Ala Leu Cys Gln Leu Ser
65                  70                  75                  80

Val Thr Ala Asp Lys Ser Arg Asn Ile Ala His Ala Arg Ala Ala Ile
                85                  90                  95

Glu Lys Ala Ala Ser Asp Gly Ala Lys Leu Val Leu Leu Pro Glu Ile
            100                 105                 110

Trp Asn Gly Pro Tyr Ser Asn Asp Ser Phe Pro Glu Tyr Ala Glu Asp
        115                 120                 125

Ile Glu Ala Gly Gly Asp Ala Ala Pro Ser Phe Ser Met Met Ser Glu
    130                 135                 140

Val Ala Arg Ser Leu Gln Ile Thr Leu Val Asp Gly Gln Leu Lys Gly
145                 150                 155                 160

Lys His Arg Lys Ile His Leu Phe Asp Ile Asp Ile Pro Gly Lys Ile
                165                 170                 175

Thr Phe Lys Glu Ser Lys Thr Leu Thr Ala Gly Gln Ser Pro Thr Val
            180                 185                 190

Val Asp Thr Asp Val Gly Arg Ile Gly Ile Gly Ile Cys Tyr Asp Ile
        195                 200                 205

Arg Phe Gln Glu Leu Ala Met Leu Tyr Ala Ala Arg Gly Ala His Leu
    210                 215                 220

Leu Cys Tyr Pro Gly Ala Phe Asn Met Thr Thr Gly Pro Leu His Trp
225                 230                 235                 240

Glu Leu Leu Gln Arg Ala Arg Gln Pro Ala Val Cys Cys Asn Val Arg
                245                 250                 255

Ser Ser Ser Arg Tyr Gln Cys Arg Leu Cys Cys Leu Gly Thr Leu His
            260                 265                 270

Ala Cys Trp Thr Phe Trp Arg Gly Asp Cys Asn Asn
        275                 280
```

<210> SEQ ID NO 10
<211> LENGTH: 329
<212> TYPE: PRT
<213> ORGANISM: Ricinus communis
<220> FEATURE:
<223> OTHER INFORMATION: castor bean cultivar Hale nitrilase and fragile
      histidine triad fusion protein, putative, locus RCOM_0706590A transcript

<400> SEQUENCE: 10

Met Ser Ala Ser Phe Asn Pro Glu Gln Ala Arg Ser Pro Pro Ala Leu
1               5                   10                  15

Pro Leu Pro Thr Pro Pro Leu Thr Lys Ala Gln Phe Leu Leu Thr Ser
            20                  25                  30

Tyr Leu Thr Ile Leu Ile Tyr Met Ile Phe Lys Ile Gly Leu Cys Gln
        35                  40                  45

Leu Leu Val Thr Pro Asp Lys Ala Lys Asn Ile Ala His Ala Arg Lys
    50                  55                  60

Ala Ile Glu Glu Ala Ala Lys Gly Ala Lys Leu Val Leu Leu Pro
65                  70                  75                  80

Glu Ile Trp Asn Ser Pro Tyr Ser Asn Asp Ser Phe Pro Val Tyr Ala
                85                  90                  95

Glu Asp Ile Asp Ala Gly His Val Ala Ser Pro Ser Thr Ala Met Leu
            100                 105                 110

Ser Gln Leu Ala Arg Leu Leu Asn Ile Thr Ile Val Gly Gly Ser Ile
        115                 120                 125

Pro Glu Arg Ser Gly Asp Arg Leu Tyr Asn Thr Cys Cys Val Phe Asp
    130                 135                 140

Thr Gln Gly Asn Leu Ile Ala Lys His Arg Lys Ile His Leu Phe Asp
145                 150                 155                 160

Ile Asp Ile Pro Gly Lys Ile Thr Phe Ile Glu Ser Lys Thr Leu Thr
                165                 170                 175

Ala Gly Glu Thr Pro Asn Ile Val Asp Thr Glu Val Gly Arg Ile Gly
            180                 185                 190

Ile Gly Ile Cys Tyr Asp Ile Arg Phe Gln Glu Leu Ala Val Leu Tyr
        195                 200                 205

Ala Ala Arg Gly Ala His Leu Ile Cys Tyr Pro Gly Ala Phe Asn Met
    210                 215                 220

Thr Thr Gly Pro Leu His Trp Glu Leu Leu Gln Arg Ala Arg Ala Ala
225                 230                 235                 240

Asp Asn Gln Leu Tyr Val Ala Thr Cys Ser Pro Ala Arg Asp Val Gly
                245                 250                 255

Ala Gly Tyr Val Ala Trp Gly His Ser Thr Leu Val Gly Pro Phe Gly
            260                 265                 270

Glu Ile Leu Ala Thr Thr Glu His Glu Gln Asp Ile Ile Ala Glu
        275                 280                 285

Ile Asp Tyr Ser Leu Ile Glu Leu Arg Ser Gln Leu Ser Thr Thr His
    290                 295                 300

Leu Pro Leu Pro Thr Pro Thr Thr Arg Asp Ser Thr Ile Glu Glu
305                 310                 315                 320

Glu Asp Asp Leu Val Tyr Ile Tyr Ile
                325

<210> SEQ ID NO 11
<211> LENGTH: 311
<212> TYPE: PRT
<213> ORGANISM: Physcomitrella patens
<220> FEATURE:
<223> OTHER INFORMATION: Physcomitrella patens subspecies patens ecotype
      Gransden 2004 moss hypothetical protein, locus PHYPADRAFT_130338

<400> SEQUENCE: 11

Met Ala Ser Asp Phe Gln Pro His Met Ala Arg Gln Pro Pro Ser Glu

```
                1               5              10              15

Ser Leu Pro Asn Ala Pro Asn Gly Gly Lys Tyr Lys Leu Ala Val Cys
                        20                  25                  30

Gln Leu Ser Val Thr Ser Asp Lys Ala Ala Asn Ile Ala His Ala Arg
                        35                  40                  45

Gln Lys Ile Glu Ala Ala Asp Ser Gly Ala Gln Leu Ile Val Leu
                        50                  55                  60

Pro Glu Met Trp Asn Cys Pro Tyr Ser Asn Asp Ser Phe Pro Thr Tyr
        65                      70                  75                  80

Ala Glu Asp Ile Asp Ala Gly Leu Glu Ala Ser Pro Ser Ser His Met
                        85                  90                  95

Leu Ser Glu Val Ala Arg Lys Lys Val Thr Ile Val Gly Gly Ser
                        100                 105                 110

Ile Pro Glu Arg Asn Asp Gly Lys Leu Tyr Asn Thr Cys Cys Val Phe
                        115                 120                 125

Asp Lys Asn Gly Glu Leu Lys Ala Lys Phe Arg Lys Ile His Leu Phe
                        130                 135                 140

Asp Ile Asp Ile Pro Gly Lys Ile Thr Phe Lys Glu Ser Asp Thr Leu
        145                     150                 155                 160

Thr Pro Gly Glu Gly Leu Cys Val Val Asp Thr Asp Val Gly Arg Ile
                        165                 170                 175

Ala Val Gly Ile Cys Tyr Asp Ile Arg Phe Pro Glu Met Ala Met Leu
                        180                 185                 190

Tyr Ser Ala Arg Gly Ala His Ile Ile Cys Tyr Pro Gly Ala Phe Asn
                        195                 200                 205

Met Thr Thr Gly Pro Leu His Trp Glu Leu Leu Gln Lys Ala Arg Ala
        210                     215                 220

Val Asp Asn Gln Ile Phe Val Val Thr Cys Ser Pro Ala Arg Asp Thr
        225                     230                 235                 240

Glu Ala Gly Tyr Ile Ala Trp Gly His Ser Thr Val Val Gly Pro Phe
                        245                 250                 255

Gly Glu Ile Leu Ala Thr Thr Glu His Glu Glu Ala Thr Ile Phe Ala
                        260                 265                 270

Asp Ile Asp Tyr Ser Gln Leu Asp Thr Arg Arg Gln Asn Met Pro Leu
                        275                 280                 285

Glu Ser Gln Arg Arg Gly Asp Leu Tyr His Leu Ile Ser Val Thr Arg
                        290                 295                 300

Lys Asp Thr Val Lys Ser Ser
        305                     310

<210> SEQ ID NO 12
<211> LENGTH: 290
<212> TYPE: PRT
<213> ORGANISM: Selaginella moellendorffii
<220> FEATURE:
<223> OTHER INFORMATION: club moss hypothetical protein, locus
      SELMODRAFT_92478

<400> SEQUENCE: 12

Met Pro Ser Ser Arg Tyr Phe Trp Phe Leu Trp Gln Phe Lys Leu Ala
        1                       5                   10                  15

Val Cys Gln Leu Ser Ile Cys Ala Asp Lys Glu Gln Asn Ile Arg His
                        20                  25                  30

Ala Arg Glu Ala Ile Gln Thr Ala Ala Asp Gly Gly Ser Lys Leu Val
                        35                  40                  45
```

```
Leu Leu Pro Glu Met Trp Asn Cys Pro Tyr Ser Asn Ala Ser Phe Pro
    50                  55                  60

Ile Tyr Ala Glu Asp Ile Asp Ala Gly Asp Ser Pro Ser Ser Lys Met
 65                  70                  75                  80

Leu Ser Asp Met Ala Lys Ser Lys Glu Val Thr Ile Ile Gly Gly Ser
                 85                  90                  95

Ile Pro Glu Arg Ser Gly Asn His Leu Tyr Asn Thr Cys Cys Ile Tyr
                100                 105                 110

Gly Lys Asp Gly Ser Leu Lys Gly Lys His Arg Lys Val His Leu Phe
            115                 120                 125

Asp Ile Asp Ile Pro Gly Lys Ile Gln Phe Lys Glu Ser Asp Thr Leu
    130                 135                 140

Thr Pro Gly Asp Lys Tyr Thr Val Val Asp Thr Asp Val Gly Arg Ile
145                 150                 155                 160

Gly Val Gly Ile Cys Tyr Asp Ile Arg Phe Pro Glu Met Ala Met Thr
                165                 170                 175

Tyr Ala Ala Arg Gly Val His Met Ile Cys Tyr Pro Gly Ala Phe Asn
                180                 185                 190

Met Thr Thr Gly Pro Ala His Trp Glu Leu Leu Gln Lys Ala Arg Ala
            195                 200                 205

Val Asp Asn Gln Leu Phe Val Ala Thr Cys Ser Pro Ala Arg Asn Pro
    210                 215                 220

Ser Ala Gly Tyr Val Ala Trp Gly His Ser Ser Val Ile Gly Pro Phe
225                 230                 235                 240

Gly Glu Ile Leu Ala Ser Thr Gly Arg Glu Glu Ala Ile Phe Tyr Ala
                245                 250                 255

Asp Ile Asp Tyr Ala Gln Ile Lys Glu Arg Arg Met Asn Met Pro Leu
                260                 265                 270

Asp His Gln Arg Arg Gly Asp Leu Tyr Gln Leu Val Asp Leu Thr Phe
            275                 280                 285

Thr Thr
    290

<210> SEQ ID NO 13
<211> LENGTH: 271
<212> TYPE: PRT
<213> ORGANISM: Medicago truncatula
<220> FEATURE:
<223> OTHER INFORMATION: barrel medic unknown protein

<400> SEQUENCE: 13

Met Ala Ala Ser Ser Ile Asn Ser Glu Leu Ala Arg Ser Pro Pro Ala
  1               5                  10                  15

Ile Pro Leu Pro Thr Pro Pro Leu Thr Asn Phe Lys Ile Gly Leu Cys
                 20                  25                  30

Gln Leu Ser Val Thr Ser Asp Lys Asp Lys Asn Ile Ala His Ala Arg
             35                  40                  45

Thr Ala Ile Gln Asp Ala Ala Ala Lys Gly Ala Lys Leu Ile Leu Leu
    50                  55                  60

Pro Glu Ile Trp Asn Ser Pro Tyr Ser Asn Asp Ser Phe Pro Val Tyr
 65                  70                  75                  80

Ala Glu Asp Ile Asp Ala Gly Gly Asp Ala Ser Pro Ser Thr Ala Met
                 85                  90                  95

Leu Ser Glu Leu Ser Ser Leu Leu Lys Ile Thr Ile Val Gly Gly Ser
                100                 105                 110
```

-continued

```
Ile Pro Glu Arg Ser Gly Asp Arg Leu Tyr Asn Thr Cys Cys Val Phe
            115                 120                 125

Gly Thr Asp Gly Lys Leu Lys Ala Lys His Arg Lys Ile His Leu Phe
    130                 135                 140

Asp Ile Asp Ile Pro Gly Lys Ile Thr Phe Ile Glu Ser Leu Thr Leu
145                 150                 155                 160

Thr Ala Gly Asp Thr Pro Thr Ile Val Asp Thr Glu Val Gly Arg Ile
                165                 170                 175

Gly Ile Gly Ile Cys Tyr Asp Ile Arg Phe Pro Glu Leu Ala Met Ile
                180                 185                 190

Tyr Ala Ala Arg Gly Ala His Leu Leu Cys Tyr Pro Gly Ala Phe Asn
            195                 200                 205

Met Thr Thr Gly Pro Leu His Trp Glu Leu Leu Gln Arg Ala Arg Ala
    210                 215                 220

Thr Asp Asn Gln Leu Tyr Val Ala Thr Cys Ser Pro Ala Arg Asp Thr
225                 230                 235                 240

Thr Gly Trp Leu Cys Gly Leu Gly Val Thr Pro Leu Leu Leu Val Leu
                245                 250                 255

Leu Glu Lys Phe Trp Leu Leu Gln Asn Ala Arg Arg Gln Pro Leu
            260                 265                 270

<210> SEQ ID NO 14
<211> LENGTH: 613
<212> TYPE: PRT
<213> ORGANISM: Chlorella variabilis
<220> FEATURE:
<223> OTHER INFORMATION: green algae strain NC64A hypothetical protein
      CHLNCDRAFT_58195, similar to hydrolase, carbon-nitrogen
      family protein, expressed

<400> SEQUENCE: 14

Met Gln Ala Leu Ala Lys Gly Met Ala Leu Val Gly Val Ala Gly Leu
1               5                   10                  15

Ser Ala Ala Ala Gly Arg Arg Ala Ala Cys Leu Arg Pro Leu Ser Ser
                20                  25                  30

Tyr Thr Ser Ala Thr Ala Asp Val Ile Asp Pro Pro Pro Pro Gln Lys
            35                  40                  45

Val Pro Pro Leu Pro Cys Cys Arg Cys Arg His Cys Cys His Arg
50                  55                  60

Leu Ala Ser Asn Gln Gln Leu Ala Arg Pro Leu Leu Ala Gly Pro Ser
65                  70                  75                  80

Ala Gln Ile Lys Val Ala Leu Cys Gln Leu Ala Val Gly Ala Asp Lys
                85                  90                  95

Gln Ala Asn Leu Thr Thr Ala Arg Ser Ala Ile Glu Glu Ala Ala Thr
            100                 105                 110

Ala Gly Ala Asp Leu Val Val Leu Pro Glu Met Trp Asn Cys Pro Tyr
        115                 120                 125

Ser Asn Asp Ser Phe Pro Thr Tyr Ala Glu Asp Val Glu Ala Gly Asp
    130                 135                 140

Ser Pro Ser Thr Ser Met Leu Ser Ala Ala Ala Ala Asn Arg Val
145                 150                 155                 160

Val Leu Val Gly Gly Ser Ile Pro Glu Arg Ala Asn Gly Gly Arg Leu
                165                 170                 175

Tyr Asn Thr Cys Phe Val Tyr Gly Arg Asp Gly Arg Leu Leu Gly Arg
            180                 185                 190

His Arg Lys Val His Leu Phe Asp Ile Asp Ile Pro Gly Lys Ile Thr
```

-continued

```
                195                 200                 205
Phe Lys Glu Ser Leu Thr Leu Thr Pro Gly Glu Gly Leu Thr Val Val
    210                 215                 220
Gly Arg Leu Gly Ile Gly Ile Cys Tyr Asp Ile Arg Phe Pro Glu Leu
225                 230                 235                 240
Ala Leu Leu Tyr Ala Ala Arg Gly Val Gln Leu Ile Val Tyr Pro Gly
                245                 250                 255
Ala Phe Asn Met Thr Thr Gly Pro Val His Trp Glu Leu Leu Gln Arg
                260                 265                 270
Ala Arg Ala Val Asp Gly Gln Leu Phe Val Ala Thr Cys Ser Pro Ala
                275                 280                 285
Arg Ser Glu Gly Thr Gly Tyr Ile Ala Trp Gly His Ser Thr Ala Val
                290                 295                 300
Gly Pro Phe Ala Glu Val Leu Ala Thr Thr Asp Glu Lys Ala Gly Ile
305                 310                 315                 320
Val Tyr Cys His Met Asp Phe Ala Gln Leu Gly Glu Arg Arg Ala Asn
                325                 330                 335
Met Pro Leu Arg His Gln Lys Arg Ala Asp Leu Tyr Ser Leu Leu Asp
                340                 345                 350
Leu Thr Arg Pro Asn Ser Leu Ser Asn Ala Gly Leu His Asn Gly Pro
                355                 360                 365
Val Gln Arg Thr Leu Ala Gly Ser Ser Gly Ile Val Gly Ser Gly Ile
                370                 375                 380
Thr Arg Gln Leu Leu Met Glu Gly Ala Lys Val Val Ala Leu Leu Arg
385                 390                 395                 400
Lys Val Asp Gln Lys Ala Gly Leu Leu Arg Asp Cys Gln Gly Ala Pro
                405                 410                 415
Ile Glu Asn Leu Tyr Pro Ala Val Val Glu Asp Val Ser Lys Glu Glu
                420                 425                 430
Gln Cys Ala Ala Phe Val His Glu Val Val Glu Gln His Gly Ala Ile
                435                 440                 445
Asp His Ala Val Ser Cys Phe Gly Ala Trp Trp Gln Gly Gly Leu Leu
                450                 455                 460
Thr Glu Gln Ser Tyr Ala Glu Phe Ser Arg Val Leu Ala Asn Phe Ala
465                 470                 475                 480
Gly Ser His Phe Thr Phe Val Lys Tyr Ile Leu Pro Ala Met Arg Gln
                485                 490                 495
Ser His Thr Ser Ser Met Leu Phe Val Thr Gly Gly Val Gly Lys Arg
                500                 505                 510
Val Leu Ser Ala Asp Ser Gly Leu Ala Thr Val Gly Ala Ala Leu
                515                 520                 525
Tyr Gly Ile Val Arg Ala Ala Gln Ala Gln Tyr Gly Arg Pro Pro
                530                 535                 540
Arg Ile Asn Glu Leu Arg Ile Phe Ala Leu Val Thr Arg His Gly Glu
545                 550                 555                 560
Met Pro Arg Ser His Ser Ser Ile Val Glu Gly Leu Arg Ala His Ser
                565                 570                 575
Asn Arg Lys Val Gly Asn Leu Ala Ala Glu Ala Leu Ala Ala Ala
                580                 585                 590
Asp Asp Glu Leu Leu Glu Val Thr Ser Glu Arg Leu Asp Gly Val Met
                595                 600                 605
Leu Met Val Gly Asp
    610
```

<210> SEQ ID NO 15
<211> LENGTH: 269
<212> TYPE: PRT
<213> ORGANISM: Volvox carteri
<220> FEATURE:
<223> OTHER INFORMATION: Volvox carteri forma nagariensis hypothetical
      protein VOLCADRAFT_73623

<400> SEQUENCE: 15

Met His Val Thr Ala Asp Lys Ala Gln Asn Leu Gln Thr Ala Lys Arg
 1               5                  10                  15

Ala Ile Glu Asp Ala Ala Ala Gln Gly Ala Lys Leu Val Val Leu Pro
            20                  25                  30

Glu Met Trp Asn Cys Pro Tyr Ser Asn Asp Ser Phe Pro Thr Tyr Ala
        35                  40                  45

Glu Asp Ile Glu Gly Gly Ala Ser Gly Ser Val Ala Met Leu Ser Ala
    50                  55                  60

Ala Ala Ala Ala Ala Cys Val Thr Leu Val Ala Gly Ser Ile Pro Glu
65                  70                  75                  80

Arg Cys Gly Asp Arg Leu Tyr Asn Thr Cys Cys Val Phe Asn Ser Arg
                85                  90                  95

Gly Glu Leu Leu Ala Lys His Arg Lys Val His Leu Phe Asp Ile Asp
            100                 105                 110

Ile Pro Gly Lys Ile Thr Phe Lys Glu Ser Leu Thr Leu Ser Pro Gly
        115                 120                 125

Pro Gly Pro Thr Val Val Asp Thr Glu Ala Gly Arg Leu Gly Ile Gly
    130                 135                 140

Ile Cys Tyr Asp Ile Arg Phe Pro Glu Leu Ala Gln Leu Tyr Ala Ala
145                 150                 155                 160

Arg Gly Cys Gln Val Leu Ile Tyr Pro Gly Ala Phe Asn Met Thr Thr
                165                 170                 175

Gly Pro Val His Trp Glu Leu Leu Ala Arg Ala Arg Ala Val Asp Asn
            180                 185                 190

Gln Ile Phe Val Ile Thr Cys Ser Pro Ala Arg Asn Pro Ser Ser Ser
        195                 200                 205

Tyr Gln Ala Trp Gly His Ser Thr Val Val Gly Pro Phe Ala Glu Ile
    210                 215                 220

Leu Ala Thr Thr Asp His Gln Pro Gly Thr Ile Tyr Thr Glu Leu Asp
225                 230                 235                 240

Tyr Ser Gln Leu Ala Glu Arg Arg Ala Asn Met Pro Leu Arg Gln Gln
                245                 250                 255

Lys Arg His Asp Leu Tyr Val Leu Leu Asp Lys Thr Ala
            260                 265

<210> SEQ ID NO 16
<211> LENGTH: 1525
<212> TYPE: DNA
<213> ORGANISM: Artificial Sequence
<220> FEATURE:
<223> OTHER INFORMATION: synthetic glycine-rich protein (GRP) promoter

<400> SEQUENCE: 16
gaaattaaac ccagggtcga cagcgcccac tatagagaaa aaattgaaat gttttgagaa      60
tcggatgatt ttttttaact attaggtcta gtttgaaaac cctatttcct aacaaaggga    120
ttttcatttt tataagagaa aataaactaa cttttcttga gaaataaaaa ttctttggaa    180

```
aaatggattt ctcaaactag ctcttacggc tagtttggaa accccaattt cacacgggat    240 tctcatttc ccaagggaaa aatgaactaa tttcccttag aaaaatgaga atcccgtggg    300
aaattgggat tttcaaagta gcccttatag tggaaataag ttatggtgtc tcgctcgtat    360
ggttatgtag ggccgcgcgt gtattccagc gccggccgca tggataccct atcgattctg    420
acttctctgt ctcaggaaaa taatacagcc acgattaacg gaacctgctg gctggatcca    480
tgattactca cttgacttca catcgatcca aattatctag cttgcacgtt catgggtcgc    540
ctcgctcgcc cgatcgatat tacgtacacc atagattagt actatatgga gtggagtgtt    600
gaatggatgc tctttattat tctagccaag ttatcaagcc gggcacttgc atcggaagga    660
gtaccagtgt acgcatcaga tcagacgata atcgatcaag atgggtacga gatttgccgc    720
ttgcttcctg ttcttgatgg gcaatctttt cgggccttga acgtcggaga atcgactata    780
cgaaatccta ggtcaactat acattggttg atgcttccgt gtagttttac cagttcatcg    840
gtctctagct tgttgtttgc gacgacttca cgtggccacg cgtttactgc gctctgctca    900
aagaaattgc ctacagtgcc tggcgtcagc tgcaggcgtt gaatccgagg tcgcgcgccg    960
cagaataagt acgagtcaaa ggctgagctg catgccgtac cggcctttat taatagctga   1020
gctctactcg ctacgtcagt atagtatagc acggtcatat atatactata gctatagctg   1080
tggggtaccg tgtccgtatc gtgaatctga agtcgaacag tgatatgcg tactatctaa   1140 taatgtcccg tgcagtaata tcactgttgc cgacgatggg aatctctagt tttgacagaa   1200
accaaagcaa ctgctagcta attaattcca gagagatcga tttctacagt gctgcaacaa   1260
tcaatgcaat tggcatcaga cgatatatgc taatggtttc tttatcgata cgtggtcaac   1320
agagctctct cgcccgccct gatcagatct catcgcacat ggacacccat ctgccaaccc   1380
aacacgggcg ggggaaccac cgtgaaacat cgcgttcatg cacgaccccc ccgcaggccg   1440
cagctataaa tacccatgca atgcaatgca gcgggtcatc atcgactcca cctggactcg   1500
ctcactggca atggctacca ccagc                                         1525
```

<210> SEQ ID NO 17
<211> LENGTH: 1615
<212> TYPE: DNA
<213> ORGANISM: Artificial Sequence
<220> FEATURE:
<223> OTHER INFORMATION: synthetic Agrobacterium rhizogenes roID
      promoter with Arabidopsis thaliana omega-amidase coding sequence
      construct

<400> SEQUENCE: 17

```
gacgtcggta ccgaatttgt tcgtgaacta ttagttgcgg gccttggcat ccgactacct     60
ctgcggcaat attatattcc ctgggcccac cgtgaaccca atttcgccta tttattcatt    120
acccccatta acattgaagt agtcatgatg ggcctgcagc acgttggtga ggctggcaca    180
actcatccat atactttctg accggatcgg cacattattg tagaaaacgc ggacccacag    240
cgcactttcc aaagcggtgc cgcgtcagaa tgcgctggca gaaaaaaatt aatccaaaag    300
taccctccaa gcagcccata taaacgcgtt tacaaatccg ctaacctcaa caatttgagc    360
agagaaaatt cgcacctaca aggcagatgg catcatcatt caatccagag caggcaagag    420
ttccttcagc attaccttta ccagcaccac cacttaccaa attcaacatc ggactttgtc    480
aattgagtgt tacttctgat aagaaaagaa acatttcaca tgctaagaaa gcaatcgaag    540
aggctgctag taagggagct aaactcgttc ttttgcctga aatatggaac tcaccataca    600
gtaacgattc ttttcctgtg tacgcagaag agatcgatgc tggaggtgat gcatctccat    660
```

```
caactgctat gctctcagaa gttagtaaga gactcaagat tacaattatc ggaggttcaa    720
ttcctgagag agttggagat aggttgtata acacatgttg cgtgttcgga tctgatggag    780
agctcaaggc taagcatagg aagattcacc tcttcgatat agatattcct ggaaagatca    840
ccttcatgga atcaaaaaca cttaccgctg gagagactcc aacaattgtt gatacagatg    900
tgggtagaat cggaataggt atatgttacg atatcaggtt ccaagaattg ctatgatat     960 atgctgcaag aggagcacat ctcttatgct accctggagc tttcaatatg actacaggtc   1020
cattgcactg ggagcttttg caaagagcta ggcaacaga  taaccagctc tatgttgcta    1080
cctgctctcc tgcaagagat tcaggagctg gttacaccgc atggggtcat tctactcttg   1140
ttggaccatt tggtgaagtg ttggctacca ctgagcacga agaggctatt ataatcgcag   1200
aaatcgatta cagtatactt gagcagagaa ggacttctct cccattaaat aggcagagga   1260
ggggtgattt ataccagtta gttgatgttc agagattaga tagtaagtga cacgtgtgaa   1320
ttacaggtga ccagctcgaa tttccccgat cgttcaaaca tttggcaata agtttcttta   1380
agattgaatc ctgttgccgg tcttgcgatg attatcatat aatttctgtt gaattacgtt   1440
aagcatgtaa taattaacat gtaatgcatg acgttattta tgagatgggt ttttatgatt   1500
agagtcccgc aattatacat ttaatacgcg atagaaaaca aaatatagcg cgcaaactag   1560
gataaattat cgcgcgcggt gtcatctatg ttactagatc gggggtaccg acgtc         1615

<210> SEQ ID NO 18
<211> LENGTH: 7
<212> TYPE: PRT
<213> ORGANISM: Artificial Sequence
<220> FEATURE:
<223> OTHER INFORMATION: synthetic conserved glutamine phenylpyruvate
      transaminase (GPT) region

<400> SEQUENCE: 18

Asn Leu Gly Gln Gly Phe Pro
 1               5

<210> SEQ ID NO 19
<211> LENGTH: 275
<212> TYPE: PRT
<213> ORGANISM: Chlamydomonas reinhardtii
<220> FEATURE:
<223> OTHER INFORMATION: Chlamydomonas reinhardtii strain CC-503 cw92
      mt+ predicted protein, partial, locus CHLREDRAFT_114854

<400> SEQUENCE: 19

Lys Val Ala Leu Cys Gln Leu His Val Thr Ala Asp Lys Glu Gln Asn
 1               5                  10                  15

Leu Arg Thr Ala Arg Lys Ala Ile Glu Asp Ala Ala Ala Gly Ala
             20                  25                  30

Lys Leu Val Val Leu Pro Glu Met Phe Asn Cys Pro Tyr Ser Asn Asp
         35                  40                  45

Ser Phe Pro Thr Tyr Ala Glu Asp Ile Glu Gly Gly Ala Ser Gly Ser
     50                  55                  60

Val Ala Ala Leu Ser Ala Ala Ala Ala Arg Val Thr Leu Val
 65                  70                  75                  80

Ala Gly Ser Ile Pro Glu Arg Cys Gln Gly Lys Leu Tyr Asn Thr Cys
                 85                  90                  95

Cys Val Phe Asp Ser Ser Gly Lys Leu Leu Ala Lys His Arg Lys Val
            100                 105                 110
```

```
His Leu Phe Asp Ile Asp Ile Pro Gly Lys Ile Thr Phe Lys Glu Ser
            115                 120                 125

Leu Thr Leu Ser Pro Gly Pro Gly Pro Thr Val Val Asp Thr Glu Ala
    130                 135                 140

Gly Arg Leu Gly Ile Gly Ile Cys Tyr Asp Ile Arg Phe Pro Glu Leu
145                 150                 155                 160

Ala Gln Ile Tyr Ala Ala Arg Gly Cys Gln Val Leu Ile Tyr Pro Gly
                165                 170                 175

Ala Phe Asn Met Thr Thr Gly Pro Val His Trp Glu Leu Leu Ala Lys
            180                 185                 190

Ala Arg Ala Val Asp Asn Gln Val Phe Val Leu Thr Cys Ser Pro Ala
        195                 200                 205

Arg Asn Pro Asp Ser Ser Tyr Gln Ala Trp Gly His Ser Thr Ala Leu
        210                 215                 220

Gly Pro Phe Ala Glu Val Leu Ala Thr Thr Glu His Ser Pro Ala Thr
225                 230                 235                 240

Val Phe Ala Glu Leu Asp Tyr Ala Gln Leu Asp Glu Arg Arg Ala Ala
                245                 250                 255

Met Pro Leu Arg Gln Gln Lys Arg His Asp Leu Tyr Leu Leu Leu Asp
            260                 265                 270

Lys Thr Ala
        275

<210> SEQ ID NO 20
<211> LENGTH: 361
<212> TYPE: PRT
<213> ORGANISM: Micromonas pusilla
<220> FEATURE:
<223> OTHER INFORMATION: green algae Micromonas pusilla strain CCMP1545
      hypothetical protein, locus MICPUCDRAFT_23156

<400> SEQUENCE: 20

Met Arg Ala Thr Lys Thr Thr Ala Ala Ala Ala Ala Ala Ala Ala Ala
1               5                   10                  15

Ser Ser Ser Gly Ala Gly Ala Pro Val Pro Phe Ala Arg Val Pro Ala
            20                  25                  30

Pro Trp Ser Ala Ser Gly Ala Ser Ala Ser Asp Ala Ala Thr Pro Thr
        35                  40                  45

Pro Thr Pro Ala Pro Arg Val Val Lys Val Ala Leu Cys Gln Leu Ala
    50                  55                  60

Cys Pro Thr Ala Asp Lys Val Ala Asn Ile Ala Arg Ala Arg Glu Ala
65                  70                  75                  80

Ile Arg Asn Ala Ala Glu Gly Gly Ala Ala Leu Val Val Leu Pro Glu
                85                  90                  95

Met Trp Asn Cys Pro Tyr Ala Asn Glu Ser Phe Pro Ala His Ala Glu
            100                 105                 110

Thr Ile Gly Ala Asn Asp Pro Thr Pro Ser Val Thr Met Leu Ser Glu
        115                 120                 125

Ala Ala Ala Ala His Asp Ile Val Leu Val Gly Gly Ser Ile Pro Glu
    130                 135                 140

Arg Gly Val Gly Val Gly Gly Gly Ala Asp Glu Glu Asp Val
145                 150                 155                 160

Leu Tyr Asn Ala Cys Cys Val Phe Asp Gly Lys Arg Gly Leu Ile Ala
                165                 170                 175

Arg His Arg Lys Thr His Leu Phe Asp Val Asp Ile Pro Gly Glu Ile
            180                 185                 190
```

Ser Phe Arg Glu Ser Asp Thr Leu Thr Glu Gly Glu Gly Leu Thr Val
    195                 200                 205

Val Asp Thr Ala Val Gly Arg Val Gly Val Gly Ile Cys Phe Asp Val
210                 215                 220

Arg Phe Gly Glu Met Ala Ala Met Ala Asn Arg Gly Ala Asp Val
225                 230                 235                 240

Leu Ile Tyr Pro Gly Ala Phe Asn Thr Val Thr Gly Pro His His Trp
                245                 250                 255

Glu Leu Leu Gln Arg Ala Arg Ala Val Asp Asn Gln Ala Arg Ser Ile
            260                 265                 270

His Trp Ser Pro Tyr Asp Arg Cys Phe Val Leu Thr Cys Ser Pro Ala
        275                 280                 285

Arg Asn Thr Thr Gly Glu Gly Tyr Gln Ala Trp Gly His Ser Thr Ala
    290                 295                 300

Val Gly Pro Phe Ala Glu Val Leu Ala Thr Thr Asp Glu Arg Pro Gly
305                 310                 315                 320

Ile Val Phe Ala Asp Leu Asp Leu Gly Glu Val Thr Arg Arg Arg
                325                 330                 335

Asn Met Pro Leu Ala Thr Gln Arg Arg Gly Asp Leu Tyr Ala Leu His
                340                 345                 350

Asp Leu Gly Ala Val Arg Gly Asp Ala
            355                 360

<210> SEQ ID NO 21
<211> LENGTH: 371
<212> TYPE: PRT
<213> ORGANISM: Ectocarpus siliculosus
<220> FEATURE:
<223> OTHER INFORMATION: brown algae Ectocarpus siliculosus strain Ec 32
      hydrolase, carbon-nitrogen family protein, locus Esi_0003_0068

<400> SEQUENCE: 21

Met Phe Leu Ala Ala Ala Arg Arg Ala Ser Pro Ile Leu Leu Ser Leu
1               5                   10                  15

Ala Val Lys Thr Ser Thr Thr Ala Ala Phe Cys Ser Pro Arg Leu Ala
            20                  25                  30

Asn Ala Arg Thr Asn Thr Ala Ala Gly Ala Thr Arg Thr Ala Tyr Ala
        35                  40                  45

Ala Cys Ser Ile Ser Arg Asn Ile Ser Leu Leu Ser Arg Pro Leu Ser
    50                  55                  60

Ser Met Ser Ala Ser Gly Ala Ser Glu Gly Ala Thr Ala Gly Ala Gly
65                  70                  75                  80

Ser Arg Arg Phe Val Val Ala Ala Cys Gln Ile Leu Cys Gly Ser Asp
                85                  90                  95

Lys Leu Ala Asn Ile Ala Thr Ala Glu Ser Ala Val Arg Asp Ala Ala
            100                 105                 110

Ala Ala Gly Ala Gln Val Val Leu Pro Glu Cys Trp Asn Gly Pro
        115                 120                 125

Tyr Asp Thr Ala Ser Phe Pro Val Tyr Ala Glu Pro Val Pro Asp Pro
    130                 135                 140

Gln Gly Asp Glu Thr Ala Ala Asp Met Pro Ser Ala Glu Gln Ser Pro
145                 150                 155                 160

Ser Ala Ala Met Leu Cys Arg Ala Ala Ala Glu Asn Lys Val Trp Leu
                165                 170                 175

Val Gly Gly Ser Val Pro Glu Ala Gly Lys Asp Gly Gly Val Tyr Asn

```
                180             185             190
Thr Cys Ile Val Val Gly Pro Ser Gly Arg Ile Val Ala Lys His Arg
            195             200             205
Lys Val His Leu Phe Asp Ile Asp Val Pro Gly Gly Ile Thr Phe Lys
            210             215             220
Glu Ser Asp Thr Leu Ser Pro Gly Asp Ser Ile Thr Thr Val Glu Thr
225             230             235             240
Pro Phe Gly Thr Ile Gly Val Gly Ile Cys Tyr Asp Met Arg Phe Pro
            245             250             255
Glu Leu Ser Met Ala Met Arg Ala Ala Gly Ser Val Leu Leu Cys Phe
            260             265             270
Pro Gly Ala Phe Asn Met Thr Thr Gly Pro Ala His Trp Glu Leu Leu
            275             280             285
Gln Arg Ala Arg Ala Leu Asp Asn Gln Cys Phe Val Val Thr Ala Ser
            290             295             300
Pro Ala Arg Asn Pro Asp Ser Lys Tyr Gln Ala Trp Gly His Ser Ser
305             310             315             320
Ile Val Asp Pro Trp Gly Thr Val Val Ala Thr Thr Glu His Glu Glu
            325             330             335
Ala Met Leu Val Ala Glu Val Asp Val Gly Arg Val Ala Glu Val Arg
            340             345             350
Thr Ser Ile Pro Val Ser Leu Gln Lys Arg Pro Asp Leu Tyr Arg Leu
            355             360             365
Glu Leu Pro
    370

<210> SEQ ID NO 22
<211> LENGTH: 313
<212> TYPE: PRT
<213> ORGANISM: Phaeodactylum tricornutum
<220> FEATURE:
<223> OTHER INFORMATION: diatom Phaeodactylum tricornutum strain CCAP
      1055/1 hypothetical protein, locus PHATRDRAFT_15536

<400> SEQUENCE: 22

Met Ser Ala Ser Arg Gln Asn Asp Asp Asp Asp Asp Asp Pro Ser
1               5              10              15
Val Leu Arg Val Ala Leu Cys Gln Leu Pro Val Thr Asn Asp Lys Ala
            20              25              30
Gln Asn His Gln Thr Ala Arg Glu Tyr Leu Asn Arg Ala Ala Asn Gln
            35              40              45
Gly Ala Arg Leu Val Val Leu Pro Glu Ile Trp Asn Ser Pro Tyr Ala
50              55              60
Thr Ala Ala Phe Pro Glu Tyr Ala Glu Gln Leu Pro Asp Val Leu Ala
65              70              75              80
Gln Asp Gly Asp Gly His Thr Gly Val Tyr Glu Ser Pro Ser Ala Asp
            85              90              95
Leu Leu Arg Glu Ser Ala Lys Glu His Lys Leu Trp Ile Val Gly Gly
            100             105             110
Ser Ile Pro Glu Arg Asp Asp Asp Lys Ile Tyr Asn Thr Ser Leu
            115             120             125
Val Phe Asp Pro Gln Gly Asn Leu Val Ala Lys His Arg Lys Met His
            130             135             140
Leu Phe Asp Ile Asp Val Pro Gly Gly Ile Thr Phe Phe Glu Ser Asp
145             150             155             160
```

```
Thr Leu Ser Pro Gly Asn Thr Val Ser His Phe Ala Thr Pro Trp Gly
                165                 170                 175

Asn Ile Gly Leu Gly Ile Cys Tyr Asp Ile Arg Phe Pro Glu Tyr Ala
            180                 185                 190

Met Leu Leu Ala Lys Glu His Asp Cys Gly Ile Leu Ile Tyr Pro Gly
            195                 200                 205

Ala Phe Asn Leu Thr Thr Gly Pro Ala His Trp Glu Leu Leu Gln Arg
        210                 215                 220

Gly Arg Ala Val Asp Asn Gln Cys Phe Val Leu Thr Ala Ser Pro Ala
225                 230                 235                 240

Arg Thr Glu Pro Pro Ser Lys Ala Gly Leu Tyr Pro His Tyr Thr Ala
                245                 250                 255

Trp Gly His Ser Thr Ala Val Ser Pro Trp Gly Glu Val Ile Ala Thr
            260                 265                 270

Thr Asn Glu Lys Ala Gly Ile Val Phe Ala Asp Leu Asp Leu Ser Lys
        275                 280                 285

Val Thr Glu Met Arg Thr Ser Ile Pro Ile Gly Lys Gln Lys Arg Thr
290                 295                 300

Asp Leu Tyr Gln Leu Val Gly Lys Ser
305                 310
```

<210> SEQ ID NO 23
<211> LENGTH: 322
<212> TYPE: PRT
<213> ORGANISM: Schizosaccharomyces pombe
<220> FEATURE:
<223> OTHER INFORMATION: fission yeast Schizosaccharomyces pombe strain
      972h-amidohydrolase, locus SPAC26A3.11

<400> SEQUENCE: 23

```
Met Asn Ser Lys Phe Phe Gly Leu Val Gln Lys Gly Thr Arg Ser Phe
1               5                   10                  15

Phe Pro Ser Leu Asn Phe Cys Tyr Thr Arg Asn Ile Met Ser Val Ser
            20                  25                  30

Ala Ser Ser Leu Val Pro Lys Asp Phe Arg Ala Phe Arg Ile Gly Leu
        35                  40                  45

Val Gln Leu Ala Asn Thr Lys Asp Lys Ser Glu Asn Leu Gln Leu Ala
    50                  55                  60

Arg Leu Lys Val Leu Glu Ala Ala Lys Asn Gly Ser Asn Val Ile Val
65                  70                  75                  80

Leu Pro Glu Ile Phe Asn Ser Pro Tyr Gly Thr Gly Tyr Phe Asn Gln
                85                  90                  95

Tyr Ala Glu Pro Ile Glu Glu Ser Ser Pro Ser Tyr Gln Ala Leu Ser
            100                 105                 110

Ser Met Ala Lys Asp Thr Lys Thr Tyr Leu Phe Gly Gly Ser Ile Pro
        115                 120                 125

Glu Arg Lys Asp Gly Lys Leu Tyr Asn Thr Ala Met Val Phe Asp Pro
    130                 135                 140

Ser Gly Lys Leu Ile Ala Val His Arg Lys Ile His Leu Phe Asp Ile
145                 150                 155                 160

Asp Ile Pro Gly Gly Val Ser Phe Arg Glu Ser Asp Ser Leu Ser Pro
                165                 170                 175

Gly Asp Ala Met Thr Met Val Asp Thr Glu Tyr Gly Lys Phe Gly Leu
            180                 185                 190

Gly Ile Cys Tyr Asp Ile Arg Phe Pro Glu Leu Ala Met Ile Ala Ala
        195                 200                 205
```

```
Arg Asn Gly Cys Ser Val Met Ile Tyr Pro Gly Ala Phe Asn Leu Ser
    210                 215                 220

Thr Gly Pro Leu His Trp Glu Leu Leu Ala Arg Ala Arg Ala Val Asp
225                 230                 235                 240

Asn Glu Met Phe Val Ala Cys Cys Ala Pro Ala Arg Asp Met Asn Ala
                245                 250                 255

Asp Tyr His Ser Trp Gly His Ser Thr Val Val Asp Pro Phe Gly Lys
            260                 265                 270

Val Ile Ala Thr Thr Asp Glu Lys Pro Ser Ile Val Tyr Ala Asp Ile
        275                 280                 285

Asp Pro Ser Val Met Ser Thr Ala Arg Asn Ser Val Pro Ile Tyr Thr
    290                 295                 300

Gln Arg Arg Phe Asp Val Tyr Ser Glu Val Leu Pro Ala Leu Lys Lys
305                 310                 315                 320

Glu Glu

<210> SEQ ID NO 24
<211> LENGTH: 292
<212> TYPE: PRT
<213> ORGANISM: Aspergillus oryzae
<220> FEATURE:
<223> OTHER INFORMATION: yellow koji mold Aspergillus oryzae strain
      RIB40 hypothetical protein, locus AOR_1_782154

<400> SEQUENCE: 24

Met Ala Ala Leu Leu Lys Gln Pro Leu Lys Leu Ala Leu Val Gln Leu
  1               5                  10                  15

Ala Ser Gly Ala Asp Lys Ala Val Asn Leu Ala His Ala Arg Thr Lys
                 20                  25                  30

Val Leu Glu Ala Ala Gln Ala Gly Ala Lys Leu Ile Val Leu Pro Glu
            35                  40                  45

Cys Phe Asn Ser Pro Tyr Gly Thr Gln Tyr Phe Pro Lys Tyr Ala Glu
        50                  55                  60

Thr Leu Leu Pro Ser Pro Pro Thr Glu Asp Gln Ser Pro Ser Tyr His
65                  70                  75                  80

Ala Leu Ser Ala Ile Ala Ala Glu Ala Lys Ala Tyr Leu Val Gly Gly
                85                  90                  95

Ser Ile Pro Glu Leu Glu Pro Thr Thr Lys Lys Tyr Tyr Asn Thr Ser
            100                 105                 110

Leu Val Phe Ser Pro Thr Gly Ser Leu Ile Gly Thr His Arg Lys Thr
        115                 120                 125

His Leu Phe Asp Ile Asp Ile Pro Gly Lys Ile Thr Phe Lys Glu Ser
    130                 135                 140

Glu Val Leu Ser Pro Gly Asn Gln Leu Thr Ile Val Asp Leu Pro Asp
145                 150                 155                 160

Tyr Gly Lys Ile Gly Leu Ala Ile Cys Tyr Asp Ile Arg Phe Pro Glu
                165                 170                 175

Ala Ala Met Ile Ala Ala Arg Lys Gly Ala Phe Ala Leu Ile Tyr Pro
            180                 185                 190

Gly Ala Phe Asn Met Thr Thr Gly Pro Met His Trp Ser Leu Leu Ala
        195                 200                 205

Arg Ala Arg Ala Val Asp Asn Gln Leu Tyr Val Gly Leu Cys Ser Pro
    210                 215                 220

Ala Arg Asp Met Glu Ala Thr Tyr His Ala Trp Gly His Ser Leu Ile
225                 230                 235                 240
```

```
Ala Asn Pro Ala Ala Glu Val Leu Val Glu Ala Glu Asp Lys Glu Thr
                245                 250                 255

Ile Val Tyr Ala Asp Leu Asp Asn Asp Thr Ile Gln Ser Thr Arg Lys
            260                 265                 270

Gly Ile Pro Val Tyr Thr Gln Arg Arg Phe Asp Leu Tyr Pro Asp Val
        275                 280                 285

Ser Ala Glu Lys
        290

<210> SEQ ID NO 25
<211> LENGTH: 306
<212> TYPE: PRT
<213> ORGANISM: Neurospora crassa
<220> FEATURE:
<223> OTHER INFORMATION: red bread mold Neurospora crassa strain OR74A
      hypothetical protein, locus NCU06726.1, similar to nit protein 2

<400> SEQUENCE: 25

Met Ala Ser Ser Thr Lys His Pro Ile Leu Leu Lys Lys Pro Val Lys
 1               5                  10                  15

Leu Ala Cys Ile Gln Leu Ala Ser Gly Ala Asp Lys Ser Ala Asn Leu
            20                  25                  30

Ser His Ala Ala Asp Lys Val Arg Glu Ala Ala Ser Gly Gly Ala Asn
        35                  40                  45

Ile Val Val Leu Pro Glu Cys Phe Asn Ser Pro Tyr Gly Cys Asp Phe
 50                  55                  60

Phe Pro Ser Tyr Ala Glu Gln Leu Leu Pro Ser Pro Pro Thr Val Glu
65                  70                  75                  80

Gln Ser Pro Ser Phe His Ala Leu Ser Ala Met Ala Arg Asp Asn Gly
                85                  90                  95

Ile Tyr Leu Val Gly Gly Ser Ile Pro Glu Leu Ala Ile Glu Glu Gly
            100                 105                 110

Thr Glu Asp Lys Lys Thr Tyr Tyr Asn Thr Ser Leu Val Phe Gly Pro
        115                 120                 125

Asp Gly Lys Leu Leu Ala Ser His Arg Lys Val His Leu Phe Asp Ile
    130                 135                 140

Asp Ile Pro Gly Lys Ile Lys Phe Lys Glu Ser Asp Val Leu Ser Pro
145                 150                 155                 160

Gly Asn Ser Val Thr Leu Val Asp Leu Pro Asp Tyr Gly Arg Ile Ala
                165                 170                 175

Val Ala Ile Cys Tyr Asp Ile Arg Phe Pro Glu Leu Ala Met Ile Ala
            180                 185                 190

Ala Arg Lys Gly Cys Phe Ala Leu Val Tyr Pro Gly Ala Phe Asn Thr
        195                 200                 205

Thr Thr Gly Pro Leu His Trp Arg Leu Gln Gly Gln Ala Arg Ala Met
    210                 215                 220

Asp Asn Gln Ile Tyr Val Ala Leu Cys Ser Pro Ala Arg Asp Ile Ser
225                 230                 235                 240

Ala Ser Tyr His Ala Tyr Gly His Ser Leu Ile Val Asp Pro Met Ala
                245                 250                 255

Arg Val Leu Val Glu Ala Glu Glu Ser Glu Thr Ile Val Ser Ala Glu
            260                 265                 270

Leu Asp Gly Thr Lys Ile Glu Glu Ala Arg Ser Gly Ile Pro Leu Arg
        275                 280                 285

Asp Gln Arg Arg Phe Asp Ile Tyr Pro Asp Val Ser Gln Ala Lys Pro
```

290                 295                 300

Phe Phe
305

<210> SEQ ID NO 26
<211> LENGTH: 285
<212> TYPE: PRT
<213> ORGANISM: Rhizobium leguminosarum
<220> FEATURE:
<223> OTHER INFORMATION: nitrogen-fixing plant microsymbiont bacteria of
      tribe Viciae Rhizobium leguminosarum biovar viciae strain 3841
      aminohydrolase, locus RL4288

<400> SEQUENCE: 26

Met Ser Phe Lys Ala Ala Ala Val Gln Met Cys Ser Gly Val Asp Pro
1               5                   10                  15

Val Arg Asn Ala Ala Ala Met Ala Arg Leu Val Arg Glu Ala Ala Gly
            20                  25                  30

Gln Gly Ala Ile Tyr Val Gln Thr Pro Glu Met Thr Gly Met Leu Gln
        35                  40                  45

Arg Asp Arg Ala Ala Ala Arg Ala Val Leu Ala Asp Glu Ala His Asp
    50                  55                  60

Ile Ile Val Lys Thr Gly Ser Asp Leu Ala Arg Glu Leu Gly Ile His
65                  70                  75                  80

Met His Val Gly Ser Thr Ala Ile Ala Leu Ala Asp Gly Lys Ile Ala
                85                  90                  95

Asn Arg Gly Phe Leu Phe Gly Pro Asp Gly Arg Ile Leu Asn Arg Tyr
            100                 105                 110

Asp Lys Ile His Met Phe Asp Val Asp Leu Asp Asn Gly Glu Ser Trp
        115                 120                 125

Arg Glu Ser Ala Ala Tyr Thr Ala Gly Ser Gly Ala Arg Val Leu Ser
    130                 135                 140

Leu Pro Phe Ala Glu Met Gly Phe Ala Ile Cys Tyr Asp Val Arg Phe
145                 150                 155                 160

Pro Ala Leu Phe Arg Ala Gln Ala Met Ala Gly Ala Glu Val Met Thr
                165                 170                 175

Val Pro Ala Ala Phe Thr Lys Gln Thr Gly Glu Ala His Trp Glu Ile
            180                 185                 190

Leu Leu Arg Ala Arg Ala Ile Glu Asn Gly Val Phe Val Ile Ala Ala
        195                 200                 205

Ala Gln Ala Gly Arg His Glu Asp Gly Arg Glu Ser Phe Gly His Ser
    210                 215                 220

Met Ile Ile Asp Pro Trp Gly Thr Val Leu Ala Ser Ala Gly Ala Thr
225                 230                 235                 240

Gly Glu Ala Val Ile Val Ala Glu Ile Asp Pro Ser Ala Val Lys Ala
                245                 250                 255

Ala His Asp Lys Ile Pro Asn Leu Arg Asn Gly Arg Glu Phe Ser Val
            260                 265                 270

Glu Lys Ile Ala Gly Ala Ile Ala Gly Gly Val Ala Ala
        275                 280                 285

<210> SEQ ID NO 27
<211> LENGTH: 285
<212> TYPE: PRT
<213> ORGANISM: Rhizobium etli
<220> FEATURE:
<223> OTHER INFORMATION: nitrogen-fixing plant microsymbiont bacteria
      Rhizobium etli strain CFN 42 aminohydrolase, locus RHE_CH03761

<400> SEQUENCE: 27

| Met | Ser | Phe | Lys | Ala | Ala | Ile | Gln | Met | Cys | Ser | Gly | Val | Asp | Pro |
| 1   |     |     |     | 5   |     |     |     |     | 10  |     |     |     |     | 15  |

Val Lys Asn Ala Ala Ser Met Ala Arg Leu Val Arg Glu Ala Ala
              20                  25                  30

Gln Gly Ala Thr Tyr Val Gln Thr Pro Glu Met Thr Gly Met Leu Gln
            35                  40                  45

Arg Asp Arg Ala Ala Ala Ala Val Leu Ala Asp Glu Ala His Asp
50                  55                  60

Ile Ile Val Lys Thr Gly Ser Glu Leu Ala Arg Glu Leu Gly Ile His
65                  70                  75                  80

Val His Val Gly Ser Thr Ala Ile Ala Leu Ser Asp Gly Lys Ile Ala
                85                  90                  95

Asn Arg Gly Phe Leu Phe Gly Pro Asp Gly Arg Ile Leu Asn Arg Tyr
                100                 105                 110

Asp Lys Ile His Met Phe Asp Val Asp Leu Asp Asn Gly Glu Ser Trp
                115                 120                 125

Arg Glu Ser Ala Ala Tyr Thr Ala Gly Ser Glu Ala Arg Val Leu Ser
130                 135                 140

Leu Pro Phe Ala Glu Met Gly Phe Ala Ile Cys Tyr Asp Val Arg Phe
145                 150                 155                 160

Pro Ala Leu Phe Arg Ala Gln Ala Val Ala Gly Ala Glu Val Met Thr
                165                 170                 175

Val Pro Ser Ser Phe Ser Arg Gln Thr Gly Glu Ala His Trp Glu Ile
                180                 185                 190

Leu Leu Arg Ala Arg Ala Ile Glu Asn Gly Val Phe Val Ile Ala Ala
                195                 200                 205

Ala Gln Ala Gly Arg His Glu Asp Gly Arg Glu Thr Phe Gly His Ser
210                 215                 220

Ile Ile Ile Asp Pro Trp Gly Thr Val Leu Ala Ser Ala Gly Ala Thr
225                 230                 235                 240

Gly Glu Ala Val Ile Leu Ala Glu Ile Asp Pro Gly Ala Val Lys Ala
                245                 250                 255

Ala His Asp Lys Ile Pro Asn Leu Arg Asp Gly Arg Glu Phe Ser Val
                260                 265                 270

Glu Lys Ile Ala Gly Ala Val Ala Gly Gly Val Ala Ala
                275                 280                 285

<210> SEQ ID NO 28
<211> LENGTH: 285
<212> TYPE: PRT
<213> ORGANISM: Rhizobium leguminosarum
<220> FEATURE:
<223> OTHER INFORMATION: nitrogen-fixing plant microsymbiont bacteria of
      South American clover Trifolium polymorphum Rhizobium
      leguminosarum biovar trifolii strain WSM1325 nitrilase/cyanide
      hydratase and apolipoprotein N-acyltransferase, locus Rleg_3821

<400> SEQUENCE: 28

Met Ser Phe Lys Ala Ala Ala Val Gln Met Cys Ser Gly Val Asp Pro
1               5                   10                  15

Val Lys Asn Ala Ala Ala Met Ala Arg Leu Val Arg Glu Ala Ala Gly
                20                  25                  30

Gln Gly Ala Thr Tyr Val Gln Thr Pro Glu Met Thr Gly Met Leu Gln
            35                  40                  45

```
Arg Asp Arg Thr Ala Ala Arg Ala Val Leu Ala Asp Glu Ala His Asp
 50                  55                  60

Ile Ile Val Lys Thr Gly Ser Glu Leu Ala Ile Glu Leu Gly Ile His
 65                  70                  75                  80

Met His Val Gly Ser Thr Ala Ile Ala Leu Ala Asp Gly Lys Ile Ala
                 85                  90                  95

Asn Arg Gly Phe Leu Phe Gly Pro Asp Gly Arg Val Leu Asn Arg Tyr
                100                 105                 110

Asp Lys Ile His Met Phe Asp Val Asp Leu Asp Asn Gly Glu Ser Trp
            115                 120                 125

Arg Glu Ser Ala Ala Tyr Thr Ala Gly Ser Glu Ala Arg Val Leu Ser
    130                 135                 140

Leu Pro Phe Ala Glu Met Gly Phe Ala Ile Cys Tyr Asp Val Arg Phe
145                 150                 155                 160

Pro Ala Leu Phe Cys Ala Gln Ala Val Ala Gly Ala Glu Val Met Thr
                165                 170                 175

Val Pro Ala Ala Phe Thr Lys Gln Thr Gly Glu Ala His Trp Glu Ile
                180                 185                 190

Leu Leu Arg Ala Arg Ala Ile Glu Asn Gly Val Phe Val Ile Ala Ala
195                 200                 205

Ala Gln Ala Gly Arg His Glu Asp Gly Arg Glu Thr Phe Gly His Ser
    210                 215                 220

Met Ile Ile Asp Pro Trp Gly Thr Val Leu Ala Ser Ala Gly Ala Thr
225                 230                 235                 240

Gly Glu Ala Val Ile Val Ala Glu Ile Asp Pro Ala Ala Val Lys Ala
                245                 250                 255

Ala His Asp Lys Ile Pro Asn Leu Arg Asn Gly Arg Glu Phe Ser Val
                260                 265                 270

Glu Lys Ile Ala Gly Ala Ile Ala Gly Gly Val Ala Ala
            275                 280                 285

<210> SEQ ID NO 29
<211> LENGTH: 292
<212> TYPE: PRT
<213> ORGANISM: Bradyrhizobium sp.
<220> FEATURE:
<223> OTHER INFORMATION: photosynthetic bacteria Bradyrhizobium sp.
      strain ORS278 nitrilase, locus BRAD00581

<400> SEQUENCE: 29

Met Ser Asn Asp Arg Ser Phe Thr Ala Ala Met Val Gln Met Arg Thr
  1               5                  10                  15

Ala Leu Leu Pro Glu Pro Ser Leu Glu Gln Gly Thr Arg Leu Ile Arg
                 20                  25                  30

Glu Ala Val Ala Gln Gly Ala Gln Tyr Val Gln Thr Pro Glu Val Ser
             35                  40                  45

Asn Met Met Gln Leu Asn Arg Thr Ala Leu Phe Glu Gln Leu Lys Ser
         50                  55                  60

Glu Glu Glu Asp Pro Ser Leu Lys Ala Tyr Arg Ala Leu Ala Lys Glu
 65                  70                  75                  80

Leu Asn Ile His Leu His Ile Gly Ser Leu Ala Leu Arg Phe Ser Ala
                 85                  90                  95

Glu Lys Ala Val Asn Arg Ser Phe Leu Ile Gly Pro Asp Gly Gln Val
                100                 105                 110

Leu Ala Ser Tyr Asp Lys Ile His Met Phe Asp Ile Asp Leu Pro Gly
            115                 120                 125
```

Gly Glu Ser Tyr Arg Glu Ser Ala Asn Tyr Gln Pro Gly Glu Thr Ala
            130                 135                 140

Val Ile Ser Asp Leu Pro Trp Gly Arg Leu Gly Leu Thr Ile Cys Tyr
145                 150                 155                 160

Asp Val Arg Phe Pro Ala Leu Tyr Arg Ala Leu Ala Glu Ser Gly Ala
                165                 170                 175

Ser Phe Ile Ser Val Pro Ser Ala Phe Thr Arg Lys Thr Gly Glu Ala
                180                 185                 190

His Trp His Thr Leu Leu Arg Ala Arg Ala Ile Glu Thr Gly Cys Phe
            195                 200                 205

Val Phe Ala Ala Ala Gln Cys Gly Leu His Glu Asn Lys Arg Glu Thr
            210                 215                 220

Phe Gly His Ser Leu Ile Ile Asp Pro Trp Gly Glu Ile Leu Ala Glu
225                 230                 235                 240

Gly Gly Val Glu Pro Gly Val Ile Leu Ala Arg Ile Asp Pro Ser Arg
                245                 250                 255

Val Glu Ser Val Arg Gln Thr Ile Pro Ser Leu Gln His Gly Arg Arg
                260                 265                 270

Phe Gly Ile Ala Asp Pro Lys Gly Gly Pro Asp Tyr Leu His Leu Val
            275                 280                 285

Arg Gly Ser Ala
    290

<210> SEQ ID NO 30
<211> LENGTH: 290
<212> TYPE: PRT
<213> ORGANISM: Sinorhizobium meliloti
<220> FEATURE:
<223> OTHER INFORMATION: nitrogen-fixing plant microsymbiont bacteria
      Sinorhizobium meliloti strain BL225C nitrilase/cyanide hydratase
      and apolipoprotein N-acyltransferase, locus SinmeBDRAFT_5722

<400> SEQUENCE: 30

Met Pro Ser Ser Arg Tyr Phe Trp Phe Leu Trp Gln Phe Lys Leu Ala
1               5                   10                  15

Val Cys Gln Leu Ser Ile Cys Ala Asp Lys Glu Gln Asn Ile Arg His
            20                  25                  30

Ala Arg Glu Ala Ile Gln Thr Ala Ala Asp Gly Gly Ser Lys Leu Val
        35                  40                  45

Leu Leu Pro Glu Met Trp Asn Cys Pro Tyr Ser Asn Ala Ser Phe Pro
50                  55                  60

Ile Tyr Ala Glu Asp Ile Asp Ala Gly Asp Ser Pro Ser Ser Lys Met
65                  70                  75                  80

Leu Ser Asp Met Ala Lys Ser Lys Glu Val Thr Ile Ile Gly Gly Ser
            85                  90                  95

Ile Pro Glu Arg Ser Gly Asn His Leu Tyr Asn Thr Cys Cys Ile Tyr
            100                 105                 110

Gly Lys Asp Gly Ser Leu Lys Gly Lys His Arg Lys Val His Leu Phe
            115                 120                 125

Asp Ile Asp Ile Pro Gly Lys Ile Gln Phe Lys Glu Ser Asp Thr Leu
            130                 135                 140

Thr Pro Gly Asp Lys Tyr Thr Val Val Asp Thr Asp Val Gly Arg Ile
145                 150                 155                 160

Gly Val Gly Ile Cys Tyr Asp Ile Arg Phe Pro Glu Met Ala Met Thr
                165                 170                 175

```
Tyr Ala Ala Arg Gly Val His Met Ile Cys Tyr Pro Gly Ala Phe Asn
            180                 185                 190

Met Thr Thr Gly Pro Ala His Trp Glu Leu Leu Gln Lys Ala Arg Ala
        195                 200                 205

Val Asp Asn Gln Leu Phe Val Ala Thr Cys Ser Pro Ala Arg Asn Pro
    210                 215                 220

Ser Ala Gly Tyr Val Ala Trp Gly His Ser Ser Val Ile Gly Pro Phe
225                 230                 235                 240

Gly Glu Ile Leu Ala Ser Thr Gly Arg Glu Ala Ile Phe Tyr Ala
                245                 250                 255

Asp Ile Asp Tyr Ala Gln Ile Lys Glu Arg Arg Met Asn Met Pro Leu
            260                 265                 270

Asp His Gln Arg Arg Gly Asp Leu Tyr Gln Leu Val Asp Leu Thr Phe
        275                 280                 285

Thr Thr
    290

<210> SEQ ID NO 31
<211> LENGTH: 285
<212> TYPE: PRT
<213> ORGANISM: Sinorhizobium meliloti
<220> FEATURE:
<223> OTHER INFORMATION: nitrogen-fixing plant microsymbiont bacteria
      Sinorhizobium meliloti strain 1021 hydrolase, locus SMe02442

<400> SEQUENCE: 31

Met Thr Phe Lys Ala Ala Val Gln Ile Cys Ser Gly Val Asp Pro
1               5                   10                  15

Ala Gly Asn Ala Glu Thr Met Ala Lys Leu Val Arg Glu Ala Ala Ser
            20                  25                  30

Arg Gly Ala Thr Tyr Val Gln Thr Pro Glu Met Thr Gly Ala Val Gln
        35                  40                  45

Arg Asp Arg Thr Gly Leu Arg Ser Val Leu Lys Asp Gly Glu Asn Asp
    50                  55                  60

Val Val Arg Glu Ala Ser Arg Leu Ala Arg Glu Leu Gly Ile Tyr
65                  70                  75                  80

Leu His Val Gly Ser Thr Pro Ile Ala Arg Ala Asp Gly Lys Ile Ala
                85                  90                  95

Asn Arg Gly Phe Leu Phe Gly Pro Asp Gly Ala Lys Ile Cys Asp Tyr
            100                 105                 110

Asp Lys Ile His Met Phe Asp Val Asp Leu Glu Asn Gly Glu Ser Trp
        115                 120                 125

Arg Glu Ser Ala Ala Tyr His Pro Gly Asn Thr Ala Arg Thr Ala Asp
    130                 135                 140

Leu Pro Phe Gly Lys Leu Gly Phe Ser Ile Cys Tyr Asp Val Arg Phe
145                 150                 155                 160

Pro Glu Leu Phe Arg Gln Gln Ala Val Ala Gly Ala Glu Ile Met Ser
                165                 170                 175

Val Pro Ala Ala Phe Thr Arg Gln Thr Gly Glu Ala His Trp Glu Ile
            180                 185                 190

Leu Leu Arg Ala Arg Ala Ile Glu Asn Gly Leu Phe Val Ile Ala Ala
        195                 200                 205

Ala Gln Ala Gly Thr His Glu Asp Gly Arg Glu Thr Phe Gly His Ser
    210                 215                 220

Met Ile Val Asp Pro Trp Gly Arg Val Leu Ala Glu Ala Gly Ala Thr
225                 230                 235                 240
```

```
Gly Glu Glu Ile Ile Val Ala Glu Ile Asp Val Ala Ala Val His Ala
                245                 250                 255

Ala Arg Ala Lys Ile Pro Asn Leu Arg Asn Ala Arg Ser Phe Val Leu
            260                 265                 270

Asp Glu Val Val Pro Val Gly Lys Gly Gly Ala Ala
        275                 280             285

<210> SEQ ID NO 32
<211> LENGTH: 312
<212> TYPE: PRT
<213> ORGANISM: Phytophthora infestans
<220> FEATURE:
<223> OTHER INFORMATION: potato blight oomycete Phytophthora infestans
      strain T30-4 carbon-nitrogen hydrolase, putative, locus
      PITG_05539

<400> SEQUENCE: 32

Met Leu Gly Arg Thr Ile Arg Ser Gln Ala Arg His Leu Arg Ser Pro
 1               5                  10                  15

Phe Leu Arg Leu Ser Ser Pro Met Ser Thr Thr Ala Pro Lys Phe Lys
            20                  25                  30

Leu Ala Leu Cys Gln Ile Ala Val Gly Asp Asp Lys Gln Lys Asn Ile
        35                  40                  45

Ala Thr Ala Thr Ala Ala Val Thr Glu Ala Ala Gln Asn Ala Ala Gln
    50                  55                  60

Val Val Ser Leu Pro Glu Cys Trp Asn Ser Pro Tyr Ala Thr Thr Ser
65                  70                  75                  80

Phe Pro Gln Tyr Ala Glu Glu Ile Pro Glu Lys Lys Ala Ala Leu Asn
                85                  90                  95

Glu Lys Glu His Pro Ser Thr Phe Ala Leu Ser Gln Leu Ala Ala Lys
            100                 105                 110

Leu Gln Ile Phe Leu Val Gly Gly Ser Ile Pro Glu Lys Asp Ala Thr
        115                 120                 125

Gly Lys Val Tyr Asn Thr Ser Val Ile Phe Ser Pro Glu Gly Glu Ile
    130                 135                 140

Leu Gly Lys His Arg Lys Val His Leu Phe Asp Ile Asp Val Pro Gly
145                 150                 155                 160

Lys Ile Thr Phe Lys Glu Ser Asp Thr Leu Ser Pro Gly Asn Ser Met
                165                 170                 175

Thr Leu Phe Asp Thr Pro Tyr Gly Lys Met Gly Val Gly Ile Cys Tyr
            180                 185                 190

Asp Ile Arg Phe Pro Glu Leu Ser Met Leu Met Lys Lys Gln Gly Ala
        195                 200                 205

Lys Val Leu Leu Phe Pro Gly Ala Phe Asn Leu Thr Thr Gly Pro Ala
    210                 215                 220

His Trp Glu Leu Leu Gln Arg Ala Arg Ala Val Asp Asn Gln Leu Tyr
225                 230                 235                 240

Val Ala Ala Thr Ser Pro Ala Arg Gly Pro Glu Gly Tyr Gln Ala
                245                 250                 255

Trp Gly His Ser Thr Val Ile Ser Pro Trp Gly Glu Val Val Ala Thr
            260                 265                 270

Cys Gly His Gly Glu Ser Ile Val Tyr Ala Glu Val Asp Leu Glu Lys
        275                 280                 285

Val Glu Glu Met Arg Arg Asn Ile Pro Thr Thr Asn Gln Thr Arg Ser
    290                 295                 300
```

Asp Leu Tyr Glu Leu Val Gln Lys
305                 310

<210> SEQ ID NO 33
<211> LENGTH: 276
<212> TYPE: PRT
<213> ORGANISM: Homo sapiens
<220> FEATURE:
<223> OTHER INFORMATION: human omega-amidase NIT2, Nit protein 2,
      nitrilase homolog 2, nitrilase family, member 2

<400> SEQUENCE: 33

Met Thr Ser Phe Arg Leu Ala Leu Ile Gln Leu Gln Ile Ser Ile
1               5                   10                  15

Lys Ser Asp Asn Val Thr Arg Ala Cys Ser Phe Ile Arg Glu Ala Ala
            20                  25                  30

Thr Gln Gly Ala Lys Ile Val Ser Leu Pro Glu Cys Phe Asn Ser Pro
        35                  40                  45

Tyr Gly Ala Lys Tyr Phe Pro Glu Tyr Ala Glu Lys Ile Pro Gly Glu
    50                  55                  60

Ser Thr Gln Lys Leu Ser Glu Val Ala Lys Glu Cys Ser Ile Tyr Leu
65                  70                  75                  80

Ile Gly Gly Ser Ile Pro Glu Glu Asp Ala Gly Lys Leu Tyr Asn Thr
                85                  90                  95

Cys Ala Val Phe Gly Pro Asp Gly Thr Leu Leu Ala Lys Tyr Arg Lys
            100                 105                 110

Ile His Leu Phe Asp Ile Asp Val Pro Gly Lys Ile Thr Phe Gln Glu
        115                 120                 125

Ser Lys Thr Leu Ser Pro Gly Asp Ser Phe Ser Thr Phe Asp Thr Pro
    130                 135                 140

Tyr Cys Arg Val Gly Leu Gly Ile Cys Tyr Asp Met Arg Phe Ala Glu
145                 150                 155                 160

Leu Ala Gln Ile Tyr Ala Gln Arg Gly Cys Gln Leu Leu Val Tyr Pro
                165                 170                 175

Gly Ala Phe Asn Leu Thr Thr Gly Pro Ala His Trp Glu Leu Leu Gln
            180                 185                 190

Arg Ser Arg Ala Val Asp Asn Gln Val Tyr Val Ala Thr Ala Ser Pro
        195                 200                 205

Ala Arg Asp Asp Lys Ala Ser Tyr Val Ala Trp Gly His Ser Thr Val
    210                 215                 220

Val Asn Pro Trp Gly Glu Val Leu Ala Lys Ala Gly Thr Glu Glu Ala
225                 230                 235                 240

Ile Val Tyr Ser Asp Ile Asp Leu Lys Lys Leu Ala Glu Ile Arg Gln
                245                 250                 255

Gln Ile Pro Val Phe Arg Gln Lys Arg Ser Asp Leu Tyr Ala Val Glu
            260                 265                 270

Met Lys Lys Pro
        275

<210> SEQ ID NO 34
<211> LENGTH: 314
<212> TYPE: PRT
<213> ORGANISM: Equus caballus
<220> FEATURE:
<223> OTHER INFORMATION: thoroughbred horse predicted omega-amidase
      NIT2-like,LOC100072286

<400> SEQUENCE: 34

```
Met Ala Ala His Ser Ile Leu Asp Leu Ser Gly Leu Asp Arg Glu Ser
 1               5                  10                  15

Gln Ile Asp Leu Gln Arg Pro Leu Lys Ala Arg Pro Gly Lys Ala Lys
            20                  25                  30

Asp Leu Ser Ser Gly Ser Ala Cys Thr Phe Arg Leu Ala Leu Ile Gln
        35                  40                  45

Leu Gln Val Ser Ser Val Lys Ser Asp Asn Leu Thr Arg Ala Cys Gly
    50                  55                  60

Leu Val Arg Glu Ala Ala Gln Gly Ala Lys Ile Val Cys Leu Pro
65                  70                  75                  80

Glu Cys Phe Asn Ser Pro Tyr Gly Thr Asn Tyr Phe Pro Gln Tyr Ala
                85                  90                  95

Glu Lys Ile Pro Gly Glu Ser Thr Gln Lys Leu Ser Glu Val Ala Lys
            100                 105                 110

Glu Cys Ser Ile Tyr Leu Ile Gly Gly Ser Ile Pro Glu Glu Asp Ala
        115                 120                 125

Gly Lys Leu Tyr Asn Thr Cys Ala Val Phe Gly Pro Asp Gly Ala Leu
    130                 135                 140

Leu Val Lys His Arg Lys Leu His Leu Phe Asp Ile Asp Val Pro Gly
145                 150                 155                 160

Lys Ile Thr Phe Gln Glu Ser Lys Thr Leu Ser Pro Gly Asp Ser Phe
                165                 170                 175

Ser Thr Phe Asp Thr Pro Tyr Cys Arg Val Gly Leu Gly Ile Cys Tyr
            180                 185                 190

Asp Leu Arg Phe Ala Glu Leu Ala Gln Ile Tyr Ala Gln Arg Gly Cys
        195                 200                 205

Gln Leu Leu Val Tyr Pro Gly Ala Phe Asn Leu Thr Thr Gly Pro Ala
    210                 215                 220

His Trp Glu Leu Leu Gln Arg Gly Arg Ala Val Asp Asn Gln Val Tyr
225                 230                 235                 240

Val Ala Thr Ala Ser Pro Ala Arg Asp Asp Lys Ala Ser Tyr Val Ala
                245                 250                 255

Trp Gly His Ser Thr Val Val Thr Pro Trp Gly Glu Val Leu Ala Thr
            260                 265                 270

Ala Gly Thr Glu Glu Met Ile Val Tyr Ser Asp Ile Asp Leu Lys Lys
        275                 280                 285

Leu Ala Glu Ile Arg Gln Gln Ile Pro Ile Phe Ser Gln Lys Arg Leu
    290                 295                 300

Asp Leu Tyr Ala Val Glu Ala Lys Lys Pro
305                 310

<210> SEQ ID NO 35
<211> LENGTH: 276
<212> TYPE: PRT
<213> ORGANISM: Xenopus tropicalis
<220> FEATURE:
<223> OTHER INFORMATION: western clawed frog omega-amilase NIT2,
      nitrilase homolog 2, nitrilase family, member 2

<400> SEQUENCE: 35

Met Ala Lys Phe Arg Leu Ser Leu Val Gln Phe Leu Val Ser Pro Val
 1               5                  10                  15

Lys Ser Glu Asn Leu Asn Arg Ala Cys Lys Leu Ile Lys Glu Ala Ala
            20                  25                  30

Gln Lys Gly Ala Gln Ile Val Ala Leu Pro Glu Cys Phe Asn Ser Pro
        35                  40                  45
```

```
Tyr Gly Thr Lys Tyr Phe Pro Glu Tyr Ala Glu Lys Ile Pro Gly Glu
        50                  55                  60

Ser Thr Glu Arg Leu Ser Gln Val Ala Lys Glu Cys Gly Ile Tyr Leu
 65                  70                  75                  80

Ile Gly Gly Ser Ile Pro Glu Glu Asp Ser Gly Lys Leu Tyr Asn Thr
                85                  90                  95

Cys Ala Val Phe Gly Pro Asp Gly Thr Leu Leu Val Lys His Arg Lys
                100                 105                 110

Ile His Leu Phe Asp Ile Asp Val Pro Gly Lys Ile Arg Phe Gln Glu
            115                 120                 125

Ser Glu Thr Leu Ser Pro Gly Asp Ser Phe Ser Val Phe Glu Thr Pro
        130                 135                 140

Tyr Cys Lys Val Gly Val Gly Ile Cys Tyr Asp Ile Arg Phe Ala Glu
145                 150                 155                 160

Leu Ala Gln Leu Tyr Ser Lys Lys Gly Cys Gln Leu Leu Val Tyr Pro
                165                 170                 175

Gly Ala Phe Asn Met Thr Thr Gly Pro Ala His Trp Glu Leu Leu Gln
                180                 185                 190

Arg Ala Arg Ala Leu Asp Asn Gln Val Tyr Val Ala Thr Ala Ser Pro
            195                 200                 205

Ala Arg Asp Glu Lys Ala Ser Tyr Val Ala Trp Gly His Ser Thr Ile
        210                 215                 220

Val Ser Pro Trp Gly Glu Val Ile Ala Lys Ala Gly Ser Glu Glu Thr
225                 230                 235                 240

Val Ile Ser Ala Asp Ile Asp Leu Glu Tyr Leu Ala Glu Ile Arg Glu
                245                 250                 255

Gln Ile Pro Ile Arg Arg Gln Arg His Asp Leu Tyr Ser Val Glu
                260                 265                 270

Glu Lys Lys Asn
        275

<210> SEQ ID NO 36
<211> LENGTH: 277
<212> TYPE: PRT
<213> ORGANISM: Danio rerio
<220> FEATURE:
<223> OTHER INFORMATION: zebrafish Nit protein 2, NIT2

<400> SEQUENCE: 36

Met Ser Lys Phe Arg Leu Ala Val Val Gln Leu His Val Ser Lys Ile
 1                5                  10                  15

Lys Ala Asp Asn Leu Gly Arg Ala Gln Thr Leu Val Thr Glu Ala Ala
                20                  25                  30

Gly Gln Gly Ala Lys Val Val Leu Pro Glu Cys Phe Asn Ser Pro
            35                  40                  45

Tyr Gly Thr Gly Phe Phe Lys Glu Tyr Ala Glu Lys Ile Pro Gly Glu
        50                  55                  60

Ser Thr Gln Val Leu Ser Glu Thr Ala Lys Lys Cys Gly Ile Tyr Leu
 65                  70                  75                  80

Val Gly Gly Ser Ile Pro Glu Glu Asp Gly Gly Lys Leu Tyr Asn Thr
                85                  90                  95

Cys Ser Val Phe Gly Pro Asp Gly Thr Leu Leu Val Thr His Arg Lys
                100                 105                 110

Ile His Leu Phe Asp Ile Asp Val Pro Gly Lys Ile Arg Phe Gln Glu
            115                 120                 125
```

-continued

Ser Glu Thr Leu Ser Pro Gly Lys Ser Leu Ser Met Phe Glu Thr Pro
    130                 135                 140

Tyr Cys Lys Val Gly Val Gly Ile Cys Tyr Asp Ile Arg Phe Ala Glu
145                 150                 155                 160

Leu Ala Gln Ile Tyr Ala Lys Lys Gly Cys Gln Leu Leu Val Tyr Pro
                165                 170                 175

Gly Ala Phe Asn Met Thr Thr Gly Pro Ala His Trp Glu Leu Leu Gln
            180                 185                 190

Arg Gly Arg Ala Val Asp Asn Gln Val Tyr Val Ala Thr Ala Ser Pro
        195                 200                 205

Ala Arg Asp Glu Thr Ala Ser Tyr Val Ala Trp Gly His Ser Ser Val
    210                 215                 220

Ile Asn Pro Trp Gly Glu Val Ile Ser Lys Ala Gly Ser Glu Glu Ser
225                 230                 235                 240

Val Val Tyr Ala Asp Ile Asp Leu Gln Tyr Leu Ala Asp Val Arg Gln
                245                 250                 255

Gln Ile Pro Ile Thr Lys Gln Arg Arg Asn Asp Leu Tyr Ser Val Asn
            260                 265                 270

Ser Val Gln Glu Gly
        275

<210> SEQ ID NO 37
<211> LENGTH: 279
<212> TYPE: PRT
<213> ORGANISM: Nematostella vectensis
<220> FEATURE:
<223> OTHER INFORMATION: starlet sea anemone strain CH2 x CH6 predicted
      protein, locus NEMVEDRAFT_v1g139747

<400> SEQUENCE: 37

Met Ala Val Pro Ile Leu Val Phe Arg Ile Gly Leu Val Gln Leu Ala
1               5                   10                  15

Val Thr Ala Asn Lys Leu Gln Asn Leu Gln Arg Ala Arg Glu Lys Ile
            20                  25                  30

Lys Glu Ala Val Ala Ala Gly Ala Lys Ile Val Ala Leu Pro Glu Cys
        35                  40                  45

Phe Asn Ser Pro Tyr Gly Thr Gln Tyr Phe Lys Asp Tyr Ala Glu Glu
    50                  55                  60

Ile Pro Gly Glu Ser Ser Asn Met Leu Ala Glu Val Ala Lys Glu Thr
65                  70                  75                  80

Gly Ala Tyr Ile Val Gly Gly Ser Ile Pro Glu Arg Ala Ser Asn Gly
                85                  90                  95

Lys Leu Tyr Asn Thr Ser Leu Ser Tyr Asp Pro Ser Gly Asn Leu Met
            100                 105                 110

Gly Lys His Arg Lys Ile His Leu Phe Asp Ile Asp Val Pro Gly Lys
        115                 120                 125

Ile Arg Phe Gln Glu Ser Glu Val Leu Ser Pro Gly Glu Asn Leu Thr
    130                 135                 140

Ile Leu Asp Thr Glu Tyr Cys Lys Ile Gly Ile Gly Ile Cys Tyr Asp
145                 150                 155                 160

Met Arg Phe Pro Glu Leu Ala Gln Leu Tyr Ala Lys Lys Gly Cys His
                165                 170                 175

Leu Leu Leu Tyr Pro Gly Ala Phe Asn Met Thr Thr Gly Pro Ala His
            180                 185                 190

Trp Glu Leu Leu Thr Arg Ala Arg Ala Leu Asp Asn Gln Leu Tyr Val

```
              195                 200                 205
Ala Thr Ile Ser Pro Ala Arg Asp Asp Asn Ala Thr Tyr Ile Ala Trp
    210                 215                 220

Gly His Ser Thr Val Val Asn Pro Trp Gly Lys Ile Val Ser Lys Ala
225                 230                 235                 240

Asp His Thr Glu Gln Ile Leu Tyr Ala Glu Ile Asp Leu Lys Tyr Leu
                245                 250                 255

Asn Glu Val Arg Ser Gln Ile Pro Val Gln Phe Gln Lys Arg Asp Asp
            260                 265                 270

Val Tyr Glu Leu Gln Val Lys
        275

<210> SEQ ID NO 38
<211> LENGTH: 276
<212> TYPE: PRT
<213> ORGANISM: Mus musculus
<220> FEATURE:
<223> OTHER INFORMATION: house mouse omega-amidase NIT2, 1190017B19Rik,
      D16Ertd502e

<400> SEQUENCE: 38

Met Ser Thr Phe Arg Leu Ala Leu Ile Gln Leu Gln Val Ser Ser Ile
1               5                  10                  15

Lys Ser Asp Asn Leu Thr Arg Ala Cys Ser Leu Val Arg Glu Ala Ala
            20                  25                  30

Lys Gln Gly Ala Asn Ile Val Ser Leu Pro Glu Cys Phe Asn Ser Pro
        35                  40                  45

Tyr Gly Thr Thr Tyr Phe Pro Asp Tyr Ala Glu Lys Ile Pro Gly Glu
    50                  55                  60

Ser Thr Gln Lys Leu Ser Glu Val Ala Lys Glu Ser Ser Ile Tyr Leu
65                  70                  75                  80

Ile Gly Gly Ser Ile Pro Glu Glu Asp Ala Gly Lys Leu Tyr Asn Thr
                85                  90                  95

Cys Ser Val Phe Gly Pro Asp Gly Ser Leu Leu Val Lys His Arg Lys
            100                 105                 110

Ile His Leu Phe Asp Ile Asp Val Pro Gly Lys Ile Thr Phe Gln Glu
        115                 120                 125

Ser Lys Thr Leu Ser Pro Gly Asp Ser Phe Ser Thr Phe Asp Thr Pro
    130                 135                 140

Tyr Cys Lys Val Gly Leu Gly Ile Cys Tyr Asp Met Arg Phe Ala Glu
145                 150                 155                 160

Leu Ala Gln Ile Tyr Ala Gln Arg Gly Cys Gln Leu Leu Val Tyr Pro
                165                 170                 175

Gly Ala Phe Asn Leu Thr Thr Gly Pro Ala His Trp Glu Leu Leu Gln
            180                 185                 190

Arg Ala Arg Ala Val Asp Asn Gln Val Tyr Val Ala Thr Ala Ser Pro
        195                 200                 205

Ala Arg Asp Asp Lys Ala Ser Tyr Val Ala Trp Gly His Ser Thr Val
    210                 215                 220

Val Asp Pro Trp Gly Gln Val Leu Thr Lys Ala Gly Thr Glu Glu Thr
225                 230                 235                 240

Ile Leu Tyr Ser Asp Ile Asp Leu Lys Lys Leu Ala Glu Ile Arg Gln
                245                 250                 255

Gln Ile Pro Ile Leu Lys Gln Lys Arg Ala Asp Leu Tyr Thr Val Glu
            260                 265                 270
```

Ser Lys Lys Pro
   275

<210> SEQ ID NO 39
<211> LENGTH: 10798
<212> TYPE: DNA
<213> ORGANISM: Artificial Sequence
<220> FEATURE:
<223> OTHER INFORMATION: synthetic pTF101.1 vector + roID-02 promoter +
      Arabidopsis omega-amidase (codon optimized) + nos terminator
      region construct

<400> SEQUENCE: 39

| | | | | | |
|---|---|---|---|---|---|
| agtactttaa | agtactttaa | agtactttaa | agtactttga | tccaacccct | ccgctgctat | 60 |
| agtgcagtcg | gcttctgacg | ttcagtgcag | ccgtcttctg | aaaacgacat | gtcgcacaag | 120 |
| tcctaagtta | cgcgacaggc | tgccgccctg | ccctttcct | ggcgttttct | tgtcgcgtgt | 180 |
| tttagtcgca | taaagtagaa | tacttgcgac | tagaaccgga | gacattacgc | catgaacaag | 240 |
| agcgccgccg | ctggcctgct | gggctatgcc | cgcgtcagca | ccgacgacca | ggacttgacc | 300 |
| aaccaacggg | ccgaactgca | cgcggccggc | tgcaccaagc | tgttttccga | gaagatcacc | 360 |
| ggcaccaggc | gcgaccgccc | ggagctggcc | aggatgcttg | accacctacg | ccctggcgac | 420 |
| gttgtgacag | tgaccaggct | agaccgcctg | gcccgcagca | cccgcgacct | actggacatt | 480 |
| gccgagcgca | tccaggaggc | cggcgcgggc | ctgcgtagcc | tggcagagcc | gtgggccgac | 540 |
| accaccacgc | cggccggccg | catggtgttg | accgtgttcg | ccggcattgc | cgagttcgag | 600 |
| cgttccctaa | tcatcgaccg | cacccggagc | gggcgcgagg | ccgccaaggc | ccgaggcgtg | 660 |
| aagtttggcc | cccgccctac | cctcaccccg | gcacagatcg | cgcacgcccg | cgagctgatc | 720 |
| gaccaggaag | gccgcaccgt | gaaagaggcg | gctgcactgc | ttggcgtgca | tcgctcgacc | 780 |
| ctgtaccgcg | cacttgagcg | cagcgaggaa | gtgacgccca | ccgaggccag | gcggcgcggt | 840 |
| gccttccgtg | aggacgcatt | gaccgaggcc | gacgccctgg | cggccgccga | gaatgaacgc | 900 |
| caagaggaac | aagcatgaaa | ccgcaccagg | acggccagga | cgaaccgttt | ttcattaccg | 960 |
| aagagatcga | ggcggagatg | atcgcggccg | ggtacgtgtt | cgagccgccc | gcgcacgtct | 1020 |
| caaccgtgcg | gctgcatgaa | atcctggccg | gtttgtctga | tgccaagctg | gcggcctggc | 1080 |
| cggccagctt | ggccgctgaa | gaaaccgagc | gccgccgtct | aaaaaggtga | tgtgtatttg | 1140 |
| agtaaaacag | cttgcgtcat | gcggtcgctg | cgtatatgat | gcgatgagta | aataaacaaa | 1200 |
| tacgcaaggg | gaacgcatga | aggttatcgc | tgtacttaac | cagaaaggcg | ggtcaggcaa | 1260 |
| gacgaccatc | gcaacccatc | tagcccgcgc | cctgcaactc | gccggggccg | atgttctgtt | 1320 |
| agtcgattcc | gatccccagg | gcagtgcccg | cgattgggcg | gccgtgcggg | aagatcaacc | 1380 |
| gctaaccgtt | gtcggcatcg | accgcccgac | gattgaccgc | gacgtgaagg | ccatcggccg | 1440 |
| gcgcgacttc | gtagtgatcg | acggagcgcc | ccaggcggcg | gacttggctg | tgtccgcgat | 1500 |
| caaggcagcc | gacttcgtgc | tgattccggt | gcagccaagc | ccttacgaca | tatgggccac | 1560 |
| cgccgacctg | gtggagctgg | ttaagcagcg | cattgaggtc | acggatggaa | ggctacaagc | 1620 |
| ggcctttgtc | gtgtcgcggg | cgatcaaagg | cacgcgcatc | ggcggtgagg | ttgccgaggc | 1680 |
| gctggccggg | tacgagctgc | ccattcttga | gtcccgtatc | acgcagcgcg | tgagctaccc | 1740 |
| aggcactgcc | gccgccggca | caaccgttct | tgaatcagaa | cccgagggcg | acgctgcccg | 1800 |
| cgaggtccag | gcgctggccg | ctgaaattaa | atcaaaactc | atttgagtta | atgaggtaaa | 1860 |
| gagaaaatga | gcaaaagcac | aaacacgcta | agtgccggcc | gtccgagcgc | acgcagcagc | 1920 |

```
aaggctgcaa cgttggccag cctggcagac acgccagcca tgaagcgggt caactttcag   1980
ttgccggcgg aggatcacac caagctgaag atgtacgcgg tacgccaagg caagaccatt   2040
accgagctgc tatctgaata catcgcgcag ctaccagagt aaatgagcaa atgaataaat   2100
gagtagatga attttagcgg ctaaaggagg cggcatggaa aatcaagaac aaccaggcac   2160
cgacgccgtg gaatgcccca tgtgtggagg aacgggcggt tggccaggcg taagcggctg   2220
ggttgtctgc cggccctgca atggcactgg aaccccaag cccgaggaat cggcgtgacg    2280
gtcgcaaacc atccggcccg gtacaaatcg cgcggcgct gggtgatgac ctggtggaga    2340
agttgaaggc cgcgcaggcc gcccagcggc aacgcatcga ggcagaagca cgccccggtg   2400
aatcgtggca agcggccgct gatcgaatcc gcaaagaatc ccggcaaccg ccggcagccg   2460
gtgcgccgtc gattaggaag ccgcccaagg gcgacgagca accagatttt ttcgttccga   2520
tgctctatga cgtgggcacc cgcgatagtc gcagcatcat ggacgtggcc gttttccgtc   2580
tgtcgaagcg tgaccgacga gctggcgagg tgatccgcta cgagcttcca gacgggcacg   2640
tagaggtttc cgcagggccg gccggcatgg ccagtgtgtg ggattacgac ctggtactga   2700
tggcggtttc ccatctaacc gaatccatga accgataccg ggaagggaag ggagacaagc   2760
ccggccgcgt gttccgtcca cacgttgcgg acgtactcaa gttctgccgg cgagccgatg   2820
gcggaaagca gaaagacgac ctggtagaaa cctgcattcg gttaaacacc acgcacgttg   2880
ccatgcagcg tacgaagaag gccaagaacg gccgcctggt gacggtatcc gagggtgaag   2940
ccttgattag ccgctacaag atcgtaaaga gcgaaaccgg gcggccggag tacatcgaga   3000
tcgagctagc tgattggatg taccgcgaga tcacagaagg caagaacccg gacgtgctga   3060
cggttcaccc cgattacttt ttgatcgatc ccggcatcgg ccgtttctc taccgcctgg     3120
cacgccgcgc gcgcaggcaa gcagaagcca gatggttgtt caagacgatc tacgaacgca   3180
gtggcagcgc cggagagttc aagaagttct gtttcaccgt gcgcaagctg atcgggtcaa   3240
atgacctgcc ggagtacgat ttgaaggagg aggcggggca ggctggcccg atcctagtca   3300
tgcgctaccg caacctgatc gagggcgaag catccgccgg ttcctaatgt acggagcaga   3360
tgctagggca aattgcccta gcaggggaaa aaggtcgaaa aggtctcttt cctgtggata   3420
gcacgtacat tgggaaccca aagccgtaca ttgggaaccg gaacccgtac attgggaacc   3480
caaagccgta cattgggaac cggtcacaca tgtaagtgac tgatatataaa agagaaaaag   3540
gcgattttc cgcctaaaac tctttaaaac ttattaaaac tcttaaaacc cgcctggcct    3600
gtgcataact gtctggccag cgcacagccg aagagctgca aaaagcgcct acccttcggt   3660
cgctgcgctc cctacgcccc gccgcttcgc gtcggcctat cgcggccgct ggccgctcaa   3720
aaatggctgg cctacggcca ggcaatctac cagggcgcgg acaagccgcg ccgtcgccac   3780
tcgaccgccg gcgcccacat caaggcaccc tgcctcgcgc gtttcggtga tgacggtgaa   3840
aacctctgac acatgcagct cccggagacg gtcacagctt gtctgtaagc ggatgccggg   3900
agcagacaag cccgtcaggg cgcgtcagcg ggtgttggcg ggtgtcgggg cgcagccatg   3960
acccagtcac gtagcgatag cggagtgtat actggcttaa ctatgcggca tcagagcaga   4020
ttgtactgag agtgcaccat atgcggtgtg aaataccgca cagatgcgta aggagaaaat   4080
accgcatcag gcgctcttcc gcttcctcgc tcactgactc gctgcgctcg tcgttcggc    4140
tgcggcgagc ggtatcagct cactcaaagg cggtaatacg gttatccaca gaatcagggg   4200
ataacgcagg aaagaacatg tgagcaaaag gccagcaaaa ggccaggaac cgtaaaaagg   4260
ccgcgttgct ggcgtttttc cataggctcc gcccccctga cgagcatcac aaaaatcgac   4320
```

-continued

```
gctcaagtca gaggtggcga aacccgacag gactataaag ataccaggcg tttcccctg     4380 gaagctccct cgtgcgctct cctgttccga ccctgccgct taccggatac ctgtccgcct    4440
ttctcccttc gggaagcgtg gcgctttctc atagctcacg ctgtaggtat ctcagttcgg    4500
tgtaggtcgt tcgctccaag ctgggctgtg tgcacgaacc ccccgttcag cccgaccgct    4560
gcgccttatc cggtaactat cgtcttgagt ccaacccggt aagacacgac ttatcgccac    4620
tggcagcagc cactggtaac aggattagca gagcgaggta tgtaggcggt gctacagagt    4680
tcttgaagtg gtggcctaac tacggctaca ctagaaggac agtatttggt atctgcgctc    4740
tgctgaagcc agttaccttc ggaaaaagag ttggtagctc ttgatccggc aaacaaacca    4800
ccgctggtag cggtggtttt tttgtttgca agcagcagat tacgcgcaga aaaaaggat    4860 ctcaagaaga tcctttgatc ttttctacgg ggtctgacgc tcagtggaac gaaaactcac    4920
gttaagggat tttggtcatg catgatatat ctcccaattt gtgtagggct tattatgcac    4980
gcttaaaaat aataaaagca gacttgacct gatagtttgg ctgtgagcaa ttatgtgctt    5040
agtgcatcta atcgcttgag ttaacgccgg cgaagcggcg tcggcttgaa cgaatttcta    5100
gctagacatt atttgccgac taccttggtg atctcgcctt tcacgtagtg gacaaattct    5160
tccaactgat ctgcgcgcga ggccaagcga tcttcttctt gtccaagata agcctgtcta    5220
gcttcaagta tgacgggctg atactgggcc ggcaggcgct ccattgccca gtcggcagcg    5280
acatccttcg gcgcgatttt gccggttact gcgctgtacc aaatgcggga caacgtaagc    5340
actacatttc gctcatcgcc agcccagtcg ggcggcgagt tccatagcgt taaggtttca    5400
tttagcgcct caaatagatc ctgttcagga accggatcaa agagttcctc cgccgctgga    5460
cctaccaagg caacgctatg ttctcttgct tttgtcagca agatagccag atcaatgtcg    5520
atcgtggctg gctcgaagat acctgcaaga atgtcattgc gctgccattc tccaaattgc    5580
agttcgcgct tagctggata acgccacgga atgatgtcgt cgtgcacaac aatggtgact    5640
tctacagcgc ggagaatctc gctctctcca ggggaagccg aagtttccaa aaggtcgttg    5700
atcaaagctc gccgcgttgt ttcatcaagc cttacggtca ccgtaaccag caaatcaata    5760
tcactgtgtg gcttcaggcc gccatccact gcggagccgt acaaatgtac ggccagcaac    5820
gtcggttcga gatggcgctc gatgacgcca actacctctg atagttgagt cgatacttcg    5880
gcgatcaccg cttcccccat gatgtttaac tttgttttag ggcgactgcc ctgctgcgta    5940
acatcgttgc tgctccataa catcaaacat cgacccacgg cgtaacgcgc ttgctgcttg    6000
gatgcccgag gcatagactg taccccaaaa aaacatgtca taacaagaag ccatgaaaac    6060
cgccactgcg ccgttaccac cgctgcgttc ggtcaaggtt ctggaccagt tgcgtgacgg    6120
cagttacgct acttgcatta cagcttacga accgaacgag gcttatgtcc actgggttcg    6180
tgcccgaatt gatcacaggc agcaacgctc tgtcatcgtt acaatcaaca tgctaccctc    6240
cgcgagatca tccgtgtttc aaacccggca gcttagttgc cgttcttccg aatagcatcg    6300
gtaacatgag caaagtctgc cgccttacaa cggctctccc gctgacgccg tcccggactg    6360
atgggctgcc tgtatcgagt ggtgattttg tgccgagctg ccggtcgggg agctgttggc    6420
tggctggtgg caggatatat tgtggtgtaa acaaattgac gcttagacaa cttaataaca    6480
cattgcggac gtttttaatg tactgaatta cgccgaatt gctctagcat tcgccattca     6540
ggctgcgcaa ctgttgggaa gggcgatcgg tgcgggcctc ttcgctatta cgccagctgg    6600
cgaaaggggg atgtgctgca aggcgattaa gttgggtaac gccagggttt tcccagtcac    6660
```

```
gacgttgtaa aacgacggcc agtgccaagc taattcttca agacgtgctc aaatcactat    6720
ttccacaccc ctatatttct attgcactcc cttttaactg ttttttatta caaaaatgcc    6780
ctggaaaatg cactcccttt tgtgtttgt tttttttgtga aacgatgttg tcaggtaatt    6840
tatttgtcag tctactatgg tggcccatta tattaatagc aactgtcggt ccaatagacg    6900
acgtcgattt tctgcatttg tttaaccacg tggattttat gacattttat attagttaat    6960
ttgtaaaacc tacccaatta aagacctcat atgttctaaa gactaatact taatgataac    7020
aattttcttt tagtgaagaa agggataatt agtaaatatg gaacaagggc agaagattta    7080
ttaaagccgc gtaagagaca caagtaggt acgtggagtg tcttaggtga cttacccaca    7140
taacataaag tgacattaac aaacatagct aatgctccta tttgaatagt gcatatcagc    7200
ataccttatt acatatagat aggagcaaac tctagctaga ttgttgagag cagatctcgg    7260
tgacgggcag gaccggacgg ggcggtaccg gcaggctgaa gtccagctgc cagaaaccca    7320
cgtcatgcca gttcccgtgc ttgaagccgc ccgcccgcag catgccgcgg gggcatatc    7380 cgagcgcctc gtgcatgcgc acgctcgggt cgttgggcag cccgatgaca cgaccacgc    7440 tcttgaagcc ctgtgcctcc agggacttca gcaggtgggt gtagagcgtg gagcccagtc    7500
ccgtccgctg gtggcggggg gagacgtaca cggtcgactc ggccgtccag tcgtaggcgt    7560
tgcgtgcctt ccagggggccc gcgtaggcga tgccggcgac ctcgccgtcc acctcggcga    7620
cgagccaggg atagcgctcc cgcagacgga cgaggtcgtc cgtccactcc tgcggttcct    7680
gcggctcggt acggaagttg accgtgcttg tctcgatgta gtggttgacg atggtgcaga    7740
ccgccggcat gtccgcctcg gtggcacggc ggatgtcggc cgggcgtcgt tctgggctca    7800
tggtagatcc cccgttcgta aatggtgaaa attttcagaa aattgctttt gctttaaaag    7860
aaatgattta aattgctgca atagaagtag aatgcttgat tgcttgagat tcgtttgttt    7920
tgtatatgtt gtgttgagaa ttaattctcg aggtcctctc caaatgaaat gaacttcctt    7980
atatagagga agggtcttgc gaaggatagt gggattgtgc gtcatccctt acgtcagtgg    8040
agatatcaca tcaatccact tgctttgaag acgtggttgg aacgtcttct ttttccacga    8100
tgctcctcgt gggtggggt ccatctttgg gaccactgtc ggtagaggca tcttgaacga    8160
tagccttttc tttatcgcaa tgatggcatt tgtaggagcc accttccttt tccactatct    8220
tcacaataaa gtgacagata gctgggcaat ggaatccgag gaggtttccg gatattaccc    8280
tttgttgaaa agtctcaatt gcccttggt cttctgagac tgtatctttg atatttttgg    8340
agtagacaag tgtgtcgtgc tccaccatgt tatcacatca atccacttgc tttgaagacg    8400
tggttggaac gtcttctttt tccacgatgc tcctcgtggg tggggtcca tctttgggac    8460 cactgtcggc agaggcatct tcaacgatgg ccttttccttt atcgcaatga tggcatttgt    8520
aggagccacc ttcctttttcc actatcttca caataaagtg acagatagct gggcaatgga    8580
atccgaggag gtttccggat attcccttt gttgaaaagt ctcaattgcc ctttggtctt    8640
ctgagactgt atctttgata ttttggagt agacaagtgt gtcgtgctcc accatgttga    8700
cctgcaggca tgcaagcttg catgcctgca ggtcgactct agaggatccc cgtcggtacc    8760
gaatttgttc gtgaactatt agttgcgggc cttggcatcc gactacctct gcggcaatat    8820
tatattccct gggcccaccg tgaacccaat ttcgcctatt tattcattac ccccattaac    8880
attgaagtag tcatgatggg cctgcagcac gttggtgagg ctggcacaac tcatccatat    8940
actttctgac cggatcggca cattattgta gaaaacgcgg acccacagcg cactttccaa    9000
agcggtgccg cgtcagaatg cgctggcaga aaaaaattaa tccaaaagta ccctccaagc    9060
```

```
agcccatata aacgcgttta caaatccgct aacctcaaca atttgagcag agaaaattcg    9120
cacctacaag gcagatggca tcatcattca atccagagca ggcaagagtt ccttcagcat    9180
tacctttacc agcaccacca cttaccaaat tcaacatcgg actttgtcaa ttgagtgtta    9240
cttctgataa gaaaagaaac atttcacatg ctaagaaagc aatcgaagag ctgctagta    9300 agggagctaa actcgttctt ttgcctgaaa tatggaactc accatacagt aacgattctt    9360
ttcctgtgta cgcagaagag atcgatgctg gaggtgatgc atctccatca actgctatgc    9420
tctcagaagt tagtaagaga ctcaagatta caattatcgg aggttcaatt cctgagagag    9480
ttggagatag gttgtataac acatgttgcg tgttcggatc tgatggagag ctcaaggcta    9540
agcataggaa gattcaccctc ttcgatatag atattcctgg aaagatcacc ttcatggaat    9600
caaaaacact taccgctgga gagactccaa caattgttga tacagatgtg ggtagaatcg    9660
gaataggtat atgttacgat atcaggttcc aagaattggc tatgatatat gctgcaagag    9720
gagcacatct cttatgctac cctggagctt tcaatatgac tacaggtcca ttgcactggg    9780
agcttttgca aagagctagg gcaacagata accagctcta tgttgctacc tgctctcctg    9840
caagagattc aggagctggt tacaccgcat ggggtcattc tactcttgtt ggaccatttg    9900
gtgaagtgtt ggctaccact gagcacgaag aggctattat aatcgcagaa atcgattaca    9960
gtatacttga gcagagaagg acttctctcc cattaaatag gcagaggagg ggtgatttat   10020
accagttagt tgatgttcag agattagata gtaagtgaca cgtgtgaatt acaggtgacc   10080
agctcgaatt tccccgatcg ttcaaacatt tggcaataaa gtttcttaag attgaatcct   10140
gttgccggtc ttgcgatgat tatcatataa tttctgttga attacgttaa gcatgtaata   10200
attaacatgt aatgcatgac gttatttatg agatgggttt ttatgattag agtcccgcaa   10260
ttatacattt aatacgcgat agaaaacaaa atatagcgcg caaactagga taaattatcg   10320
cgcgcggtgt catctatgtt actagatcgg gggtaccgac gggtaccgag ctcgaattcg   10380
taatcatggt catagctgtt tcctgtgtga aattgttatc cgctcacaat tccacacaac   10440
atacgagccg gaagcataaa gtgtaaagcc tggggtgcct aatgagtgag ctaactcaca   10500
ttaattgcgt tgcgctcact gcccgctttc cagtcgggaa acctgtcgtg ccagctgcat   10560
taatgaatcg gccaacgcgc ggggagaggc ggtttgcgta ttggagcttg agcttggatc   10620
agattgtcgt ttcccgcctt cagtttaaac tatcagtgtt tgacaggata tattggcggg   10680
taaacctaag agaaaagagc gtttattaga ataacggata tttaaaaggg cgtgaaaagg   10740
tttatccgtt cgtccatttg tatgtgcatg ccaaccacag ggttcccctc gggatcaa     10798
```

<210> SEQ ID NO 40
<211> LENGTH: 11845
<212> TYPE: DNA
<213> ORGANISM: Artificial Sequence
<220> FEATURE:
<223> OTHER INFORMATION: synthetic GPT 6c construct; Cambia 2201 with tomato rubisco SSU promoter + GPT (-45) truncated (deleted chloroplast targeting sequence), codon optimized for Arabidopsis + nos terminator

<400> SEQUENCE: 40

```
cccgcgcgtt ggccgattca ttaatgcagc tggcacgaca ggtttcccga ctggaaagcg      60
ggcagtgagc gcaacgcaat taatgtgagt tagctcactc attaggcacc ccaggcttta    120
cactttatgc ttccggctcg tatgttgtgt ggaattgtga gcggataaca atttcacaca    180
ggaaacagct atgaccatga ttacgaattc gagctcggta cccggggatc ctctagatct    240
```

```
agagaattca tcgatgtttg aatcctcctt aaagttttc tctggagaaa ctgtagtaat      300
tttactttgt tgtgttccct tcatcttttg aattaatggc atttgtttta atactaatct      360
gcttctgaaa cttgtaatgt atgtatatca gtttcttata atttatccaa gtaatatctt      420
ccattctcta tgcaattgcc tgcataagct cgacaaaaga gtacatcaac ccctcctcct      480
ctggactact ctagctaaac ttgaatttcc ccttaagatt atgaaattga tatatcctta      540
acaaacgact ccttctgttg gaaaatgtag tacttgtctt tcttcttttg ggtatatata      600
gtttatatac accatactat gtacaacatc caagtagagt gaaatggata catgtacaag      660
acttatttga ttgattgatg acttgagttg cctaggagt aacaaattct taggtcaata      720
aatcgttgat ttgaaattaa tctctctgtc ttagacagat aggaattatg acttccaatg      780
gtccagaaag caaagttcgc actgagggta tacttggaat tgagacttgc acaggtccag      840
aaaccaaagt tcccatcgag ctctaaaatc acatctttgg aatgaaattc aattagagat      900
aagttgcttc atagcatagg taaaatggaa gatgtgaagt aacctgcaat aatcagtgaa      960
atgacattaa tacactaaat acttcatatg taattatcct ttccaggtta acaatactct     1020
ataaagtaag aattatcaga aatgggctca tcaaactttt gtactatgta tttcatataa     1080
ggaagtataa ctatacataa gtgtatacac aactttattc ctattttgta aaggtggaga     1140
gactgttttc gatggatcta aagcaatatg tctataaaat gcattgatat aataattatc     1200
tgagaaaatc cagaattggc gttggattat ttcagccaaa tagaagtttg taccatactt     1260
gttgattcct tctaagttaa ggtgaagtat cattcataaa cagttttccc caaagtacta     1320
ctcaccaagt ttcccttttgt agaattaaca gttcaaatat atggcgcaga aattactcta     1380
tgcccaaaac caaacgagaa agaaacaaaa tacaggggtt gcagacttta ttttcgtgtt     1440
agggtgtgtt ttttcatgta attaatcaaa aaatattatg acaaaaacat ttatacatat     1500
ttttactcaa cactctgggt atcagggtgg gttgtgttcg acaatcaata tggaaaggaa     1560 gtatttcct tatttttta gttaatattt tcagttatac caaacatacc ttgtgatatt     1620 attttaaaa atgaaaaact cgtcagaaag aaaagcaaa agcaacaaaa aaattgcaag     1680 tatttttta aaaagaaaaa aaaacatat cttgtttgtc agtatgggaa gtttgagata     1740
aggacgagtg aggggttaaa attcagtggc cattgatttt gtaatgccaa gaaccacaaa     1800
atccaatggt taccattcct gtaagatgag gtttgctaac tcttttttgtc cgttagatag     1860 gaagccttat cactatatat acaaggcgtc ctaataaccct cttagtaacc aattatttca     1920
gcaactagta tggcgactca aaatgagtca acacaaaagc ctgttcaggt ggctaagaga     1980
cttgagaagt ttaaaactac aattttcact caaatgtcta tcctcgcagt taagcacgga     2040
gctattaatc ttggacaggg ttttcctaac ttcgatggtc cagattttcgt gaaagaagct     2100 gcaattcaag caatcaagga tggaaaaaat cagtatgcta gaggatacgg tattcctcag     2160
ttgaactctg ctatcgctgc aagattcaga gaagatacag acttgttgt ggatccagaa     2220 aaagaggtta ctgtgacatc aggttgtact gaggctattg ctgcagctat gctcggactt     2280
attaaccctg gagatgaagt tatccttttt gcaccattct atgattctta cgaggctaca     2340
ttgtcaatgg caggagctaa ggtgaaaggt attactctca gacctccaga tttctctatc     2400
cctttggaag agctcaaggc agctgttact aataagacaa gagctatctt gatgaatact     2460
cctcataacc caacaggaaa gatgtttact agagaagagc tcgaaactat tgcttctctt     2520
tgcatcgaga acgatgtttt ggtgttctca gatgaagtgt atgataaact cgcatttgag     2580
```

```
atggatcaca tttctatcgc ttcacttcca ggaatgtacg aaagaactgt tactatgaat     2640
tctttgggaa agactttttc tctcacagga tggaaaattg gttgggcaat cgctcctcca     2700
catctcacat ggggtgttag acaagcacac tcttatctta ctttcgcaac ttcaacacct     2760
gctcagtggg cagctgtggc agctcttaag gctccagaat cttacttcaa ggagttgaag     2820
agagattaca acgttaagaa agaaacactt gtgaagggat tgaaagaggt tggttttaca     2880
gtgttccctt cttcaggaac ttactttgtt gtggcagatc atactccatt cggtatggaa     2940
aacgatgttg cttttttgtga gtatcttatt gaagaggttg gagttgtggc tatccctaca     3000
tctgtgtttt accttaatcc agaagaggga aagaatcttg ttagatttgc attctgcaaa     3060
gatgaagaga ctttgagagg tgctattgag aggatgaagc aaaaactcaa gagaaaagtt     3120
tgacacgtgt gaattacagg tgaccagctc gaatttcccc gatcgttcaa acatttggca     3180
ataaagtttc ttaagattga atcctgttgc cggtcttgcg atgattatca tataatttct     3240
gttgaattac gttaagcatg taataattaa catgtaatgc atgacgttat ttatgagatg     3300
ggttttatg attagagtcc cgcaattata catttaatac gcgatagaaa acaaaatata     3360
gcgcgcaaac taggataaat tatcgcgcgc ggtgtcatct atgttactag atcgggaatt     3420
aaactatcag tgtttgacag gatatattgg cgggtaaacc taagagaaaa gagcgtttat     3480
tagaataacg gatatttaaa agggcgtgaa aaggtttatc cgttcgtcca tttgtatgtg     3540
catgccaacc acagggttcc cctcgggatc aaagtacttt gatccaaccc ctccgctgct     3600
atagtgcagt cggcttctga cgttcagtgc agccgtcttc tgaaaacgac atgtcgcaca     3660
agtcctaagt tacgcgacag gctgccgccc tgcccttttc ctggcgtttt cttgtcgcgt     3720
gttttagtcg cataaagtag aatacttgcg actagaaccg gagacattac gccatgaaca     3780
agagcgccgc cgctggcctg ctgggctatg cccgcgtcag caccgacgac caggacttga     3840
ccaaccaacg ggccgaactg cacgcggccg gctgcaccaa gctgttttcc gagaagatca     3900
ccggcaccag cgcgaccgc ccggagctgg ccaggatgct tgaccaccta cgccctggcg     3960
acgttgtgac agtgaccagg ctagaccgcc tggcccgcag cacccgcgac ctactggaca     4020
ttgccgagcg catccaggag gccggcgcgg gcctgcgtag cctggcagag ccgtgggccg     4080
acaccaccac gccggccggc cgcatggtgt tgaccgtgtt cgccggcatt gccgagttcg     4140
agcgttccct aatcatcgac cgcacccgga gcgggcgcga ggccgccaag gcccgaggcg     4200
tgaagtttgg cccccgccct accctcaccc cggcacagat cgcgcacgcc cgcgagctga     4260
tcgaccagga aggccgcacc gtgaaagagg cggctgcact gcttggcgtg catcgctcga     4320
ccctgtaccg cgcacttgag cgcagcgagg aagtgacgcc caccgaggcc aggcggcgcg     4380
gtgccttccg tgaggacgca ttgaccgagg ccgacgccct ggcggccgcc gagaatgaac     4440
gccaagagga caagcatga accgcacca ggacggccag gacgaaccgt ttttcattac     4500
cgaagagatc gaggcggaga tgatcgcggc cgggtacgtg ttcgagccgc ccgcgcacgt     4560
ctcaaccgtg cggctgcatg aaatcctggc cggtttgtct gatgccaagc tggcggcctg     4620
gccggccagc ttggccgctg aagaaaccga gcgccgccgt ctaaaaaggt gatgtgtatt     4680
tgagtaaaac agcttgcgtc atgcggtcgc tgcgtatatg atgcgatgag taaataaaca     4740
aatacgcaag gggaacgcat gaaggttatc gctgtactta accagaaagg cgggtcaggc     4800
aagacgacca tcgcaaccca tctagcccgc gccctgcaac tcgccggggc cgatgttctg     4860
ttagtcgatt ccgatcccca gggcagtgcc cgcgattggg cggccgtgcg gaagatcaa     4920
ccgctaaccg ttgtcggcat cgaccgcccg acgattgacc gcgacgtgaa ggccatcggc     4980
```

```
cggcgcgact tcgtagtgat cgacggagcg ccccaggcgg cggacttggc tgtgtccgcg    5040
atcaaggcag ccgacttcgt gctgattccg gtgcagccaa gcccttacga catatgggcc    5100
accgccgacc tggtggagct ggttaagcag cgcattgagg tcacggatgg aaggctacaa    5160
gcggcctttg tcgtgtcgcg ggcgatcaaa ggcacgcgca tcggcggtga ggttgccgag    5220
gcgctggccg ggtacgagct gcccattctt gagtcccgta tcacgcagcg cgtgagctac    5280
ccaggcactg ccgccgccgg cacaaccgtt cttgaatcag aacccgaggg cgacgctgcc    5340
cgcgaggtcc aggcgctggc cgctgaaatt aaatcaaaac tcatttgagt taatgaggta    5400
aagagaaaat gagcaaaagc acaaacacgc taagtgccgg ccgtccgagc gcacgcagca    5460
gcaaggctgc aacgttggcc agcctggcag acacgccagc catgaagcgg gtcaactttc    5520
agttgccggc ggaggatcac accaagctga agatgtacgc ggtacgccaa ggcaagacca    5580
ttaccgagct gctatctgaa tacatcgcgc agctaccaga gtaaatgagc aaatgaataa    5640
atgagtagat gaattttagc ggctaaagga ggcggcatgg aaaatcaaga caaccaggc    5700 accgacgccg tggaatgccc catgtgtgga ggaacgggcg gttggccagg cgtaagcggc    5760
tgggttgtct gccggccctg caatggcact ggaaccccca gcccgagga atcggcgtga    5820 cggtcgcaaa ccatccggcc cggtacaaat cggcgcggcg ctgggtgatg acctggtgga    5880
gaagttgaag gccgcgcagg ccgcccagcg gcaacgcatc gaggcagaag cacgccccgg    5940
tgaatcgtgg caagcggccg ctgatcgaat ccgcaaagaa tcccggcaac cgccggcagc    6000
cggtgcgccg tcgattagga agccgcccaa gggcgacgag caaccagatt ttttcgttcc    6060
gatgctctat gacgtgggca cccgcgatag tcgcagcatc atggacgtgg ccgttttccg    6120
tctgtcgaag cgtgaccgac gagctggcga ggtgatccgc tacgagcttc agacgggca    6180 cgtagaggtt tccgcagggc cggccggcat ggccagtgtg tgggattacg acctggtact    6240
gatggcggtt tccatctaa ccgaatccat gaaccgatac cgggaaggga agggagacaa    6300
gcccggccgc gtgttccgtc cacacgttgc ggacgtactc aagttctgcc ggcgagccga    6360
tggcggaaag cagaaagacg acctggtaga aacctgcatt cggttaaaca ccacgcacgt    6420
tgccatgcag cgtacgaaga aggccaagaa cggccgcctg gtgacggtat ccgagggtga    6480
agccttgatt agccgctaca agatcgtaaa gagcgaaacc gggcggccgg agtacatcga    6540
gatcgagcta gctgattgga tgtaccgcga gatcacagaa ggcaagaacc cggacgtgct    6600
gacggttcac cccgattact ttttgatcga tcccggcatc ggccgttttc tctaccgcct    6660
ggcacgccgc gccgcaggca aggcagaagc cagatggttg ttcaagacga tctacgaacg    6720
cagtggcagc gccggagagt tcaagaagtt ctgtttcacc gtgcgcaagc tgatcgggtc    6780
aaatgacctg ccgagtacg atttgaagga ggaggcgggg caggctggcc cgatcctagt    6840
catgcgctac cgcaacctga tcgagggcga agcatccgcc ggttcctaat gtacggagca    6900
gatgctaggg caaattgccc tagcagggga aaaggtcga aaaggtctct ttcctgtgga    6960
tagcacgtac attgggaacc caaagccgta cattgggaac cggaaccgt acattgggaa    7020 cccaaagccg tacattggga accggtcaca catgtaagtg actgatataa aagagaaaaa    7080
aggcgatttt tccgcctaaa actctttaaa acttattaaa actcttaaaa cccgcctggc    7140
ctgtgcataa ctgtctggcc agcgcacagc cgaagagctg caaaaagcgc ctacccttcg    7200
gtcgctgcgc tccctacgcc ccgccgcttc gcgtcggcct atcgcggccg ctggccgctc    7260
aaaaatggct ggcctacggc caggcaatct accagggcgc ggacaagccg cgccgtcgcc    7320
```

-continued

```
actcgaccgc cggcgcccac atcaaggcac cctgcctcgc gcgtttcggt gatgacggtg    7380
aaaacctctg acacatgcag ctcccggaga cggtcacagc ttgtctgtaa gcggatgccg    7440
ggagcagaca agcccgtcag ggcgcgtcag cgggtgttgg cgggtgtcgg ggcgcagcca    7500
tgacccagtc acgtagcgat agcggagtgt atactggctt aactatgcgg catcagagca    7560
gattgtactg agagtgcacc atatgcggtg tgaaataccg cacagatgcg taaggagaaa    7620
ataccgcatc aggcgctctt ccgcttcctc gctcactgac tcgctgcgct cggtcgttcg    7680
gctgcggcga gcggtatcag ctcactcaaa ggcggtaata cggttatcca cagaatcagg    7740
ggataacgca ggaaagaaca tgtgagcaaa aggccagcaa aaggccagga accgtaaaaa    7800
ggccgcgttg ctggcgtttt tccataggct ccgcccccct gacgagcatc acaaaaatcg    7860
acgctcaagt cagaggtggc gaaacccgac aggactataa agataccagg cgtttccccc    7920
tggaagctcc ctcgtgcgct ctcctgttcc gaccctgccg cttaccggat acctgtccgc    7980
ctttctccct tcgggaagcg tggcgctttc tcatagctca cgctgtaggt atctcagttc    8040
ggtgtaggtc gttcgctcca agctgggctg tgtgcacgaa ccccccgttc agcccgaccg    8100
ctgcgcctta tccggtaact atcgtcttga gtccaacccg gtaagacacg acttatcgcc    8160
actggcagca gccactggta acaggattag cagagcgagg tatgtaggcg gtgctacaga    8220
gttcttgaag tggtggccta actacggcta cactagaagg acagtatttg gtatctgcgc    8280
tctgctgaag ccagttacct tcggaaaaag agttggtagc tcttgatccg gcaaacaaac    8340
caccgctggt agcggtggtt tttttgtttg caagcagcag attacgcgca gaaaaaaagg    8400
atctcaagaa gatcctttga tcttttctac ggggtctgac gctcagtgga acgaaaactc    8460
acgttaaggg attttggtca tgcatgatat atctcccaat tgtgtaggg cttattatgc    8520 acgcttaaaa ataataaaag cagacttgac ctgatagttt ggctgtgagc aattatgtgc    8580
ttagtgcatc taatcgcttg agttaacgcc ggcgaagcgg cgtcggcttg aacgaatttc    8640
tagctagagg atcgcaccaa taactgcctt aaaaaaatta cgccccgccc tgccactcat    8700
cgcagtactg ttgtaattca ttaagcattc tgccgacatg gaagccatca caaacggcat    8760
gatgaacctg aatcgccagc ggcatcagca ccttgtcgcc ttgcgtataa tatttgccca    8820
ttgtgaaaac gggggcgaag aagttgtcca tattggccac gtttaaatca aaactggtga    8880
aactcaccca gggattggct gagacgaaaa acatattctc aataaaccct ttagggaaat    8940
aggccaggtt ttcaccgtaa cacgccacat cttgcgaata tatgtgtaga aactgccgga    9000
aatcgtcgtg gtattcactc cagagcgatg aaaacgtttc agtttgctca tggaaaacgg    9060
tgtaacaagg gtgaacacta tcccatatca ccagctcacc gtctttcatt gccatacgga    9120
actccggatg agcattcatc aggcgggcaa gaatgtgaat aaaggccgga taaaacttgt    9180
gcttattttt ctttacggtc tttaaaaagg ccgtaatatc cagctgaacg gtctggttat    9240
aggtacattg agcaactgac tgaaatgcct caaaatgttc tttacgatgc cattgggata    9300
tatcaacggt ggtatatcca gtgattttttt tctccatgat gtttaacttt gttttagggc    9360
gactgccctg ctgcgtaaca tcgttgctgc tccataacat caaacatcga cccacggcgt    9420
aacgcgcttg ctgcttggat gcccgaggca tagactgtac cccaaaaaaa catgtcataa    9480
caagaagcca tgaaaaccgc cactgcgccg ttaccaccgc tgcgttcggt caaggttctg    9540
gaccagttgc gtgacggcag ttacgctact tgcattacag cttacgaacc gaacgaggct    9600
tatgtccact gggttcgtgc ccgaattgat cacaggcagc aacgctctgt catcgttaca    9660
atcaacatgc taccctccgc gagatcatcc gtgtttcaaa cccggcagct tagttgccgt    9720
```

```
tcttccgaat agcatcggta acatgagcaa agtctgccgc cttacaacgg ctctcccgct    9780
gacgccgtcc cggactgatg ggctgcctgt atcgagtggt gattttgtgc cgagctgccg    9840
gtcggggagc tgttggctgg ctggtggcag gatatattgt ggtgtaaaca aattgacgct    9900
tagacaactt aataacacat tgcgacgtt tttaatgtac tgaattaacg ccgaattaat    9960
tcggggatc tggattttag tactggattt tggttttagg aattagaaat tttattgata   10020
gaagtatttt acaaatacaa atacatacta agggtttctt atatgctcaa cacatgagcg   10080
aaaccctata ggaaccctaa ttcccttatc tgggaactac tcacacatta ttatggagaa   10140
actcgagctt gtcgatcgac tctagctaga ggatcgatcc gaaccccaga gtcccgctca   10200
gaagaactcg tcaagaaggc gatagaaggc gatgcgctgc gaatcgggag cggcgatacc   10260
gtaaagcacg aggaagcggt cagcccattc gccgccaagc tcttcagcaa tatcacgggt   10320
agccaacgct atgtcctgat agcggtccgc cacacccagc cggccacagt cgatgaatcc   10380
agaaaagcgg ccattttcca ccatgatatt cggcaagcag gcatcgccat gtgtcacgac   10440
gagatcctcg ccgtcgggca tgcgcgcctt gagcctggcg aacagttcgg ctggcgcgag   10500
cccctgatgc tcttcgtcca gatcatcctg atcgacaaga ccggcttcca tccgagtacg   10560
tgctcgctcg atgcgatgtt tcgcttggtg gtcgaatggg caggtagccg gatcaagcgt   10620
atgcagccgc cgcattgcat cagccatgat ggatactttc tcggcaggag caaggtgaga   10680
tgacaggaga tcctgccccg gcacttcgcc caatagcagc cagtcccttc ccgcttcagt   10740
gacaacgtcg agcacagctg cgcaaggaac gcccgtcgtg gccagccacg atagccgcgc   10800
tgcctcgtcc tggagttcat tcagggcacc ggacaggtcg gtcttgacaa aaagaaccgg   10860
gcgcccctgc gctgacagcc ggaacacggc ggcatcagag cagccgattg tctgttgtgc   10920
ccagtcatag ccgaatagcc tctccaccca agcggccgga gaacctgcgt gcaatccatc   10980
ttgttcaatc cccatggtcg atcgacagat ctgcgaaagc tcgagagaga tagatttgta   11040
gagagagact ggtgatttca gcgtgtcctc tccaaatgaa atgaacttcc ttatatagag   11100
gaaggtcttg cgaaggatag tgggattgtg cgtcatccct tacgtcagtg gagatatcac   11160
atcaatccac ttgctttgaa gacgtggttg gaacgtcttc tttttccacg atgctcctcg   11220
tgggtggggg tccatctttg ggaccactgt cggcagaggc atcttgaacg atagcctttc   11280
ctttatcgca atgatggcat ttgtaggtgc caccttcctt ttctactgtc ttttgatga   11340
agtgacagat agctgggcaa tggaatccga ggaggtttcc cgatattacc ctttgttgaa   11400
aagtctcaat agccctttgg tcttctgaga ctgtatcttt gatattcttg gagtagacga   11460
gagtgtcgtg ctccaccatg ttatcacatc aatccacttg ctttgaagac gtggttggaa   11520
cgtcttcttt ttccacgatg ctcctcgtgg gtggggtcc atctttggga ccactgtcgg   11580
cagaggcatc ttgaacgata gcctttcctt tatcgcaatg atggcatttg taggtgccac   11640
cttccttttc tactgtcctt ttgatgaagt gacagatagc tgggcaatgg aatccgagga   11700
ggtttcccga tattacccctt tgttgaaaag tctcaatagc cctttggtct tctgagactg   11760
tatctttgat attcttggag tagacgagag tgtcgtgctc caccatgttg gcaagctgct   11820
ctagccaata cgcaaaccgc ctctc                                          11845
```

<210> SEQ ID NO 41
<211> LENGTH: 11845
<212> TYPE: DNA
<213> ORGANISM: Artificial Sequence
<220> FEATURE:

<223> OTHER INFORMATION: synthetic GPT 9c construct; Cambia 2201 +
tomato rubisco SSU promoter + GPT (-45) truncated (deleted
chloroplast targeting sequence) F:V mutation codon optimized for
Arabidopsis + nos terminator; GPT transgene expression vector
construct (9c)

<400> SEQUENCE: 41

```
cccgcgcgtt ggccgattca ttaatgcagc tggcacgaca ggtttcccga ctggaaagcg      60
ggcagtgagc gcaacgcaat taatgtgagt tagctcactc attaggcacc ccaggcttta     120
cactttatgc ttccggctcg tatgttgtgt ggaattgtga gcggataaca atttcacaca     180
ggaaacagct atgaccatga ttacgaattc gagctcggta cccggggatc ctctagatct     240
agagaattca tcgatgtttg aatcctcctt aaagtttttc tctggagaaa ctgtagtaat     300
tttactttgt tgtgttccct tcatcttttg aattaatggc atttgtttta atactaatct     360
gcttctgaaa cttgtaatgt atgtatatca gtttcttata atttatccaa gtaatatctt     420
ccattctcta tgcaattgcc tgcataagct cgacaaaaga gtacatcaac ccctcctcct     480
ctggactact ctagctaaac ttgaatttcc ccttaagatt atgaaattga tatatcctta     540
acaaacgact ccttctgttg gaaaatgtag tacttgtctt tcttcttttg ggtatatata     600
gtttatatac accatactat gtacaacatc aagtagagt gaaatggata catgtacaag      660
acttatttga ttgattgatg acttgagttg ccttaggagt aacaaattct taggtcaata     720
aatcgttgat ttgaaattaa tctctctgtc ttagacagat aggaattatg acttccaatg     780
gtccagaaag caaagttcgc actgagggta tacttggaat tgagacttgc acaggtccag     840
aaaccaaagt tccatcgag ctctaaaatc acatctttgg aatgaaattc aattagagat       900
aagttgcttc atagcatagg taaaatggaa gatgtgaagt aacctgcaat aatcagtgaa     960
atgacattaa tacactaaat acttcatatg taattatcct ttccaggtta acaatactct    1020
ataaagtaag aattatcaga aatgggctca tcaaactttt gtactatgta tttcatataa    1080
ggaagtataa ctatacataa gtgtatacac aactttattc ctattttgta aaggtggaga    1140
gactgttttc gatggatcta aagcaatatg tctataaaat gcattgatat aataattatc    1200
tgagaaaatc cagaattggc gttggattat ttcagcccaaa tagaagtttg taccatactt   1260
gttgattcct tctaagttaa ggtgaagtat cattcataaa cagttttccc caaagtacta    1320
ctcaccaagt ttcccttgt agaattaaca gttcaaatat atggcgcaga aattactcta    1380
tgcccaaaac caaacgagaa agaaacaaaa tacaggggtt gcagacttta ttttcgtgtt    1440
agggtgtgtt ttttcatgta attaatcaaa aaatattatg acaaaacat ttatacatat     1500
ttttactcaa cactctgggt atcagggtgg gttgtgttcg acaatcaata tggaaaggaa    1560
gtattttcct tatttttta gttaatattt tcagttatac caaacatacc ttgtgatatt    1620
attttttaaaa atgaaaaact cgtcagaaag aaaaagcaaa agcaacaaaa aaattgcaag   1680
tatttttaa aaagaaaaa aaaaacatat cttgtttgtc agtatgggaa gtttgagata       1740
aggacgagtg agggggttaaa attcagtggc cattgatttt gtaatgccaa gaaccacaaa   1800
atccaatggt taccattcct gtaagatgag gtttgctaac tcttttttgtc cgttagatag   1860
gaagccttat cactatatat acaaggcgtc ctaataacct cttagtaacc aattatttca    1920
gcaactagta tggcgactca aaatgagtca acacaaaagc ctgttcaggt ggctaagaga    1980
cttgagaagt ttaaaactac aattttcact caaatgtcta tcctcgcagt taagcacgga    2040
gctattaatc ttggacaggg tgttcctaac ttcgatggtc cagatttcgt gaaagaagct    2100
gcaattcaag caatcaagga tggaaaaaat cagtatgcta gaggatacgg tattcctcag    2160
```

```
ttgaactctg ctatcgctgc aagattcaga gaagatacag gacttgttgt ggatccagaa   2220
aaagaggtta ctgtgacatc aggttgtact gaggctattg ctgcagctat gctcggactt   2280
attaaccctg gagatgaagt tatcctttt gcaccattct atgattctta cgaggctaca    2340
ttgtcaatgg caggagctaa ggtgaaaggt attactctca gacctccaga tttctctatc   2400
cctttggaag agctcaaggc agctgttact aataagacaa gagctatctt gatgaatact   2460
cctcataacc caacaggaaa gatgtttact agagaagagc tcgaaactat tgcttctctt   2520
tgcatcgaga acgatgtttt ggtgttctca gatgaagtgt atgataaact cgcatttgag   2580
atggatcaca tttctatcgc ttcacttcca ggaatgtacg aaagaactgt tactatgaat   2640
tctttgggaa agacttttc tctcacagga tggaaaattg gtgggcaat cgctcctcca     2700
catctcacat ggggtgttag acaagcacac tcttatctta ctttcgcaac ttcaacacct   2760
gctcagtggg cagctgtggc agctcttaag gctccagaat cttacttcaa ggagttgaag   2820
agagattaca acgttaagaa agaaacactt gtgaagggat tgaaagaggt tggttttaca   2880
gtgttccctt cttcaggaac ttactttgtt gtggcagatc atactccatt cggtatggaa   2940
aacgatgttg cttttgtga gtatcttatt gaagaggttg gagttgtggc tatccctaca    3000
tctgtgtttt accttaatcc agaagaggga aagaatcttg ttagatttgc attctgcaaa   3060
gatgaagaga ctttgagagg tgctattgag aggatgaagc aaaaactcaa gagaaaagtt   3120
tgacacgtgt gaattacagg tgaccagctc gaatttcccc gatcgttcaa acatttggca   3180
ataaagtttc ttaagattga atcctgttgc cggtcttgcg atgattatca tataatttct   3240
gttgaattac gttaagcatg taataattaa catgtaatgc atgacgttat ttatgagatg   3300
ggttttatg attagagtcc cgcaattata catttaatac gcgatagaaa acaaaatata    3360
gcgcgcaaac taggataaat tatcgcgcgc ggtgtcatct atgttactag atcgggaatt   3420
aaactatcag tgtttgacag gatatattgg cgggtaaacc taagagaaaa gagcgtttat   3480
tagaataacg gatatttaaa agggcgtgaa aaggtttatc cgttcgtcca tttgtatgtg   3540
catgccaacc acagggttcc cctcgggatc aaagtacttt gatccaaccc ctccgctgct   3600
atagtgcagt cggcttctga cgttcagtgc agccgtcttc tgaaaacgac atgtcgcaca   3660
agtcctaagt tacgcgacag gctgccgccc tgccctttc ctggcgtttt cttgtcgcgt    3720
gttttagtcg cataaagtag aatacttgcg actagaaccg gagacattac gccatgaaca   3780
agagcgccgc cgctggcctg ctgggctatg cccgcgtcag caccgacgac caggacttga   3840
ccaaccaacg ggccgaactg cacgcggccg gctgcaccaa gctgttttcc gagaagatca   3900
ccggcaccag gcgcgaccgc ccggagctgg ccaggatgct tgaccaccta cgccctggcg   3960
acgttgtgac agtgaccagg ctagaccgcc tggcccgcag cacccgcgac ctactggaca   4020
ttgccgagcg catccaggag gccggcgcgg gcctgcgtag cctggcagag ccgtgggccg   4080
acaccaccac gccggccggc cgcatggtgt tgaccgtgtt cgccggcatt gccgagttcg   4140
agcgttccct aatcatcgac cgcacccgga gcgggcgcga ggccgccaag gcccgaggcg   4200
tgaagtttgg cccccgccct accctcaccc cggcacagat cgcgcacgcc cgcgagctga   4260
tcgaccagga aggccgcacc gtgaaagagg cggctgcact gcttggcgtg catcgctcga   4320
ccctgtaccg cgcacttgag cgcagcgagg aagtgacgcc caccgaggcc aggcggcgcg   4380
gtgccttccg tgaggacgca ttgaccgagg ccgacgccct ggcggccgcc gagaatgaac   4440
gccaagagga acaagcatga aaccgcacca ggacggccag gacgaaccgt ttttcattac   4500
```

```
cgaagagatc gaggcggaga tgatcgcggc cgggtacgtg ttcgagccgc ccgcgcacgt    4560
ctcaaccgtg cggctgcatg aaatcctggc cggtttgtct gatgccaagc tggcggcctg    4620
gccggccagc ttggccgctg aagaaaccga cgccgccgt ctaaaaaggt gatgtgtatt     4680
tgagtaaaac agcttgcgtc atgcggtcgc tgcgtatatg atgcgatgag taaataaaca    4740
aatacgcaag gggaacgcat gaaggttatc gctgtactta accagaaagg cgggtcaggc    4800
aagacgacca tcgcaaccca tctagcccgc gccctgcaac tcgccgggc cgatgttctg     4860
ttagtcgatt ccgatcccca gggcagtgcc cgcgattggg cggccgtgcg ggaagatcaa    4920
ccgctaaccg ttgtcggcat cgaccgcccg acgattgacc gcgacgtgaa ggccatcggc    4980
cggcgcgact tcgtagtgat cgacggagcg ccccaggcgg cggacttggc tgtgtccgcg    5040
atcaaggcag ccgacttcgt gctgattccg gtgcagccaa gcccttacga catatgggcc    5100
accgccgacc tggtggagct ggttaagcag cgcattgagg tcacggatgg aaggctacaa    5160
gcggcctttg tcgtgtcgcg ggcgatcaaa ggcacgcgca tcggcggtga ggttgccgag    5220
gcgctggccg gtacgagct gcccattctt gagtcccgta tcacgcagcg cgtgagctac     5280
ccaggcactg ccgccgccgg cacaaccgtt cttgaatcag aacccgaggg cgacgctgcc    5340
cgcgaggtcc aggcgctggc cgctgaaatt aaatcaaaac tcatttgagt taatgaggta    5400
aagagaaaat gagcaaaagc acaaacacgc taagtgccgg ccgtccgagc gcacgcagca    5460
gcaaggctgc aacgttggcc agcctggcag acacgccagc catgaagcgg gtcaactttc    5520
agttgccggc ggaggatcac accaagctga agatgtacgc ggtacgccaa ggcaagacca    5580
ttaccgagct gctatctgaa tacatcgcgc agctaccaga gtaaatgagc aaatgaataa    5640
atgagtagat gaattttagc ggctaaagga ggcggcatgg aaaatcaaga caaccaggc    5700
accgacgccg tggaatgccc catgtgtgga ggaacgggcg gttggccagg cgtaagcggc    5760
tgggttgtct gccggccctg caatggcact ggaaccccca gcccgagga atcggcgtga     5820
cggtcgcaaa ccatccggcc cggtacaaat cggcgcggcg ctgggtgatg acctggtgga    5880
gaagttgaag gccgcgcagg ccgcccagcg gcaacgcatc gaggcagaag cacgccccgg    5940
tgaatcgtgg caagcggccg ctgatcgaat ccgcaaagaa tcccggcaac cgccggcagc    6000
cggtgcgccg tcgattagga agccgcccaa gggcgacgag caaccagatt ttttcgttcc    6060
gatgctctat gacgtgggca cccgcgatag tcgcagcatc atggacgtgg ccgttttccg    6120
tctgtcgaag cgtgaccgac gagctggcga ggtgatccgc tacgagcttc agacgggca    6180
cgtagaggtt tccgcagggc cggccggcat ggccagtgtg tgggattacg acctggtact    6240
gatggcggtt tccatctaa ccgaatccat gaaccgatac cgggaaggga agggagacaa    6300
gcccggccgc gtgttccgtc cacacgttgc ggacgtactc aagttctgcc ggcgagccga    6360
tggcggaaag cagaaagacg acctggtaga aacctgcatt cggttaaaca ccacgcacgt    6420
tgccatgcag cgtacgaaga aggccaagaa cggccgcctg gtgacggtat ccagggtga    6480
agccttgatt agccgctaca agatcgtaaa gagcgaaacc gggcggccgg agtacatcga    6540
gatcgagcta gctgattgga tgtaccgcga gatcacagaa ggcaagaacc cggacgtgct    6600
gacggttcac cccgattact ttttgatcga tcccggcatc ggccgttttc tctaccgcct    6660
ggcacgccgc gccgcaggca aggcagaagc cagatggttg ttcaagacga tctacgaacg    6720
cagtggcagc gccggagagt tcaagaagtt ctgtttcacc gtgcgcaagc tgatcgggtc    6780
aaatgacctg ccggagtacg atttgaagga ggaggcgggg caggctggcc cgatcctagt    6840
catgcgctac cgcaacctga tcgagggcga agcatccgcc ggttcctaat gtacggagca    6900
```

```
gatgctaggg caaattgccc tagcagggga aaaaggtcga aaaggtctct ttcctgtgga   6960
tagcacgtac attgggaacc caaagccgta cattgggaac cggaacccgt acattgggaa   7020
cccaaagccg tacattggga accggtcaca catgtaagtg actgatataa aagagaaaaa   7080
aggcgatttt tccgcctaaa actctttaaa acttattaaa actcttaaaa cccgcctggc   7140
ctgtgcataa ctgtctggcc agcgcacagc cgaagagctg caaaaagcgc ctacccttcg   7200
gtcgctgcgc tccctacgcc ccgccgcttc gcgtcggcct atcgcggccg ctggccgctc   7260
aaaaatggct ggcctacggc caggcaatct accagggcgc ggacaagccg cgccgtcgcc   7320
actcgaccgc cggcgcccac atcaaggcac cctgcctcgc gcgtttcggt gatgacggtg   7380
aaaacctctg acacatgcag ctcccggaga cggtcacagc ttgtctgtaa gcggatgccg   7440
ggagcagaca gcccgtcag ggcgcgtcag cgggtgttgg cgggtgtcgg ggcgcagcca   7500
tgacccagtc acgtagcgat agcggagtgt atactggctt aactatgcgg catcagagca   7560
gattgtactg agagtgcacc atatgcggtg tgaaataccg cacagatgcg taaggagaaa   7620
ataccgcatc aggcgctctt ccgcttcctc gctcactgac tcgctgcgct cggtcgttcg   7680
gctgcggcga gcggtatcag ctcactcaaa ggcggtaata cggttatcca cagaatcagg   7740
ggataacgca ggaaagaaca tgtgagcaaa aggccagcaa aaggccagga accgtaaaaa   7800
ggccgcgttg ctggcgtttt tccataggct ccgcccccct gacgagcatc acaaaaatcg   7860
acgctcaagt cagaggtggc gaaacccgac aggactataa agataccagg cgtttccccc   7920
tggaagctcc ctcgtgcgct ctcctgttcc gaccctgccg cttaccggat acctgtccgc   7980
ctttctccct tcgggaagcg tggcgctttc tcatagctca cgctgtaggt atctcagttc   8040
ggtgtaggtc gttcgctcca agctgggctg tgtgcacgaa ccccccgttc agcccgaccg   8100
ctgcgcctta tccggtaact atcgtcttga gtccaacccg gtaagacacg acttatcgcc   8160
actggcagca gccactggta acaggattag cagagcgagg tatgtaggcg gtgctacaga   8220
gttcttgaag tggtggccta actacggcta cactagaagg acagtatttg gtatctgcgc   8280
tctgctgaag ccagttacct tcggaaaaag agttggtagc tcttgatccg gcaaacaaac   8340
caccgctggt agcggtggtt tttttgtttg caagcagcag attacgcgca gaaaaaaagg   8400
atctcaagaa gatcctttga tcttttctac ggggtctgac gctcagtgga acgaaaactc   8460
acgttaaggg attttggtca tgcatgatat atctcccaat ttgtgtaggg cttattatgc   8520
acgcttaaaa ataataaaag cagacttgac ctgatagttt ggctgtgagc aattatgtgc   8580
ttagtgcatc taatcgcttg agttaacgcc ggcgaagcgg cgtcggcttg aacgaatttc   8640
tagctagagg atcgcaccaa taactgcctt aaaaaaatta cgccccgccc tgccactcat   8700
cgcagtactg ttgtaattca ttaagcattc tgccgacatg gaagccatca caaacggcat   8760
gatgaacctg aatcgccagc ggcatcagca ccttgtcgcc ttgcgtataa tatttgccca   8820
ttgtgaaaac ggggcgaag aagttgtcca tattggccac gtttaaatca aaactggtga   8880
aactcaccca gggattggct gagacgaaaa acatattctc aataaaccct ttagggaaat   8940
aggccaggtt ttcaccgtaa cacgccacat cttgcgaata tatgtgtaga aactgccgga   9000
aatcgtcgtg gtattcactc cagagcgatg aaaacgtttc agtttgctca tggaaaacgg   9060
tgtaacaagg gtgaacacta tcccatatca ccagctcacc gtctttcatt gccatacgga   9120
actccgatg agcattcatc aggcgggcaa gaatgtgaat aaaggccgga taaaacttgt   9180
gcttattttt ctttacggtc tttaaaaagg ccgtaatatc cagctgaacg gtctggttat   9240
```

```
aggtacattg agcaactgac tgaaatgcct caaaatgttc tttacgatgc cattgggata    9300
tatcaacggt ggtatatcca gtgattttt tctccatgat gtttaacttt gttttagggc     9360
gactgccctg ctgcgtaaca tcgttgctgc tccataacat caaacatcga cccacggcgt    9420
aacgcgcttg ctgcttggat gcccgaggca tagactgtac cccaaaaaaa catgtcataa    9480
caagaagcca tgaaaaccgc cactgcgccg ttaccaccgc tgcgttcggt caaggttctg    9540
gaccagttgc gtgacggcag ttacgctact tgcattacag cttacgaacc gaacgaggct    9600
tatgtccact gggttcgtgc ccgaattgat cacaggcagc aacgctctgt catcgttaca    9660
atcaacatgc taccctccgc gagatcatcc gtgtttcaaa cccggcagct tagttgccgt    9720
tcttccgaat agcatcggta acatgagcaa agtctgccgc cttacaacgg ctctcccgct    9780
gacgccgtcc cggactgatg gctgcctgt atcgagtggt gattttgtgc cgagctgccg     9840
gtcggggagc tgttggctgg ctggtggcag gatatattgt ggtgtaaaca aattgacgct    9900
tagacaactt aataacacat tgcggacgtt tttaatgtac tgaattaacg ccgaattaat    9960
tcggggatc tggattttag tactggattt tggttttagg aattagaaat tttattgata    10020
gaagtatttt acaaatacaa atacatacta agggtttctt atatgctcaa cacatgagcg    10080
aaaccctata ggaaccctaa ttcccttatc tgggaactac tcacacatta ttatggagaa    10140
actcgagctt gtcgatcgac tctagctaga ggatcgatcc gaaccccaga gtcccgctca    10200
gaagaactcg tcaagaaggc gatagaaggc gatgcgctgc gaatcgggag cggcgatacc    10260
gtaaagcacg aggaagcggt cagcccattc gccgccaagc tcttcagcaa tatcacgggt    10320
agccaacgct atgtcctgat agcggtccgc cacacccagc cggccacagt cgatgaatcc    10380
agaaaagcgg ccattttcca ccatgatatt cggcaagcag gcatcgccat gtgtcacgac    10440
gagatcctcg ccgtcgggca tgcgcgcctt gagcctggcg aacagttcgg ctggcgcgag    10500
cccctgatgc tcttcgtcca gatcatcctg atcgacaaga ccggcttcca tccgagtacg    10560
tgctcgctcg atgcgatgtt tcgcttggtg gtcgaatggg caggtagccg gatcaagcgt    10620
atgcagccgc cgcattgcat cagccatgat ggatactttc tcggcaggag caaggtgaga    10680
tgacaggaga tcctgccccg gcacttcgcc caatagcagc cagtcccttc ccgcttcagt    10740
gacaacgtcg agcacagctg cgcaaggaac gcccgtcgtg gccagccacg atagccgcgc    10800
tgcctcgtcc tggagttcat tcagggcacc ggacaggtcg gtcttgacaa aaagaaccgg    10860
gcgcccctgc gctgacagcc ggaacacggc ggcatcagag cagccgattg tctgttgtgc    10920
ccagtcatag ccgaatagcc tctccaccca agcggccgga gaacctgcgt gcaatccatc    10980
ttgttcaatc cccatggtcg atcgacagat ctgcgaaagc tcgagagaga tagatttgta    11040
gagagagact ggtgatttca gcgtgtcctc tccaaatgaa atgaacttcc ttatatagag    11100
gaaggtcttg cgaaggatag tgggattgtg cgtcatccct tacgtcagtg gagatatcac    11160
atcaatccac ttgctttgaa gacgtggttg gaacgtcttc tttttccacg atgctcctcg    11220
tgggtggggg tccatctttg ggaccactgt cggcagaggc atcttgaacg atagcctttc    11280
ctttatcgca atgatggcat ttgtaggtgc caccttcctt ttctactgtc cttttgatga    11340
agtgacagat agctgggcaa tggaatccga ggaggtttcc cgatattacc ctttgttgaa    11400
aagtctcaat agccctttgg tcttctgaga ctgtatcttt gatattcttg gagtagacga    11460
gagtgtcgtg ctccaccatg ttatcacatc aatccacttg ctttgaagac gtggttggaa    11520
cgtcttcttt ttccacgatg ctcctcgtgg gtggggtcc atctttggga ccactgtcgg    11580
cagaggcatc ttgaacgata gcctttcctt tatcgcaatg atggcatttg taggtgccac    11640
```

```
cttcctttc  tactgtcctt  ttgatgaagt  gacagatagc  tgggcaatgg  aatccgagga    11700
ggtttcccga  tattacccctt  tgttgaaaag  tctcaatagc  cctttggtct  tctgagactg   11760
tatctttgat  attcttggag  tagacgagag  tgtcgtgctc  caccatgttg  gcaagctgct   11820
ctagccaata  cgcaaaccgc  ctctc                                            11845

<210> SEQ ID NO 42
<211> LENGTH: 1780
<212> TYPE: DNA
<213> ORGANISM: Artificial Sequence
<220> FEATURE:
<223> OTHER INFORMATION: synthetic GPT 5c construct; Cambia 1305.1 with
      rbcS3C promoter + catI intron with full-length codon optimized
      Arabidopsis GPT gene

<400> SEQUENCE: 42
aaaaaagaaa  aaaaaaacat  atcttgtttg  tcagtatggg  aagtttgaga  taaggacgag      60
tgaggggtta  aaattcagtg  gccattgatt  ttgtaatgcc  aagaaccaca  aaatccaatg    120
gttaccattc  ctgtaagatg  aggtttgcta  actcttttg   tccgttagat  aggaagcctt    180
atcactatat  atacaaggcg  tcctaataac  ctcttagtaa  ccaattattt  cagcaccatg    240
gtagatctga  gggtaaattt  ctagttttc   tccttcattt  tcttggttag  gacccttttc    300 tcttttatt   tttttgagct  ttgatctttc  tttaaactga  tctatttttt  aattgattgg    360
ttatggtgta  aatattacat  agctttaact  gataatctga  ttactttatt  tcgtgtgtct    420
atgatgatga  tgatagttac  agaaccgacg  aactagtatg  tacctggaca  taaatggtgt    480
gatgatcaaa  cagtttagct  tcaaagcctc  tcttctccca  ttctcttcta  atttccgaca    540
aagctccgcc  aaaatccatc  gtcctatcgg  agccaccatg  accacagttt  cgactcagaa    600
cgagtctact  caaaaacccg  tccaggtggc  gaagagatta  gagaagttca  agactactat    660
tttcactcaa  atgagcatat  tggcagttaa  acatggagcg  atcaatttag  gccaaggctt    720
tcccaatttc  gacggtcctg  attttgttaa  agaagctgcg  atccaagcta  ttaaagatgg    780
taaaaaccag  tatgctcgtg  gatacggcat  tcctcagctc  aactctgcta  tagctgcgcg    840
gtttcgtgaa  gatacgggtc  ttgttgttga  tcctgagaaa  gaagttactg  ttacatctgg    900
ttgcacagaa  gccatagctg  cagctatgtt  gggtttaata  aaccctggtg  atgaagtcat    960
tctctttgca  ccgtttatg   attcctatga  agcaacactc  tctatggctg  gtgctaaagt   1020
aaaaggaatc  actttacgtc  caccggactt  ctccatccct  ttggaagagc  ttaaagctgc   1080
ggtaactaac  aagactcgag  ccatccttat  gaacactccg  cacaacccga  ccggaagat    1140 gttcactagg  gaggagcttg  aaaccattgc  atctctctgc  attgaaaacg  atgtgcttgt   1200
gttctcggat  gaagtatacg  ataagcttgc  gtttgaaatg  gatcacattt  ctatagcttc   1260
tcttcccggt  atgtatgaaa  gaactgtgac  catgaattcc  ctgggaaaga  ctttctcttt   1320
aaccggatgg  aagatcggct  gggcgattgc  gccgcctcat  ctgacttggg  gagttcgaca   1380
agcacactct  tacctcacat  cgccacatca  aacaccagca  caatgggcag  ccgttgcagc   1440
tctcaaggca  ccagagtctt  acttcaaaga  gctgaaaaga  gattacaatg  tgaaaaagga   1500
gactctggtt  aagggtttga  aggaagtcgg  atttacagtt  ttcccatcga  gcgggactta   1560
ctttgtggtt  gctgatcaca  ctccatttgg  aatggagaac  gatgttgctt  tctgtgagta   1620
tcttattgaa  gaagttgggg  tcgttgcgat  cccaacgagc  gtcttttatc  tgaatccaga   1680
agaagggaag  aatttggtta  ggtttgcgtt  ctgtaaagac  gaagagacgt  tgcgtggtgc   1740
```

```
aattgagagg atgaagcaga agcttaagag aaaagtctga            1780
```

<210> SEQ ID NO 43
<211> LENGTH: 11960
<212> TYPE: DNA
<213> ORGANISM: Artificial Sequence
<220> FEATURE:
<223> OTHER INFORMATION: synthetic GS 4c construct; Cambia 1305.1 with
      rbcS3C tomato rubisco small subunit promoter + catI intron +
      Arabidopsis GS1 coding region + nos terminator

<400> SEQUENCE: 43

```
ggtaccgttt gaatcctcct taaagttttt ctctggagaa actgtagtaa ttttactttg        60
ttgtgttccc ttcatctttt gaattaatgg catttgtttt aatactaatc tgcttctgaa       120
acttgtaatg tatgtatatc agtttcttat aatttatcca agtaatatct tccattctct       180
atgcaattgc ctgcataagc tcgacaaaag agtacatcaa cccctcctcc tctggactac       240
tctagctaaa cttgaatttc cccttaagat tatgaaattg atatatcctt aacaaacgac       300
tccttctgtt ggaaaatgta gtacttgtct ttcttctttt gggtatatat agtttatata       360
caccatacta tgtacaacat ccaagtagag tgaaatggat acatgtacaa gacttatttg       420
attgattgat gacttgagtt gccttaggag taacaaattc ttaggtcaat aaatcgttga       480
tttgaaatta atctctctgt cttagacaga taggaattat gacttccaat ggtccagaaa       540
gcaaagttcg cactgagggt atacttggaa ttgagacttg cacaggtcca gaaaccaaag       600
ttcccatcga gctctaaaat cacatctttg gaatgaaatt caattagaga taagttgctt       660
catagcatag gtaaaatgga agatgtgaag taacctgcaa taatcagtga atgacatta        720
atacactaaa tacttcatat gtaattatcc tttccaggtt aacaatactc tataaagtaa       780
gaattatcag aaatgggctc atcaaacttt tgtactatgt atttcatata ggaagtata        840
actatacata agtgtataca caactttatt cctattttgt aaaggtggag agactgtttt       900
cgatggatct aaagcaatat gtctataaaa tgcattgata taataattat ctgagaaaat       960
ccagaattgg cgttggatta tttcagccaa atagaagttt gtaccatact tgttgattcc      1020
ttctaagtta aggtgaagta tcattcataa acagttttcc ccaaagtact actcaccaag      1080
tttcccttg tagaattaac agttcaaata tatggcgcag aaattactct atgcccaaaa       1140
ccaaacgaga aagaaacaaa atacaggggt tgcagacttt attttcgtgt tagggtgtgt      1200
tttttcatgt aattaatcaa aaaatattat gacaaaaaca tttatacata tttttactca      1260
acactctggg tatcagggtg ggttgtgttc gacaatcaat atggaaagga agtattttcc      1320
ttattttttt agttaatatt ttcagttata ccaaacatac cttgtgatat tattttttaaa     1380
aatgaaaaac tcgtcagaaa gaaaaagcaa agcaacaaa aaaattgcaa gtatttttta       1440
aaaagaaaa aaaaaacata tcttgtttgt cagtatggga agtttgagat aaggacgagt       1500
gagggggttaa aattcagtgg ccattgattt tgtaatgcca agaaccacaa aatccaatgg     1560
ttaccattcc tgtaagatga ggtttgctaa ctctttttgt ccgttagata ggaagcctta      1620
tcactatata tacaaggcgt cctaataacc tcttagtaac caattatttc agcaccatgg      1680
tagatctgag ggtaaatttc tagttttttct ccttcatttt cttggttagg acccttttct    1740
cttttatttt ttttgagctt tgatcttcct ttaaactgat ctattttta attgattggt      1800
tatggtgtaa atattacata gctttaactg ataatctgat tacttatttt cgtgtgtcta      1860
tgatgatgat gatagttaca gaaccgacga actagtatgt ctctgctctc agatctcgtt     1920
aacctcaacc tcaccgatgc caccgggaaa atcatcgccg aatacatatg gatcggtgga     1980
```

-continued

```
tctggaatgg atatcagaag caaagccagg acactaccag gaccagtgac tgatccatca    2040
aagcttccca agtggaacta cgacggatcc agcaccggtc aggctgctgg agaagacagt    2100
gaagtcattc tataccctca ggcaatattc aaggatccct tcaggaaagg caacaacatc    2160
ctggtgatgt gtgatgctta caccagct ggtgatccta ttccaaccaa caagaggcac      2220
aacgctgcta agatcttcag ccaccccgac gttgccaagg aggagccttg gtatgggatt    2280
gagcaagaat acactttgat gcaaaaggat gtgaactggc caattggttg gcctgttggt    2340
ggctaccctg gccctcaggg accttactac tgtggtgtgg gagctgacaa agccattggt    2400
cgtgacattg tggatgctca ctacaaggcc tgtctttacg ccggtattgg tatttctggt    2460
atcaatggag aagtcatgcc aggccagtgg gagttccaag tcggccctgt tgagggtatt    2520
agttctggtg atcaagtctg ggttgctcga taccttctcg agaggatcac tgagatctct    2580
ggtgtaattg tcagcttcga cccgaaacca gtcccgggtg actggaatgg agctggagct    2640
cactgcaact acagcactaa gacaatgaga acgatggag gattagaagt gatcaagaaa     2700
gcgatagggga agcttcagct gaaacacaaa gaacacattg ctgcttacgg tgaaggaaac   2760
gagcgtcgtc tcactggaaa gcacgaaacc gcagacatca acacattctc ttggggagtc   2820
gcgaaccgtg gagcgtcagt gagagtggga cgtgacacag agaaggaagg taaagggtac   2880
ttcgaagaca gaaggccagc ttctaacatg gatccttacg ttgtcacctc catgatcgct   2940
gagacgacca tactcggttg acacgtgtga attggtgacc agctcgaatt ccccgatcg    3000
ttcaaacatt tggcaataaa gtttcttaag attgaatcct gttgccggtc ttgcgatgat   3060
tatcatataa tttctgttga attacgttaa gcatgtaata attaacatgt aatgcatgac   3120
gttatttatg agatgggttt ttatgattag agtcccgcaa ttatacattt aatacgcgat   3180
agaaaacaaa atatagcgcg caaactagga taaattatcg cgcgcggtgt catctatgtt   3240
actagatcgg gaattaaact atcagtgttt gacaggatat attggcgggt aaacctaaga   3300
gaaaagagcg tttattagaa taacggatat ttaaagggc gtgaaaaggt ttatccgttc    3360
gtccatttgt atgtgcatgc caaccacagg gttcccctcg ggatcaaagt actttgatcc   3420
aacccctccg ctgctatagt gcagtcggct tctgacgttc agtgcagccg tcttctgaaa   3480
acgacatgtc gcacaagtcc taagttacgc gacaggctgc cgccctgccc ttttcctggc   3540
gttttcttgt cgcgtgtttt agtcgcataa agtagaatac ttgcgactag aaccggagac   3600
attacgccat gaacaagagc gccgccgctg gcctgctggg ctatgcccgc gtcagcaccg   3660
acgaccagga cttgaccaac caacgggccg aactgcacgc ggccggctgc accaagctgt   3720
tttccgagaa gatcaccggc accaggcgcg accgcccgga gctggccagg atgcttgacc   3780
acctacgccc tggcgacgtt gtgacagtga ccaggctaga ccgcctggcc cgcagcaccc   3840
gcgacctact ggacattgcc gagcgcatcc aggaggccgg cgcgggcctg cgtagcctgg   3900
cagagccgtg ggccgacacc accacgccgg ccggccgcat ggtgttgacc gtgttcgccg   3960
gcattgccga gttcgagcgt tccctaatca tcgaccgcac ccggagcggg cgcgaggccg   4020
ccaaggcccg aggcgtgaag tttggcccccc gccctaccct caccccggca cagatcgcgc   4080
acgcccgcga gctgatcgac caggaaggcc gcaccgtgaa agaggcggct gcactgcttg   4140
gcgtgcatcg ctcgaccctg taccgcgcac ttgagcgcag cgaggaagtg acgcccaccg   4200
aggccaggcg gcgcggtgcc ttccgtgagg acgcattgac cgaggccgac gccctggcgg   4260
ccgccgagaa tgaacgccaa gaggaacaag catgaaaccg caccaggacg gccaggacga   4320
```

```
accgtttttc attaccgaag agatcgaggc ggagatgatc gcggccgggt acgtgttcga    4380
gccgcccgcg cacgtctcaa ccgtgcggct gcatgaaatc ctggccggtt tgtctgatgc    4440
caagctggcg gcctggccgg ccagcttggc cgctgaagaa accgagcgcc gccgtctaaa    4500
aaggtgatgt gtatttgagt aaaacagctt cgtcatgcg gtcgctgcgt atatgatgcg     4560
atgagtaaat aaacaaatac gcaaggggaa cgcatgaagg ttatcgctgt acttaaccag    4620
aaaggcgggc caggcaagac gaccatcgca acccatctag cccgcgccct gcaactcgcc    4680
ggggccgatg ttctgttagt cgattccgat ccccagggca gtgcccgcga ttgggcggcc    4740
gtgcgggaag atcaaccgct aaccgttgtc ggcatcgacc gcccgacgat tgaccgcgac    4800
gtgaaggcca tcggccggcg cgacttcgta gtgatcgacg gagcgcccca ggcggcggac    4860
ttggctgtgt ccgcgatcaa ggcagccgac ttcgtgctga ttccggtgca gccaagccct    4920
tacgacatat gggccaccgc cgacctggtg gagctggtta agcagcgcat tgaggtcacg    4980
gatggaaggc tacaagcggc ctttgtcgtg tcgcgggcga tcaaaggcac gcgcatcggc    5040
ggtgaggttg ccgaggcgct ggccgggtac gagctgccca ttcttgagtc ccgtatcacg    5100
cagcgcgtga gctacccagg cactgccgcc gccggcacaa ccgttcttga atcagaaccc    5160
gagggcgacg ctgcccgcga ggtccaggcg ctggccgctg aaattaaatc aaaactcatt    5220
tgagttaatg aggtaaagag aaaatgagca aaagcacaaa cacgctaagt gccggccgtc    5280
cgagcgcacg cagcagcaag gctgcaacgt tggccagcct ggcagacacg ccagccatga    5340
agcgggtcaa ctttcagttg ccggcggagg atcacaccaa gctgaagatg tacgcggtac    5400
gccaaggcaa gaccattacc gagctgctat ctgaatacat cgcgcagcta ccagagtaaa    5460
tgagcaaatg aataaatgag tagatgaatt ttagcggcta aggaggcgg catggaaaat    5520
caagaacaac caggcaccga cgccgtggaa tgccccatgt gtggaggaac gggcggttgg    5580
ccaggcgtaa gcggctgggt tgtctgccgg ccctgcaatg gcactggaac ccccaagccc    5640
gaggaatcgg cgtgacggtc gcaaaccatc cggcccggta caaatcggcg cggcgctggg    5700
tgatgacctg gtggagaagt tgaaggccgc gcaggccgcc cagcggcaac gcatcgaggc    5760
agaagcacgc cccggtgaat cgtggcaagc ggccgctgat cgaatccgca aagaatcccg    5820
gcaaccgccg gcagccggtg cgccgtcgat taggaagccg cccaagggcg acgagcaacc    5880
agatttttc gttccgatgc tctatgacgt gggcacccgc gatagtgca gcatcatgga     5940
cgtggccgtt ttccgtctgt cgaagcgtga ccgacgagct ggcgaggtga tccgctacga    6000
gcttccagac gggcacgtag aggtttccgc agggccggcc ggcatggcca gtgtgtggga    6060
ttacgacctg gtactgatgg cggtttccca tctaaccgaa tccatgaacc gataccggga    6120
agggaaggga gacaagcccg ccgcgtgtt ccgtccacac gttgcggacg tactcaagtt     6180
ctgccggcga gccgatggcg gaaagcagaa agacgacctg gtagaaacct gcattcggtt    6240
aaacaccacg cacgttgcca tgcagcgtac gaagaaggcc aagaacggcc gcctggtgac    6300
ggtatccgag ggtgaagcct tgattagccg ctacaagatc gtaaagagcg aaaccgggcg    6360
gccggagtac atcgagatcg agctagctga ttggatgtac cgcgagatca cagaaggcaa    6420
gaacccggac gtgctgacgg ttcaccccga ttactttttg atcgatcccg gcatcggccg    6480
ttttctctac cgcctggcac gccgcgccgc aggcaaggca gaagccagat ggttgttcaa    6540
gacgatctac gaacgcagtg gcagcgccgg agagttcaag aagttctgtt tcaccgtgcg    6600
caagctgatc gggtcaaatg acctgccgga gtacgatttg aaggaggagg cggggcaggc    6660
tggcccgatc ctagtcatgc gctaccgcaa cctgatcgag ggcgaagcat ccgccggttc    6720
```

```
ctaatgtacg gagcagatgc tagggcaaat tgccctagca gggaaaaag gtcgaaaagg      6780 tctctttcct gtggatagca cgtacattgg gaacccaaag ccgtacattg ggaaccggaa      6840
cccgtacatt gggaacccaa agccgtacat tgggaaccgg tcacacatgt aagtgactga      6900
tataaaagag aaaaaaggcg attttttccgc ctaaaactct ttaaaactta ttaaaactct      6960
taaaacccgc ctggcctgtg cataactgtc tggccagcgc acagccgaag agctgcaaaa      7020
agcgcctacc cttcggtcgc tgcgctccct acgccccgcc gcttcgcgtc ggcctatcgc      7080
ggccgctggc cgctcaaaaa tggctggcct acggccaggc aatctaccag ggcgcggaca      7140
agccgcgccg tcgccactcg accgccggcg cccacatcaa ggcaccctgc ctcgcgcgtt      7200
tcggtgatga cggtgaaaac ctctgacaca tgcagctccc ggagacggtc acagcttgtc      7260
tgtaagcgga tgccgggagc agacaagccc gtcaggcgc gtcagcgggt gttggcgggt       7320
gtcggggcgc agccatgacc cagtcacgta gcgatagcgg agtgtatact ggcttaacta      7380
tgcggcatca gagcagattg tactgagagt gcaccatatg cggtgtgaaa taccgcacag      7440
atgcgtaagg agaaaatacc gcatcaggcg ctcttccgct tcctcgctca ctgactcgct      7500
gcgctcggtc gttcggctgc ggcgagcggt atcagctcac tcaaaggcgg taatacggtt      7560
atccacagaa tcaggggata acgcaggaaa gaacatgtga gcaaaaggcc agcaaaaggc      7620
caggaaccgt aaaaaggccg cgttgctggc gtttttccat aggctccgcc ccctgacga     7680 gcatcacaaa aatcgacgct caagtcagag gtggcgaaac ccgacaggac tataaagata      7740
ccaggcgttt ccccctggaa gctccctcgt gcgctctcct gttccgaccc tgccgcttac      7800
cggatacctg tccgccttc tcccttcggg aagcgtggcg ctttctcata gctcacgctg       7860
taggtatctc agttcggtgt aggtcgttcg ctccaagctg ggctgtgtgc acgaaccccc      7920
cgttcagccc gaccgctgcg ccttatccgg taactatcgt cttgagtcca acccggtaag      7980
acacgactta tcgccactgg cagcagccac tggtaacagg attagcagag cgaggtatgt      8040
aggcggtgct acagagttct tgaagtggtg gcctaactac ggctacacta aaggacagt       8100 atttggtatc tgcgctctgc tgaagccagt taccttcgga aaaagagttg gtagctcttg      8160
atccggcaaa caaaccaccg ctggtagcgg tggttttttt gtttgcaagc agcagattac      8220
gcgcagaaaa aaaggatctc aagaagatcc tttgatcttt tctacggggt ctgacgctca      8280
gtggaacgaa aactcacgtt aagggatttt ggtcatgcat tctaggtact aaaacaattc      8340
atccagtaaa atataatatt ttattttctc ccaatcaggc ttgatcccca gtaagtcaaa      8400
aaatagctcg acatactgtt cttccccgat atcctccctg atcgaccgga cgcagaaggc      8460
aatgtcatac cacttgtccg ccctgccgct tctcccaaga tcaataaagc cacttacttt      8520
gccatctttc acaaagatgt tgctgtctcc caggtcgccg tgggaaaaga caagttcctc      8580
ttcgggcttt tccgtctttaaaaaatcata cagctcgcgc ggatctttaa atggagtgtc      8640
ttcttcccag ttttcgcaat ccacatcggc cagatcgtta ttcagtaagt aatccaattc      8700
ggctaagcgg ctgtctaagc tattcgtata gggacaatcc gatatgtcga tggagtgaaa      8760
gagcctgatg cactccgcat acagctcgat aatcttttca gggctttgtt catcttcata      8820
ctcttccgag caaaggacgc catcggcctc actcatgagc agattgctcc agccatcatg      8880
ccgttcaaag tgcaggacct ttggaacagg cagctttcct tccagccata gcatcatgtc      8940
cttttcccgt tccacatcat aggtggtccc tttataccgg ctgtccgtca ttttaaata      9000 taggttttca ttttctccca ccagcttata taccttagca ggagacattc cttccgtatc      9060
```

```
ttttacgcag cggtattttt cgatcagttt tttcaattcc ggtgatattc tcattttagc   9120
catttattat ttccttcctc ttttctacag tatttaaaga tacccaaga  agctaattat   9180
aacaagacga actccaattc actgttcctt gcattctaaa accttaaata ccagaaaaca   9240
gcttttcaa  agttgttttc aaagttggcg tataacatag tatcgacgga gccgattttg   9300
aaaccgcggt gatcacaggc agcaacgctc tgtcatcgtt acaatcaaca tgctaccctc   9360
cgcgagatca tccgtgtttc aaacccggca gcttagttgc cgttcttccg aatagcatcg   9420
gtaacatgag caaagtctgc cgccttacaa cggctctccc gctgacgccg tcccggactg   9480
atgggctgcc tgtatcgagt ggtgattttg tgccgagctg ccggtcgggg agctgttggc   9540
tggctggtgg caggatatat tgtggtgtaa acaaattgac gcttagacaa cttaataaca   9600
cattgcggac gttttaatg  tactgaatta acgccgaatt aattcggggg atctggattt   9660
tagtactgga ttttggtttt aggaattaga aattttattg atagaagtat tttacaaata   9720
caaatacata ctaagggttt cttatatgct caacacatga gcgaaaccct ataggaaccc   9780
taattcccctt atctgggaac tactcacaca ttattatgga gaaactcgag cttgtcgatc   9840
gacagatccg gtcggcatct actctatttc tttgccctcg gacgagtgct ggggcgtcgg   9900
tttccactat cggcgagtac ttctacacag ccatcggtcc agacggccgc gcttctgcgg   9960
gcgatttgtg tacgcccgac agtcccggct ccggatcgga cgattgcgtc gcatcgaccc  10020
tgcgcccaag ctgcatcatc gaaattgccg tcaaccaagc tctgatagag ttggtcaaga  10080
ccaatgcgga gcatatacgc ccggagtcgt ggcgatcctg caagctccgg atgcctccgc  10140
tcgaagtagc gcgtctgctg ctccatacaa gccaaccacg gcctcagaa  gaagatgttg  10200
gcgacctcgt attgggaatc cccgaacatc gcctcgctcc agtcaatgac cgctgttatg  10260
cggccattgt ccgtcaggac attgttggag ccgaaatccg cgtgcacgag gtgccggact  10320
tcggggcagt cctcggccca agcatcagc  tcatcgagag cctgcgcgac ggacgcactg  10380
acggtgtcgt ccatcacagt ttgccagtga tacacatggg gatcagcaat cgcgcatatg  10440
aaatcacgcc atgtagtgta ttgaccgatt ccttgcggtc cgaatgggcc gaacccgctc  10500
gtctggctaa gatcggccgc agcgatcgca tccatagcct ccgcgaccgg ttgtagaaca  10560
gcggcagtt  cggtttcagg caggtcttgc aacgtgacac cctgtgcacg gcgggagatg  10620
caataggtca ggctctcgct aaactcccca atgtcaagca cttccggaat cgggagcgcg  10680
gccgatgcaa agtgccgata acataacga  tctttgtaga aaccatcggc gcagctattt  10740
acccgcagga catatccacg ccctcctaca tcgaagctga agcacgaga  ttcttcgccc  10800
tccgagagct gcatcaggtc ggagacgctg tcgaactttt cgatcagaaa cttctcgaca  10860
gacgtcgcgg tgagttcagg cttttcata  tctcattgcc ccccgggatc tgcgaaagct  10920
cgagagagat agatttgtag agagagactg gtgatttcag cgtgtcctct ccaaatgaaa  10980
tgaacttcct tatatagagg aaggtcttgc gaaggatagt gggattgtgc gtcatcccctt  11040
acgtcagtgg agatatcaca tcaatccact tgctttgaag acgtggttgg aacgtcttct  11100
tttccacga  tgctcctcgt gggtgggggt ccatctttgg gaccactgtc ggcagaggca  11160
tcttgaacga tagcctttcc tttatcgcaa tgatggcatt tgtaggtgcc accttccttt  11220
tctactgtcc ttttgatgaa gtgacagata gctgggcaat ggaatccgag gaggtttccc  11280
gatattaccc tttgttgaaa agtctcaata gcccttggt  cttctgagac tgtatctttg  11340
atattcttgg agtagacgag agtgtcgtgc tccaccatgt tatcacatca atccacttgc  11400
tttgaagacg tggttggaac gtcttctttt tccacgatgc tcctcgtggg tgggggtcca  11460
```

```
tctttgggac cactgtcggc agaggcatct tgaacgatag cctttccttt atcgcaatga   11520
tggcatttgt aggtgccacc ttccttttct actgtccttt tgatgaagtg acagatagct   11580
gggcaatgga atccgaggag gtttcccgat attacccttt gttgaaaagt ctcaatagcc   11640
ctttggtctt ctgagactgt atctttgata ttcttggagt agacgagagt gtcgtgctcc   11700
accatgttgg caagctgctc tagccaatac gcaaaccgcc tctccccgcg cgttggccga   11760
ttcattaatg cagctggcac gacaggtttc ccgactggaa agcgggcagt gagcgcaacg   11820
caattaatgt gagttagctc actcattagg cacccaggc tttacacttt atgcttccgg   11880
ctcgtatgtt gtgtggaatt gtgagcggat aacaatttca cacaggaaac agctatgacc   11940
atgattacga attcgagctc                                                11960
```

```
<210> SEQ ID NO 44
<211> LENGTH: 394
<212> TYPE: PRT
<213> ORGANISM: Artificial Sequence
<220> FEATURE:
<223> OTHER INFORMATION: synthetic plant omega-amidase consensus
      sequence
<220> FEATURE:
<221> NAME/KEY: VARIANT
<222> LOCATION: (1)...(1)
<223> OTHER INFORMATION: Xaa = Met or absent
<220> FEATURE:
<221> NAME/KEY: VARIANT
<222> LOCATION: (2)...(2)
<223> OTHER INFORMATION: Xaa = Lys or absent
<220> FEATURE:
<221> NAME/KEY: VARIANT
<222> LOCATION: (3)...(3)
<223> OTHER INFORMATION: Xaa = Ser or absent
<220> FEATURE:
<221> NAME/KEY: VARIANT
<222> LOCATION: (4)...(4)
<223> OTHER INFORMATION: Xaa = Ala, Met or absent
<220> FEATURE:
<221> NAME/KEY: VARIANT
<222> LOCATION: (5)...(5)
<223> OTHER INFORMATION: Xaa = Ile, Lys or absent
<220> FEATURE:
<221> NAME/KEY: VARIANT
<222> LOCATION: (6)...(6)
<223> OTHER INFORMATION: Xaa = Ser or absent
<220> FEATURE:
<221> NAME/KEY: VARIANT
<222> LOCATION: (7)...(7)
<223> OTHER INFORMATION: Xaa = Ser, Ala or absent
<220> FEATURE:
<221> NAME/KEY: VARIANT
<222> LOCATION: (8)...(8)
<223> OTHER INFORMATION: Xaa = Thr, Ala or absent
<220> FEATURE:
<221> NAME/KEY: VARIANT
<222> LOCATION: (9)...(9)
<223> OTHER INFORMATION: Xaa = Thr, Leu or absent
<220> FEATURE:
<221> NAME/KEY: VARIANT
<222> LOCATION: (10)...(10)
<223> OTHER INFORMATION: Xaa = Thr, Ser or absent
<220> FEATURE:
<221> NAME/KEY: VARIANT
<222> LOCATION: (11)...(11)
<223> OTHER INFORMATION: Xaa = Leu, Ala, Met or absent
<220> FEATURE:
<221> NAME/KEY: VARIANT
<222> LOCATION: (12)...(12)
<223> OTHER INFORMATION: Xaa = Leu, Val or absent
<220> FEATURE:
<221> NAME/KEY: VARIANT
<222> LOCATION: (13)...(13)
<223> OTHER INFORMATION: Xaa = Ser, Leu, Ala, Met or absent
```

```
<220> FEATURE:
<221> NAME/KEY: VARIANT
<222> LOCATION: (14)...(14)
<223> OTHER INFORMATION: Xaa = Ser, Ala, Thr or absent
<220> FEATURE:
<221> NAME/KEY: VARIANT
<222> LOCATION: (15)...(15)
<223> OTHER INFORMATION: Xaa = Lys, Ser, Ala, Pro or absent
<220> FEATURE:
<221> NAME/KEY: VARIANT
<222> LOCATION: (16)...(16)
<223> OTHER INFORMATION: Xaa = Asn, Thr, Ala, Leu or absent
<220> FEATURE:
<221> NAME/KEY: VARIANT
<222> LOCATION: (17)...(17)
<223> OTHER INFORMATION: Xaa = Leu, Ala or absent
<220> FEATURE:
<221> NAME/KEY: VARIANT
<222> LOCATION: (18)...(18)
<223> OTHER INFORMATION: Xaa = Ser, Ala or absent
<220> FEATURE:
<221> NAME/KEY: VARIANT
<222> LOCATION: (19)...(19)
<223> OTHER INFORMATION: Xaa = Leu, Tyr, Ala or absent
<220> FEATURE:
<221> NAME/KEY: VARIANT
<222> LOCATION: (20)...(20)
<223> OTHER INFORMATION: Xaa = Lys, Ala, Ser or absent
<220> FEATURE:
<221> NAME/KEY: VARIANT
<222> LOCATION: (21)...(21)
<223> OTHER INFORMATION: Xaa = Leu, Ser, Ala or absent
<220> FEATURE:
<221> NAME/KEY: VARIANT
<222> LOCATION: (22)...(22)
<223> OTHER INFORMATION: Xaa = His, Pro, Thr or Arg or absent
<220> FEATURE:
<221> NAME/KEY: VARIANT
<222> LOCATION: (23)...(23)
<223> OTHER INFORMATION: Xaa = Leu, Pro, Ala, Val or absent
<220> FEATURE:
<221> NAME/KEY: VARIANT
<222> LOCATION: (24)...(24)
<223> OTHER INFORMATION: Xaa = Asn, His, Thr, Val or absent
<220> FEATURE:
<221> NAME/KEY: VARIANT
<222> LOCATION: (25)...(25)
<223> OTHER INFORMATION: Xaa = His, Leu, Ala or absent
<220> FEATURE:
<221> NAME/KEY: VARIANT
<222> LOCATION: (26)...(26)
<223> OTHER INFORMATION: Xaa = Ser, Asn, Ala or absent
<220> FEATURE:
<221> NAME/KEY: VARIANT
<222> LOCATION: (27)...(27)
<223> OTHER INFORMATION: Xaa = Pro, Leu, Ala or absent
<220> FEATURE:
<221> NAME/KEY: VARIANT
<222> LOCATION: (29)...(29)
<223> OTHER INFORMATION: Xaa = Ser, Arg, Leu or absent
<220> FEATURE:
<221> NAME/KEY: VARIANT
<222> LOCATION: (30)...(30)
<223> OTHER INFORMATION: Xaa = Arg, Pro, Ala or absent
<220> FEATURE:
<221> NAME/KEY: VARIANT
<222> LOCATION: (31)...(31)
<223> OTHER INFORMATION: Xaa = Leu, Ala, Pro, Lys or absent
<220> FEATURE:
<221> NAME/KEY: VARIANT
<222> LOCATION: (32)...(32)
<223> OTHER INFORMATION: Xaa = Pro, Thr, Gly, Ser or absent
<220> FEATURE:
<221> NAME/KEY: VARIANT
<222> LOCATION: (33)...(33)
<223> OTHER INFORMATION: Xaa = Ser, Ala, Leu or absent
<220> FEATURE:
<221> NAME/KEY: VARIANT
<222> LOCATION: (34)...(34)
```

```
<223> OTHER INFORMATION: Xaa = Ser, Val, Lys, Ile or absent
<220> FEATURE:
<221> NAME/KEY: VARIANT
<222> LOCATION: (35)...(35)
<223> OTHER INFORMATION: Xaa = Leu, Ala or absent
<220> FEATURE:
<221> NAME/KEY: VARIANT
<222> LOCATION: (36)...(36)
<223> OTHER INFORMATION: Xaa = Phe, Cys, Ser or absent
<220> FEATURE:
<221> NAME/KEY: VARIANT
<222> LOCATION: (37)...(37)
<223> OTHER INFORMATION: Xaa = Arg, Ala or absent
<220> FEATURE:
<221> NAME/KEY: VARIANT
<222> LOCATION: (38)...(38)
<223> OTHER INFORMATION: Xaa = Ser, Gly, Val or absent
<220> FEATURE:
<221> NAME/KEY: VARIANT
<222> LOCATION: (39)...(39)
<223> OTHER INFORMATION: Xaa = Lys, Leu, Arg, Gly or absent
<220> FEATURE:
<221> NAME/KEY: VARIANT
<222> LOCATION: (40)...(40)
<223> OTHER INFORMATION: Xaa = Ser, Leu, Ala, Arg or absent
<220> FEATURE:
<221> NAME/KEY: VARIANT
<222> LOCATION: (41)...(41)
<223> OTHER INFORMATION: Xaa = Asn, Pro, Arg, Leu or absent
<220> FEATURE:
<221> NAME/KEY: VARIANT
<222> LOCATION: (42)...(42)
<223> OTHER INFORMATION: Xaa = Thr, Val, Ser or absent
<220> FEATURE:
<221> NAME/KEY: VARIANT
<222> LOCATION: (43)...(43)
<223> OTHER INFORMATION: Xaa = His, Ser, Ala or absent
<220> FEATURE:
<221> NAME/KEY: VARIANT
<222> LOCATION: (44)...(44)
<223> OTHER INFORMATION: Xaa = Phe, Thr, Ser or absent
<220> FEATURE:
<221> NAME/KEY: VARIANT
<222> LOCATION: (45)...(45)
<223> OTHER INFORMATION: Xaa = Pro or absent
<220> FEATURE:
<221> NAME/KEY: VARIANT
<222> LOCATION: (46)...(46)
<223> OTHER INFORMATION: Xaa = Ser or absent
<220> FEATURE:
<221> NAME/KEY: VARIANT
<222> LOCATION: (47)...(48)
<223> OTHER INFORMATION: Xaa = Leu or absent
<220> FEATURE:
<221> NAME/KEY: VARIANT
<222> LOCATION: (49)...(49)
<223> OTHER INFORMATION: Xaa = Pro or absent
<220> FEATURE:
<221> NAME/KEY: VARIANT
<222> LOCATION: (50)...(50)
<223> OTHER INFORMATION: Xaa = Arg, Pro or absent
<220> FEATURE:
<221> NAME/KEY: VARIANT
<222> LOCATION: (51)...(51)
<223> OTHER INFORMATION: Xaa = Asn, Ser, Lys or absent
<220> FEATURE:
<221> NAME/KEY: VARIANT
<222> LOCATION: (52)...(52)
<223> OTHER INFORMATION: Xaa = Asn, Pro, Gly, Arg or absent
<220> FEATURE:
<221> NAME/KEY: VARIANT
<222> LOCATION: (53)...(53)
<223> OTHER INFORMATION: Xaa = Ser, Phe, Leu or absent
<220> FEATURE:
<221> NAME/KEY: VARIANT
<222> LOCATION: (54)...(54)
<223> OTHER INFORMATION: Xaa = Thr, His, Pro or absent
<220> FEATURE:
<221> NAME/KEY: VARIANT
```

```
<222> LOCATION: (55)...(55)
<223> OTHER INFORMATION: Xaa = His, Thr, Leu, Ala or absent
<220> FEATURE:
<221> NAME/KEY: VARIANT
<222> LOCATION: (56)...(56)
<223> OTHER INFORMATION: Xaa = Asn, Gln, Arg or absent
<220> FEATURE:
<221> NAME/KEY: VARIANT
<222> LOCATION: (57)...(57)
<223> OTHER INFORMATION: Xaa = Gln, Leu, Arg or absent
<220> FEATURE:
<221> NAME/KEY: VARIANT
<222> LOCATION: (58)...(58)
<223> OTHER INFORMATION: Xaa = Lys, Arg, Val, Leu or absent
<220> FEATURE:
<221> NAME/KEY: VARIANT
<222> LOCATION: (59)...(59)
<223> OTHER INFORMATION: Xaa = Ser, Thr, Arg or absent
<220> FEATURE:
<221> NAME/KEY: VARIANT
<222> LOCATION: (60)...(60)
<223> OTHER INFORMATION: Xaa = Gln, Ala, Ile or absent
<220> FEATURE:
<221> NAME/KEY: VARIANT
<222> LOCATION: (61)...(61)
<223> OTHER INFORMATION: Xaa = Ile, Lys, Met, Ser or absent
<220> FEATURE:
<221> NAME/KEY: VARIANT
<222> LOCATION: (62)...(62)
<223> OTHER INFORMATION: Xaa = His, Ile, Ala, Tyr or absent
<220> FEATURE:
<221> NAME/KEY: VARIANT
<222> LOCATION: (64)...(64)
<223> OTHER INFORMATION: Xaa = Pro, Ala, Asn or absent
<220> FEATURE:
<221> NAME/KEY: VARIANT
<222> LOCATION: (65)...(65)
<223> OTHER INFORMATION: Xaa = Met, Ile, Ser, Pro, Tyr or absent
<220> FEATURE:
<221> NAME/KEY: VARIANT
<222> LOCATION: (66)...(66)
<223> OTHER INFORMATION: Xaa = Ala, Ser, Met, Asn or absent
<220> FEATURE:
<221> NAME/KEY: VARIANT
<222> LOCATION: (71)...(71)
<223> OTHER INFORMATION: Xaa = Asn, Met, Lys or absent
<220> FEATURE:
<221> NAME/KEY: VARIANT
<222> LOCATION: (90)...(90)
<223> OTHER INFORMATION: Xaa = Asn, Lys, Gly or absent
<220> FEATURE:
<221> NAME/KEY: VARIANT
<222> LOCATION: (91)...(91)
<223> OTHER INFORMATION: Xaa = Ala or absent
<220> FEATURE:
<221> NAME/KEY: VARIANT
<222> LOCATION: (92)...(92)
<223> OTHER INFORMATION: Xaa = Gln or absent
<220> FEATURE:
<221> NAME/KEY: VARIANT
<222> LOCATION: (93)...(93)
<223> OTHER INFORMATION: Xaa = Phe or absent
<220> FEATURE:
<221> NAME/KEY: VARIANT
<222> LOCATION: (94)...(95)
<223> OTHER INFORMATION: Xaa = Leu or absent
<220> FEATURE:
<221> NAME/KEY: VARIANT
<222> LOCATION: (96)...(96)
<223> OTHER INFORMATION: Xaa = Thr or absent
<220> FEATURE:
<221> NAME/KEY: VARIANT
<222> LOCATION: (97)...(97)
<223> OTHER INFORMATION: Xaa = Ser or absent
<220> FEATURE:
<221> NAME/KEY: VARIANT
<222> LOCATION: (98)...(98)
<223> OTHER INFORMATION: Xaa = Tyr or absent
<220> FEATURE:
```

```
<221> NAME/KEY: VARIANT
<222> LOCATION: (99)...(99)
<223> OTHER INFORMATION: Xaa = Leu or absent
<220> FEATURE:
<221> NAME/KEY: VARIANT
<222> LOCATION: (100)...(100)
<223> OTHER INFORMATION: Xaa = Thr or absent
<220> FEATURE:
<221> NAME/KEY: VARIANT
<222> LOCATION: (101)...(101)
<223> OTHER INFORMATION: Xaa = Ile or absent
<220> FEATURE:
<221> NAME/KEY: VARIANT
<222> LOCATION: (102)...(102)
<223> OTHER INFORMATION: Xaa = Leu or absent
<220> FEATURE:
<221> NAME/KEY: VARIANT
<222> LOCATION: (103)...(103)
<223> OTHER INFORMATION: Xaa = Ile or absent
<220> FEATURE:
<221> NAME/KEY: VARIANT
<222> LOCATION: (104)...(104)
<223> OTHER INFORMATION: Xaa = Tyr or absent
<220> FEATURE:
<221> NAME/KEY: VARIANT
<222> LOCATION: (105)...(105)
<223> OTHER INFORMATION: Xaa = Met or absent
<220> FEATURE:
<221> NAME/KEY: VARIANT
<222> LOCATION: (106)...(106)
<223> OTHER INFORMATION: Xaa = Ile, Lys or absent
<220> FEATURE:
<221> NAME/KEY: VARIANT
<222> LOCATION: (183)...(183)
<223> OTHER INFORMATION: Xaa = Leu, Ala, Arg or Ser
<220> FEATURE:
<221> NAME/KEY: VARIANT
<222> LOCATION: (213)...(213)
<223> OTHER INFORMATION: Xaa = Lys, Asn, Glu or Gln
<220> FEATURE:
<221> NAME/KEY: VARIANT
<222> LOCATION: (361)...(361)
<223> OTHER INFORMATION: Xaa = Ala, Leu, Val, Gln or Glu
<220> FEATURE:
<221> NAME/KEY: VARIANT
<222> LOCATION: (365)...(365)
<223> OTHER INFORMATION: Xaa = Leu, Asn, Ser, Phe or absent
<220> FEATURE:
<221> NAME/KEY: VARIANT
<222> LOCATION: (366)...(366)
<223> OTHER INFORMATION: Xaa = Ser or absent
<220> FEATURE:
<221> NAME/KEY: VARIANT
<222> LOCATION: (367)...(368)
<223> OTHER INFORMATION: Xaa = Thr or absent
<220> FEATURE:
<221> NAME/KEY: VARIANT
<222> LOCATION: (369)...(369)
<223> OTHER INFORMATION: Xaa = His or absent
<220> FEATURE:
<221> NAME/KEY: VARIANT
<222> LOCATION: (373)...(373)
<223> OTHER INFORMATION: Xaa = Pro, Thr, Leu, Asn, Gln, Glu or absent
<220> FEATURE:
<221> NAME/KEY: VARIANT
<222> LOCATION: (374)...(374)
<223> OTHER INFORMATION: Xaa = Thr, Lys, Asn, Arg, Tyr, His or absent
<220> FEATURE:
<221> NAME/KEY: VARIANT
<222> LOCATION: (390)...(390)
<223> OTHER INFORMATION: Xaa = Val, Lys, Asp, Gly or absent
<220> FEATURE:
<221> NAME/KEY: VARIANT
<222> LOCATION: (392)...(392)
<223> OTHER INFORMATION: Xaa = Ile, Asp, Gln, Lys, Ala or absent
<220> FEATURE:
<221> NAME/KEY: VARIANT
<222> LOCATION: (393)...(393)
<223> OTHER INFORMATION: Xaa = Tyr, Ser, Glu, Lys or absent
```

```
<220> FEATURE:
<221> NAME/KEY: VARIANT
<222> LOCATION: (394)...(394)
<223> OTHER INFORMATION: Xaa = Ile, His or absent

<400> SEQUENCE: 44
```

| | | | | | | | | | | | | | | |
|---|---|---|---|---|---|---|---|---|---|---|---|---|---|---|
| Xaa<br>1 | Xaa | Xaa | Xaa | Xaa<br>5 | Xaa | Xaa | Xaa | Xaa | Xaa<br>10 | Xaa | Xaa | Xaa | Xaa | Xaa<br>15 |
| Xaa | Xaa | Xaa | Xaa | Xaa<br>20 | Xaa | Xaa | Xaa | Xaa | Xaa<br>25 | Leu | Xaa | Xaa | Xaa | Xaa<br>30 |
| Xaa | Xaa | Xaa | Xaa | Xaa<br>35 | Xaa | Xaa | Xaa | Xaa | Xaa<br>40 | Xaa | Xaa | Xaa | Xaa | Xaa<br>45 |
| Xaa | Xaa | Xaa | Xaa | Xaa<br>50 | Xaa | Xaa | Xaa | Xaa | Xaa<br>55 | Xaa | Xaa | Xaa | Thr | Xaa<br>60 |
| Xaa | Xaa | Ala | Ser | Ser | Phe | Xaa<br>70 | Pro | Glu | Gln | Ala | Arg<br>75 | Ser | Pro | Pro | Ala<br>80 |
| Leu | Pro | Leu | Pro | Thr<br>85 | Pro | Pro | Leu | Thr | Xaa<br>90 | Xaa | Xaa | Xaa | Xaa | Xaa<br>95 |
| Xaa | Xaa | Xaa | Xaa | Xaa<br>100 | Xaa | Xaa | Xaa | Xaa | Phe<br>105 | Lys | Ile | Gly | Leu<br>110 | Cys |
| Gln | Leu | Ser | Val | Thr<br>115 | Ala | Asp | Lys | Asp | Arg<br>120 | Asn | Ile | Ala | His | Ala<br>125 | Arg |
| Lys | Ala | Ile<br>130 | Glu | Glu | Ala | Ala | Lys<br>135 | Gly | Ala | Lys | Leu | Val<br>140 | Leu | Leu |
| Pro<br>145 | Glu | Ile | Trp | Asn | Ser<br>150 | Pro | Tyr | Ser | Asn | Asp<br>155 | Ser | Phe | Pro | Val | Tyr<br>160 |
| Ala | Glu | Asp | Ile | Asp<br>165 | Ala | Gly | Gly | Asp | Ala<br>170 | Ser | Pro | Ser | Thr | Ala<br>175 | Met |
| Leu | Ser | Glu | Val | Ala<br>180 | Arg | Xaa | Leu | Lys | Ile<br>185 | Thr | Ile | Val | Gly<br>190 | Gly Ser |
| Ile | Pro | Glu | Arg<br>195 | Ser | Gly | Asp | Arg | Leu<br>200 | Tyr | Asn | Thr | Cys | Cys<br>205 | Val | Phe |
| Gly | Ser | Asp<br>210 | Gly | Xaa | Leu | Lys<br>215 | Ala | Lys | His | Arg | Lys<br>220 | Ile | His | Leu | Phe |
| Asp<br>225 | Ile | Asp | Ile | Pro | Gly<br>230 | Lys | Ile | Thr | Phe | Ile<br>235 | Glu | Ser | Lys | Thr | Leu<br>240 |
| Thr | Ala | Gly | Asp | Thr<br>245 | Pro | Thr | Ile | Val | Asp<br>250 | Thr | Glu | Val | Gly | Arg<br>255 | Ile |
| Gly | Ile | Gly | Ile<br>260 | Cys | Tyr | Asp | Ile | Arg<br>265 | Phe | Gln | Glu | Leu | Ala<br>270 | Met | Leu |
| Tyr | Ala | Ala | Arg<br>275 | Gly | Ala | His | Leu | Leu<br>280 | Cys | Tyr | Pro | Gly | Ala<br>285 | Phe | Asn |
| Met<br>290 | Thr | Thr | Gly | Pro | Leu<br>295 | His | Trp | Glu | Leu | Leu<br>300 | Gln | Arg | Ala | Arg | Ala |
| Ala<br>305 | Asp | Asn | Gln | Leu | Tyr<br>310 | Val | Ala | Thr | Cys | Ser<br>315 | Pro | Ala | Arg | Asp | Thr<br>320 |
| Gly | Ala | Gly | Tyr | Val<br>325 | Ala | Trp | Gly | His | Ser<br>330 | Thr | Leu | Val | Gly | Pro<br>335 | Phe |
| Gly | Glu | Val | Leu | Ala<br>340 | Thr | Thr | Glu | His | Glu<br>345 | Glu | Ala | Ile | Ile<br>350 | Ile | Ala |
| Glu | Ile | Asp | Tyr<br>355 | Ser | Leu | Ile | Glu | Xaa<br>360 | Arg | Arg | Gln | Xaa | Xaa<br>365 | Xaa | Xaa |
| Xaa | Leu | Pro<br>370 | Leu | Xaa | Xaa | Gln<br>375 | Arg | Arg | Gly | Asp | Leu<br>380 | Tyr | Gln | Leu | Val |

Asp Val Gln Arg Leu Xaa Ser Xaa Xaa Xaa
385                 390

<210> SEQ ID NO 45
<211> LENGTH: 318
<212> TYPE: PRT
<213> ORGANISM: Artificial Sequence
<220> FEATURE:
<223> OTHER INFORMATION: synthetic animal omega-amidase consensus
      sequence
<220> FEATURE:
<221> NAME/KEY: VARIANT
<222> LOCATION: (1)...(1)
<223> OTHER INFORMATION: Xaa = Met or absent
<220> FEATURE:
<221> NAME/KEY: VARIANT
<222> LOCATION: (2)...(3)
<223> OTHER INFORMATION: Xaa = Ala or absent
<220> FEATURE:
<221> NAME/KEY: VARIANT
<222> LOCATION: (4)...(4)
<223> OTHER INFORMATION: Xaa = His or absent
<220> FEATURE:
<221> NAME/KEY: VARIANT
<222> LOCATION: (5)...(5)
<223> OTHER INFORMATION: Xaa = Ser or absent
<220> FEATURE:
<221> NAME/KEY: VARIANT
<222> LOCATION: (6)...(6)
<223> OTHER INFORMATION: Xaa = Ile or absent
<220> FEATURE:
<221> NAME/KEY: VARIANT
<222> LOCATION: (7)...(7)
<223> OTHER INFORMATION: Xaa = Leu or absent
<220> FEATURE:
<221> NAME/KEY: VARIANT
<222> LOCATION: (8)...(8)
<223> OTHER INFORMATION: Xaa = Asp or absent
<220> FEATURE:
<221> NAME/KEY: VARIANT
<222> LOCATION: (9)...(9)
<223> OTHER INFORMATION: Xaa = Leu or absent
<220> FEATURE:
<221> NAME/KEY: VARIANT
<222> LOCATION: (10)...(10)
<223> OTHER INFORMATION: Xaa = Ser or absent
<220> FEATURE:
<221> NAME/KEY: VARIANT
<222> LOCATION: (11)...(11)
<223> OTHER INFORMATION: Xaa = Gly or absent
<220> FEATURE:
<221> NAME/KEY: VARIANT
<222> LOCATION: (12)...(12)
<223> OTHER INFORMATION: Xaa = Leu or absent
<220> FEATURE:
<221> NAME/KEY: VARIANT
<222> LOCATION: (13)...(13)
<223> OTHER INFORMATION: Xaa = Asp or absent
<220> FEATURE:
<221> NAME/KEY: VARIANT
<222> LOCATION: (14)...(14)
<223> OTHER INFORMATION: Xaa = Arg or absent
<220> FEATURE:
<221> NAME/KEY: VARIANT
<222> LOCATION: (15)...(15)
<223> OTHER INFORMATION: Xaa = Glu or absent
<220> FEATURE:
<221> NAME/KEY: VARIANT
<222> LOCATION: (16)...(16)
<223> OTHER INFORMATION: Xaa = Ser or absent
<220> FEATURE:
<221> NAME/KEY: VARIANT
<222> LOCATION: (17)...(17)
<223> OTHER INFORMATION: Xaa = Gln, Met or absent
<220> FEATURE:
<221> NAME/KEY: VARIANT
<222> LOCATION: (18)...(18)
<223> OTHER INFORMATION: Xaa = Ile, Ala or absent -continued

```
<220> FEATURE:
<221> NAME/KEY: VARIANT
<222> LOCATION: (19)...(19)
<223> OTHER INFORMATION: Xaa = Asp, Ser or absent
<220> FEATURE:
<221> NAME/KEY: VARIANT
<222> LOCATION: (20)...(20)
<223> OTHER INFORMATION: Xaa = Leu, Ser or absent
<220> FEATURE:
<221> NAME/KEY: VARIANT
<222> LOCATION: (21)...(21)
<223> OTHER INFORMATION: Xaa = Gln, Phe or absent
<220> FEATURE:
<221> NAME/KEY: VARIANT
<222> LOCATION: (22)...(22)
<223> OTHER INFORMATION: Xaa = Arg, Asn or absent
<220> FEATURE:
<221> NAME/KEY: VARIANT
<222> LOCATION: (23)...(23)
<223> OTHER INFORMATION: Xaa = Pro or absent
<220> FEATURE:
<221> NAME/KEY: VARIANT
<222> LOCATION: (24)...(24)
<223> OTHER INFORMATION: Xaa = Leu, Glu or absent
<220> FEATURE:
<221> NAME/KEY: VARIANT
<222> LOCATION: (25)...(25)
<223> OTHER INFORMATION: Xaa = Lys, Gln or absent
<220> FEATURE:
<221> NAME/KEY: VARIANT
<222> LOCATION: (26)...(26)
<223> OTHER INFORMATION: Xaa = Ala or absent
<220> FEATURE:
<221> NAME/KEY: VARIANT
<222> LOCATION: (27)...(27)
<223> OTHER INFORMATION: Xaa = Arg or absent
<220> FEATURE:
<221> NAME/KEY: VARIANT
<222> LOCATION: (28)...(28)
<223> OTHER INFORMATION: Xaa = Phe, Val or absent
<220> FEATURE:
<221> NAME/KEY: VARIANT
<222> LOCATION: (29)...(29)
<223> OTHER INFORMATION: Xaa = Gly, Pro or absent
<220> FEATURE:
<221> NAME/KEY: VARIANT
<222> LOCATION: (30)...(30)
<223> OTHER INFORMATION: Xaa = Lys, Ser or absent
<220> FEATURE:
<221> NAME/KEY: VARIANT
<222> LOCATION: (31)...(31)
<223> OTHER INFORMATION: Xaa = Ala or absent
<220> FEATURE:
<221> NAME/KEY: VARIANT
<222> LOCATION: (32)...(32)
<223> OTHER INFORMATION: Xaa = Lys, Leu or absent
<220> FEATURE:
<221> NAME/KEY: VARIANT
<222> LOCATION: (33)...(33)
<223> OTHER INFORMATION: Xaa = Asp, Pro or absent
<220> FEATURE:
<221> NAME/KEY: VARIANT
<222> LOCATION: (34)...(34)
<223> OTHER INFORMATION: Xaa = Leu or absent
<220> FEATURE:
<221> NAME/KEY: VARIANT
<222> LOCATION: (35)...(35)
<223> OTHER INFORMATION: Xaa = Ser, Pro or absent
<220> FEATURE:
<221> NAME/KEY: VARIANT
<222> LOCATION: (36)...(36)
<223> OTHER INFORMATION: Xaa = Ser, Ala or absent
<220> FEATURE:
<221> NAME/KEY: VARIANT
<222> LOCATION: (37)...(37)
<223> OTHER INFORMATION: Xaa = Gly, Pro or absent
<220> FEATURE:
<221> NAME/KEY: VARIANT
<222> LOCATION: (38)...(38)
```

```
<223> OTHER INFORMATION: Xaa = Ser, Pro or absent
<220> FEATURE:
<221> NAME/KEY: VARIANT
<222> LOCATION: (70)...(70)
<223> OTHER INFORMATION: Xaa = Lys, Ala, Thr, Gly, Gln or Ser
<220> FEATURE:
<221> NAME/KEY: VARIANT
<222> LOCATION: (77)...(77)
<223> OTHER INFORMATION: Xaa = Ser, Cys, Val, Ala or Leu
<220> FEATURE:
<221> NAME/KEY: VARIANT
<222> LOCATION: (89)...(89)
<223> OTHER INFORMATION: Xaa = Thr, Asn, Lys, Gly or Asp
<220> FEATURE:
<221> NAME/KEY: VARIANT
<222> LOCATION: (101)...(102)
<223> OTHER INFORMATION: Xaa = Gly or absent
<220> FEATURE:
<221> NAME/KEY: VARIANT
<222> LOCATION: (103)...(103)
<223> OTHER INFORMATION: Xaa = Asp or absent
<220> FEATURE:
<221> NAME/KEY: VARIANT
<222> LOCATION: (104)...(104)
<223> OTHER INFORMATION: Xaa = Ala or absent
<220> FEATURE:
<221> NAME/KEY: VARIANT
<222> LOCATION: (105)...(105)
<223> OTHER INFORMATION: Xaa = Ser or absent
<220> FEATURE:
<221> NAME/KEY: VARIANT
<222> LOCATION: (265)...(265)
<223> OTHER INFORMATION: Xaa = Asp, Thr, Asn, Ser or Gly
<220> FEATURE:
<221> NAME/KEY: VARIANT
<222> LOCATION: (288)...(288)
<223> OTHER INFORMATION: Xaa = Lys, Gln, Glu or Ser
<220> FEATURE:
<221> NAME/KEY: VARIANT
<222> LOCATION: (289)...(289)
<223> OTHER INFORMATION: Xaa = Lys, Tyr or Ile
<220> FEATURE:
<221> NAME/KEY: VARIANT
<222> LOCATION: (299)...(299)
<223> OTHER INFORMATION: Xaa = Leu, Phe, Thr, Arg, Asn or absent
<220> FEATURE:
<221> NAME/KEY: VARIANT
<222> LOCATION: (304)...(304)
<223> OTHER INFORMATION: Xaa = Ala, Leu, Asn, His, Gly or absent
<220> FEATURE:
<221> NAME/KEY: VARIANT
<222> LOCATION: (311)...(311)
<223> OTHER INFORMATION: Xaa = Ser, Ala, Glu, Asp or absent
<220> FEATURE:
<221> NAME/KEY: VARIANT
<222> LOCATION: (314)...(314)
<223> OTHER INFORMATION: Xaa = Pro, Glu, Asn, Arg or absent
<220> FEATURE:
<221> NAME/KEY: VARIANT
<222> LOCATION: (315)...(315)
<223> OTHER INFORMATION: Xaa = Gly, Leu or absent
<220> FEATURE:
<221> NAME/KEY: VARIANT
<222> LOCATION: (316)...(316)
<223> OTHER INFORMATION: Xaa = Asp or absent
<220> FEATURE:
<221> NAME/KEY: VARIANT
<222> LOCATION: (317)...(317)
<223> OTHER INFORMATION: Xaa = Ser or absent
<220> FEATURE:
<221> NAME/KEY: VARIANT
<222> LOCATION: (318)...(318)
<223> OTHER INFORMATION: Xaa = Lys or absent

<400> SEQUENCE: 45

Xaa Xaa Xaa Xaa Xaa Xaa Xaa Xaa Xaa Xaa Xaa Xaa Xaa Xaa Xaa Xaa
 1               5                   10                  15
```

```
Xaa Xaa Xaa Xaa Xaa Xaa Xaa Xaa Xaa Xaa Xaa Xaa
            20                  25                  30

Xaa Xaa Xaa Xaa Xaa Xaa Met Ser Lys Phe Arg Leu Ala Leu Ile Gln
            35                  40                  45

Leu Gln Val Ser Ser Ile Lys Ser Asp Asn Leu Arg Ala Cys Ser Leu
 50                  55                  60

Val Arg Glu Ala Ala Xaa Gln Gly Ala Lys Ile Val Xaa Leu Pro Glu
 65                  70                  75                  80

Cys Phe Asn Ser Pro Tyr Gly Thr Xaa Tyr Phe Pro Glu Tyr Ala Glu
                85                  90                  95

Lys Ile Pro Gly Xaa Xaa Xaa Xaa Glu Ser Thr Gln Lys Leu Ser
                100                 105                 110

Glu Val Ala Lys Glu Cys Ile Tyr Leu Ile Gly Gly Ser Ile Pro Glu
                115                 120                 125

Glu Asp Ala Gly Lys Leu Tyr Asn Thr Cys Ala Val Phe Gly Pro Asp
                130                 135                 140

Gly Thr Leu Leu Val Lys His Arg Lys Ile His Leu Phe Asp Ile Asp
145                 150                 155                 160

Val Pro Gly Lys Ile Thr Phe Gln Glu Ser Lys Thr Leu Ser Pro Gly
                165                 170                 175

Asp Phe Ser Thr Phe Asp Thr Pro Tyr Cys Lys Val Gly Leu Gly Ile
                180                 185                 190

Cys Tyr Asp Ile Arg Phe Ala Glu Leu Ala Gln Ile Tyr Ala Gln Arg
                195                 200                 205

Gly Cys Gln Leu Leu Val Tyr Pro Gly Ala Phe Asn Leu Thr Thr Gly
210                 215                 220

Pro Ala His Trp Glu Leu Leu Gln Arg Ala Arg Ala Asp Asn Gln Val
225                 230                 235                 240

Tyr Val Ala Thr Ala Ser Pro Ala Arg Asp Asp Lys Ala Ser Tyr Val
                245                 250                 255

Ala Trp Gly His Ser Thr Val Val Xaa Pro Trp Gly Glu Val Leu Ala
                260                 265                 270

Lys Ala Gly Thr Glu Glu Thr Ile Leu Tyr Ala Asp Ile Asp Leu Xaa
                275                 280                 285

Xaa Leu Ala Glu Ile Arg Gln Ile Pro Ile Xaa Lys Gln Arg Arg Xaa
 290                 295                 300

Asp Leu Tyr Thr Val Glu Xaa Lys Lys Xaa Xaa Xaa Xaa
305                 310                 315

<210> SEQ ID NO 46
<211> LENGTH: 369
<212> TYPE: PRT
<213> ORGANISM: Arabidopsis thaliana
<220> FEATURE:
<223> OTHER INFORMATION: Arabidopsis full-length omega-amidase,
      AT5g12040/F14F18_210

<400> SEQUENCE: 46

Met Lys Ser Ala Ile Ser Ser Ser Leu Phe Phe Asn Ser Lys Asn Leu
 1               5                  10                  15

Leu Asn Pro Asn Pro Leu Ser Arg Phe Ile Ser Leu Ser Asn Phe
                20                  25                  30

Leu Pro Lys Leu Ser Pro Arg Ser Ile Thr Ser His Thr Leu Lys Leu
                35                  40                  45

Pro Ser Ser Ser Thr Ser Ala Leu Arg Ser Ile Ser Ser Met Ala
 50                  55                  60
```

```
Ser Ser Phe Asn Pro Glu Gln Ala Arg Val Pro Ser Ala Leu Pro Leu
 65                  70                  75                  80
Pro Ala Pro Pro Leu Thr Lys Phe Asn Ile Gly Leu Cys Gln Leu Ser
             85                  90                  95
Val Thr Ser Asp Lys Lys Arg Asn Ile Ser His Ala Lys Lys Ala Ile
            100                 105                 110
Glu Glu Ala Ala Ser Lys Gly Ala Lys Leu Val Leu Leu Pro Glu Ile
            115                 120                 125
Trp Asn Ser Pro Tyr Ser Asn Asp Ser Phe Pro Val Tyr Ala Glu Glu
        130                 135                 140
Ile Asp Ala Gly Gly Asp Ala Ser Pro Ser Thr Ala Met Leu Ser Glu
145                 150                 155                 160
Val Ser Lys Arg Leu Lys Ile Thr Ile Ile Gly Gly Ser Ile Pro Glu
                165                 170                 175
Arg Val Gly Asp Arg Leu Tyr Asn Thr Cys Cys Val Phe Gly Ser Asp
            180                 185                 190
Gly Glu Leu Lys Ala Lys His Arg Lys Ile His Leu Phe Asp Ile Asp
            195                 200                 205
Ile Pro Gly Lys Ile Thr Phe Met Glu Ser Lys Thr Leu Thr Ala Gly
        210                 215                 220
Glu Thr Pro Thr Ile Val Asp Thr Asp Val Gly Arg Ile Gly Ile Gly
225                 230                 235                 240
Ile Cys Tyr Asp Ile Arg Phe Gln Glu Leu Ala Met Ile Tyr Ala Ala
                245                 250                 255
Arg Gly Ala His Leu Leu Cys Tyr Pro Gly Ala Phe Asn Met Thr Thr
            260                 265                 270
Gly Pro Leu His Trp Glu Leu Leu Gln Arg Ala Arg Ala Thr Asp Asn
        275                 280                 285
Gln Leu Tyr Val Ala Thr Cys Ser Pro Ala Arg Asp Ser Gly Ala Gly
        290                 295                 300
Tyr Thr Ala Trp Gly His Ser Thr Leu Val Gly Pro Phe Gly Glu Val
305                 310                 315                 320
Leu Ala Thr Thr Glu His Glu Glu Ala Ile Ile Ile Ala Glu Ile Asp
                325                 330                 335
Tyr Ser Ile Leu Glu Gln Arg Arg Thr Ser Leu Pro Leu Asn Arg Gln
            340                 345                 350
Arg Arg Gly Asp Leu Tyr Gln Leu Val Asp Val Gln Arg Leu Asp Ser
            355                 360                 365
Lys
```